(12) United States Patent
Winston, Jr. et al.

(10) Patent No.: US 7,649,083 B2
(45) Date of Patent: Jan. 19, 2010

(54) HEPATOCYTE GROWTH FACTOR (HGF) BINDING ANTIBODY

(75) Inventors: William M. Winston, Jr., Marlborough, MA (US); S. Kirk Wright, Waltham, MA (US); May Han, Brookline, MA (US); Lyne Breault, Roslindale, MA (US); Jie Lin, West Roxbury, MA (US); Bijan Etemad-Gilbertson, Jamaica Plain, MA (US); Christine Knuehl, Natick, MA (US); Jeno Gyuris, Winchester, MA (US); Arnold Horwitz, San Leandro, CA (US)

(73) Assignees: AVEO Pharmaceuticals, Inc., Cambridge, MA (US); XOMA Technology Ltd., Berkeley, CA (US)

( * ) Notice: Subject to any disclaimer, the term of this patent is extended or adjusted under 35 U.S.C. 154(b) by 228 days.

(21) Appl. No.: 11/757,059

(22) Filed: Jun. 1, 2007

(65) Prior Publication Data

US 2008/0108565 A1 May 8, 2008

Related U.S. Application Data

(60) Provisional application No. 60/810,714, filed on Jun. 2, 2006, provisional application No. 60/860,509, filed on Nov. 21, 2006.

(51) Int. Cl.
*C07K 16/00* (2006.01)
*C07K 16/24* (2006.01)
(52) U.S. Cl. .............................. 530/388.24; 530/387.1; 530/388.1; 530/388.15
(58) Field of Classification Search ........................ None
See application file for complete search history.

(56) References Cited

U.S. PATENT DOCUMENTS

| 5,707,624 | A | 1/1998 | Nickoloff et al. |
| 5,766,886 | A | 6/1998 | Studnicka et al. |
| 5,997,868 | A | 12/1999 | Goldberg et al. |
| 6,432,406 | B1 | 8/2002 | Goldberg et al. |
| 6,881,557 | B2 | 4/2005 | Foote |
| 7,220,410 | B2 | 5/2007 | Kim et al. |
| 2008/0038256 | A1 | 2/2008 | Chung et al. |
| 2008/0038257 | A1 | 2/2008 | May et al. |

FOREIGN PATENT DOCUMENTS

| WO | WO-01/034650 | 5/2001 |
| WO | WO-2005/017107 | 2/2005 |
| WO | WO-2005/044848 | 5/2005 |
| WO | WO-2005/107800 | 11/2005 |
| WO | WO-2006/130773 | 12/2006 |
| WO | WO-2007/115049 | 10/2007 |

OTHER PUBLICATIONS

Burgess et al. "Fully Human Monoclonal Antibodies to Hepatocyte Growth Factor With Therapeutic Potential Against Hepatocyte Growth Factor/C-Met-Dependent Human Tumors" (2006) Cancer Res. 66:3, pp. 1721-1729.
Burr et al. "Anti-Hepatocyte Growth Factor Antibody Inhibits Hepatocyte Proliferation During Liver Regeneration" Journal of Pathology, Chicester, Sussex, GB, vol. 185, (Jul. 1998) pp. 298-302.
Cao et al. "Neutralizing monoclonal antibodies to hepatocyte growth factor/scatter factor (HGF/SF) display antitumor activity in animal models" Proc. Natl. Acad. Sci. 2001 USA 98: 7443-7448.
Hwang et al. "Use of human germline genes in a CDR homology-based approach to antibody humanization" Methods. May 2005;36(1):35-42.
Kim et al. "Systemic anti-hepatocyte growth factor monoclonal antibody thereapy induces the regression of intracranial glioma axenografts" (2006) Clinical Cancer Research 12:1292-1298.
R&D Systems, Inc. 1999 Catalog, p. 185, Cat. #MAB294, anti-human HGF monoclonal antibody.
Rubin et al. "Hepatocyte growth factor/scatter factor and its receptor, the c-met proto-oncogene product" Biochim Biophys Acta. Dec. 23, 1993;1155(3):357-71.
Studnicka et al. "Human-engineered monoclonal antibodies retain full specific binding activity by preserving non-CDR complementarity-modulating residues" Protein Eng. Jun. 1994;7(6):805-14.
Tan et al. ""Superhumanized" antibodies: reduction of immunogenic potential by complementarity-determining region grafting with human germline sequences: application to an anti-CD28" J lmmunol. Jul. 15, 2002;169(2):1119-25.
Zaccolo et al. "Dimerization of FAB Fragments Enables Ready Screening of Phage Antibodies that Affect Hepatocyte Growth Factor/Scatter Factor Activity on Target Cells" European Journal of Immunology, vol. 27, No. 3, (1997), pp. 618-623.
International Search Report for PCT/2007/012950 dated Apr. 15, 2008.
International Search Report for PCT/2007/012939 dated Jan. 30, 2008.

*Primary Examiner*—Phillip Gambel
*Assistant Examiner*—Sharon Wen
(74) *Attorney, Agent, or Firm*—Goodwin Procter LLP

(57) ABSTRACT

The present invention provides a family of binding proteins that bind and neutralize the activity of hepatocyte growth factor (HGF), in particular human HGF. The binding proteins can be used as diagnostic and/or therapeutic agents. With regard to their therapeutic activity, the binding proteins can be used to treat certain HGF responsive disorders, for example, certain HGF responsive tumors.

9 Claims, 9 Drawing Sheets

Complete Heavy Chain Variable Region Amino Acid Alignments

| Antibody | Signal Peptide | CDR1 | CDR2 |
|---|---|---|---|
| 1A3 | MNFGLRLIFLVLVLKGVKC EVQLVESGGGLVQPGGSLKLSCAASEFTFS | NYYMS | WVRQTPEKRLQWVA YISPGGGSSYYPASVKG RFTISRDNAKNTLYL |
| 2B8 | MGWSYIILFLFLVATATDVHS QVQLQQPGAELVKPGTSVKLSCKASGYTFT | TYWMH | WVNQRPGQGLEWIGE INPTNGHTNYNEKFKS KATLTVDKSSSTAYM |
| 2F8 | MEWSWVFLFLLSVTAGVHC QVQLKQSGAELVRPGTSVKMSCKASGYTFT | TYYIH | WVNQRPGQGLEWIGK IGPGSGSTYYNEMFKD KATLTVDTSSSTAYM |
| 3B6 | MEWPCIFLFLLSVTEGVHS QVQLQQSGAELVRPGSSVKISCKASGYVFS | SYWMN | WVKQRPGQGLEWIGQ IYPGDGDSNYNGNFKG KATLTADKSSSTAYM |
| 3D11 | MAVPVLFLCLVAFPSCVLS QVQLKESGPGLVAPSQSLSITCTVSGFSLIT | SYSLH | WVRQPPGKGLEWLGVIWAG-GNTNYNSSLMS RLTIRKDNSKSQVFL |
| 1D3 | MNFGLRLIFLVLVLKGVKC EVQLVESGGGLVQPGGSLKLSCAASGFTFS | DYYMS | WVRQTPEKRLEWVA YISSGGGSTYYPDSVKG RFTISRDNAKNTLYL |
| 1F3 | MNFGLRLIFLVLVLKGVKC EVQLVESGGGLVQSGGLVQSGGSTYYPDSVKGRFTISRDNAKNTLYL |  |  |
| 1F3 | MNFGLRLIFLVLVLKGVKC EVQLVESGGGLVQSGGGLVQPGGSLKLSCAASGFTFS | NYFMS | WVRQTPEKRLEWVA YISSGGGSTYYPDSVKG RFTISRDNAKNTLYL |
| 3A12 | MNFGLRLIFLVLVLKGVKC EVQLVESGGGLVQPGGSLKISCAASGFTFS | NYFMS | WVRQTPEKRLEWVA YISSGGGSTYYPDSVKG RFTISRDNAKNTLYL |

CDR3

(1A3 cont.)    QMSSLKSEDTAMYYCAR QGDGYYGDYAMDY WGQGTSVTVSS  (SEQ ID NO: 2)
(2B8 cont.)    QLSSLTSEDSAVYYCARNY----VGSIFDY WGQGTTLTVSS  (SEQ ID NO: 12)
(2F8 cont.)    QLSSLTSDDSAVYFCARRG----LGRGFDY WGQGTTLTVSS  (SEQ ID NO: 22)
(3B6 cont.)    QLSSLTSEDSAVYFCASQLG--LRENYFDY WGQGTTLTVSS  (SEQ ID NO: 32)
(3D11 cont.)   KMNSLQTDDTAMYYCARER------FAY WGQGTLVTVSA  (SEQ ID NO: 42)
(1D3 cont.)    QMSSLKSEDTAIYYCVR QGDGYYGDYAMDY WGQGTSVIVSS  (SEQ ID NO: 52)
(1F3 cont.)    QMSSLKSEDTAMYYCVR QGDGYYGDYAMDY WGQGTSVTVSS  (SEQ ID NO: 62)
(3A12 cont.)   QMNSLKSEDTAMYYCVR QGDGYYGDYAMDY WGQGTSVTVSS  (SEQ ID NO: 72)

FIG. 2

Heavy Chain CDR Amino Acid Alignments

| Antibody | CDR1 | | CDR2 | | CDR3 | |
|---|---|---|---|---|---|---|
| 1A3 | NYYMS | (SEQ ID NO: 5) | YISPGGGSSYYPASVKG | (SEQ ID NO: 6) | QGDGYYGDYAMDY | (SEQ ID NO: 7) |
| 2B8 | TYWMH | (SEQ ID NO: 15) | EINPTNGHTNYNEKFKS | (SEQ ID NO: 16) | NY~~~VGSIFDY | (SEQ ID NO: 17) |
| 2F8 | TYYIH | (SEQ ID NO: 25) | KIGPGSGSTYYNEMFKD | (SEQ ID NO: 26) | RG~~~LGRGFDY | (SEQ ID NO: 27) |
| 3B6 | SYWMN | (SEQ ID NO: 35) | QIYPGDGDSNYNGNFKG | (SEQ ID NO: 36) | QLG~~LRENYFDY | (SEQ ID NO: 37) |
| 3D11 | SYSLH | (SEQ ID NO: 45) | VIWAG~GNTNYNSSLMS | (SEQ ID NO: 46) | ER~~~~~~FAY | (SEQ ID NO: 47) |
| 1D3 | DYYMS | (SEQ ID NO: 55) | YISSGGGSTYYPDSVKG | (SEQ ID NO: 56) | QGDGYYGDYAMDY | (SEQ ID NO: 57) |
| 1F3 | NYFMS | (SEQ ID NO: 65) | YISSGGGSTYYPDSVKG | (SEQ ID NO: 66) | QGDGYYGDYAMDY | (SEQ ID NO: 67) |
| 3A12 | NYFMS | (SEQ ID NO: 75) | YISSGGGSTYYPDSVKG | (SEQ ID NO: 76) | QGDGYYGDYAMDY | (SEQ ID NO: 77) |

FIG. 3

Complete Light (Kappa) Chain Variable Region Amino Acid Alignments

| Antibody | Signal Peptide | CDR1 | CDR2 |
|---|---|---|---|
| 1A3 | --MSVPTQVLGLLLLWLLTDARC | DIQMTQSPASLSVSVGETVTITC RASENIY----SNLA WYQQKQGKSPQLLVY AATNLAD GVPSRFSGSGSGTQFSLK |
| 2B8 | --MESQTLVFISILLLWLYGADGNIVMTQSPKSMSMSVGERVTLSC KASENVV----SYVS WYQQKPAQSPKLLIY GASNRNT GVPDRFTGSGSATDFTLT |
| 2F8 | --METDTILLWVLLLWVPGSTG DIVLTQSPASLAVSLGQRATISC KASQSVDYDGNSYIN WYQQKPGQPPKVLIY VASNLES GIPARFSGSGSGTDFTLN |
| 3B6 | MDMRTPAQFLGILLLWFPGIKC DIKMTQSPSSMYASLGERVTITC KASQDIK----SYLS WFQQKPGKSPKTLIY RVNRLVD GVPSRFSGSGSGTQDSSLT |
| 3D11 | MDFQVQIFSFLLISASVKISRG QIVLTQSPAIMSAYPGEKVTMTC SASSSVS----YMH WYQQKSGTSPKRWIY DTSKLAS GVPARFSGSGSGTSYSLT |
| 1D3 | --MSVPTQVLGLLLLWLLTDVRC DIQMTQSPASLSVSVGETVTITC RTSENIY----SNLA WYQQKQGKSPQLLIY AATNLAD GVPSRFSGSGSGTQFSLR |
| 1F3 | --MSVPTQVLGLLLLWLLTDARC DIQMTQSPASLSVSVGETVTITC RASENIY----SNLA WYQQKQGKSPQLLVY DATHLPD GVPSRFSGSGSGTQFSLK |
| 3A12 | --MSVPTQVLGLLLLWLLTDARC DIQMTQSPASLSVSVGETVTITC RASENIY----INLA WYQQKQGKSPQLLVH AATKLAD GVPSRFSGSGSGTQYSLK |

CDR3

| | | |
|---|---|---|
| (1A3 cont.) | INSLQSEDFGTYYC QHFWGTPYT FGGGTKLEIK | (SEQ ID NO: 4) |
| (2B8 cont.) | ISSVRAEDLADYHC GQSYNYPYT FGGGTRLEIK | (SEQ ID NO: 14) |
| (2F8 cont.) | IHPVEEEDAATYYC QQSIEDPPT FGAGTKLELK | (SEQ ID NO: 24) |
| (3B6 cont.) | ITSLENEDMGIYYC LQYDEFPFT FGAGTKLELK | (SEQ ID NO: 34) |
| (3D11 cont.) | ISSMEAEDAATYYC QQWSSNPLT FGGGTKLEIK | (SEQ ID NO: 44) |
| (1D3 cont.) | INSLQSEDFGRYYC QHFWGTPYT FGGGTKLEIK | (SEQ ID NO: 54) |
| (1F3 cont.) | INSLQSEDFGSYYC QHFWGTPYT FGGGTKLEIK | (SEQ ID NO: 64) |
| (3A12 cont.) | INSLQSEDFGSYYC QHFWGTPYT FGGGTKLEIK | (SEQ ID NO: 74) |

FIG. 4

Light (Kappa) Chain CDR Amino Acid Alignments

| Antibody | CDR1 | | CDR2 | | CDR3 | |
|---|---|---|---|---|---|---|
| 1A3 | RASENIY~~~~SNLA | (SEQ ID NO: 8) | AATNLAD | (SEQ ID NO: 9) | QHFWGTPYT | (SEQ ID NO: 10) |
| 1D3 | RTSENIY~~~~SNLA | (SEQ ID NO: 58) | AATNLAD | (SEQ ID NO: 59) | QHFWGTPYT | (SEQ ID NO: 60) |
| 2B8 | KASENVV~~~~SYVS | (SEQ ID NO: 18) | GASNRNT | (SEQ ID NO: 19) | GQSYNYPYT | (SEQ ID NO: 20) |
| 2F8 | KASQSVDYDGNSYIN | (SEQ ID NO: 28) | VASNLES | (SEQ ID NO: 29) | QQSIEDPPT | (SEQ ID NO: 30) |
| 3D11 | SASSSVS~~~~~~YMH | (SEQ ID NO: 48) | DTSKLAS | (SEQ ID NO: 49) | QQWSSNPLT | (SEQ ID NO: 50) |
| 3B6 | KASQDIK~~~~SYLS | (SEQ ID NO: 38) | RVNRLVD | (SEQ ID NO: 39) | LQYDEFFT | (SEQ ID NO: 40) |
| 1F3 | RASENIY~~~~SNLA | (SEQ ID NO: 68) | DATHLPD | (SEQ ID NO: 69) | QHFWGTPYT | (SEQ ID NO: 70) |
| 3A12 | RASENIY~~~~INLA | (SEQ ID NO: 78) | AATKLAD | (SEQ ID NO: 79) | QHFWGTPYT | (SEQ ID NO: 80) |

FIG. 5

| Kappa | Heavy | ka (1/Ms) | STDEV | kd (1/s) | STDEV | KD (pM) | STDEV |
|---|---|---|---|---|---|---|---|
| Chimeric 2B8 | Chimeric 2B8 | $2.3 \times 10^6$ | | $2.7 \times 10^{-5}$ | | 11.6 | |
| Hu2B8_Kv1-39.1 | Chimeric 2B8 | $2.8 \times 10^6$ | | $3.9 \times 10^{-5}$ | | 13.6 | |
| Hu2B8_Kv3-15.1 | Chimeric 2B8 | $3.1 \times 10^6$ | | $1.7 \times 10^{-5}$ | | 5.5 | |
| Chimeric 2B8 | Hu2B8_Hv1-f.1 | $2.4 \times 10^6$ | | $1.6 \times 10^{-3}$ | | 662.5 | |
| Chimeric 2B8 | Hu2B8_Hv5-a.1 | $2.4 \times 10^6$ | | $1.1 \times 10^{-5}$ | | 4.4 | |
| Chimeric 2B8 | Hu2B8_Hv5-51.1 | $2.1 \times 10^6$ | | $3.4 \times 10^{-5}$ | | 16.3 | |
| Hu2B8_Kv1-39.1 | Hu2B8_Hv1-f.1 | $7.1 \times 10^6$ | | $2.1 \times 10^{-3}$ | | 294.0 | |
| Hu2B8_Kv1-39.1 | Hu2B8_Hv5-a.1 | $2.6 \times 10^6$ | | $3.8 \times 10^{-5}$ | | 14.7 | |
| Hu2B8_Kv1-39.1 | Hu2B8_Hv5-51.1 | $2.0 \times 10^6$ | $4.2 \times 10^5$ | $1.7 \times 10^{-5}$ | $1.4 \times 10^{-5}$ | 8.1 | 5.3 |
| Hu2B8_Kv3-15.1 | Hu2B8_Hv1-f.1 | $7.8 \times 10^6$ | | $3.7 \times 10^{-3}$ | | 465.8 | |
| Hu2B8_Kv3-15.1 | Hu2B8_Hv5-a.1 | $2.2 \times 10^6$ | | $5.9 \times 10^{-5}$ | | 26.9 | |
| Hu2B8_Kv3-15.1 | Hu2B8_Hv5-51.1 | $1.9 \times 10^6$ | $4.7 \times 10^5$ | $2.3 \times 10^{-5}$ | $6.3 \times 10^{-6}$ | 12.0 | 0.4 |

Fig. 8

SEQUENCE LISTING

<160> NUMBER OF SEQ ID NOS: 216

<210> SEQ ID NO 1
<211> LENGTH: 424
<212> TYPE: DNA
<213> ORGANISM: Artificial Sequence
<220> FEATURE:
<223> OTHER INFORMATION: Synthetic Heavy Chain Variable Region 1A3

<400> SEQUENCE: 1

```
atgaactttg ggctcagatt gattttcctt gtccttgttt taaaaggtgt gaagtgtgaa      60
gtgcagctgg tggagtctgg gggaggctta gtgcagcctg agggtccct gaaactctcc      120
tgtgcagcct ctgaattcac tttcagtaac tattacatgt cttgggttcg ccagactcca      180
gagaagaggc tgcagtgggt cgcatacatt agtcctggtg gtggtagctc ctactatcca      240
gccagtgtga aggtcgatt caccatctcc agagacaatg ccaagaacac cctgtacctg      300
caaatgagca gtctgaagtc tgaggacaca gccatgtatt actgtgcaag acaaggggat      360
ggttactacg ggactatgc tatggactac tggggtcaag gaacctcagt caccgtctcc      420
tcag                                                                   424
```

<210> SEQ ID NO 2
<211> LENGTH: 141
<212> TYPE: PRT
<213> ORGANISM: Artificial Sequence
<220> FEATURE:
<223> OTHER INFORMATION: Synthetic Heavy Chain Variable Region 1A3

<400> SEQUENCE: 2

Met Asn Phe Gly Leu Arg Leu Ile Phe Leu Val Leu Val Leu Lys Gly
1               5                   10                  15

Val Lys Cys Glu Val Gln Leu Val Glu Ser Gly Gly Gly Leu Val Gln
            20                  25                  30

Pro Gly Gly Ser Leu Lys Leu Ser Cys Ala Ala Ser Glu Phe Thr Phe
        35                  40                  45

Ser Asn Tyr Tyr Met Ser Trp Val Arg Gln Thr Pro Glu Lys Arg Leu
    50                  55                  60

Gln Trp Val Ala Tyr Ile Ser Pro Gly Gly Gly Ser Ser Tyr Tyr Pro
65                  70                  75                  80

Ala Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Gln Gly Asp Gly Tyr Tyr Gly Asp Tyr Ala Met
        115                 120                 125

Asp Tyr Trp Gly Gln Gly Thr Ser Val Thr Val Ser Ser
    130                 135                 140

<210> SEQ ID NO 3
<211> LENGTH: 382
<212> TYPE: DNA
<213> ORGANISM: Artificial Sequence
<220> FEATURE:
<223> OTHER INFORMATION: Synthetic Light (kappa) Chain Variable Region
      1A3

<400> SEQUENCE: 3

```
atgagtgtgc ccactcaggt cctggggttg ctgctgctgt ggcttacaga tgccagatgt      60
```

```
gacatccaga tgactcagtc tccagcctcc ctatctgttt ctgtgggaga aactgtcacc    120
atcacatgtc gagcaagtga aatatttat agtaatttag catggtatca gcagaaacag    180
ggaaaatctc ctcagctcct ggtctatgct gcaacaaact tagcagatgg tgtgccatca    240
aggttcagtg gcagtggatc aggcacacag ttttcccctca agatcaacag cctgcagtct    300
gaagattttg gacttatta ctgtcaacat ttttggggta ctccgtacac gttcggaggg    360
gggaccaagc tggaaataaa ac                                             382
```

```
<210> SEQ ID NO 4
<211> LENGTH: 127
<212> TYPE: PRT
<213> ORGANISM: Artificial Sequence
<220> FEATURE:
<223> OTHER INFORMATION: Synthetic Light (kappa) Chain Variable Region
      1A3

<400> SEQUENCE: 4

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Ser Glu Asp Phe Gly Thr Tyr Tyr Cys Gln His Phe Trp
            100                 105                 110

Gly Thr Pro Tyr Thr Phe Gly Gly Gly Thr Lys Leu Glu Ile Lys
        115                 120                 125

<210> SEQ ID NO 5
<211> LENGTH: 5
<212> TYPE: PRT
<213> ORGANISM: Artificial Sequence
<220> FEATURE:
<223> OTHER INFORMATION: Synthetic Heavy Chain CDR1 1A3

<400> SEQUENCE: 5

Asn Tyr Tyr Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Heavy Chain CDR2 1A3

<400> SEQUENCE: 6

Tyr Ile Ser Pro Gly Gly Gly Ser Ser Tyr Tyr Pro Ala Ser Val Lys
1               5                   10                  15
Gly

<210> SEQ ID NO 7
<211> LENGTH: 13
```

```
<212> TYPE: PRT
<213> ORGANISM: Artificial Sequence
<220> FEATURE:
<223> OTHER INFORMATION: Synthetic Heavy Chain CDR3 1A3

<400> SEQUENCE: 7

Gln Gly Asp Gly Tyr Tyr Gly Asp Tyr Ala Met Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Light (kappa) Chain CDR1 1A3

<400> SEQUENCE: 8

Arg Ala Ser Glu Asn Ile Tyr Ser Asn Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Light (kappa) Chain CDR2 1A3

<400> SEQUENCE: 9

Ala Ala Thr Asn Leu Ala Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Light (kappa) Chain CDR3 1A3

<400> SEQUENCE: 10

Gln His Phe Trp Gly Thr Pro Tyr Thr
1               5

<210> SEQ ID NO 11
<211> LENGTH: 412
<212> TYPE: DNA
<213> ORGANISM: Artificial Sequence
<220> FEATURE:
<223> OTHER INFORMATION: Synthetic Heavy Chain Variable Region 2B8

<400> SEQUENCE: 11
atgggatgga gctatatcat cctcttttg gtagcaacag ctacagatgt ccactcccag      60
gtccaactgc agcagcctgg ggctgaactg gtgaagcctg gacttcagt gaagctgtcc     120 tgcaaggctt ctggctacac cttcaccacc tactggatgc actgggtgaa tcagaggcct    180
ggacaaggcc ttgagtggat tggagagatt aatcctacca acggtcatac taactacaat    240
gagaagttca gagcaaggc cacactgact gtagacaaat cctccagcac agcctacatg     300
caactcagca gcctgacatc tgaggactct gcggtctatt actgtgcaag aaactatgtt    360
ggtagcatct ttgactactg gggccaaggc accactctca cagtctcctc ag            412

<210> SEQ ID NO 12
<211> LENGTH: 137
<212> TYPE: PRT
<213> ORGANISM: Artificial Sequence
<220> FEATURE:
```

```
<223> OTHER INFORMATION: Synthetic Heavy Chain Variable Region 2B8

<400> SEQUENCE: 12

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Thr Ser Val Lys Leu Ser Cys Lys Ala Ser Gly Tyr Thr Phe
        35                  40                  45

Thr Thr Tyr Trp Met His Trp Val Asn Gln Arg Pro Gly Gln Gly Leu
    50                  55                  60

Glu Trp Ile Gly Glu Ile Asn Pro Thr Asn Gly His Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asn Tyr Val Gly Ser Ile Phe Asp Tyr Trp Gly
        115                 120                 125

Gln Gly Thr Thr Leu Thr Val Ser Ser
    130                 135

<210> SEQ ID NO 13
<211> LENGTH: 382
<212> TYPE: DNA
<213> ORGANISM: Artificial Sequence
<220> FEATURE:
<223> OTHER INFORMATION: Synthetic Light (kappa) Chain Variable Region
      2B8

<400> SEQUENCE: 13
atggaatcac agactctggt cttcatatcc atactgctct ggttatatgg tgctgatggg     60
aacattgtaa tgacccaatc tcccaaatcc atgtccatgt cagtaggaga gagggtcacc    120
ttgagctgca aggccagtga gaatgtggtt tcttatgtat cctggtatca acagaaacca    180
gcgcagtctc ctaaactgct gatatacggg gcatccaacc ggaacactgg ggtccccgat    240
cgcttcacag gcagtggatc tgcaacagat ttcactctga ccatcagcag tgtgcgggct    300
gaagaccttg cagattatca ctgtgggcag agttacaact atccgtacac gttcggaggg    360
gggaccaggc tggaaataaa ac                                             382

<210> SEQ ID NO 14
<211> LENGTH: 127
<212> TYPE: PRT
<213> ORGANISM: Artificial Sequence
<220> FEATURE:
<223> OTHER INFORMATION: Synthetic Light (kappa) Chain Variable Region
      2B8

<400> SEQUENCE: 14

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
        35                  40                  45

Val Val Ser Tyr Val Ser Trp Tyr Gln Gln Lys Pro Ala Gln Ser Pro
    50                  55                  60
```

```
Lys Leu Leu Ile Tyr Gly Ala Ser Asn Arg Asn Thr Gly Val Pro Asp
 65                  70                  75                  80

Arg Phe Thr Gly Ser Gly Ser Ala Thr Asp Phe Thr Leu Thr Ile Ser
                 85                  90                  95

Ser Val Arg Ala Glu Asp Leu Ala Asp Tyr His Cys Gly Gln Ser Tyr
            100                 105                 110

Asn Tyr Pro Tyr Thr Phe Gly Gly Gly Thr Arg Leu Glu Ile Lys
        115                 120                 125

<210> SEQ ID NO 15
<211> LENGTH: 5
<212> TYPE: PRT
<213> ORGANISM: Artificial Sequence
<220> FEATURE:
<223> OTHER INFORMATION: Synthetic Heavy Chain CDR1 2B8

<400> SEQUENCE: 15

Thr Tyr Trp Met His
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic Heavy Chain CDR2 2B8

<400> SEQUENCE: 16

Glu Ile Asn Pro Thr Asn Gly His Thr Asn Tyr Asn Glu Lys Phe Lys
1               5                   10                  15

Ser

<210> SEQ ID NO 17
<211> LENGTH: 9
<212> TYPE: PRT
<213> ORGANISM: Artificial Sequence
<220> FEATURE:
<223> OTHER INFORMATION: Synthetic Heavy Chain CDR3 2B8

<400> SEQUENCE: 17

Asn Tyr Val Gly Ser Ile Phe Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic Light (kappa) Chain CDR1 2B8

<400> SEQUENCE: 18

Lys Ala Ser Glu Asn Val Val Ser Tyr Val Ser
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Light (kappa) Chain CDR2 2B8

<400> SEQUENCE: 19

Gly Ala Ser Asn Arg Asn Thr
1               5
```

<210> SEQ ID NO 20
<211> LENGTH: 9
<212> TYPE: PRT
<213> ORGANISM: Artificial Sequence
<220> FEATURE:
<223> OTHER INFORMATION: Synthetic Light (kappa) Chain CDR3 2B8

<400> SEQUENCE: 20

Gly Gln Ser Tyr Asn Tyr Pro Tyr Thr
1               5

<210> SEQ ID NO 21
<211> LENGTH: 412
<212> TYPE: DNA
<213> ORGANISM: Artificial Sequence
<220> FEATURE:
<223> OTHER INFORMATION: Synthetic Heavy Chain Variable Region 2F8

<400> SEQUENCE: 21
atggaatgga gctgggtctt tctcttcctc ctgtcagtaa ctgcaggtgt ccactgccag      60
gtccagctga agcagtctgg agctgagctg gtgaggcctg ggacttcagt gaagatgtcc    120
tgcaaggctt ctggctacac cttcactacc tactatatac actgggtgaa tcagaggcct    180
ggacagggcc ttgagtggat tggaaagatt ggtcctggaa gtggtagtac ttactacaat    240
gagatgttca agacaaggc cacattgact gtagacacat cctccagcac agcctacatg    300
cagctcagca gcctgacatc tgacgactct gcggtctatt tctgtgcaag aaggggactg    360
ggacgtggct tgactactg ggccaaggc accactctca cagtctcctc ag              412

<210> SEQ ID NO 22
<211> LENGTH: 137
<212> TYPE: PRT
<213> ORGANISM: Artificial Sequence
<220> FEATURE:
<223> OTHER INFORMATION: Synthetic Heavy Chain Variable Region 2F8

<400> SEQUENCE: 22

Met Glu Trp Ser Trp Val Phe Leu Phe Leu Leu Ser Val Thr Ala Gly
1               5                   10                  15

Val His Cys Gln Val Gln Leu Lys Gln Ser Gly Ala Glu Leu Val Arg
                20                  25                  30

Pro Gly Thr Ser Val Lys Met Ser Cys Lys Ala Ser Gly Tyr Thr Phe
            35                  40                  45

Thr Thr Tyr Tyr Ile His Trp Val Asn Gln Arg Pro Gly Gln Gly Leu
        50                  55                  60

Glu Trp Ile Gly Lys Ile Gly Pro Gly Ser Gly Ser Thr Tyr Tyr Asn
65                  70                  75                  80

Glu Met Phe Lys Asp Lys Ala Thr Leu Thr Val Asp Thr Ser Ser Ser
                85                  90                  95

Thr Ala Tyr Met Gln Leu Ser Ser Leu Thr Ser Asp Asp Ser Ala Val
            100                 105                 110

Tyr Phe Cys Ala Arg Arg Gly Leu Gly Arg Gly Phe Asp Tyr Trp Gly
        115                 120                 125

Gln Gly Thr Thr Leu Thr Val Ser Ser
    130                 135

<210> SEQ ID NO 23
<211> LENGTH: 394
<212> TYPE: DNA
<213> ORGANISM: Artificial Sequence -continued

```
<220> FEATURE:
<223> OTHER INFORMATION: Synthetic Light (kappa) Chain Variable Region
      2F8

<400> SEQUENCE: 23
atggagacag acacaatcct gctatgggtg ctgctgctct gggttccagg ctccactggt      60
gacattgtgc tgacccaatc tccagcttct ttggctgtgt ctctagggca gagggccacc     120
atctcctgca aggccagcca aagtgttgat tatgatggta atagttatat caactggtac     180
caacagaaac caggacagcc acccaaagtc ctcatctatg ttgcatccaa tctagaatct     240
gggatcccag ccaggtttag tggcagtggg tctgggacag acttcaccct caacatccat     300
cctgtggagg aggaggatgc tgcaacctat tactgtcagc aaagtattga ggatcctccc     360
acgttcggtg ctgggaccaa gctggagctg aaac                                 394

<210> SEQ ID NO 24
<211> LENGTH: 131
<212> TYPE: PRT
<213> ORGANISM: Artificial Sequence
<220> FEATURE:
<223> OTHER INFORMATION: Synthetic Light (kappa) Chain Variable Region
      2F8

<400> SEQUENCE: 24

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asn Ser Tyr Ile Asn Trp Tyr Gln Gln Lys Pro
    50                  55                  60

Gly Gln Pro Pro Lys Val Leu Ile Tyr Val Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Ile Glu Asp Pro Pro Thr Phe Gly Ala Gly Thr Lys Leu
        115                 120                 125

Glu Leu Lys
    130

<210> SEQ ID NO 25
<211> LENGTH: 5
<212> TYPE: PRT
<213> ORGANISM: Artificial Sequence
<220> FEATURE:
<223> OTHER INFORMATION: Synthetic Heavy Chain CDR1 2F8

<400> SEQUENCE: 25

Thr Tyr Tyr Ile His
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic Heavy Chain CDR2 2F8
```

```
<400> SEQUENCE: 26

Lys Ile Gly Pro Gly Ser Gly Ser Thr Tyr Tyr Asn Glu Met Phe Lys
1               5                   10                  15
Asp

<210> SEQ ID NO 27
<211> LENGTH: 9
<212> TYPE: PRT
<213> ORGANISM: Artificial Sequence
<220> FEATURE:
<223> OTHER INFORMATION: Synthetic Heavy Chain CDR3 2F8

<400> SEQUENCE: 27

Arg Gly Leu Gly Arg Gly Phe Asp Tyr
1               5

<210> SEQ ID NO 28
<211> LENGTH: 15
<212> TYPE: PRT
<213> ORGANISM: Artificial Sequence
<220> FEATURE:
<223> OTHER INFORMATION: Synthetic Light (kappa) Chain CDR1 2F8

<400> SEQUENCE: 28

Lys Ala Ser Gln Ser Val Asp Tyr Asp Gly Asn Ser Tyr Ile Asn
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Synthetic Light (kappa) Chain CDR2 2F8

<400> SEQUENCE: 29

Val Ala Ser Asn Leu Glu Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Light (kappa) Chain CDR3 2F8

<400> SEQUENCE: 30

Gln Gln Ser Ile Glu Asp Pro Pro Thr
1               5

<210> SEQ ID NO 31
<211> LENGTH: 418
<212> TYPE: DNA
<213> ORGANISM: Artificial Sequence
<220> FEATURE:
<223> OTHER INFORMATION: Synthetic Heavy Chain Variable Region 3B6

<400> SEQUENCE: 31
atggaatggc cttgtatctt tctcttcctc ctgtcagtaa ctgaaggtgt ccactcccag      60
gttcagctgc agcagtctgg ggctgaactg gtgaggcctg gtcctcagt gaagatttcc     120 tgcaaggctt ctggctatgt attcagtagc tactggatga actgggtgaa gcagaggcct     180
ggacagggtc ttgagtggat tggacagatt tatcctggag atggtgatag taactacaat     240
ggaaacttca aggtaaagc cacactgact gcagacaaat cctccagtac agcctacatg     300
```

```
cagctcagca gcctaacatc tgaggactct gcggtctatt tctgtgcatc ccagctcggg    360
ctacgtgaga actactttga ctactggggc caaggcacca ctctcacagt ctcctcag     418
```

<210> SEQ ID NO 32
<211> LENGTH: 139
<212> TYPE: PRT
<213> ORGANISM: Artificial Sequence
<220> FEATURE:
<223> OTHER INFORMATION: Synthetic Heavy Chain Variable Region 3B6

<400> SEQUENCE: 32

Met Glu Trp Pro Cys Ile Phe Leu Phe Leu Leu Ser Val Thr Glu Gly
1               5                   10                  15

Val His Ser Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Val Phe
        35                  40                  45

Ser Ser Tyr Trp Met Asn Trp Val Lys Gln Arg Pro Gly Gln Gly Leu
    50                  55                  60

Glu Trp Ile Gly Gln Ile Tyr Pro Gly Asp Gly Asp Ser Asn Tyr Asn
65                  70                  75                  80

Gly Asn Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Ser Gln Leu Gly Leu Arg Glu Asn Tyr Phe Asp Tyr
        115                 120                 125

Trp Gly Gln Gly Thr Thr Leu Thr Val Ser Ser
    130                 135

<210> SEQ ID NO 33
<211> LENGTH: 388
<212> TYPE: DNA
<213> ORGANISM: Artificial Sequence
<220> FEATURE:
<223> OTHER INFORMATION: Synthetic Light (kappa) Chain Variable Region
      3B6

<400> SEQUENCE: 33

```
atggacatga ggacccctgc tcagtttctt ggaatcttgt tgctctggtt tccaggtatc     60
aaatgtgaca tcaagatgac ccagtctcca tcttccatgt atgcatctct aggagagaga    120
gtcacaatca cttgcaaggc gagtcaggac attaaaagct atttaagctg gttccagcag    180
aaaccaggga aatctcctaa gaccctgatc tatcgtgtaa acagattggt agatggggtc    240
ccatcaaggt tcagtggcag tggatctggg caagattctt ctctcaccat caccagcctg    300
gagaatgaag atatgggaat ttattattgt ctacagtatg atgagtttcc gttcacgttc    360 ggaggggga ccaagctgga aataaagc                                        388
```

<210> SEQ ID NO 34
<211> LENGTH: 129
<212> TYPE: PRT
<213> ORGANISM: Artificial Sequence
<220> FEATURE:
<223> OTHER INFORMATION: Synthetic Light (kappa) Chain Variable Region
      3B6

<400> SEQUENCE: 34

Met Asp Met Arg Thr Pro Ala Gln Phe Leu Gly Ile Leu Leu Leu Trp
1               5                   10                  15

```
Phe Pro Gly Ile Lys Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Lys Ser Tyr Leu Ser Trp Phe Gln Gln Lys Pro Gly Lys
    50                  55                  60

Ser Pro Lys Thr Leu Ile Tyr Arg Val Asn Arg Leu Val Asp Gly Val
65                  70                  75                  80

Pro Ser Arg Phe Ser Gly Ser Gly Ser Gly Gln Asp Ser Ser Leu Thr
                85                  90                  95

Ile Thr Ser Leu Glu Asn Glu Asp Met Gly Ile Tyr Tyr Cys Leu Gln
            100                 105                 110

Tyr Asp Glu Phe Pro Phe Thr Phe Gly Gly Gly Thr Lys Leu Glu Ile
        115                 120                 125

Lys

<210> SEQ ID NO 35
<211> LENGTH: 5
<212> TYPE: PRT
<213> ORGANISM: Artificial Sequence
<220> FEATURE:
<223> OTHER INFORMATION: Synthetic Heavy Chain CDR1 3B6

<400> SEQUENCE: 35

Ser Tyr Trp Met Asn
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic Heavy Chain CDR2 3B6

<400> SEQUENCE: 36

Gln Ile Tyr Pro Gly Asp Gly Asp Ser Asn Tyr Asn Gly Asn Phe Lys
1               5                   10                  15

Gly

<210> SEQ ID NO 37
<211> LENGTH: 11
<212> TYPE: PRT
<213> ORGANISM: Artificial Sequence
<220> FEATURE:
<223> OTHER INFORMATION: Synthetic Heavy Chain CDR3 3B6

<400> SEQUENCE: 37

Gln Leu Gly Leu Arg Glu Asn Tyr Phe Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Light (kappa) Chain CDR1 3B6

<400> SEQUENCE: 38

Lys Ala Ser Gln Asp Ile Lys Ser Tyr Leu Ser
1               5                   10
```

```
<210> SEQ ID NO 39
<211> LENGTH: 7
<212> TYPE: PRT
<213> ORGANISM: Artificial Sequence
<220> FEATURE:
<223> OTHER INFORMATION: Synthetic Light (kappa) Chain CDR2 3B6

<400> SEQUENCE: 39

Arg Val Asn Arg Leu Val Asp
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Light (kappa) Chain CDR3 3B6

<400> SEQUENCE: 40

Leu Gln Tyr Asp Glu Phe Pro Phe Thr
1               5

<210> SEQ ID NO 41
<211> LENGTH: 397
<212> TYPE: DNA
<213> ORGANISM: Artificial Sequence
<220> FEATURE:
<223> OTHER INFORMATION: Synthetic Heavy Chain Variable Region 3D11

<400> SEQUENCE: 41
atggctgtcc cggtgctgtt cctctgcctg gttgcatttc caagctgtgt cctgtcccag      60
gtacagctga aggagtcagg acctggcctg gtggcgccct cacagagcct gtccatcact     120
tgcactgtct ctgggttttc attaaccagc tatagtttac actgggttcg ccagcctcca     180
ggaaagggtc tggaatggct gggagtaata tgggctggtg aaacacaaa ttataattcg      240 tctctcatgt ccagactgac catcaggaaa gacaactcca agagccaagt tttcttaaaa     300
atgaacagtc tgcaaactga tgacacagcc atgtactact gtgccagaga gaggtttgct     360
tactggggcc aagggactct ggtcactgtc tctgcag                              397

<210> SEQ ID NO 42
<211> LENGTH: 132
<212> TYPE: PRT
<213> ORGANISM: Artificial Sequence
<220> FEATURE:
<223> OTHER INFORMATION: Synthetic Heavy Chain Variable Region 3D11

<400> SEQUENCE: 42

Met Ala Val Pro Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ser Tyr Ser Leu His Trp Val Arg Gln Pro Pro Gly Lys Gly Leu
    50                  55                  60

Glu Trp Leu Gly Val Ile Trp Ala Gly Gly Asn Thr Asn Tyr Asn Ser
65                  70                  75                  80

Ser Leu Met Ser Arg Leu Thr Ile Arg Lys Asp Asn Ser Lys Ser Gln
                85                  90                  95

Val Phe Leu Lys Met Asn Ser Leu Gln Thr Asp Asp Thr Ala Met Tyr
            100                 105                 110
```

```
Tyr Cys Ala Arg Glu Arg Phe Ala Tyr Trp Gly Gln Gly Thr Leu Val
        115                 120                 125

Thr Val Ser Ala
    130

<210> SEQ ID NO 43
<211> LENGTH: 385
<212> TYPE: DNA
<213> ORGANISM: Artificial Sequence
<220> FEATURE:
<223> OTHER INFORMATION: Synthetic Light (kappa) Chain Variable Region
      3D11

<400> SEQUENCE: 43
atggattttc aagtgcagat tttcagcttc ctgctaatca gtgcctcagt caaaatatcc      60
agaggacaaa ttgttctcac ccagtctcca gcaatcatgt ctgcatatcc aggggagaag    120
gtcaccatga cctgcagtgc cagctcaagt gtaagttaca tgcactggta ccagcagaag    180
tcaggcacct cccccaaaag atggatttat gacacatcca aactggcttc tggagtccct    240
gctcgcttca gtggcagtgg gtctgggacc tcttactccc tcacaatcag tagtatggag    300
gctgaagatg ctgccactta ttactgccag cagtggagta gtaacccact cacgttcggt    360
gctgggacca agctggagct gaaac                                          385

<210> SEQ ID NO 44
<211> LENGTH: 128
<212> TYPE: PRT
<213> ORGANISM: Artificial Sequence
<220> FEATURE:
<223> OTHER INFORMATION: Synthetic Light (kappa) Chain Variable Region
      3D11

<400> SEQUENCE: 44

Met Asp Phe Gln Val Gln Ile Phe Ser Phe Leu Leu Ile Ser Ala Ser
1               5                   10                  15

Val Lys Ile Ser Arg Gly Gln Ile Val Leu Thr Gln Ser Pro Ala Ile
            20                  25                  30

Met Ser Ala Tyr Pro Gly Glu Lys Val Thr Met Thr Cys Ser Ala Ser
        35                  40                  45

Ser Ser Val Ser Tyr Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

<210> SEQ ID NO 45
<211> LENGTH: 5
<212> TYPE: PRT
<213> ORGANISM: Artificial Sequence
<220> FEATURE:
<223> OTHER INFORMATION: Synthetic Heavy Chain CDR1 3D11

<400> SEQUENCE: 45

Ser Tyr Ser Leu His
1               5
```

<210> SEQ ID NO 46
<211> LENGTH: 16
<212> TYPE: PRT
<213> ORGANISM: Artificial Sequence
<220> FEATURE:
<223> OTHER INFORMATION: Synthetic Heavy Chain CDR2 3D11

<400> SEQUENCE: 46

Val Ile Trp Ala Gly Gly Asn Thr Asn Tyr Asn Ser Ser Leu Met Ser
1               5                   10                  15

<210> SEQ ID NO 47
<211> LENGTH: 5
<212> TYPE: PRT
<213> ORGANISM: Artificial Sequence
<220> FEATURE:
<223> OTHER INFORMATION: Synthetic Heavy Chain CDR3 3D11

<400> SEQUENCE: 47

Glu Arg Phe Ala Tyr
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic Light (kappa) Chain CDR1 3D11

<400> SEQUENCE: 48

Ser Ala Ser Ser Ser Val Ser Tyr Met His
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic Light (kappa) Chain CDR2 3D11

<400> SEQUENCE: 49

Asp Thr Ser Lys Leu Ala Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Light (kappa) Chain CDR3 3D11

<400> SEQUENCE: 50

Gln Gln Trp Ser Ser Asn Pro Leu Thr
1               5

<210> SEQ ID NO 51
<211> LENGTH: 424
<212> TYPE: DNA
<213> ORGANISM: Artificial Sequence
<220> FEATURE:
<223> OTHER INFORMATION: Synthetic Heavy Chain Variable Region 1D3

<400> SEQUENCE: 51
atgaactttg ggctcagatt gattttcctt gtccttgttt taaaaggtgt gaagtgtgaa      60
gtgcagctgg tggagtctgg gggaggctta gtgcagcctg agggtccct gaaactctcc      120

```
tgtgcagcct ctggattcac tttcagtgac tattacatgt cttgggttcg ccagactcca      180
gagaagaggc tggagtgggt cgcatacatt agtagtggtg gtggtagcac ctactatcca      240
gacagtgtga agggtcgatt caccatctcc cgagacaatg ccaagaacac cctgtacctg      300
caaatgagca gtctgaagtc tgaggacaca gccatatatt actgtgtgag acaaggggat      360
ggttattacg ggactatgc tatggactac tggggtcaag gaacctcagt catcgtctcc       420
tcag                                                                  424

<210> SEQ ID NO 52
<211> LENGTH: 141
<212> TYPE: PRT
<213> ORGANISM: Artificial Sequence
<220> FEATURE:
<223> OTHER INFORMATION: Synthetic Heavy Chain Variable Region 1D3

<400> SEQUENCE: 52

Met Asn Phe Gly Leu Arg Leu Ile Phe Leu Val Leu Val Leu Lys Gly
 1               5                  10                  15

Val Lys Cys Glu Val Gln Leu Val Glu Ser Gly Gly Gly Leu Val Gln
             20                  25                  30

Pro Gly Gly Ser Leu Lys Leu Ser Cys Ala Ala Ser Gly Phe Thr Phe
         35                  40                  45

Ser Asp Tyr Tyr Met Ser Trp Val Arg Gln Thr Pro Glu Lys Arg Leu
     50                  55                  60

Glu Trp Val Ala Tyr Ile Ser Ser Gly Gly Gly Ser Thr Tyr Tyr Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Ile
            100                 105                 110

Tyr Tyr Cys Val Arg Gln Gly Asp Gly Tyr Tyr Gly Asp Tyr Ala Met
        115                 120                 125

Asp Tyr Trp Gly Gln Gly Thr Ser Val Ile Val Ser Ser
    130                 135                 140

<210> SEQ ID NO 53
<211> LENGTH: 382
<212> TYPE: DNA
<213> ORGANISM: Artificial Sequence
<220> FEATURE:
<223> OTHER INFORMATION: Synthetic Light (kappa) Chain Variable Region
      1D3

<400> SEQUENCE: 53
atgagtgtgc ccactcaggt cctggggttg ctgctgctgt ggcttacaga tgtcagatgt       60
gacatccaga tgactcagtc tccagcctcc ctatctgtat ctgtgggaga aactgtcacc      120
atcacatgtc gaacaagtga aaatatttac agtaatttag cgtggtatca gcagaaacag      180
ggaaaatctc ctcagctcct aatctatgct gcaacaaact tagcagatgg tgtgccatca      240
aggttcagtg gcagtggatc aggcacacag ttttccctca ggatcaacag cctgcagtct      300
gaagattttg ggaggtatta ctgtcaacat ttttggggga ctccgtacac gttcggaggg      360
gggaccaaac tggaaataaa ac                                              382

<210> SEQ ID NO 54
<211> LENGTH: 127
<212> TYPE: PRT
```

```
<213> ORGANISM: Artificial Sequence
<220> FEATURE:
<223> OTHER INFORMATION: Synthetic Light (kappa) Chain Variable Region
      1D3

<400> SEQUENCE: 54

Met Ser Val Pro Thr Gln Val Leu Gly Leu Leu Leu Leu Trp Leu Thr
1               5                   10                  15

Asp Val Arg Cys Asp Ile Gln Met Thr Gln Ser Pro Ala Ser Leu Ser
            20                  25                  30

Val Ser Val Gly Glu Thr Val Thr Ile Thr Cys Arg Thr Ser Glu Asn
        35                  40                  45

Ile Tyr Ser Asn Leu Ala Trp Tyr Gln Gln Lys Gln Gly Lys Ser Pro
50                  55                  60

Gln Leu Leu Ile Tyr Ala Ala Thr Asn Leu Ala Asp Gly Val Pro Ser
65                  70                  75                  80

Arg Phe Ser Gly Ser Gly Ser Gly Thr Gln Phe Ser Leu Arg Ile Asn
                85                  90                  95

Ser Leu Gln Ser Glu Asp Phe Gly Arg Tyr Tyr Cys Gln His Phe Trp
            100                 105                 110

Gly Thr Pro Tyr Thr Phe Gly Gly Gly Thr Lys Leu Glu Ile Lys
        115                 120                 125

<210> SEQ ID NO 55
<211> LENGTH: 5
<212> TYPE: PRT
<213> ORGANISM: Artificial Sequence
<220> FEATURE:
<223> OTHER INFORMATION: Synthetic Heavy Chain CDR1 1D3

<400> SEQUENCE: 55

Asp Tyr Tyr Met Ser
1               5

<210> SEQ ID NO 56
<211> LENGTH: 17
<212> TYPE: PRT
<213> ORGANISM: Artificial Sequence
<220> FEATURE:
<223> OTHER INFORMATION: Synthetic Heavy Chain CDR2 1D3

<400> SEQUENCE: 56

Tyr Ile Ser Ser Gly Gly Gly Ser Thr Tyr Tyr Pro Asp Ser Val Lys
1               5                   10                  15

Gly

<210> SEQ ID NO 57
<211> LENGTH: 13
<212> TYPE: PRT
<213> ORGANISM: Artificial Sequence
<220> FEATURE:
<223> OTHER INFORMATION: Synthetic Heavy Chain CDR3 1D3

<400> SEQUENCE: 57

Gln Gly Asp Gly Tyr Tyr Gly Asp Tyr Ala Met Asp Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic Light (kappa) Chain CDR1 1D3
```

```
<400> SEQUENCE: 58

Arg Thr Ser Glu Asn Ile Tyr Ser Asn Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Synthetic Light (kappa) Chain CDR2 1D3

<400> SEQUENCE: 59

Ala Ala Thr Asn Leu Ala Asp
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Light (kappa) Chain CDR3 1D3

<400> SEQUENCE: 60

Gln His Phe Trp Gly Thr Pro Tyr Thr
1               5

<210> SEQ ID NO 61
<211> LENGTH: 424
<212> TYPE: DNA
<213> ORGANISM: Artificial Sequence
<220> FEATURE:
<223> OTHER INFORMATION: Synthetic Heavy Chain Variable Region 1F3

<400> SEQUENCE: 61
atgaactttg ggctcagatt gattttcctt gtccttgttt taaaaggtgt gaagtgtgag      60
gtgcagctgg tggagtctgg gggaggctta gtgcagtctg agggtccct gaaactctcc     120 tgtgcggcct ctggattcac tttcagtaac tatttcatgt cttgggttcg ccagactcca    180
gagaagaggc tggagtgggt cgcatatatt agtagtggtg gtggtagcac ctactatcca    240
gacagtgtga aggtcgatt caccatctct agagacaatg ccaagaacac cctgtacctg    300
caaatgagca gtctgaagtc tgaggacaca gccatgtatt actgtgtaag acaaggggat    360
ggttactacg ggactatgc tatggactac tggggtcaag gaacctcagt caccgtctcc    420
tcag                                                                 424

<210> SEQ ID NO 62
<211> LENGTH: 141
<212> TYPE: PRT
<213> ORGANISM: Artificial Sequence
<220> FEATURE:
<223> OTHER INFORMATION: Synthetic Heavy Chain Variable Region 1F3

<400> SEQUENCE: 62

Met Asn Phe Gly Leu Arg Leu Ile Phe Leu Val Leu Val Leu Lys Gly
1               5                   10                  15

Val Lys Cys Glu Val Gln Leu Val Glu Ser Gly Gly Gly Leu Val Gln
            20                  25                  30

Ser Gly Gly Ser Leu Lys Leu Ser Cys Ala Ala Ser Gly Phe Thr Phe
        35                  40                  45

Ser Asn Tyr Phe Met Ser Trp Val Arg Gln Thr Pro Glu Lys Arg Leu
    50                  55                  60
```

Glu Trp Val Ala Tyr Ile Ser Ser Gly Gly Ser Thr Tyr Tyr Pro
65                  70                  75                  80

Asp Ser Val Lys Gly Arg Phe Thr Ile Ser Arg Asp Asn Ala Lys Asn
            85                  90                  95

Thr Leu Tyr Leu Gln Met Ser Ser Leu Lys Ser Glu Asp Thr Ala Met
            100                 105                 110

Tyr Tyr Cys Val Arg Gln Gly Asp Gly Tyr Tyr Gly Asp Tyr Ala Met
            115                 120                 125

Asp Tyr Trp Gly Gln Gly Thr Ser Val Thr Val Ser Ser
    130                 135                 140

<210> SEQ ID NO 63
<211> LENGTH: 382
<212> TYPE: DNA
<213> ORGANISM: Artificial Sequence
<220> FEATURE:
<223> OTHER INFORMATION: Synthetic Light (kappa) Chain Variable Region 1F3

<400> SEQUENCE: 63
atgagtgtgc ccactcaggt cctggggttg ctgctgctgt ggcttacaga tgccagatgt     60
gacatccaga tgactcagtc tccagcctcc ctatctgtat ctgtgggaga aactgtcacc    120
atcacatgtc gagcaagtga aaatatttac agtaatttag catggtatca gcagaaacag    180
ggaaaatctc ctcagctcct ggtctatgat gcaacacact accagatggg tgtgccatca    240
aggttcagtg gcagtggatc aggcacacag ttttcccctca agatcaacag cctgcagtct    300
gaagattttg ggagttatta ctgtcaacat ttttggggta ctccgtacac gtttggaggg    360
gggaccagac tggaaattaa ac                                             382

<210> SEQ ID NO 64
<211> LENGTH: 127
<212> TYPE: PRT
<213> ORGANISM: Artificial Sequence
<220> FEATURE:
<223> OTHER INFORMATION: Synthetic Light (kappa) Chain Variable Region 1F3

<400> SEQUENCE: 64

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Asp Ala Thr His Leu Pro Asp Gly Val Pro Ser
65                  70                  75                  80

Arg Phe Ser Gly Ser Gly Ser Gly Thr Gln Phe Ser Leu Lys Ile Asn
            85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Gly Thr Arg Leu Glu Ile Lys
        115                 120                 125

<210> SEQ ID NO 65
<211> LENGTH: 5

```
<212> TYPE: PRT
<213> ORGANISM: Artificial Sequence
<220> FEATURE:
<223> OTHER INFORMATION: Synthetic Heavy Chain CDR1 1F3

<400> SEQUENCE: 65

Asn Tyr Phe Met Ser
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic Heavy Chain CDR2 1F3

<400> SEQUENCE: 66

Tyr Ile Ser Ser Gly Gly Gly Ser Thr Tyr Tyr Pro Asp Ser Val Lys
1               5                   10                  15
Gly

<210> SEQ ID NO 67
<211> LENGTH: 13
<212> TYPE: PRT
<213> ORGANISM: Artificial Sequence
<220> FEATURE:
<223> OTHER INFORMATION: Synthetic Heavy Chain CDR3 1F3

<400> SEQUENCE: 67

Gln Gly Asp Gly Tyr Tyr Gly Asp Tyr Ala Met Asp Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Light (kappa) Chain CDR1 1F3

<400> SEQUENCE: 68

Arg Ala Ser Glu Asn Ile Tyr Ser Asn Leu Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic Light (kappa) Chain CDR2 1F3

<400> SEQUENCE: 69

Asp Ala Thr His Leu Pro Asp
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Light (kappa) Chain CDR3 1F3

<400> SEQUENCE: 70

Gln His Phe Trp Gly Thr Pro Tyr Thr
1               5

<210> SEQ ID NO 71
```

<211> LENGTH: 424
<212> TYPE: DNA
<213> ORGANISM: Artificial Sequence
<220> FEATURE:
<223> OTHER INFORMATION: Synthetic Heavy Chain Variable Region 3A12

<400> SEQUENCE: 71

```
atgaactttg ggctcagatt gattttcctt gtccttgttt taaaaggtgt gaagtgtgaa      60
gtgcagctgg tggagtctgg gggaggctta gtgcagcctg agggtccct gaaaatctcc      120
tgtgcagcct ctggatttac tttcagtaac tatttcatgt cttgggttcg ccagactcca     180
gagaagaggc tggagtgggt cgcatacatt agtagtggtg gtggtagcac ctactatcca     240
gacagtgtga aggtcgatt caccatctcc agagacaatg ccagaacac cctgtacctg       300
caaatgaaca gtctgaagtc tgaggacaca gccatgtatt actgtgtaag acaaggagat     360
ggttactatg ggactatgc tatggactac tggggtcaag aacctcagt caccgtctcc       420
tcag                                                                   424
```

<210> SEQ ID NO 72
<211> LENGTH: 141
<212> TYPE: PRT
<213> ORGANISM: Artificial Sequence
<220> FEATURE:
<223> OTHER INFORMATION: Synthetic Heavy Chain Variable Region 3A12

<400> SEQUENCE: 72

```
Met Asn Phe Gly Leu Arg Leu Ile Phe Leu Val Leu Val Leu Lys Gly
1               5                   10                  15

Val Lys Cys Glu Val Gln Leu Val Glu Ser Gly Gly Gly Leu Val Gln
            20                  25                  30

Pro Gly Gly Ser Leu Lys Ile Ser Cys Ala Ala Ser Gly Phe Thr Phe
        35                  40                  45

Ser Asn Tyr Phe Met Ser Trp Val Arg Gln Thr Pro Glu Lys Arg Leu
    50                  55                  60

Glu Trp Val Ala Tyr Ile Ser Ser Gly Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Lys Ser Glu Asp Thr Ala Met
            100                 105                 110

Tyr Tyr Cys Val Arg Gln Gly Asp Gly Tyr Tyr Gly Asp Tyr Ala Met
        115                 120                 125

Asp Tyr Trp Gly Gln Gly Thr Ser Val Thr Val Ser Ser
    130                 135                 140
```

<210> SEQ ID NO 73
<211> LENGTH: 382
<212> TYPE: DNA
<213> ORGANISM: Artificial Sequence
<220> FEATURE:
<223> OTHER INFORMATION: Synthetic Light (kappa) Chain Variable Region 3A12

<400> SEQUENCE: 73

```
atgagtgtgc ccactcaggt cctggggttg ctgctgctgt ggcttacaga tgccagatgt      60
gacatccaga tgactcagtc gccagcctcc ctatctgtat ctgtgggaga aactgtcacc      120
atcacatgtc gagcaagtga gaatatttac attaatttag catggtatca gcagaaacag     180
ggaaaatctc ctcagctcct ggtccatgct gcaacaaagt tagcagatgg tgtgccatca     240
```

```
aggttcagtg cagtggatc aggcacacag tattccctca agatcaacag cctgcagtct    300
gaagattttg ggagttatta ctgtcaacat ttttggggta ctccgtacac gttcggaggg    360
gggaccaaac tagaaataaa ac                                             382
```

```
<210> SEQ ID NO 74
<211> LENGTH: 127
<212> TYPE: PRT
<213> ORGANISM: Artificial Sequence
<220> FEATURE:
<223> OTHER INFORMATION: Synthetic Light (kappa) Chain Variable Region
      3A12

<400> SEQUENCE: 74
```

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ile Asn Leu Ala Trp Tyr Gln Gln Lys Gln Gly Lys Ser Pro
    50                  55                  60

Gln Leu Leu Val His Ala Ala Thr Lys Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Pro Tyr Thr Phe Gly Gly Thr Lys Leu Glu Ile Lys
        115                 120                 125

```
<210> SEQ ID NO 75
<211> LENGTH: 5
<212> TYPE: PRT
<213> ORGANISM: Artificial Sequence
<220> FEATURE:
<223> OTHER INFORMATION: Synthetic Heavy Chain CDR1 3A12

<400> SEQUENCE: 75
```

Asn Tyr Phe Met Ser
1               5

```
<210> SEQ ID NO 76
<211> LENGTH: 17
<212> TYPE: PRT
<213> ORGANISM: Artificial Sequence
<220> FEATURE:
<223> OTHER INFORMATION: Synthetic Heavy Chain CDR2 3A12

<400> SEQUENCE: 76
```

Tyr Ile Ser Ser Gly Gly Gly Ser Thr Tyr Tyr Pro Asp Ser Val Lys
1               5                   10                  15

Gly

```
<210> SEQ ID NO 77
<211> LENGTH: 13
<212> TYPE: PRT
<213> ORGANISM: Artificial Sequence
<220> FEATURE:
<223> OTHER INFORMATION: Synthetic Heavy Chain CDR3 3A12

<400> SEQUENCE: 77
```

Gln Gly Asp Gly Tyr Tyr Gly Asp Tyr Ala Met Asp Tyr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Light (kappa) Chain CDR1 3A12

<400> SEQUENCE: 78

Arg Ala Ser Glu Asn Ile Tyr Ile Asn Leu Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Synthetic Light (kappa) Chain CDR2 3A12

<400> SEQUENCE: 79

Ala Ala Thr Lys Leu Ala Asp
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Light (kappa) Chain CDR3 3A12

<400> SEQUENCE: 80

Gln His Phe Trp Gly Thr Pro Tyr Thr
1               5

<210> SEQ ID NO 81
<211> LENGTH: 974
<212> TYPE: DNA
<213> ORGANISM: Artificial Sequence
<220> FEATURE:
<223> OTHER INFORMATION: Reference Mouse IgG1 Heavy Chain Constant
      Region (J00453)

<400> SEQUENCE: 81
ccaaaacgac accccatctg tctatccact ggcccctgga tctgctgccc aaactaact       60 ccatggtgac cctgggatgc ctggtcaagg gctatttccc tgagccagtg acagtgacct     120
ggaactctgg atccctgtcc agcggtgtgc acaccttccc agctgtcctg agtctgacc      180 tctacactct gagcagctca gtgactgtcc cctccagccc tcggcccagc gagaccgtca     240
cctgcaacgt tgcccacccg gccagcagca ccaaggtgga caagaaaatt gtgcccaggg     300
attgtggttg taagccttgc atatgtacag tcccagaagt atcatctgtc ttcatcttcc     360
ccccaaagcc caaggatgtg ctcaccatta ctctgactcc taaggtcacg tgtgttgtgg     420
tagacatcag caaggatgat cccgaggtcc agttcagctg gtttgtagat gatgtggagg     480
tgcacacagc tcagacgcaa ccccgggagg agcagttcaa cagcactttc cgctcagtca     540
gtgaacttcc catcatgcac caggactggc tcaatggcaa ggagttcaaa tgcagggtca     600
acagtgcagc tttccctgcc ccatcgaga aaaccatctc caaaccaaa ggcagaccga      660 aggctccaca ggtgtacacc attccacctc caaggagca gatggccaag ataaagtca      720 gtctgacctg catgataaca gacttcttcc ctgaagacat tactgtggag tggcagtgga     780

```
atgggcagcc agcggagaac tacaagaaca ctcagcccat catgaacacg aatggctctt    840
acttcgtcta cagcaagctc aatgtgcaga agagcaactg ggaggcagga aatactttca    900
cctgctctgt gttacatgag ggcctgcaca accaccatac tgagaagagc ctctcccact    960
ctcctggtaa atga                                                      974

<210> SEQ ID NO 82
<211> LENGTH: 974
<212> TYPE: DNA
<213> ORGANISM: Artificial Sequence
<220> FEATURE:
<223> OTHER INFORMATION: Mouse IgG1 Heavy Chain Constant Region for 1A3,
      1D3, 1F3, and 2B8

<400> SEQUENCE: 82
ccaaaacgac accccatctg tctatccact ggcccctgg atctgctgcc caaactaact     60
ccatggtgac cctgggatgc ctggtcaagg gctatttccc tgagccagtg acagtgacct    120
ggaactctgg atccctgtcc agcggtgtgc acaccttccc agctgtcctg cagtctgacc    180
tctacactct gagcagctca gtgactgtcc cctccagcac ctggcccagc gagaccgtca    240
cctgcaacgt tgcccacccg gccagcagca ccaaggtgga caagaaaatt gtgcccaggg    300
attgtggttg taagccttgc atatgtacag tcccagaagt atcatctgtc ttcatcttcc    360
ccccaaagcc caaggatgtg ctcaccatta ctctgactcc taaggtcacg tgtgttgtgg    420
tagacatcag caaggatgat cccgaggtcc agttcagctg gtttgtagat gatgtggagg    480
tgcacacagc tcagacgcaa ccccgggagg agcagttcaa cagcactttc cgctcagtca    540
gtgaacttcc catcatgcac caggactggc tcaatggcaa ggagttcaaa tgcagggtca    600
acagtgcagc tttccctgcc cccatcgaga aaaccatctc caaaaccaaa ggcagaccga    660
aggctccaca ggtgtacacc attccacctc ccaaggagca gatggccaag gataaagtca    720
gtctgacctg catgataaca gacttcttcc ctgaagacat tactgtggag tggcagtgga    780
atgggcagcc agcggagaac tacaagaaca ctcagcccat catggacaca gatggctctt    840
acttcgtcta cagcaagctc aatgtgcaga agagcaactg ggaggcagga aatactttca    900
cctgctctgt gttacatgag ggcctgcaca accaccatac tgagaagagc ctctcccact    960
ctcctggtaa atga                                                      974

<210> SEQ ID NO 83
<211> LENGTH: 323
<212> TYPE: DNA
<213> ORGANISM: Artificial Sequence
<220> FEATURE:
<223> OTHER INFORMATION: Mouse Kappa Light Chain Constant Region

<400> SEQUENCE: 83
gggctgatgc tgcaccaact gtatccatct tcccaccatc cagtgagcag ttaacatctg    60
gaggtgcctc agtcgtgtgc ttcttgaaca acttctaccc caaagacatc aatgtcaagt    120
ggaagattga tggcagtgaa cgacaaaatg gcgtcctgaa cagttggact gatcaggaca    180
gcaaagacag cacctacagc atgagcagca ccctcacgtt gaccaaggac gagtatgaac    240
gacataacag ctatacctgt gaggccactc acaagacatc aacttcaccc attgtcaaga    300
gcttcaacag gaatgagtgt tag                                            323

<210> SEQ ID NO 84
<211> LENGTH: 323
```

<212> TYPE: DNA
<213> ORGANISM: Artificial Sequence
<220> FEATURE:
<223> OTHER INFORMATION: Synthetic Mouse Kappa Light Chain Constant
      Region with Mutation

<400> SEQUENCE: 84
gggctgatgc tgcaccaact gtatccatct tcccaccatc cagtgagcag ttaacatctg      60
gaggtgcctc agtcgtgtgc ttcttgaaca acttctaccc caaagacatc aatgtcaagt     120
ggaagattga tggcagtgaa cgacaaaatg gcgtcctgaa cagttggact gatcaggaca     180
gcaaagacag cacctacagc atgagcagca ccctcatgtt gaccaaggac gagtatgaac     240
gacataacag ctatacctgt gaggccactc acaagacatc aacttcaccc attgtcaaga     300
gcttcaacag gaatgagtgt tag                                              323

<210> SEQ ID NO 85
<211> LENGTH: 30
<212> TYPE: DNA
<213> ORGANISM: Artificial Sequence
<220> FEATURE:
<223> OTHER INFORMATION: Synthetic oligonucleotide primer BD SMART II A

<400> SEQUENCE: 85
aagcagtggt atcaacgcag agtacgcggg                                        30

<210> SEQ ID NO 86
<211> LENGTH: 27
<212> TYPE: DNA
<213> ORGANISM: Artificial Sequence
<220> FEATURE:
<223> OTHER INFORMATION: Synthetic oligonucleotide primer RACE CDS
<220> FEATURE:
<221> NAME/KEY: misc_feature
<222> LOCATION: (27)..(27)
<223> OTHER INFORMATION: n is a, c, g, t or u

<400> SEQUENCE: 86 ttttttttttt ttttttttttt tttttvn                                         27

<210> SEQ ID NO 87
<211> LENGTH: 45
<212> TYPE: DNA
<213> ORGANISM: Artificial Sequence
<220> FEATURE:
<223> OTHER INFORMATION: Synthetic oligonucleotide primer of Universal
      Primer Mix A

<400> SEQUENCE: 87
ctaatacgac tcactatagg gcaagcagtg gtatcaacgc agagt                       45

<210> SEQ ID NO 88
<211> LENGTH: 22
<212> TYPE: DNA
<213> ORGANISM: Artificial Sequence
<220> FEATURE:
<223> OTHER INFORMATION: Synthetic oligonucleotide primer of Universal
      Primer Mix A

<400> SEQUENCE: 88
ctaatacgac tcactatagg gc                                                22

<210> SEQ ID NO 89
<211> LENGTH: 21
<212> TYPE: DNA
<213> ORGANISM: Artificial Sequence

```
<220> FEATURE:
<223> OTHER INFORMATION: Synthetic IgG1 Constant Region specific primer

<400> SEQUENCE: 89
tatgcaaggc ttacaaccac a                                             21

<210> SEQ ID NO 90
<211> LENGTH: 28
<212> TYPE: DNA
<213> ORGANISM: Artificial Sequence
<220> FEATURE:
<223> OTHER INFORMATION: Synthetic IgG1 Constant Region specific primer

<400> SEQUENCE: 90
gccagtggat agacagatgg gggtgtcg                                      28

<210> SEQ ID NO 91
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 91
ctcattcctg ttgaagctct tgacaat                                       27

<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 92
cgactgaggc acctccagat gtt                                           23

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide primer T7

<400> SEQUENCE: 93
taatacgact cactataggg                                               20

<210> SEQ ID NO 94
<211> LENGTH: 17
<212> TYPE: DNA
<213> ORGANISM: Artificial Sequence
<220> FEATURE:
<223> OTHER INFORMATION: Synthetic oligonucleotide primer M13 Forward

<400> SEQUENCE: 94
gtaaaacgac ggccagt                                                  17

<210> SEQ ID NO 95
<211> LENGTH: 18
<212> TYPE: DNA
<213> ORGANISM: Artificial Sequence
<220> FEATURE:
<223> OTHER INFORMATION: Synthetic oligonucleotide primer M13 Reverse

<400> SEQUENCE: 95
caggaaacag ctatgacc                                                 18
```

<210> SEQ ID NO 96
<211> LENGTH: 63
<212> TYPE: DNA
<213> ORGANISM: Artificial Sequence
<220> FEATURE:
<223> OTHER INFORMATION: Synthetic oligonucleotide forward primer

<400> SEQUENCE: 96
ggggacaagt tgtacaaaa aagcaggctg ccaccatgaa ctttgggctc agattgattt    60
tcc                                                                 63

<210> SEQ ID NO 97
<211> LENGTH: 54
<212> TYPE: DNA
<213> ORGANISM: Artificial Sequence
<220> FEATURE:
<223> OTHER INFORMATION: Synthetic oligonucleotide reverse primer

<400> SEQUENCE: 97
ggggaccact ttgtacaaga aagctgggtt catttaccag gagagtggga gagg          54

<210> SEQ ID NO 98
<211> LENGTH: 62
<212> TYPE: DNA
<213> ORGANISM: Artificial Sequence
<220> FEATURE:
<223> OTHER INFORMATION: Synthetic oligonucleotide forward primer

<400> SEQUENCE: 98
ggggacaagt tgtacaaaa aagcaggctg ccaccatggg atggagctat atcatcctct    60
tt                                                                  62

<210> SEQ ID NO 99
<211> LENGTH: 53
<212> TYPE: DNA
<213> ORGANISM: Artificial Sequence
<220> FEATURE:
<223> OTHER INFORMATION: Synthetic oligonucleotide reverse primer

<400> SEQUENCE: 99
ggggaccact ttgtacaaga aagctgggtt catttaccag gagagtggga gag           53

<210> SEQ ID NO 100
<211> LENGTH: 62
<212> TYPE: DNA
<213> ORGANISM: Artificial Sequence
<220> FEATURE:
<223> OTHER INFORMATION: Synthetic oligonucleotide forward primer

<400> SEQUENCE: 100
ggggacaagt tgtacaaaa aagcaggctg ccaccatgga atcacagact ctggtcttca    60
ta                                                                  62

<210> SEQ ID NO 101
<211> LENGTH: 54
<212> TYPE: DNA
<213> ORGANISM: Artificial Sequence
<220> FEATURE:
<223> OTHER INFORMATION: Synthetic oligonucleotide reverse primer

<400> SEQUENCE: 101
ggggaccact ttgtacaaga aagctgggtc taacactcat tcctgttgaa gctc          54

<210> SEQ ID NO 102
<211> LENGTH: 30
<212> TYPE: DNA
<213> ORGANISM: Artificial Sequence
<220> FEATURE:
<223> OTHER INFORMATION: Synthetic oligonucleotide 5 prime hHGF NheI
      primer

<400> SEQUENCE: 102
actggctagc atgtgggtga ccaaactcct                                    30

<210> SEQ ID NO 103
<211> LENGTH: 46
<212> TYPE: DNA
<213> ORGANISM: Artificial Sequence
<220> FEATURE:
<223> OTHER INFORMATION: Synthetic oligonucleotide 3 prime hHGF NotI his
      tag primer

<400> SEQUENCE: 103
gtgatggtga tggtgatggc ggccgcatga ctgtggtacc ttatat                  46

<210> SEQ ID NO 104
<211> LENGTH: 30
<212> TYPE: DNA
<213> ORGANISM: Artificial Sequence
<220> FEATURE:
<223> OTHER INFORMATION: Synthetic oligonucleotide 5 prime His IgFc
      primer

<400> SEQUENCE: 104 actgcggcc gccatcacca tcaccatcac                                     30

<210> SEQ ID NO 105
<211> LENGTH: 31
<212> TYPE: DNA
<213> ORGANISM: Artificial Sequence
<220> FEATURE:
<223> OTHER INFORMATION: Synthetic oligonucleotide 3 prime IgFc BamHI
      primer

<400> SEQUENCE: 105
actgggatcc tcactattta cccggggaca g                                  31

<210> SEQ ID NO 106
<211> LENGTH: 27
<212> TYPE: DNA
<213> ORGANISM: Artificial Sequence
<220> FEATURE:
<223> OTHER INFORMATION: Synthetic hHGF-Fc (G555E) sense primer

<400> SEQUENCE: 106
catgatgtcc acgaaagagg agatgag                                       27

<210> SEQ ID NO 107
<211> LENGTH: 27
<212> TYPE: DNA
<213> ORGANISM: Artificial Sequence
<220> FEATURE:
<223> OTHER INFORMATION: Synthetic hHGF-Fc (G555E) antisense primer

<400> SEQUENCE: 107
ctcatctcct ctttcgtgga catcatg                                       27

<210> SEQ ID NO 108
<211> LENGTH: 37
<212> TYPE: DNA

<213> ORGANISM: Artificial Sequence
<220> FEATURE:
<223> OTHER INFORMATION: Synthetic hHGF-Fc (C561R) sense primer

<400> SEQUENCE: 108
ggaagaggag atgagaaacg caaacaggtt ctcaatg        37

<210> SEQ ID NO 109
<211> LENGTH: 37
<212> TYPE: DNA
<213> ORGANISM: Artificial Sequence
<220> FEATURE:
<223> OTHER INFORMATION: Synthetic hHGF-Fc (C561R) antisense primer

<400> SEQUENCE: 109
cattgagaac ctgtttgcgt ttctcatctc ctcttcc        37

<210> SEQ ID NO 110
<211> LENGTH: 29
<212> TYPE: DNA
<213> ORGANISM: Artificial Sequence
<220> FEATURE:
<223> OTHER INFORMATION: Synthetic Fragment 1 Primer for mHGF alpha
      chain 5 prime NheI

<400> SEQUENCE: 110
atcggctagc atgatgtggg ggaccaaac                  29

<210> SEQ ID NO 111
<211> LENGTH: 36
<212> TYPE: DNA
<213> ORGANISM: Artificial Sequence
<220> FEATURE:
<223> OTHER INFORMATION: Synthetic Fragment 1 Primer for mHGF alpha
      chain 5 prime NheI

<400> SEQUENCE: 111
ggttttgttt tgttgacgcc caacatttac cctaag          36

<210> SEQ ID NO 112
<211> LENGTH: 36
<212> TYPE: DNA
<213> ORGANISM: Artificial Sequence
<220> FEATURE:
<223> OTHER INFORMATION: Synthetic Fragment 2 Primer for hHGF beta chain
      aa V495-L585

<400> SEQUENCE: 112
ccaaaacaaa acaactgcgg gttgtaaatg ggattc          36

<210> SEQ ID NO 113
<211> LENGTH: 40
<212> TYPE: DNA
<213> ORGANISM: Artificial Sequence
<220> FEATURE:
<223> OTHER INFORMATION: Synthetic Fragment 2 Primer for hHGF beta chain
      aa V495-L585

<400> SEQUENCE: 113
tctagaccaa aattacttcg aacgagctgg acgttaggac      40

<210> SEQ ID NO 114
<211> LENGTH: 40
<212> TYPE: DNA
<213> ORGANISM: Artificial Sequence
<220> FEATURE:
<223> OTHER INFORMATION: Synthetic Fragment 3 Primer for mHGF beta chain C-terminus 3 prime NotI

<400> SEQUENCE: 114
agatctggtt ttaatgaagc ttgctcgacc tgcaatcctg                                    40

<210> SEQ ID NO 115
<211> LENGTH: 48
<212> TYPE: DNA
<213> ORGANISM: Artificial Sequence
<220> FEATURE:
<223> OTHER INFORMATION: Synthetic Fragment 3 Primer for mHGF beta chain
      C-terminus 3 prime NotI

<400> SEQUENCE: 115
cactaccact accactaccg ccggcgtgtt gaacatacag ttttaatg                           48

<210> SEQ ID NO 116
<211> LENGTH: 38
<212> TYPE: DNA
<213> ORGANISM: Artificial Sequence
<220> FEATURE:
<223> OTHER INFORMATION: Synthetic mutagenesis primer 1

<400> SEQUENCE: 116
catcaccatc accatcacta agcgggtctg gtgccacg                                      38

<210> SEQ ID NO 117
<211> LENGTH: 38
<212> TYPE: DNA
<213> ORGANISM: Artificial Sequence
<220> FEATURE:
<223> OTHER INFORMATION: Synthetic mutagenesis primer 2

<400> SEQUENCE: 117
cgtggcacca gacccgctta gtgatggtga tggtgatg                                      38

<210> SEQ ID NO 118
<211> LENGTH: 2922
<212> TYPE: DNA
<213> ORGANISM: Artificial Sequence
<220> FEATURE:
<223> OTHER INFORMATION: nucleotide sequence of synthetic hHGF-Fc
      protein

<400> SEQUENCE: 118
atgtgggtga ccaaactcct gccagccctg ctgctgcagc atgtcctcct gcatctcctc             60
ctgctcccca tcgccatccc ctatgcagag ggacaaagga aagaagaaa tacaattcat             120 gaattcaaaa aatcagcaaa gactacccta tcaaaatag atccagcact gaagataaaa             180
accaaaaaag tgaatactgc agaccaatgt gctaatagat gtactaggaa taaaggactt             240
ccattcactt gcaaggcttt tgtttttgat aaagcaagaa acaatgcct ctggttcccc              300 ttcaatagca tgtcaagtgg agtgaaaaaa gaatttggcc atgaatttga cctctatgaa             360
aacaaagact acattagaaa ctgcatcatt ggtaaaggac gcagctacaa gggaacagta             420
tctatcacta gagtggcat caaatgtcag ccctggagtt ccatgatacc acacgaacac              480 agcttttttgc cttcgagcta tcggggtaaa gacctacagg aaaactactg tcgaaatcct             540
cgaggggaag aagggggacc ctggtgtttc acaagcaatc cagaggtacg ctacgaagtc             600
tgtgacattc tcagtgttc agaagttgaa tgcatgacct gcaatgggga gagttatcga              660
ggtctcatgg atcatacaga atcaggcaag atttgtcagc gctgggatca tcagacacca             720
caccggcaca aattcttgcc tgaaagatat cccgacaagg gctttgatga taattattgc             780

-continued

| | |
|---|---|
| cgcaatcccg atggccagcc gaggccatgg tgctatactc ttgaccctca cacccgctgg | 840 |
| gagtactgtg caattaaaac atgcgctgac aatactatga atgacactga tgttcctttg | 900 |
| gaaacaactg aatgcatcca aggtcaagga aaggctaca ggggcactgt caataccatt | 960 |
| tggaatggaa ttccatgtca gcgttgggat tctcagtatc ctcacgagca tgacatgact | 1020 |
| cctgaaaatt tcaagtgcaa ggacctacga gaaaattact gccgaaatcc agatgggtct | 1080 |
| gaatcaccct ggtgttttac cactgatcca acatccgag ttggctactg ctcccaaatt | 1140 |
| ccaaactgtg atatgtcaca tggacaagat tgttatcgtg gaatggcaa aaattatatg | 1200 |
| ggcaacttat cccaaacaag atctggacta acatgttcaa tgtgggacaa gaacatggaa | 1260 |
| gacttacatc gtcatatctt ctgggaacca gatgcaagta agctgaatga gaattactgc | 1320 |
| cgaaatccag atgatgatgc tcatggaccc tggtgctaca cgggaaatcc actcattcct | 1380 |
| tgggattatt gccctatttc tcgttgtgaa ggtgatacca cacctacaat agtcaattta | 1440 |
| gaccatcccg taatatcttg tgccaaaacg aaacaattgc gagttgtaaa tgggattcca | 1500 |
| acacgaacaa acataggatg gatggttagt ttgagataca gaaataaaca tatctgcgga | 1560 |
| ggatcattga taaaggagag ttgggttctt actgcacgac agtgtttccc ttctcgagac | 1620 |
| ttgaaagatt atgaagcttg gcttggaatt catgatgtcc acggaagagg agatgagaaa | 1680 |
| tgcaaacagg ttctcaatgt ttcccagctg gtatatggcc ctgaaggatc agatctggtt | 1740 |
| taatgaagc ttgccaggcc tgctgtcctg gatgattttg ttagtacgat tgatttacct | 1800 |
| aattatggat gcacaattcc tgaaaagacc agttgcagtg tttatggctg gggctacact | 1860 |
| ggattgatca actatgatgg cctattacga gtggcacatc tctatataat gggaaatgag | 1920 |
| aaatgcagcc agcatcatcg agggaaggtg actctgaatg agtctgaaat atgtgctggg | 1980 |
| gctgaaaaga ttggatcagg accatgtgag ggggattatg gtggcccact tgtttgtgag | 2040 |
| caacataaaa tgagaatggt tcttggtgtc attgttcctg gtcgtggatg tgccattcca | 2100 |
| aatcgtcctg gtattttgt ccgagtagca tattatgcaa aatggataca caaaattatt | 2160 |
| ttaacatata aggtaccaca gtcatgcggc cgccatcacc atcaccatca ctccgcgggt | 2220 |
| ctggtgccac gcggtagtga caaactcac acatgcccac cgtgcccagc acctgaactc | 2280 |
| ctgggggac cgtcagtctt cctcttcccc ccaaaaccca aggacaccct catgatctcc | 2340 |
| cggacccctg aggtcacatg cgtggtggtg gacgtgagcc acgaagaccc tgaggtcaag | 2400 |
| ttcaactggt acgtggacgg cgtggaggtg cataatgcca agacaaagcc gcgggaggag | 2460 |
| cagtacaaca gcacgtaccg tgtggtcagc gtcctcaccg tcctgcacca ggactggctg | 2520 |
| aatggcaagg agtacaagtg caaggtctcc aacaaagccc tcccagcccc catcgagaaa | 2580 |
| accatctcca aagccaaagg gcagccccga gaaccacagg tgtacaccct gcccccatcc | 2640 |
| cgggaggaga tgaccaagaa ccaggtcagc ctgacctgcc tggtcaaagg cttctatccc | 2700 |
| agcgacatcg ccgtggagtg ggagagcaat gggcagccgg agaacaacta caagaccacg | 2760 |
| cctcccgtgc tggactccga cggctccttc ttcctctata gcaagctcac cgtggacaag | 2820 |
| agcaggtggc agcaggggaa cgtcttctca tgctccgtga tgcatgaggc tctgcacaac | 2880 |
| cactacacgc agaagagcct ctccctgtcc ccgggtaaat ag | 2922 |

<210> SEQ ID NO 119
<211> LENGTH: 919
<212> TYPE: PRT
<213> ORGANISM: Artificial Sequence
<220> FEATURE:

<223> OTHER INFORMATION: amino acid sequence of synthetic hHGF-Fc protein

<400> SEQUENCE: 119

| | | | | | | | | | | | | | | |
|---|---|---|---|---|---|---|---|---|---|---|---|---|---|---|
| Pro | Ala | Leu | Lys | Ile | Lys | Thr | Lys | Lys | Val | Asn | Thr | Ala | Asp | Gln | Cys |
| 1 | | | | 5 | | | | | 10 | | | | | 15 | |
| Ala | Asn | Arg | Cys | Thr | Arg | Asn | Lys | Gly | Leu | Pro | Phe | Thr | Cys | Lys | Ala |
| | | | 20 | | | | | 25 | | | | | 30 | | |
| Phe | Val | Phe | Asp | Lys | Ala | Arg | Lys | Gln | Cys | Leu | Trp | Phe | Pro | Phe | Asn |
| | | | 35 | | | | | 40 | | | | | 45 | | |
| Ser | Met | Ser | Ser | Gly | Val | Lys | Lys | Glu | Phe | Gly | His | Glu | Phe | Asp | Leu |
| | 50 | | | | | 55 | | | | | 60 | | | | |
| Tyr | Glu | Asn | Lys | Asp | Tyr | Ile | Arg | Asn | Cys | Ile | Ile | Gly | Lys | Gly | Arg |
| 65 | | | | | 70 | | | | | 75 | | | | | 80 |
| Ser | Tyr | Lys | Gly | Thr | Val | Ser | Ile | Thr | Lys | Ser | Gly | Ile | Lys | Cys | Gln |
| | | | | 85 | | | | | 90 | | | | | 95 | |
| Pro | Trp | Ser | Ser | Met | Ile | Pro | His | Glu | His | Ser | Phe | Leu | Pro | Ser | Ser |
| | | | 100 | | | | | 105 | | | | | 110 | | |
| Tyr | Arg | Gly | Lys | Asp | Leu | Gln | Glu | Asn | Tyr | Cys | Arg | Asn | Pro | Arg | Gly |
| | | 115 | | | | | 120 | | | | | 125 | | | |
| Glu | Glu | Gly | Gly | Pro | Trp | Cys | Phe | Thr | Ser | Asn | Pro | Glu | Val | Arg | Tyr |
| 130 | | | | | 135 | | | | | 140 | | | | | |
| Glu | Val | Cys | Asp | Ile | Pro | Gln | Cys | Ser | Glu | Val | Glu | Cys | Met | Thr | Cys |
| 145 | | | | | 150 | | | | | 155 | | | | | 160 |
| Asn | Gly | Glu | Ser | Tyr | Arg | Gly | Leu | Met | Asp | His | Thr | Glu | Ser | Gly | Lys |
| | | | | 165 | | | | | 170 | | | | | 175 | |
| Ile | Cys | Gln | Arg | Trp | Asp | His | Gln | Thr | Pro | His | Arg | His | Lys | Phe | Leu |
| | | | 180 | | | | | 185 | | | | | 190 | | |
| Pro | Glu | Arg | Tyr | Pro | Asp | Lys | Gly | Phe | Asp | Asp | Asn | Tyr | Cys | Arg | Asn |
| | | 195 | | | | | 200 | | | | | 205 | | | |
| Pro | Asp | Gly | Gln | Pro | Arg | Pro | Trp | Cys | Tyr | Thr | Leu | Asp | Pro | His | Thr |
| 210 | | | | | 215 | | | | | 220 | | | | | |
| Arg | Trp | Glu | Tyr | Cys | Ala | Ile | Lys | Thr | Cys | Ala | Asp | Asn | Thr | Met | Asn |
| 225 | | | | | 230 | | | | | 235 | | | | | 240 |
| Asp | Thr | Asp | Val | Pro | Leu | Glu | Thr | Thr | Glu | Cys | Ile | Gln | Gly | Gln | Gly |
| | | | | 245 | | | | | 250 | | | | | 255 | |
| Glu | Gly | Tyr | Arg | Gly | Thr | Val | Asn | Thr | Ile | Trp | Asn | Gly | Ile | Pro | Cys |
| | | | 260 | | | | | 265 | | | | | 270 | | |
| Gln | Arg | Trp | Asp | Ser | Gln | Tyr | Pro | His | Glu | His | Asp | Met | Thr | Pro | Glu |
| | | 275 | | | | | 280 | | | | | 285 | | | |
| Asn | Phe | Lys | Cys | Lys | Asp | Leu | Arg | Glu | Asn | Tyr | Cys | Arg | Asn | Pro | Asp |
| 290 | | | | | 295 | | | | | 300 | | | | | |
| Gly | Ser | Glu | Ser | Pro | Trp | Cys | Phe | Thr | Thr | Asp | Pro | Asn | Ile | Arg | Val |
| 305 | | | | | 310 | | | | | 315 | | | | | 320 |
| Gly | Tyr | Cys | Ser | Gln | Ile | Pro | Asn | Cys | Asp | Met | Ser | His | Gly | Gln | Asp |
| | | | | 325 | | | | | 330 | | | | | 335 | |
| Cys | Tyr | Arg | Gly | Asn | Gly | Lys | Asn | Tyr | Met | Gly | Asn | Leu | Ser | Gln | Thr |
| | | | 340 | | | | | 345 | | | | | 350 | | |
| Arg | Ser | Gly | Leu | Thr | Cys | Ser | Met | Trp | Asp | Lys | Asn | Met | Glu | Asp | Leu |
| | | 355 | | | | | 360 | | | | | 365 | | | |
| His | Arg | His | Ile | Phe | Trp | Glu | Pro | Asp | Ala | Ser | Lys | Leu | Asn | Glu | Asn |
| 370 | | | | | 375 | | | | | 380 | | | | | |
| Tyr | Cys | Arg | Asn | Pro | Asp | Asp | Ala | His | Gly | Pro | Trp | Cys | Tyr | Thr |
| 385 | | | | | 390 | | | | | 395 | | | | | 400 |

-continued

```
Gly Asn Pro Leu Ile Pro Trp Asp Tyr Cys Pro Ile Ser Arg Cys Glu
            405                 410                 415
Gly Asp Thr Thr Pro Thr Ile Val Asn Leu Asp His Pro Val Ile Ser
        420                 425                 430
Cys Ala Lys Thr Lys Gln Leu Arg Val Val Asn Gly Ile Pro Thr Arg
    435                 440                 445
Thr Asn Ile Gly Trp Met Val Ser Leu Arg Tyr Arg Asn Lys His Ile
450                 455                 460
Cys Gly Gly Ser Leu Ile Lys Glu Ser Trp Val Leu Thr Ala Arg Gln
465                 470                 475                 480
Cys Phe Pro Ser Arg Asp Leu Lys Asp Tyr Glu Ala Trp Leu Gly Ile
                485                 490                 495
His Asp Val His Gly Arg Gly Asp Glu Lys Cys Lys Gln Val Leu Asn
            500                 505                 510
Val Ser Gln Leu Val Tyr Gly Pro Glu Gly Ser Asp Leu Val Leu Met
        515                 520                 525
Lys Leu Ala Arg Pro Ala Val Leu Asp Asp Phe Val Ser Thr Ile Asp
    530                 535                 540
Leu Pro Asn Tyr Gly Cys Thr Ile Pro Glu Lys Thr Ser Cys Ser Val
545                 550                 555                 560
Tyr Gly Trp Gly Tyr Thr Gly Leu Ile Asn Tyr Asp Gly Leu Leu Arg
                565                 570                 575
Val Ala His Leu Tyr Ile Met Gly Asn Glu Lys Cys Ser Gln His His
            580                 585                 590
Arg Gly Lys Val Thr Leu Asn Glu Ser Glu Ile Cys Ala Gly Ala Glu
        595                 600                 605
Lys Ile Gly Ser Gly Pro Cys Glu Gly Asp Tyr Gly Gly Pro Leu Val
    610                 615                 620
Cys Glu Gln His Lys Met Arg Met Val Leu Gly Val Ile Val Pro Gly
625                 630                 635                 640
Arg Gly Cys Ala Ile Pro Asn Arg Pro Gly Ile Phe Val Arg Val Ala
                645                 650                 655
Tyr Tyr Ala Lys Trp Ile His Lys Ile Ile Leu Thr Tyr Lys Val Pro
            660                 665                 670
Gln Ser Cys Gly Arg His His His His His Ser Ala Gly Leu Val
        675                 680                 685
Pro Arg Gly Ser Asp Lys Thr His Thr Cys Pro Pro Cys Pro Ala Pro
    690                 695                 700
Glu Leu Leu Gly Gly Pro Ser Val Phe Leu Phe Pro Pro Lys Pro Lys
705                 710                 715                 720
Asp Thr Leu Met Ile Ser Arg Thr Pro Glu Val Thr Cys Val Val Val
                725                 730                 735
Asp Val Ser His Glu Asp Pro Glu Val Lys Phe Asn Trp Tyr Val Asp
            740                 745                 750
Gly Val Glu Val His Asn Ala Lys Thr Lys Pro Arg Glu Glu Gln Tyr
        755                 760                 765
Asn Ser Thr Tyr Arg Val Val Ser Val Leu Thr Val Leu His Gln Asp
    770                 775                 780
Trp Leu Asn Gly Lys Glu Tyr Lys Cys Lys Val Ser Asn Lys Ala Leu
785                 790                 795                 800
Pro Ala Pro Ile Glu Lys Thr Ile Ser Lys Ala Lys Gly Gln Pro Arg
                805                 810                 815
```

```
Glu Pro Gln Val Tyr Thr Leu Pro Pro Ser Arg Glu Glu Met Thr Lys
                820                 825                 830
Asn Gln Val Ser Leu Thr Cys Leu Val Lys Gly Phe Tyr Pro Ser Asp
            835                 840                 845
Ile Ala Val Glu Trp Glu Ser Asn Gly Gln Pro Glu Asn Asn Tyr Lys
        850                 855                 860
Thr Thr Pro Pro Val Leu Asp Ser Asp Gly Ser Phe Phe Leu Tyr Ser
865                 870                 875                 880
Lys Leu Thr Val Asp Lys Ser Arg Trp Gln Gln Gly Asn Val Phe Ser
                885                 890                 895
Cys Ser Val Met His Glu Ala Leu His Asn His Tyr Thr Gln Lys Ser
            900                 905                 910
Leu Ser Leu Ser Pro Gly Lys
        915

<210> SEQ ID NO 120
<211> LENGTH: 2901
<212> TYPE: DNA
<213> ORGANISM: Artificial Sequence
<220> FEATURE:
<223> OTHER INFORMATION: Synthetic mhm (V495-L585)-Fc chimeric protein

<400> SEQUENCE: 120
atgatgtggg ggaccaaact tctgccggtc ctgttgctgc agcatgtcct cctgcacctc      60
ctcctgcttc atgtcgccat ccctatgca gaaggacaga gaaaagaag aaatacactt      120
catgaattta aaaagtcagc aaaaactact cttaccaagg aagacccatt actgaagatt     180
aaaaccaaaa aagtgaactc tgcagatgag tgtgccaaca ggtgtatcag gaacaggggc     240
tttacgttca cttgcaaggc cttcgttttt gataagtcaa gaaaacgatg ctactggtat     300
cctttcaata gtatgtcaag tggagtgaaa aagggtttg gccatgaatt tgacctctat     360
gaaaacaaag actatattag aaactgcatc attggtaaag gaggcagcta taagggacg     420
gtatccatca ctaagagtgg catcaaatgc cagccttgga attccatgat cccccatgaa     480
cacagctatc gcgtaaaga cctacaggaa aactactgtc gaaatcctcg aggggaagaa     540
gggggaccct ggtgtttcac aagcaatcca gaggtacgct acgaagtctg tgacattcct     600
cagtgttcag aagttgaatg catgacctgc aatggtgaaa gctacagagg tcccatggat     660
cacacagaat caggcaagac ttgtcagcgc tgggaccagc agacaccaca ccggcacaag     720
ttcttgccag aaagatatcc cgacaagggc tttgatgata ttattgccg caatcctgat     780
ggcaagccga ggccatggtg ctacactctt gaccctgaca ccccttggga gtattgtgca     840
attaaaacgt cgctcacag tgctgtgaat gagactgatg tccctatgga aacaactgaa     900
tgcattcaag gccaaggaga aggttacagg ggaaccagca taccatttg aatggaatt      960
ccctgtcagc gttgggattc gcagtaccct cacaagcatg atatcactcc cgagaacttc    1020
aaaatgcaagg accttagaga aaattattgc cgcaatccag atggggctga atcaccatgg    1080
tgttttacca ctgacccaaa catccgagtt ggctactgct ctcaaattcc caagtgtgac    1140
gtgtcaagtg gacaagattg ttatcgtggc aatgggaaaa attacatggg caacttatcc    1200
aaaacaaggt ctggacttac atgttccatg tgggacaaga atatggagga tttacaccgt    1260
catatcttct gggagccaga tgctagcaaa ttgaataaga attactgccg gaatcctgat    1320
gatgatgccc atggacctg gtgctacacg gggaatcctc ttattccttg ggattattgc    1380
cctatttccc gttgtgaagg agatactaca cctacaattg tcaatttgga ccatcctgta    1440
```

-continued

```
atatcctgtg ccaaaacaaa acaactgcgg gttgtaaatg ggattccaac acgaacaaac   1500
ataggatgga tggttagttt gagatacaga aataaacata tctgcggagg atcattgata   1560
aaggagagtt gggttcttac tgcacgacag tgtttccctt ctcgagactt gaaagattat   1620
gaagcttggc ttggaattca tgatgtccac ggaagaggag atgagaaatg caaacaggtt   1680
ctcaatgttt cccagctggt atatggccct gaaggatcag atctggtttt aatgaagctt   1740
gctcgacctg caatcctgga taactttgtc agtacaattg atttacctag ttatggttgt   1800
acaatccctg aaaagaccac ttgcagtatt tacggctggg gctacactgg attgatcaac   1860
gcggatggtt tattacgagt agctcatctg tatattatgg ggaatgagaa atgcagtcag   1920
caccatcaag gcaaggtgac tttgaatgag tctgagttat gtgctggggc tgaaaagatt   1980
ggatcaggac catgtgaggg agattatggt ggcccactca tttgtgaaca acacaaaatg   2040
agaatggttc ttggtgtcat tgttcctggt cgtggatgtg ccatcccaaa tcgtcctggt   2100
atttttgttc gagtagcata ttatgcaaaa tggatacaca agtaattttt gacatacaag   2160
ttgtgcggcc gccatcacca tcaccatcac tccgcgggtc tggtgccacg cggtagtgac   2220
aaaactcaca catgcccacc gtgcccagca cctgaactcc tggggggacc gtcagtcttc   2280
ctcttccccc caaaacccaa ggacaccctc atgatctccc ggacccctga ggtcacatgc   2340
gtggtggtgg acgtgagcca cgaagaccct gaggtcaagt tcaactggta cgtggacggc   2400
gtggaggtgc ataatgccaa gacaaagccg cgggaggagc agtacaacag cacgtaccgt   2460
gtggtcagcg tcctcaccgt cctgcaccag gactggctga atggcaagga gtacaagtgc   2520
aaggtctcca acaaagccct cccagccccc atcgagaaaa ccatctccaa agccaaaggg   2580
cagccccgag aaccacaggt gtacaccctg cccccatccc gggaggagat gaccaagaac   2640
caggtcagcc tgacctgcct ggtcaaaggc ttctatccca gcgacatcgc cgtggagtgg   2700
gagagcaatg ggcagccgga gaacaactac aagaccacgc ctcccgtgct ggactccgac   2760
ggctccttct tcctctatag caagctcacc gtggacaaga gcaggtggca gcaggggaac   2820
gtcttctcat gctccgtgat gcatgaggct ctgcacaacc actacacgca gaagagcctc   2880
tccctgtccc cgggtaaata g                                              2901
```

<210> SEQ ID NO 121
<211> LENGTH: 911
<212> TYPE: PRT
<213> ORGANISM: Artificial Sequence
<220> FEATURE:
<223> OTHER INFORMATION: synthetic mhm-Fc Active form

<400> SEQUENCE: 121

```
Pro Leu Leu Lys Ile Lys Thr Lys Lys Val Asn Ser Ala Asp Glu Cys
1               5                   10                  15

Ala Asn Arg Cys Ile Arg Asn Arg Gly Phe Thr Phe Thr Cys Lys Ala
                20                  25                  30

Phe Val Phe Asp Lys Ser Arg Lys Arg Cys Tyr Trp Tyr Pro Phe Asn
            35                  40                  45

Ser Met Ser Ser Gly Val Lys Lys Gly Phe Gly His Glu Phe Asp Leu
        50                  55                  60

Tyr Glu Asn Lys Asp Tyr Ile Arg Asn Cys Ile Ile Gly Lys Gly Gly
65                  70                  75                  80

Ser Tyr Lys Gly Thr Val Ser Ile Thr Lys Ser Gly Ile Lys Cys Gln
                85                  90                  95

Pro Trp Asn Ser Met Ile Pro His Glu His Ser Tyr Arg Gly Lys Asp
```

-continued

```
                100                 105                 110
Leu Gln Glu Asn Tyr Cys Arg Asn Pro Arg Gly Glu Glu Gly Gly Pro
            115                 120                 125

Trp Cys Phe Thr Ser Asn Pro Glu Val Arg Tyr Glu Val Cys Asp Ile
130                 135                 140

Pro Gln Cys Ser Glu Val Glu Cys Met Thr Cys Asn Gly Glu Ser Tyr
145                 150                 155                 160

Arg Gly Pro Met Asp His Thr Glu Ser Gly Lys Thr Cys Gln Arg Trp
                165                 170                 175

Asp Gln Gln Thr Pro His Arg His Lys Phe Leu Pro Glu Arg Tyr Pro
            180                 185                 190

Asp Lys Gly Phe Asp Asp Asn Tyr Cys Arg Asn Pro Asp Gly Lys Pro
            195                 200                 205

Arg Pro Trp Cys Tyr Thr Leu Asp Pro Asp Thr Pro Trp Glu Tyr Cys
            210                 215                 220

Ala Ile Lys Thr Cys Ala His Ser Ala Val Asn Glu Thr Asp Val Pro
225                 230                 235                 240

Met Glu Thr Thr Glu Cys Ile Gln Gly Gln Gly Glu Gly Tyr Arg Gly
                245                 250                 255

Thr Ser Asn Thr Ile Trp Asn Gly Ile Pro Cys Gln Arg Trp Asp Ser
            260                 265                 270

Gln Tyr Pro His Lys His Asp Ile Thr Pro Glu Asn Phe Lys Cys Lys
            275                 280                 285

Asp Leu Arg Glu Asn Tyr Cys Arg Asn Pro Asp Gly Ala Glu Ser Pro
            290                 295                 300

Trp Cys Phe Thr Asp Pro Asn Ile Arg Val Gly Tyr Cys Ser Gln
305                 310                 315                 320

Ile Pro Lys Cys Asp Val Ser Ser Gly Gln Asp Cys Tyr Arg Gly Asn
            325                 330                 335

Gly Lys Asn Tyr Met Gly Asn Leu Ser Lys Thr Arg Ser Gly Leu Thr
            340                 345                 350

Cys Ser Met Trp Asp Lys Asn Met Glu Asp Leu His Arg His Ile Phe
            355                 360                 365

Trp Glu Pro Asp Ala Ser Lys Leu Asn Lys Asn Tyr Cys Arg Asn Pro
            370                 375                 380

Asp Asp Asp Ala His Gly Pro Trp Cys Tyr Thr Gly Asn Pro Leu Ile
385                 390                 395                 400

Pro Trp Asp Tyr Cys Pro Ile Ser Arg Cys Glu Gly Asp Thr Thr Pro
            405                 410                 415

Thr Ile Val Asn Leu Asp His Pro Val Ile Ser Cys Ala Lys Thr Lys
            420                 425                 430

Gln Leu Arg Val Val Asn Gly Ile Pro Thr Arg Thr Asn Ile Gly Trp
            435                 440                 445

Met Val Ser Leu Arg Tyr Arg Asn Lys His Ile Cys Gly Gly Ser Leu
            450                 455                 460

Ile Lys Glu Ser Trp Val Leu Thr Ala Arg Gln Cys Phe Pro Ser Arg
465                 470                 475                 480

Asp Leu Lys Asp Tyr Glu Ala Trp Leu Gly Ile His Asp Val His Gly
            485                 490                 495

Arg Gly Asp Glu Lys Cys Lys Gln Val Leu Asn Val Ser Gln Leu Val
            500                 505                 510

Tyr Gly Pro Glu Gly Ser Asp Leu Val Leu Met Lys Leu Ala Arg Pro
            515                 520                 525
```

```
Ala Ile Leu Asp Asn Phe Val Ser Thr Ile Asp Leu Pro Ser Tyr Gly
    530                 535                 540

Cys Thr Ile Pro Glu Lys Thr Thr Cys Ser Ile Tyr Gly Trp Gly Tyr
545                 550                 555                 560

Thr Gly Leu Ile Asn Ala Asp Gly Leu Leu Arg Val Ala His Leu Tyr
                565                 570                 575

Ile Met Gly Asn Glu Lys Cys Ser Gln His His Gln Gly Lys Val Thr
            580                 585                 590

Leu Asn Glu Ser Glu Leu Cys Ala Gly Ala Glu Lys Ile Gly Ser Gly
        595                 600                 605

Pro Cys Glu Gly Asp Tyr Gly Gly Pro Leu Ile Cys Glu Gln His Lys
    610                 615                 620

Met Arg Met Val Leu Gly Val Ile Val Pro Arg Gly Cys Ala Ile
625                 630                 635                 640

Pro Asn Arg Pro Gly Ile Phe Val Arg Val Ala Tyr Tyr Ala Lys Trp
                645                 650                 655

Ile His Lys Val Ile Leu Thr Tyr Lys Leu Cys Gly Arg His His His
            660                 665                 670

His His His Ser Ala Gly Leu Val Pro Arg Gly Ser Asp Lys Thr His
        675                 680                 685

Thr Cys Pro Pro Cys Pro Ala Pro Glu Leu Leu Gly Gly Pro Ser Val
    690                 695                 700

Phe Leu Phe Pro Pro Lys Pro Lys Asp Thr Leu Met Ile Ser Arg Thr
705                 710                 715                 720

Pro Glu Val Thr Cys Val Val Val Asp Val Ser His Glu Asp Pro Glu
                725                 730                 735

Val Lys Phe Asn Trp Tyr Val Asp Gly Val Glu Val His Asn Ala Lys
            740                 745                 750

Thr Lys Pro Arg Glu Glu Gln Tyr Asn Ser Thr Tyr Arg Val Val Ser
        755                 760                 765

Val Leu Thr Val Leu His Gln Asp Trp Leu Asn Gly Lys Glu Tyr Lys
    770                 775                 780

Cys Lys Val Ser Asn Lys Ala Leu Pro Ala Pro Ile Glu Lys Thr Ile
785                 790                 795                 800

Ser Lys Ala Lys Gly Gln Pro Arg Glu Pro Gln Val Tyr Thr Leu Pro
                805                 810                 815

Pro Ser Arg Glu Glu Met Thr Lys Asn Gln Val Ser Leu Thr Cys Leu
            820                 825                 830

Val Lys Gly Phe Tyr Pro Ser Asp Ile Ala Val Glu Trp Glu Ser Asn
        835                 840                 845

Gly Gln Pro Glu Asn Asn Tyr Lys Thr Thr Pro Pro Val Leu Asp Ser
    850                 855                 860

Asp Gly Ser Phe Phe Leu Tyr Ser Lys Leu Thr Val Asp Lys Ser Arg
865                 870                 875                 880

Trp Gln Gln Gly Asn Val Phe Ser Cys Ser Val Met His Glu Ala Leu
                885                 890                 895

His Asn His Tyr Thr Gln Lys Ser Leu Ser Leu Ser Pro Gly Lys
            900                 905                 910

<210> SEQ ID NO 122
<211> LENGTH: 1398
<212> TYPE: DNA
<213> ORGANISM: Artificial Sequence
<220> FEATURE:
```

<223> OTHER INFORMATION: Full length Heavy Chain (1A3 Variable Region and IgG1 Constant Region)

<400> SEQUENCE: 122

```
atgaactttg ggctcagatt gattttcctt gtccttgttt taaaaggtgt gaagtgtgaa      60
gtgcagctgg tggagtctgg gggaggctta gtgcagcctg agggtccct gaaactctcc     120
tgtgcagcct ctgaattcac tttcagtaac tattacatgt cttgggttcg ccagactcca    180
gagaagaggc tgcagtgggt cgcatacatt agtcctggtg gtggtagctc ctactatcca    240
gccagtgtga agggtcgatt caccatctcc agagacaatg ccaagaacac cctgtacctg    300
caaatgagca gtctgaagtc tgaggacaca gccatgtatt actgtgcaag acaaggggat    360
ggttactacg gggactatgc tatggactac tggggtcaag gaacctcagt caccgtctcc    420
tcagccaaaa cgacaccccc atctgtctat ccactggccc ctggatctgc tgcccaaact    480
aactccatgg tgaccctggg atgcctggtc aagggctatt ccctgagcc agtgacagtg     540
acctggaact ctggatccct gtccagcggt gtgcacacct tcccagctgt cctgcagtct    600
gacctctaca ctctgagcag ctcagtgact gtccccctcca gcacctggcc cagcgagacc    660
gtcacctgca acgttgccca ccggccagc agcaccaagg tggacaagaa aattgtgccc     720
agggattgtg gttgtaagcc ttgcatatgt acagtcccag aagtatcatc tgtcttcatc    780
ttccccccaa agcccaagga tgtgctcacc attactctga ctcctaaggt cacgtgtgtt    840
gtggtagaca tcagcaagga tgatcccgag gtccagttca gctggtttgt agatgatgtg    900
gaggtgcaca cagctcagac gcaacccgg gaggagcagt tcaacagcac tttccgctca     960
gtcagtgaac ttcccatcat gcaccaggac tggctcaatg gcaaggagtt caaatgcagg   1020
gtcaacagtg cagctttccc tgcccccatc gagaaaacca tctccaaaac caaggcaga   1080
ccgaaggctc cacaggtgta caccattcca cctcccaagg agcagatggc caaggataaa   1140
gtcagtctga cctgcatgat aacagacttc ttccctgaag acattactgt ggagtggcag   1200
tggaatgggc agccagcgga gaactacaag aacactcagc ccatcatgga cacagatggc   1260
tcttacttcg tctacagcaa gctcaatgtg cagaagagca ctgggaggc aggaaatact    1320
ttcacctgct ctgtgttaca tgagggcctg cacaaccacc atactgagaa gagcctctcc   1380
cactctcctg gtaaatga                                                1398
```

<210> SEQ ID NO 123
<211> LENGTH: 446
<212> TYPE: PRT
<213> ORGANISM: Artificial Sequence
<220> FEATURE:
<223> OTHER INFORMATION: Full Length 1A3 Heavy Chain (1A3 Variable Region and IgG1 Constant Region)

<400> SEQUENCE: 123

```
Glu Val Gln Leu Val Glu Ser Gly Gly Gly Leu Val Gln Pro Gly Gly
1               5                   10                  15

Ser Leu Lys Leu Ser Cys Ala Ala Ser Glu Phe Thr Phe Ser Asn Tyr
            20                  25                  30

Tyr Met Ser Trp Val Arg Gln Thr Pro Glu Lys Arg Leu Gln Trp Val
        35                  40                  45

Ala Tyr Ile Ser Pro Gly Gly Gly Ser Ser Tyr Tyr Pro Ala Ser Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Lys Ser Glu Asp Thr Ala Met Tyr Tyr Cys
                85                  90                  95

Ala Arg Gln Gly Asp Gly Tyr Tyr Gly Asp Tyr Ala Met Asp Tyr Trp
            100                 105                 110

Gly Gln Gly Thr Ser Val Thr Val Ser Ser Ala Lys Thr Thr Pro Pro
            115                 120                 125

Ser Val Tyr Pro Leu Ala Pro Gly Ser Ala Ala Gln Thr Asn Ser Met
        130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Gly Val His Thr Phe Pro
            165                 170                 175

Ala Val Leu Gln Ser Asp Leu Tyr Thr Leu Ser Ser Ser Val Thr Val
        180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
        210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
        290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 124
<211> LENGTH: 705
<212> TYPE: DNA
<213> ORGANISM: Artificial Sequence
<220> FEATURE:
<223> OTHER INFORMATION: Full Length Light Chain (1A3 Kappa Variable
      Region and Constant Region)

<400> SEQUENCE: 124
```

```
atgagtgtgc ccactcaggt cctggggttg ctgctgctgt ggcttacaga tgccagatgt    60
gacatccaga tgactcagtc tccagcctcc ctatctgttt ctgtgggaga aactgtcacc   120
atcacatgtc gagcaagtga gaatatttat agtaatttag catggtatca gcagaaacag   180
ggaaaatctc ctcagctcct ggtctatgct gcaacaaact tagcagatgg tgtgccatca   240
aggttcagtg gcagtggatc aggcacacag ttttcccctca agatcaacag cctgcagtct   300
gaagattttg ggacttatta ctgtcaacat ttttggggta ctccgtacac gttcggaggg   360
gggaccaagc tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcatg   600
ttgaccaagg acgagtatga acgacataac agctatacct gtgaggccac tcacaagaca   660
tcaacttcac ccattgtcaa gagcttcaac aggaatgagt gttag                   705
```

<210> SEQ ID NO 125
<211> LENGTH: 214
<212> TYPE: PRT
<213> ORGANISM: Artificial Sequence
<220> FEATURE:
<223> OTHER INFORMATION: Full Length Light Chain (1A3 Kappa Variable
       Region and Constant Region)

<400> SEQUENCE: 125

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Thr Tyr Tyr Cys Gln His Phe Trp Gly Thr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Met Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 126
<211> LENGTH: 1386
<212> TYPE: DNA
<213> ORGANISM: Artificial Sequence
<220> FEATURE:
<223> OTHER INFORMATION: Full Length Heavy Chain (2B8 Variable Region and IgG1 Constant Region)

<400> SEQUENCE: 126

```
atgggatgga gctatatcat cctcttttg gtagcaacag ctacagatgt ccactcccag      60
gtccaactgc agcagcctgg ggctgaactg gtgaagcctg ggacttcagt gaagctgtcc    120
tgcaaggctt ctggctacac cttcaccacc tactggatgc actgggtgaa tcagaggcct    180
ggacaaggcc ttgagtggat tggagagatt aatcctacca acggtcatac taactacaat    240
gagaagttca gagcaaggc cacactgact gtagacaaat cctccagcac agcctacatg    300
caactcagca gcctgacatc tgaggactct gcggtctatt actgtgcaag aaactatgtt    360
ggtagcatct ttgactactg gggccaaggc accactctca cagtctcctc agccaaaacg    420
acacccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca gcgagaccgt cacctgcaac    660
gttgcccacc cggccagcag caccaaggtg gacaagaaaa ttgtgcccag ggattgtggt    720
tgtaagcctt gcatatgtac agtcccagaa gtatcatctg tcttcatctt ccccccaaag    780
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacgc aaccccggga ggagcagttc aacagcactt tccgctcagt cagtgaactt    960
cccatcatgc accaggactg gctcaatggc aaggagttca atgcagggt caacagtgca   1020
gctttccctg cccccatcga gaaaaccatc tccaaaacca aggcagacc gaaggctcca   1080
caggtgtaca ccattccacc tcccaaggag cagatggcca aggataaagt cagtctgacc   1140
tgcatgataa cagacttctt ccctgaagac attactgtgg agtggcagtg aatgggcag   1200
ccagcggaga actacaagaa cactcagccc atcatggaca cagatggctc ttacttcgtc   1260
tacagcaagc tcaatgtgca gaagagcaac tgggaggcag gaaatacttt cacctgctct   1320
gtgttacatg agggcctgca caaccaccat actgagaaga gcctctccca ctctcctggt   1380
aaatga                                                              1386
```

<210> SEQ ID NO 127
<211> LENGTH: 442
<212> TYPE: PRT
<213> ORGANISM: Artificial Sequence
<220> FEATURE:
<223> OTHER INFORMATION: Full Length Heavy Chain (2B8 Variable Region and IgG1 Constant Region)

<400> SEQUENCE: 127

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Asn Gln Arg Pro Gly Gln Gly Leu Glu Trp Ile
        35                  40                  45

Gly Glu Ile Asn Pro Thr Asn Gly His Thr Asn Tyr Asn Glu Lys Phe

```
                50                  55                  60
Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asn Tyr Val Gly Ser Ile Phe Asp Tyr Trp Gly Gln Gly Thr
                100                 105                 110

Thr Leu Thr Val Ser Ser Ala Lys Thr Thr Pro Pro Ser Val Tyr Pro
            115                 120                 125

Leu Ala Pro Gly Ser Ala Ala Gln Thr Asn Ser Met Val Thr Leu Gly
        130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 128
<211> LENGTH: 705
<212> TYPE: DNA
<213> ORGANISM: Artificial Sequence
```

```
<220> FEATURE:
<223> OTHER INFORMATION: Full Length Light Chain (2B8 Kappa Variable
      Region and Constant Region)

<400> SEQUENCE: 128
atggaatcac agactctggt cttcatatcc atactgctct ggttatatgg tgctgatggg      60
aacattgtaa tgacccaatc tcccaaatcc atgtccatgt cagtaggaga gagggtcacc     120
ttgagctgca aggccagtga aaatgtggtt tcttatgtat cctggtatca acagaaacca     180
gcgcagtctc ctaaactgct gatatacggg gcatccaacc ggaacactgg ggtccccgat     240
cgcttcacag gcagtggatc tgcaacagat ttcactctga ccatcagcag tgtgcgggct     300
gaagaccttg cagattatca ctgtgggcag agttacaact atccgtacac gttcggaggg     360
gggaccaggc tggaaataaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                     705

<210> SEQ ID NO 129
<211> LENGTH: 214
<212> TYPE: PRT
<213> ORGANISM: Artificial Sequence
<220> FEATURE:
<223> OTHER INFORMATION: Full Length Light Chain (2B8 Kappa Variable
      Region and Constant Region)

<400> SEQUENCE: 129

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Val Ser Tyr
            20                  25                  30

Val Ser Trp Tyr Gln Gln Lys Pro Ala Gln Ser Pro Lys Leu Leu Ile
        35                  40                  45

Tyr Gly Ala Ser Asn Arg Asn Thr Gly Val Pro Asp Arg Phe Thr Gly
    50                  55                  60

Ser Gly Ser Ala Thr Asp Phe Thr Leu Thr Ile Ser Ser Val Arg Ala
65                  70                  75                  80

Glu Asp Leu Ala Asp Tyr His Cys Gly Gln Ser Tyr Asn Tyr Pro Tyr
                85                  90                  95

Thr Phe Gly Gly Gly Thr Arg Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205
```

Phe Asn Arg Asn Glu Cys
    210

<210> SEQ ID NO 130
<211> LENGTH: 1386
<212> TYPE: DNA
<213> ORGANISM: Artificial Sequence
<220> FEATURE:
<223> OTHER INFORMATION: Full Length Heavy Chain (2F8 Variable Region
      and IgG1 Constant Region)

<400> SEQUENCE: 130

```
atggaatgga gctgggtctt tctcttcctc ctgtcagtaa ctgcaggtgt ccactgccag      60
gtccagctga agcagtctgg agctgagctg gtgaggcctg ggacttcagt gaagatgtcc     120
tgcaaggctt ctggctacac cttcactacc tactatatac actgggtgaa tcagaggcct     180
ggacagggcc ttgagtggat tggaaagatt ggtcctggaa gtggtagtac ttactacaat     240
gagatgttca agacaaggc cacattgact gtagacacat cctccagcac agcctacatg     300
cagctcagca gcctgacatc tgacgactct gcggtctatt tctgtgcaag aaggggactg     360
ggacgtggct ttgactactg gggccaaggc accactctca cagtctcctc agccaaaacg     420
acaccccat ctgtctatcc actggcccct ggatctgctg cccaaactaa ctccatggtg     480
accctgggat gcctggtcaa gggctatttc cctgagccag tgacagtgac ctggaactct     540
ggatccctgt ccagcggtgt gcacaccttc ccagctgtcc tgcagtctga cctctacact     600
ctgagcagct cagtgactgt cccctccagc acctggccca gcgagaccgt cacctgcaac     660
gttgcccacc cggccagcag caccaaggtg gacaagaaaa ttgtgcccag ggattgtggt     720
tgtaagcctt gcatatgtac agtcccagaa gtatcatctg tcttcatctt ccccccaaag     780
cccaaggatg tgctcaccat tactctgact cctaaggtca cgtgtgttgt ggtagacatc     840
agcaaggatg atcccgaggt ccagttcagc tggtttgtag atgatgtgga ggtgcacaca     900
gctcagacgc aaccccggga ggagcagttc aacagcactt tccgctcagt cagtgaactt     960
cccatcatgc accaggactg gctcaatggc aaggagttca atgcagggt caacagtgca    1020
gctttccctg ccccatcga gaaaaccatc tccaaaacca aggcagacc gaaggctcca    1080
caggtgtaca ccattccacc tcccaaggag cagatggcca aggataaagt cagtctgacc    1140
tgcatgataa cagacttctt ccctgaagac attactgtgg agtggcagtg gaatgggcag    1200
ccagcggaga actacaagaa cactcagccc atcatggaca gatggctc ttacttcgtc    1260
tacagcaagc tcaatgtgca gaagagcaac tgggaggcag gaaatacttt cacctgctct    1320
gtgttacatg agggcctgca caaccaccat actgagaaga gcctctccca ctctcctggt    1380
aaatga                                                             1386
```

<210> SEQ ID NO 131
<211> LENGTH: 442
<212> TYPE: PRT
<213> ORGANISM: Artificial Sequence
<220> FEATURE:
<223> OTHER INFORMATION: Full Length Heavy Chain (2F8 Variable Region
      and IgG1 Constant Region)

<400> SEQUENCE: 131

Gln Val Gln Leu Lys Gln Ser Gly Ala Glu Leu Val Arg Pro Gly Thr
1               5                   10                  15

Ser Val Lys Met Ser Cys Lys Ala Ser Gly Tyr Thr Phe Thr Thr Tyr
            20                  25                  30

```
Tyr Ile His Trp Val Asn Gln Arg Pro Gly Gln Gly Leu Glu Trp Ile
         35                  40                  45
Gly Lys Ile Gly Pro Gly Ser Gly Ser Thr Tyr Tyr Asn Glu Met Phe
 50                  55                  60
Lys Asp Lys Ala Thr Leu Thr Val Asp Thr Ser Ser Ser Thr Ala Tyr
 65                  70                  75                  80
Met Gln Leu Ser Ser Leu Thr Ser Asp Asp Ser Ala Val Tyr Phe Cys
                 85                  90                  95
Ala Arg Arg Gly Leu Gly Arg Gly Phe Asp Tyr Trp Gly Gln Gly Thr
                100                 105                 110
Thr Leu Thr Val Ser Ser Ala Lys Thr Thr Pro Pro Ser Val Tyr Pro
            115                 120                 125
Leu Ala Pro Gly Ser Ala Ala Gln Thr Asn Ser Met Val Thr Leu Gly
        130                 135                 140
Cys Leu Val Lys Gly Tyr Phe Pro Glu Pro Val Thr Val Thr Trp Asn
145                 150                 155                 160
Ser Gly Ser Leu Ser Ser Gly Val His Thr Phe Pro Ala Val Leu Gln
                165                 170                 175
Ser Asp Leu Tyr Thr Leu Ser Ser Ser Val Thr Val Pro Ser Ser Thr
            180                 185                 190
Trp Pro Ser Glu Thr Val Thr Cys Asn Val Ala His Pro Ala Ser Ser
        195                 200                 205
Thr Lys Val Asp Lys Lys Ile Val Pro Arg Asp Cys Gly Cys Lys Pro
    210                 215                 220
Cys Ile Cys Thr Val Pro Glu Val Ser Ser Val Phe Ile Phe Pro Pro
225                 230                 235                 240
Lys Pro Lys Asp Val Leu Thr Ile Thr Leu Thr Pro Lys Val Thr Cys
                245                 250                 255
Val Val Val Asp Ile Ser Lys Asp Asp Pro Glu Val Gln Phe Ser Trp
            260                 265                 270
Phe Val Asp Asp Val Glu Val His Thr Ala Gln Thr Gln Pro Arg Glu
        275                 280                 285
Glu Gln Phe Asn Ser Thr Phe Arg Ser Val Ser Glu Leu Pro Ile Met
    290                 295                 300
His Gln Asp Trp Leu Asn Gly Lys Glu Phe Lys Cys Arg Val Asn Ser
305                 310                 315                 320
Ala Ala Phe Pro Ala Pro Ile Glu Lys Thr Ile Ser Lys Thr Lys Gly
                325                 330                 335
Arg Pro Lys Ala Pro Gln Val Tyr Thr Ile Pro Pro Pro Lys Glu Gln
            340                 345                 350
Met Ala Lys Asp Lys Val Ser Leu Thr Cys Met Ile Thr Asp Phe Phe
        355                 360                 365
Pro Glu Asp Ile Thr Val Glu Trp Gln Trp Asn Gly Gln Pro Ala Glu
    370                 375                 380
Asn Tyr Lys Asn Thr Gln Pro Ile Met Asp Thr Asp Gly Ser Tyr Phe
385                 390                 395                 400
Val Tyr Ser Lys Leu Asn Val Gln Lys Ser Asn Trp Glu Ala Gly Asn
                405                 410                 415
Thr Phe Thr Cys Ser Val Leu His Glu Gly Leu His Asn His His Thr
            420                 425                 430
Glu Lys Ser Leu Ser His Ser Pro Gly Lys
        435                 440
```

<210> SEQ ID NO 132
<211> LENGTH: 717
<212> TYPE: DNA
<213> ORGANISM: Artificial Sequence
<220> FEATURE:
<223> OTHER INFORMATION: Full Length Light Chain (2F8 Kappa Variable
      Region and Constant Region)

<400> SEQUENCE: 132

```
atggagacag acacaatcct gctatgggtg ctgctgctct gggttccagg ctccactggt      60
gacattgtgc tgacccaatc tccagcttct ttggctgtgt ctctagggca gagggccacc     120
atctcctgca aggccagcca agtgttgat tatgatggta atagttatat caactggtac      180
caacagaaac caggacagcc acccaaagtc ctcatctatg ttgcatccaa tctagaatct     240
gggatcccag ccaggtttag tggcagtggg tctgggacag acttcaccct caacatccat     300
cctgtggagg aggaggatgc tgcaacctat tactgtcagc aaagtattga ggatcctccc     360
acgttcggtg ctgggaccaa gctggagctg aaacggctg atgctgcacc aactgtatcc      420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata cagctatac ctgtgaggcc      660
actcacaaga gatcaacttc acccattgtc aagagcttca caggaatga gtgttag         717
```

<210> SEQ ID NO 133
<211> LENGTH: 218
<212> TYPE: PRT
<213> ORGANISM: Artificial Sequence
<220> FEATURE:
<223> OTHER INFORMATION: Full Length Light Chain (2F8 Kappa Variable
      Region and Constant Region)

<400> SEQUENCE: 133

```
Asp Ile Val Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
                20                  25                  30
Gly Asn Ser Tyr Ile Asn Trp Tyr Gln Gln Lys Pro Gly Gln Pro Pro
            35                  40                  45
Lys Val Leu Ile Tyr Val Ala Ser Asn Leu Glu Ser Gly Ile Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln Gln Ser Ile
                85                  90                  95
Glu Asp Pro Pro Thr Phe Gly Ala Gly Thr Lys Leu Glu Leu Lys Arg
                100                 105                 110
Ala Asp Ala Ala Pro Thr Val Ser Ile Phe Pro Pro Ser Ser Glu Gln
            115                 120                 125
Leu Thr Ser Gly Gly Ala Ser Val Val Cys Phe Leu Asn Asn Phe Tyr
        130                 135                 140
Pro Lys Asp Ile Asn Val Lys Trp Lys Ile Asp Gly Ser Glu Arg Gln
145                 150                 155                 160
Asn Gly Val Leu Asn Ser Trp Thr Asp Gln Asp Ser Lys Asp Ser Thr
                165                 170                 175
```

Tyr Ser Met Ser Ser Thr Leu Thr Leu Thr Lys Asp Glu Tyr Glu Arg
        180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 134
<211> LENGTH: 1392
<212> TYPE: DNA
<213> ORGANISM: Artificial Sequence
<220> FEATURE:
<223> OTHER INFORMATION: Full Length Heavy Chain (3B6 Variable Region
      and IgG1 Constant Region)

<400> SEQUENCE: 134

```
atggaatggc cttgtatctt tctcttcctc ctgtcagtaa ctgaaggtgt ccactcccag      60
gttcagctgc agcagtctgg ggctgaactg gtgaggcctg gtcctcagt gaagatttcc     120
tgcaaggctt ctggctatgt attcagtagc tactggatga actgggtgaa gcagaggcct    180
ggacagggtc ttgagtggat tgacagatt tatcctggag atggtgatag taactacaat    240
ggaaacttca agggtaaagc cacactgact gcagacaaat cctccagtac agcctacatg    300
cagctcagca gcctaacatc tgaggactct gcggtctatt tctgtgcatc ccagctcggg    360
ctacgtgaga actactttga ctactggggc caaggcacca ctctcacagt ctcctcagcc    420
aaaacgacac cccatcctgt ctatccactg gcccctggat ctgctgccca actaactcc    480
atggtgaccc tgggatgcct ggtcaagggc tatttccctg agccagtgac agtgacctgg    540
aactctggat ccctgtccag cggtgtgcac accttccag ctgtcctgca gtctgacctc    600
tacactctga gcagctcagt gactgtcccc tccagcacct ggcccagcga gaccgtcacc    660
tgcaacgttg cccacccggc cagcagcacc aaggtggaca gaaaaattgt gcccagggat    720
tgtggttgta agccttgcat atgtacagtc ccagaagtat catctgtctt catcttcccc    780
ccaaagccca aggatgtgct caccattact ctgactccta aggtcacgtg tgttgtggta    840
gacatcagca aggatgatcc cgaggtccag ttcagctggt ttgtagatga tgtggaggtg    900
cacacagctc agacgcaacc ccgggaggag cagttcaaca gcactttccg ctcagtcagt    960
gaacttccca tcatgcacca ggactggctc aatggcaagg agttcaaatg cagggtcaac   1020
agtgcagctt tccctgcccc catcgagaaa accatctcca aaaccaaagg cagaccgaag   1080
gctccacagg tgtacaccat tccacctccc aaggagcaga tggccaagga taaagtcagt   1140
ctgacctgca tgataacaga cttcttccct gaagacatta ctgtggagtg gcagtggaat   1200
gggcagccag cggagaacta caagaacact cagcccatca tggacacaga tggctcttac   1260
ttcgtctaca gcaagctcaa tgtgcagaag agcaactggg aggcaggaaa tactttcacc   1320
tgctctgtgt tacatgaggg cctgcacaac accatactg agaagagcct ctcccactct   1380
cctggtaaat ga                                                       1392
```

<210> SEQ ID NO 135
<211> LENGTH: 444
<212> TYPE: PRT
<213> ORGANISM: Artificial Sequence
<220> FEATURE:
<223> OTHER INFORMATION: Full Length Heavy Chain (3B6 Variable Region
      and IgG1 Constant egion)

<400> SEQUENCE: 135

-continued

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Val Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Ser Asn Tyr Asn Gly Asn Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Gln Leu Gly Leu Arg Glu Asn Tyr Phe Asp Tyr Trp Gly Gln
                100                 105                 110

Gly Thr Thr Leu Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
                180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
```

420         425         430
His Thr Glu Lys Ser Leu Ser His Ser Pro Gly Lys
        435                 440

<210> SEQ ID NO 136
<211> LENGTH: 711
<212> TYPE: DNA
<213> ORGANISM: Artificial Sequence
<220> FEATURE:
<223> OTHER INFORMATION: Full Length Light Chain (3B6 Kappa Variable
      Region and Constant Region)

<400> SEQUENCE: 136
atggacatga ggacccctgc tcagtttctt ggaatcttgt tgctctggtt tccaggtatc      60
aaatgtgaca tcaagatgac ccagtctcca tcttccatgt atgcatctct aggagagaga     120
gtcacaatca cttgcaaggc gagtcaggac attaaaagct atttaagctg gttccagcag     180
aaaccaggga atctcctaa gaccctgatc tatcgtgtaa acagattggt agatggggtc      240
ccatcaaggt tcagtggcag tggatctggg caagattctt ctctcaccat caccagcctg     300
gagaatgaag atatgggaat ttattattgt ctacagtatg atgagtttcc gttcacgttc     360 ggaggggga ccaagctgga aataaagcgg gctgatgctg caccaactgt atccatcttc      420
ccaccatcca gtgagcagtt aacatctgga ggtgcctcag tcgtgtgctt cttgaacaac     480
ttctacccca agacatcaa tgtcaagtgg aagattgatg gcagtgaacg acaaaatggc      540
gtcctgaaca gttggactga tcaggacagc aaagacagca cctacagcat gagcagcacc     600
ctcacgttga ccaaggacga gtatgaacga cataacagct atacctgtga ggccactcac     660
aagacatcaa cttcacccat tgtcaagagc ttcaacagga atgagtgtta g              711

<210> SEQ ID NO 137
<211> LENGTH: 214
<212> TYPE: PRT
<213> ORGANISM: Artificial Sequence
<220> FEATURE:
<223> OTHER INFORMATION: Full Length Light Chain (3B6 Kappa Variable
      Region and Constant Region)

<400> SEQUENCE: 137

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Phe Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Gln Asp Ser Ser Leu Thr Ile Thr Ser Leu Glu Asn
65                  70                  75                  80

Glu Asp Met Gly Ile Tyr Tyr Cys Leu Gln Tyr Asp Glu Phe Pro Phe
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu

```
                145                 150                 155                 160
Asn Ser Trp Thr Asp Gln Asp Ser Lys Asp Ser Thr Tyr Ser Met Ser
                    165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 138
<211> LENGTH: 1361
<212> TYPE: DNA
<213> ORGANISM: Artificial Sequence
<220> FEATURE:
<223> OTHER INFORMATION: Full Length Heavy Chain (3D11 Variable Region
      and IgG1 Constant Region)

<400> SEQUENCE: 138
atggctgtcc cggtgctgtt cctctgcctg gttgcatttc caagctgtgt cctgtcccag      60
gtacagctga aggagtcagg acctggcctg gtggcgccct cacagagcct gtccatcact     120
tgcactgtct ctgggttttc attaaccagc tatagtttac actgggttcg ccagcctcca     180
ggaaagggtc tggaatggct gggagtaata tgggctggtg aaacacaaa ttataattcg      240 tctctcatgt ccagactgac catcaggaaa gacaactcca agagccaagt tttcttaaaa     300
atgaacagtc tgcaaactga tgacacagcc atgtactact gtgccagaga gaggtttgct     360
tactggggcc aagggactct ggtcactgtc tctgcagcca aaacgacacc cccatctgtc     420
tatccactgg cccctggatc tgctgcccaa actaactcca tggtgaccct gggatgcctg     480
gtcaagggct atttccctga gccagtgaca gtgacctgga ctctggatcc cctgtccagc     540
ggtgtgcaca ccttcccagc tgtcctgcag tctgacctct acactctgag cagctcagtg     600
actgtcccct ccagcacctg gcccagcgag accgtcacct gcaacgttgc ccacccggcc     660
agcagcacca aggtggacaa gaaaattgtg cccagggatt gtggttgtaa gccttgcata     720
tgtacagtcc cagaagtatc atctgtcttc atcttccccc caaagcccaa ggatgtgctc     780
accattactc tgactcctaa ggtcacgtgt gttgtggtag acatcagcaa ggatgatccc     840
gaggtccagt tcagctggtt tgtagatgat gtggaggtgc acacagctca gacgcaaccc     900
cgggaggagc agttcaacag cactttccgc tcagtcagtg aacttcccat catgcaccag     960
gactggctca atggcaagga gttcaaatgc agggtcaaca gtgcagcttt ccctgccccc    1020
atcgagaaaa ccatctccaa aaccaaaggc agaccgaagg ctccacaggt gtacaccatt    1080
ccacctccca aggagcagat ggccaaggat aaagtcagtc tgacctgcat gataacagac    1140
ttcttccctg aagacattac tgtggagtgg cagtggaatg gcagccagc ggagaactac     1200 aagaacactc agcccatcat ggacacagat ggctcttact tcgtctacag caagctcaat    1260
gtgcagaaga gcaactggga ggcaggaaat actttcacct gctctgtgtt acatgagggc    1320
ctgcacaacc accatactga tcccactctc ctggtaaatg a                        1361

<210> SEQ ID NO 139
<211> LENGTH: 437
<212> TYPE: PRT
<213> ORGANISM: Artificial Sequence
<220> FEATURE:
<223> OTHER INFORMATION: Full Length Heavy Chain (3D11 Variable Region
      and IgG1 Constant Region)
```

<400> SEQUENCE: 139

| | | | | | | | | | | | | | | | |
|---|---|---|---|---|---|---|---|---|---|---|---|---|---|---|---|
|Gln|Val|Gln|Leu|Lys|Glu|Ser|Gly|Pro|Gly|Leu|Val|Ala|Pro|Ser|Gln|
|1| | | |5| | | | |10| | | | |15| |
|Ser|Leu|Ser|Ile|Thr|Cys|Thr|Val|Ser|Gly|Phe|Ser|Leu|Thr|Ser|Tyr|
| | | | |20| | | | |25| | | | |30| |
|Ser|Leu|His|Trp|Val|Arg|Gln|Pro|Pro|Gly|Lys|Gly|Leu|Glu|Trp|Leu|
| | | |35| | | | |40| | | | |45| | |
|Gly|Val|Ile|Trp|Ala|Gly|Gly|Asn|Thr|Asn|Tyr|Asn|Ser|Ser|Leu|Met|
| |50| | | | |55| | | | |60| | | | |
|Ser|Arg|Leu|Thr|Ile|Arg|Lys|Asp|Asn|Ser|Lys|Ser|Gln|Val|Phe|Leu|
|65| | | | |70| | | | |75| | | | |80|
|Lys|Met|Asn|Ser|Leu|Gln|Thr|Asp|Asp|Thr|Ala|Met|Tyr|Tyr|Cys|Ala|
| | | | |85| | | | |90| | | | |95| |
|Arg|Glu|Arg|Phe|Ala|Tyr|Trp|Gly|Gln|Gly|Thr|Leu|Val|Thr|Val|Ser|
| | | | |100| | | | |105| | | | |110| |
|Ala|Ala|Lys|Thr|Thr|Pro|Pro|Ser|Val|Tyr|Pro|Leu|Ala|Pro|Gly|Ser|
| | | |115| | | | |120| | | | |125| | |
|Ala|Ala|Gln|Thr|Asn|Ser|Met|Val|Thr|Leu|Gly|Cys|Leu|Val|Lys|Gly|
| | |130| | | | |135| | | | |140| | | |
|Tyr|Phe|Pro|Glu|Pro|Val|Thr|Val|Thr|Trp|Asn|Ser|Gly|Ser|Leu|Ser|
|145| | | | |150| | | | |155| | | | |160|
|Ser|Gly|Val|His|Thr|Phe|Pro|Ala|Val|Leu|Gln|Ser|Asp|Leu|Tyr|Thr|
| | | | |165| | | | |170| | | | |175| |
|Leu|Ser|Ser|Ser|Val|Thr|Val|Pro|Ser|Ser|Thr|Trp|Pro|Ser|Glu|Thr|
| | | |180| | | | |185| | | | |190| | |
|Val|Thr|Cys|Asn|Val|Ala|His|Pro|Ala|Ser|Ser|Thr|Lys|Val|Asp|Lys|
| | |195| | | | |200| | | | |205| | | |
|Lys|Ile|Val|Pro|Arg|Asp|Cys|Gly|Cys|Lys|Pro|Cys|Ile|Cys|Thr|Val|
| |210| | | | |215| | | | |220| | | | |
|Pro|Glu|Val|Ser|Ser|Val|Phe|Ile|Phe|Pro|Pro|Lys|Pro|Lys|Asp|Val|
|225| | | | |230| | | | |235| | | | |240|
|Leu|Thr|Ile|Thr|Leu|Thr|Pro|Lys|Val|Thr|Cys|Val|Val|Val|Asp|Ile|
| | | | |245| | | | |250| | | | |255| |
|Ser|Lys|Asp|Asp|Pro|Glu|Val|Gln|Phe|Ser|Trp|Phe|Val|Asp|Asp|Val|
| | | |260| | | | |265| | | | |270| | |
|Glu|Val|His|Thr|Ala|Gln|Thr|Gln|Pro|Arg|Glu|Glu|Gln|Phe|Asn|Ser|
| | |275| | | | |280| | | | |285| | | |
|Thr|Phe|Arg|Ser|Val|Ser|Glu|Leu|Pro|Ile|Met|His|Gln|Asp|Trp|Leu|
| |290| | | | |295| | | | |300| | | | |
|Asn|Gly|Lys|Glu|Phe|Lys|Cys|Arg|Val|Asn|Ser|Ala|Ala|Phe|Pro|Ala|
|305| | | | |310| | | | |315| | | | |320|
|Pro|Ile|Glu|Lys|Thr|Ile|Ser|Lys|Thr|Lys|Gly|Arg|Pro|Lys|Ala|Pro|
| | | | |325| | | | |330| | | | |335| |
|Gln|Val|Tyr|Thr|Ile|Pro|Pro|Lys|Glu|Gln|Met|Ala|Lys|Asp|Lys|
| | | |340| | | | |345| | | | |350| | |
|Val|Ser|Leu|Thr|Cys|Met|Ile|Thr|Asp|Phe|Phe|Pro|Glu|Asp|Ile|Thr|
| | |355| | | | |360| | | | |365| | | |
|Val|Glu|Trp|Gln|Trp|Asn|Gly|Gln|Pro|Ala|Glu|Asn|Tyr|Lys|Asn|Thr|
| |370| | | | |375| | | | |380| | | | |
|Gln|Pro|Ile|Met|Asp|Thr|Asp|Gly|Ser|Tyr|Phe|Val|Tyr|Ser|Lys|Leu|
|385| | | | |390| | | | |395| | | | |400|
|Asn|Val|Gln|Lys|Ser|Asn|Trp|Glu|Ala|Gly|Asn|Thr|Phe|Thr|Cys|Ser|

```
                405                 410                 415
Val Leu His Glu Gly Leu His Asn His His Thr Glu Lys Ser Leu Ser
        420                 425                 430

His Ser Pro Gly Lys
        435

<210> SEQ ID NO 140
<211> LENGTH: 708
<212> TYPE: DNA
<213> ORGANISM: Artificial Sequence
<220> FEATURE:
<223> OTHER INFORMATION: Full Length Light Chain (3D11 Kappa Variable
      Region and Constant Region)

<400> SEQUENCE: 140
atggattttc aagtgcagat tttcagcttc ctgctaatca gtgcctcagt caaaatatcc    60
agaggacaaa ttgttctcac ccagtctcca gcaatcatgt ctgcatatcc aggggagaag   120
gtcaccatga cctgcagtgc cagctcaagt gtaagttaca tgcactggta ccagcagaag   180
tcaggcacct cccccaaaag atggatttat gacacatcca aactggcttc tggagtccct   240
gctcgcttca gtggcagtgg gtctgggacc tcttactccc tcacaatcag tagtatggag   300
gctgaagatg ctgccactta ttactgccag cagtggagta gtaacccact cacgttcggt   360
gctgggacca agctggagct gaaacgggct gatgctgcac caactgtatc catcttccca   420
ccatccagtg agcagttaac atctggaggt gcctcagtcg tgtgcttctt gaacaacttc   480
taccccaaag acatcaatgt caagtggaag attgatggca gtgaacgaca aaatggcgtc   540
ctgaacagtt ggactgatca ggacagcaaa gacagcacct acagcatgag cagcaccctc   600
acgttgacca ggacgagta tgaacgacat aacagctata cctgtgaggc cactcacaag   660
acatcaactt cacccattgt caagagcttc aacaggaatg agtgttag              708

<210> SEQ ID NO 141
<211> LENGTH: 213
<212> TYPE: PRT
<213> ORGANISM: Artificial Sequence
<220> FEATURE:
<223> OTHER INFORMATION: Full Length Light Chain (3D11 Kappa Variable
      Region and Constant Region)

<400> SEQUENCE: 141

Gln Ile Val Leu Thr Gln Ser Pro Ala Ile Met Ser Ala Tyr Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
```

```
                130                 135                 140
Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 142
<211> LENGTH: 1398
<212> TYPE: DNA
<213> ORGANISM: Artificial Sequence
<220> FEATURE:
<223> OTHER INFORMATION: Full Length Heavy Chain (1D3 Variable Region
      and IgG1 Constant Region)

<400> SEQUENCE: 142
atgaactttg ggctcagatt gattttcctt gtccttgttt taaaaggtgt gaagtgtgaa      60
gtgcagctgg tggagtctgg gggaggctta gtgcagcctg agggtccct gaaactctcc     120 tgtgcagcct ctggattcac tttcagtgac tattacatgt cttgggttcg ccagactcca    180
gagaagaggc tggagtgggt cgcatacatt agtagtggtg gtggtagcac ctactatcca    240
gacagtgtga agggtcgatt caccatctcc cgagacaatg ccaagaacac cctgtacctg    300
caaatgagca gtctgaagtc tgaggacaca gccatatatt actgtgtgag acaagggat    360 ggttattacg gggactatgc tatggactac tggggtcaag gaacctcagt catcgtctcc    420
tcagccaaaa cgacaccccc atctgtctat ccactggccc ctggatctgc tgcccaaact    480
aactccatgg tgaccctggg atgcctggtc aagggctatt tccctgagcc agtgacagtg    540
acctggaact ctggatccct gtccagcggt gtgcacacct tcccagctgt cctgcagtct    600
gacctctaca ctctgagcag ctcagtgact gtcccctcca gcacctggcc cagcgagacc    660
gtcacctgca acgttgccca cccggccagc agcaccaagg tggacaagaa aattgtgccc    720
agggattgtg gttgtaagcc ttgcatatgt acagtcccag aagtatcatc tgtcttcatc    780
ttccccccaa agcccaagga tgtgctcacc attactctga ctcctaaggt cacgtgtgtt    840
gtggtagaca tcagcaagga tgatcccgag gtccagttca gctggtttgt agatgatgtg    900
gaggtgcaca cagctcagac gcaaccccgg gaggagcagt tcaacagcac tttccgctca    960
gtcagtgaac ttcccatcat gcaccaggac tggctcaatg gcaaggagtt caaatgcagg   1020
gtcaacagtg cagctttccc tgcccccatc gagaaaacca tctccaaaac caaaggcaga   1080
ccgaaggctc cacaggtgta caccattcca cctcccaagg agcagatggc caaggataaa   1140
gtcagtctga cctgcatgat aacagacttc ttccctgaag acattactgt ggagtggcag   1200
tggaatgggc agccagcgga gaactacaag aacactcagc ccatcatgga cacagatggc   1260
tcttacttcg tctacagcaa gctcaatgtg cagaagagca ctgggaggc aggaaatact   1320 ttcacctgct ctgtgttaca tgagggcctg cacaaccacc atactgagaa gagcctctcc   1380
cactctcctg gtaaatga                                                 1398

<210> SEQ ID NO 143
<211> LENGTH: 446
```

```
<212> TYPE: PRT
<213> ORGANISM: Artificial Sequence
<220> FEATURE:
<223> OTHER INFORMATION: Full Length Heavy chain (1D3 Variable Region
      and IgG1 Constant Region)

<400> SEQUENCE: 143
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | | | | | | | | | | | | | | |
| Ser | Leu | Lys | Leu | Ser | Cys | Ala | Ala | Ser | Gly | Phe | Thr | Phe | Ser | Asp |
| | | | 20 | | | | | 25 | | | | | 30 | |
| Tyr | | | | | | | | | | | | | | |
| Tyr | Met | Ser | Trp | Val | Arg | Gln | Thr | Pro | Glu | Lys | Arg | Leu | Glu | Trp |
| | | | 35 | | | | | 40 | | | | | 45 | |
| Val | | | | | | | | | | | | | | |
| Ala | Tyr | Ile | Ser | Ser | Gly | Gly | Ser | Thr | Tyr | Tyr | Pro | Asp | Ser | Val |
| 50 | | | | | 55 | | | | | 60 | | | | |
| Lys | Gly | Arg | Phe | Thr | Ile | Ser | Arg | Asp | Asn | Ala | Lys | Asn | Thr | Leu |
| 65 | | | | | 70 | | | | | 75 | | | | 80 |
| Tyr | | | | | | | | | | | | | | |
| Leu | Gln | Met | Ser | Ser | Leu | Lys | Ser | Glu | Asp | Thr | Ala | Ile | Tyr | Tyr |
| | | | | 85 | | | | | 90 | | | | | 95 |
| Cys | | | | | | | | | | | | | | |
| Val | Arg | Gln | Gly | Asp | Gly | Tyr | Tyr | Gly | Asp | Tyr | Ala | Met | Asp | Tyr |
| | | | | 100 | | | | | 105 | | | | | 110 |
| Trp | | | | | | | | | | | | | | |
| Gly | Gln | Gly | Thr | Ser | Val | Ile | Val | Ser | Ser | Ala | Lys | Thr | Thr | Pro |
| | | | 115 | | | | | 120 | | | | | 125 | |
| Pro | | | | | | | | | | | | | | |
| Ser | Val | Tyr | Pro | Leu | Ala | Pro | Gly | Ser | Ala | Ala | Gln | Thr | Asn | Ser |
| | 130 | | | | | 135 | | | | | 140 | | | |
| Met | | | | | | | | | | | | | | |
| Val | Thr | Leu | Gly | Cys | Leu | Val | Lys | Gly | Tyr | Phe | Pro | Glu | Pro | Val |
| 145 | | | | | 150 | | | | | 155 | | | | | 160 |
| Thr | | | | | | | | | | | | | | |
| Val | Thr | Trp | Asn | Ser | Gly | Ser | Leu | Ser | Ser | Gly | Val | His | Thr | Phe |
| | | | 165 | | | | | 170 | | | | | 175 | |
| Pro | | | | | | | | | | | | | | |
| Ala | Val | Leu | Gln | Ser | Asp | Leu | Tyr | Thr | Leu | Ser | Ser | Ser | Val | Thr |
| | | | 180 | | | | | 185 | | | | | 190 | |
| Val | | | | | | | | | | | | | | |
| Pro | Ser | Ser | Thr | Trp | Pro | Ser | Glu | Thr | Val | Thr | Cys | Asn | Val | Ala |
| | | | 195 | | | | | 200 | | | | | 205 | |
| His | | | | | | | | | | | | | | |
| Pro | Ala | Ser | Ser | Thr | Lys | Val | Asp | Lys | Lys | Ile | Val | Pro | Arg | Asp |
| | 210 | | | | | 215 | | | | | 220 | | | |
| Cys | | | | | | | | | | | | | | |
| Gly | Cys | Lys | Pro | Cys | Ile | Cys | Thr | Val | Pro | Glu | Val | Ser | Ser | Val |
| 225 | | | | | 230 | | | | | 235 | | | | | 240 |
| Phe | | | | | | | | | | | | | | |
| Ile | Phe | Pro | Pro | Lys | Pro | Lys | Asp | Val | Leu | Thr | Ile | Thr | Leu | Thr |
| | | | | 245 | | | | | 250 | | | | | 255 |
| Pro | | | | | | | | | | | | | | |
| Lys | Val | Thr | Cys | Val | Val | Val | Asp | Ile | Ser | Lys | Asp | Asp | Pro | Glu |
| | | | | 260 | | | | | 265 | | | | | 270 |
| Val | | | | | | | | | | | | | | |
| Gln | Phe | Ser | Trp | Phe | Val | Asp | Asp | Val | Glu | Val | His | Thr | Ala | Gln |
| | | | 275 | | | | | 280 | | | | | 285 | |
| Thr | | | | | | | | | | | | | | |
| Gln | Pro | Arg | Glu | Glu | Gln | Phe | Asn | Ser | Thr | Phe | Arg | Ser | Val | Ser |
| | 290 | | | | | 295 | | | | | 300 | | | |
| Glu | | | | | | | | | | | | | | |
| Leu | Pro | Ile | Met | His | Gln | Asp | Trp | Leu | Asn | Gly | Lys | Glu | Phe | Lys |
| 305 | | | | | 310 | | | | | 315 | | | | | 320 |
| Cys | | | | | | | | | | | | | | |
| Arg | Val | Asn | Ser | Ala | Ala | Phe | Pro | Ala | Pro | Ile | Glu | Lys | Thr | Ile |
| | | | | 325 | | | | | 330 | | | | | 335 |
| Ser | | | | | | | | | | | | | | |
| Lys | Thr | Lys | Gly | Arg | Pro | Lys | Ala | Pro | Gln | Val | Tyr | Thr | Ile | Pro |
| | | | 340 | | | | | 345 | | | | | 350 | |
| Pro | | | | | | | | | | | | | | |
| Pro | Lys | Glu | Gln | Met | Ala | Lys | Asp | Lys | Val | Ser | Leu | Thr | Cys | Met |
| | | | | 355 | | | | | 360 | | | | | 365 |
| Ile | | | | | | | | | | | | | | |
| Thr | Asp | Phe | Phe | Pro | Glu | Asp | Ile | Thr | Val | Glu | Trp | Gln | Trp | Asn |
| | | | 370 | | | | | 375 | | | | | 380 | |
| Gly | | | | | | | | | | | | | | |

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 144
<211> LENGTH: 705
<212> TYPE: DNA
<213> ORGANISM: Artificial Sequence
<220> FEATURE:
<223> OTHER INFORMATION: Full Length Light Chain (1D3 Kappa Variable
      Region and Constant Region)

<400> SEQUENCE: 144

```
atgagtgtgc ccactcaggt cctggggttg ctgctgctgt ggcttacaga tgtcagatgt    60
gacatccaga tgactcagtc tccagcctcc ctatctgtat ctgtgggaga aactgtcacc   120
atcacatgtc gaacaagtga gaatatttac agtaatttag cgtggtatca gcagaaacag   180
ggaaaatctc ctcagctcct aatctatgct gcaacaaact tagcagatgg tgtgccatca   240
aggttcagtg gcagtggatc aggcacacag ttttccctca ggatcaacag cctgcagtct   300
gaagattttg ggaggtatta ctgtcaacat tttgggggga ctccgtacac gttcggaggg   360
gggaccaaac tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gttag                   705
```

<210> SEQ ID NO 145
<211> LENGTH: 214
<212> TYPE: PRT
<213> ORGANISM: Artificial Sequence
<220> FEATURE:
<223> OTHER INFORMATION: Full Length Light Chain (1D3 Kappa Variable
      Region and Constant Region)

<400> SEQUENCE: 145

Asp Ile Gln Met Thr Gln Ser Pro Ala Ser Leu Ser Val Ser Val Gly
1               5                   10                  15

Glu Thr Val Thr Ile Thr Cys Arg Thr Ser Glu Asn Ile Tyr Ser Asn
                20                  25                  30

Leu Ala Trp Tyr Gln Gln Lys Gln Gly Lys Ser Pro Gln Leu Leu Ile
            35                  40                  45

Tyr Ala Ala Thr Asn Leu Ala Asp Gly Val Pro Ser Arg Phe Ser Gly
        50                  55                  60

Ser Gly Ser Gly Thr Gln Phe Ser Leu Arg Ile Asn Ser Leu Gln Ser
65                  70                  75                  80

Glu Asp Phe Gly Arg Tyr Tyr Cys Gln His Phe Trp Gly Thr Pro Tyr
                85                  90                  95

Thr Phe Gly Gly Gly Thr Lys Leu Glu Ile Lys Arg Ala Asp Ala Ala
                100                 105                 110

```
Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 146
<211> LENGTH: 1398
<212> TYPE: DNA
<213> ORGANISM: Artificial Sequence
<220> FEATURE:
<223> OTHER INFORMATION: Full Length Heavy Chain (1F3 Variable Region
      and IgG1 Constant Region)

<400> SEQUENCE: 146
atgaactttg ggctcagatt gattttcctt gtccttgttt taaaaggtgt gaagtgtgag      60
gtgcagctgg tggagtctgg gggaggctta gtgcagtctg agggtccct gaaactctcc     120 tgtgcggcct ctggattcac tttcagtaac tatttcatgt cttgggttcg ccagactcca     180
gagaagaggc tggagtgggt cgcatatatt agtagtggtg gtggtagcac ctactatcca     240
gacagtgtga aggtcgatt caccatctct agagacaatg ccagaacac cctgtacctg      300 caaatgagca gtctgaagtc tgaggacaca gccatgtatt actgtgtaag acaaggggat     360
ggttactacg gggactatgc tatggactac tggggtcaag gaacctcagt caccgtctcc     420
tcagccaaaa cgacaccccc atctgtctat ccactggccc ctggatctgc tgcccaaact     480
aactccatgg tgaccctggg atgcctggtc aagggctatt ccctgagcc agtgacagtg     540 acctggaact ctggatccct gtccagcggt gtgcacacct tcccagctgt cctgcagtct     600
gacctctaca ctctgagcag ctcagtgact gtcccctcca gcacctggcc cagcgagacc     660
gtcacctgca acgttgccca ccggccagc agcaccaagg tggacaagaa aattgtgccc     720
agggattgtg gttgtaagcc ttgcatatgt acagtcccag aagtatcatc tgtcttcatc     780 ttcccccaa agcccaagga tgtgctcacc attactctga ctcctaaggt cacgtgtgtt     840
gtggtagaca tcagcaagga tgatcccgag gtccagttca gctggtttgt agatgatgtg     900
gaggtgcaca cagctcagac gcaaccccgg gaggagcagt tcaacagcac tttccgctca     960
gtcagtgaac ttcccatcat gcaccaggac tggctcaatg gcaaggagtt caaatgcagg    1020
gtcaacagtg cagctttccc tgcccccatc gagaaaacca tctccaaaac caaaggcaga    1080
ccgaaggctc cacaggtgta caccattcca cctcccaagg agcagatggc caaggataaa    1140
gtcagtctga cctgcatgat aacagacttc ttccctgaag acattactgt ggagtggcag    1200
tggaatgggc agccagcgga gaactacaag aacactcagc ccatcatgga cacagatggc    1260
tcttacttcg tctacagcaa gctcaatgtg cagaagagca ctgggaggc aggaaatact    1320 ttcacctgct ctgtgttaca tgagggcctg cacaaccacc atactgagaa gagcctctcc    1380
```
cactctcctg gtaaatga                                                1398

<210> SEQ ID NO 147
<211> LENGTH: 446
<212> TYPE: PRT
<213> ORGANISM: Artificial Sequence
<220> FEATURE:
<223> OTHER INFORMATION: Full Length Heavy Chain (1F3 Variable Region
      and IgG1 Constant Region)

<400> SEQUENCE: 147

```
Glu Val Gln Leu Val Glu Ser Gly Gly Leu Val Gln Ser Gly Gly
 1               5                  10                  15

Ser Leu Lys Leu Ser Cys Ala Ala Ser Gly Phe Thr Phe Ser Asn Tyr
            20                  25                  30

Phe Met Ser Trp Val Arg Gln Thr Pro Glu Lys Arg Leu Glu Trp Val
        35                  40                  45

Ala Tyr Ile Ser Ser Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg Gln Gly Asp Gly Tyr Tyr Gly Asp Tyr Ala Met Asp Tyr Trp
            100                 105                 110

Gly Gln Gly Thr Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350
```

```
Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
            405                 410                 415

Glu Ala Gly Asn Thr Phe Thr Cys Ser Val Leu His Glu Gly Leu His
                420                 425                 430

Asn His His Thr Glu Lys Ser Leu Ser His Ser Pro Gly Lys
            435                 440                 445
```

<210> SEQ ID NO 148
<211> LENGTH: 705
<212> TYPE: DNA
<213> ORGANISM: Artificial Sequence
<220> FEATURE:
<223> OTHER INFORMATION: Full Length Light Chain (1F3 Kappa Variable
      Region and Constant Region)

<400> SEQUENCE: 148

```
atgagtgtgc ccactcaggt cctggggttg ctgctgctgt ggcttacaga tgccagatgt      60
gacatccaga tgactcagtc tccagcctcc ctatctgtat ctgtgggaga aactgtcacc     120
atcacatgtc gagcaagtga gaatatttac agtaatttag catggtatca gcagaaacag     180
ggaaaatctc ctcagctcct ggtctatgat gcaacacact accagatgg tgtgccatca      240 aggttcagtg gcagtggatc aggcacacag ttttcccctca agatcaacag cctgcagtct     300
gaagattttg ggagttatta ctgtcaacat ttttggggta ctccgtacac gtttggaggg     360
gggaccagac tggaaattaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                     705
```

<210> SEQ ID NO 149
<211> LENGTH: 214
<212> TYPE: PRT
<213> ORGANISM: Artificial Sequence
<220> FEATURE:
<223> OTHER INFORMATION: Full Length Light Chain (1F3 Kappa Variable
      Region and Constant Region)

<400> SEQUENCE: 149

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Asp Ala Thr His Leu Pro Asp Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80
```

```
Glu Asp Phe Gly Ser Tyr Tyr Cys Gln His Phe Trp Gly Thr Pro Tyr
                85                  90                  95

Thr Phe Gly Gly Gly Thr Arg Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210
```

<210> SEQ ID NO 150
<211> LENGTH: 1398
<212> TYPE: DNA
<213> ORGANISM: Artificial Sequence
<220> FEATURE:
<223> OTHER INFORMATION: Full Length Heavy Chain (3A12 Variable Region
      and IgG1 Constant Region)

<400> SEQUENCE: 150

```
atgaactttg ggctcagatt gattttcctt gtccttgttt taaaaggtgt gaagtgtgaa    60
gtgcagctgg tggagtctgg gggaggctta gtgcagcctg agggtccct  gaaaatctcc   120
tgtgcagcct ctggatttac tttcagtaac tatttcatgt cttgggttcg ccagactcca   180
gagaagaggc tggagtgggt cgcatacatt agtagtggtg gtggtagcac ctactatcca   240
gacagtgtga aggtcgatt  caccatctcc agagacaatg ccaagaacac cctgtacctg   300
caaatgaaca gtctgaagtc tgaggacaca gccatgtatt actgtgtaag acaaggagat   360
ggttactatg ggactatgc  tatggactac tggggtcaag gaacctcagt caccgtctcc   420
tcagccaaaa cgacaccccc atctgtctat ccactggccc ctggatctgc tgcccaaact   480
aactccatgg tgaccctggg atgcctggtc aagggctatt tccctgagcc agtgacagtg   540
acctggaact ctggatccct gtccagcggt gtgcacacct tcccagctgt cctgcagtct   600
gacctctaca ctctgagcag ctcagtgact gtccccctcca gcacctggcc cagcgagacc   660
gtcacctgca acgttgccca cccggccagc agcaccaagg tggacaagaa aattgtgccc   720
agggattgtg gttgtaagcc ttgcatatgt acagtcccag aagtatcatc tgtcttcatc   780
ttccccccaa agcccaagga tgtgctcacc attactctga ctcctaaggt cacgtgtgtt   840
gtggtagaca tcagcaagga tgatcccgag gtccagttca gctggtttgt agatgatgtg   900
gaggtgcaca cagctcagac gcaacccccgg gaggagcagt tcaacagcac tttccgctca   960
gtcagtgaac ttcccatcat gcaccaggac tggctcaatg gcaaggagtt caaatgcagg  1020
gtcaacagtg cagctttccc tgcccccatc gagaaaacca tctccaaaac caaaggcaga  1080
ccgaaggctc cacaggtgta caccattcca cctcccaagg agcagatggc caaggataaa  1140
gtcagtctga cctgcatgat aacagacttc ttccctgaag acattactgt ggagtggcag  1200
tggaatgggc agccagcgga gaactacaag aacactcagc ccatcatgga cacagatggc  1260
```

```
tcttacttcg tctacagcaa gctcaatgtg cagaagagca actgggaggc aggaaatact    1320
ttcacctgct ctgtgttaca tgagggcctg cacaaccacc atactgagaa gagcctctcc    1380
cactctcctg gtaaatga                                                  1398
```

<210> SEQ ID NO 151
<211> LENGTH: 446
<212> TYPE: PRT
<213> ORGANISM: Artificial Sequence
<220> FEATURE:
<223> OTHER INFORMATION: Full Length Heavy Chain (3A12 Variable Region
and IgG1 Constant Region)

<400> SEQUENCE: 151

```
Glu Val Gln Leu Val Glu Ser Gly Gly Gly Leu Val Gln Pro Gly Gly
1               5                   10                  15

Ser Leu Lys Ile Ser Cys Ala Ala Ser Gly Phe Thr Phe Ser Asn Tyr
            20                  25                  30

Phe Met Ser Trp Val Arg Gln Thr Pro Glu Lys Arg Leu Glu Trp Val
        35                  40                  45

Ala Tyr Ile Ser Ser Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Val Arg Gln Gly Asp Gly Tyr Tyr Gly Asp Tyr Ala Met Asp Tyr Trp
            100                 105                 110

Gly Gln Gly Thr Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
```

```
                    325                 330                 335
Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
        370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 152
<211> LENGTH: 705
<212> TYPE: DNA
<213> ORGANISM: Artificial Sequence
<220> FEATURE:
<223> OTHER INFORMATION: Full Length Light Chain (3A12 Kappa Variable
      Region and Constant Region)

<400> SEQUENCE: 152
atgagtgtgc ccactcaggt cctggggttg ctgctgctgt ggcttacaga tgccagatgt      60
gacatccaga tgactcagtc gccagcctcc ctatctgtat ctgtgggaga aactgtcacc     120
atcacatgtc gagcaagtga gaatatttac attaatttag catggtatca gcagaaacag     180
ggaaaatctc ctcagctcct ggtccatgct gcaacaaagt tagcagatgg tgtgccatca     240
aggttcagtg gcagtggatc aggcacacag tattccctca agatcaacag cctgcagtct     300
gaagattttg ggagttatta ctgtcaacat ttttggggta ctccgtacac gttcggaggg     360
gggaccaaac tagaaataaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                     705

<210> SEQ ID NO 153
<211> LENGTH: 214
<212> TYPE: PRT
<213> ORGANISM: Artificial Sequence
<220> FEATURE:
<223> OTHER INFORMATION: Full Length Light Chain (3A12 Kappa Variable
      Region and Constant Region)

<400> SEQUENCE: 153

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ile Asn
            20                  25                  30

Leu Ala Trp Tyr Gln Gln Lys Gln Gly Lys Ser Pro Gln Leu Leu Val
        35                  40                  45

His Ala Ala Thr Lys Leu Ala Asp Gly Val Pro Ser Arg Phe Ser Gly
```

```
                    50                  55                  60
Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Gly Thr Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 154
<211> LENGTH: 1404
<212> TYPE: DNA
<213> ORGANISM: Artificial Sequence
<220> FEATURE:
<223> OTHER INFORMATION: Full Length Chimeric 2B8 Heavy Chain

<400> SEQUENCE: 154

| | | | | |
|---|---|---|---|---|
| atgggatgga gctatatcat cctcttttg gtagcaacag ctacagatgt ccactcccag | 60 |
| gtccaactgc agcagcctgg ggctgaactg gtgaagcctg gacttcagt gaagctgtcc | 120 |
| tgcaaggctt ctggctacac cttcaccacc tactggatgc actgggtgaa tcagaggcct | 180 |
| ggacaaggcc ttgagtggat tggagagatt aatcctacca cggtcatac taactacaat | 240 |
| gagaagttca agagcaaggc cacactgact gtagacaaat cctccagcac agcctacatg | 300 |
| caactcagca gcctgacatc tgaggactct gcggtctatt actgtgcaag aaactatgtt | 360 |
| ggtagcatct ttgactactg gggccaaggc accactctca ccgtctcctc agcctccacc | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga agttgagcc aaatcttgt | 720 |
| gacaaaactc acacatgccc accgtgccca gcacctgaac tcctgggggg accgtcagtc | 780 |
| ttcctcttcc cccccaaaacc caaggacacc ctcatgatct cccggacccc tgaggtcaca | 840 |
| tgcgtggtgg tggacgtgag ccacgaagac cctgaggtca agttcaactg gtacgtggac | 900 |
| ggcgtggagg tgcataatgc caagacaaag ccgcgggagg agcagtacaa cagcacgtac | 960 |
| cgtgtggtca gcgtcctcac cgtcctgcac caggactggc tgaatggcaa ggagtacaag | 1020 |
| tgcaaggtct ccaacaaagc cctcccagcc ccatcgaga aaaccatctc caaagccaaa | 1080 |
| gggcagcccc gagaaccaca ggtgtacacc ctgcccccat cccgggatga gctgaccaag | 1140 |

-continued

```
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atga                                          1404
```

<210> SEQ ID NO 155
<211> LENGTH: 448
<212> TYPE: PRT
<213> ORGANISM: Artificial Sequence
<220> FEATURE:
<223> OTHER INFORMATION: Full Length Chimeric 2B8 Heavy Chain

<400> SEQUENCE: 155

```
Gln Val Gln Leu Gln Gln Pro Gly Ala Glu Leu Val Lys Pro Gly Thr
  1               5                  10                  15

Ser Val Lys Leu Ser Cys Lys Ala Ser Gly Tyr Thr Phe Thr Thr Tyr
             20                  25                  30

Trp Met His Trp Val Asn Gln Arg Pro Gly Gln Gly Leu Glu Trp Ile
         35                  40                  45

Gly Glu Ile Asn Pro Thr Asn Gly His Thr Asn Tyr Asn Glu Lys Phe
     50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asn Tyr Val Gly Ser Ile Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 156
<211> LENGTH: 705
<212> TYPE: DNA
<213> ORGANISM: Artificial Sequence
<220> FEATURE:
<223> OTHER INFORMATION: Full Length Chimeric 2B8 Light Chain

<400> SEQUENCE: 156
atggaatcac agactctggt cttcatatcc atactgctct ggttatatgg tgctgatggg      60
aacattgtaa tgacccaatc tcccaaatcc atgtccatgt cagtaggaga gagggtcacc     120
ttgagctgca aggccagtga aaatgtggtt tcttatgtat cctggtatca acagaaacca     180
gcgcagtctc ctaaactgct gatatacggg gcatccaacc ggaacactgg ggtcccgat      240
cgcttcacag gcagtggatc tgcaacagat ttcactctga ccatcagcag tgtgcgggct     300
gaagaccttg cagattatca ctgtgggcag agttacaact atccgtacac gttcggaggg     360
gggaccaggc tggaaataaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600
ctgagcaaag cagactacga gaaacacaaa gtctacgcct gcgaagtcac ccatcagggc     660
ctgagctcgc ccgtcacaaa gagcttcaac aggggagagt gttga                     705

<210> SEQ ID NO 157
<211> LENGTH: 214
<212> TYPE: PRT
<213> ORGANISM: Artificial Sequence
<220> FEATURE:
<223> OTHER INFORMATION: Full Length Chimeric 2B8 Light Chain

<400> SEQUENCE: 157

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Val Ser Tyr
            20                  25                  30

Val Ser Trp Tyr Gln Gln Lys Pro Ala Gln Ser Pro Lys Leu Leu Ile
        35                  40                  45
```

Tyr Gly Ala Ser Asn Arg Asn Thr Gly Val Pro Asp Arg Phe Thr Gly
    50                  55                  60

Ser Gly Ser Ala Thr Asp Phe Thr Leu Thr Ile Ser Ser Val Arg Ala
65                  70                  75                  80

Glu Asp Leu Ala Asp Tyr His Cys Gly Gln Ser Tyr Asn Tyr Pro Tyr
                85                  90                  95

Thr Phe Gly Gly Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 158
<211> LENGTH: 412
<212> TYPE: DNA
<213> ORGANISM: Artificial Sequence
<220> FEATURE:
<223> OTHER INFORMATION: Synthetic Humanized Hu2B8 Hv1-f.1 Heavy Chain
      Variable Region

<400> SEQUENCE: 158
atggactgca cctggaggat cctcctcttg gtggcagcag ctacaggcac ccacgccgag      60
gtccagctgg tacagtctgg ggctgaggtg aagaagcctg ggctacagt gaaaatctcc     120 tgcaaggttt ctggatacac cttcaccacc tactggatgc actgggtgca acaggcccct    180
ggaaaagggc ttgagtggat gggagagatt aatcctacca acggtcatac taactacaat    240
gagaagttcc agggcagagt caccataacc gcggacacgt ctacagacac agcctacatg    300
gagctgagca gcctgagatc tgaggacacg gccgtgtatt actgtgcaac aaactatgtt    360
ggtagcatct ttgactactg gggccaagga accctggtca ccgtctcctc ag            412

<210> SEQ ID NO 159
<211> LENGTH: 118
<212> TYPE: PRT
<213> ORGANISM: Artificial Sequence
<220> FEATURE:
<223> OTHER INFORMATION: Synthetic Humanized Hu2B8 Hv1-f.1 Heavy Chain
      Variable Region

<400> SEQUENCE: 159

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Thr Tyr
            20                  25                  30

Trp Met His Trp Val Gln Gln Ala Pro Gly Lys Gly Leu Glu Trp Met
        35                  40                  45

Gly Glu Ile Asn Pro Thr Asn Gly His Thr Asn Tyr Asn Glu Lys Phe

```
                50                  55                  60
Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asn Tyr Val Gly Ser Ile Phe Asp Tyr Trp Gly Gln Gly Thr
                100                 105                 110

Leu Val Thr Val Ser Ser
            115

<210> SEQ ID NO 160
<211> LENGTH: 992
<212> TYPE: DNA
<213> ORGANISM: Artificial Sequence
<220> FEATURE:
<223> OTHER INFORMATION: Synthetic Human IgG1 Heavy Chain Constant
      Region

<400> SEQUENCE: 160
cctccaccaa gggcccatcg gtcttccccc tggcaccctc ctccaagagc acctctgggg    60
gcacagcggc cctgggctgc ctggtcaagg actacttccc cgaaccggtg acggtgtcgt   120
ggaactcagg cgccctgacc agcggcgtgc acaccttccc ggctgtccta cagtcctcag   180
gactctactc cctcagcagc gtggtgaccg tgccctccag cagcttgggc acccagacct   240
acatctgcaa cgtgaatcac aagcccagca acaccaaggt ggacaagaaa gttgagccca   300
aatcttgtga caaaactcac acatgcccac cgtgcccagc acctgaactc ctggggggac   360
cgtcagtctt cctcttcccc ccaaaaccca aggacaccct catgatctcc cggacccctg   420
aggtcacatg cgtggtggtg gacgtgagcc acgaagaccc tgaggtcaag ttcaactggt   480
acgtggacgg cgtggaggtg cataatgcca agacaaagcc gcgggaggag cagtacaaca   540
gcacgtaccg tgtggtcagc gtcctcaccg tcctgcacca ggactggctg aatggcaagg   600
agtacaagtg caaggtctcc aacaaagccc tcccagcccc catcgagaaa accatctcca   660
aagccaaagg gcagccccga gaaccacagg tgtacaccct gcccccatcc cgggatgagc   720
tgaccaagaa ccaggtcagc ctgacctgcc tggtcaaagg cttctatccc agcgacatcg   780
ccgtggagtg ggagagcaat gggcagccgg agaacaacta caagaccacg cctcccgtgc   840
tggactccga cggctccttc ttcctctaca gcaagctcac cgtggacaag agcaggtggc   900
agcaggggaa cgtcttctca tgctccgtga tgcatgaggc tctgcacaac cactacacgc   960
agaagagcct ctccctgtct ccgggtaaat ga                                 992

<210> SEQ ID NO 161
<211> LENGTH: 330
<212> TYPE: PRT
<213> ORGANISM: Artificial Sequence
<220> FEATURE:
<223> OTHER INFORMATION: Synthetic Human IgG1 Heavy Chain Constant
      Region

<400> SEQUENCE: 161

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45
```

```
Gly Val His Thr Phe Pro Ala Val Leu Gln Ser Ser Gly Leu Tyr Ser
     50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 162
<211> LENGTH: 1404
<212> TYPE: DNA
<213> ORGANISM: Artificial Sequence
<220> FEATURE:
<223> OTHER INFORMATION: Full Length Humanized Hu2B8 Heavy Chain
      (Hv1f.1 Variable Region)

<400> SEQUENCE: 162
atggactgca cctggaggat cctcctcttg gtggcagcag ctacaggcac ccacgccgag      60
gtccagctgg tacagtctgg ggctgaggtg aagaagcctg ggctacagt gaaaatctcc     120 tgcaaggttt ctggatacac cttcaccacc tactggatgc actgggtgca acaggcccct    180
ggaaaagggc ttgagtggat gggagagatt aatcctacca acgtcatac taactacaat    240 gagaagttcc agggcagagt caccataacc gcggacacgt ctacagacac agcctacatg    300
gagctgagca gcctgagatc tgaggacacg gccgtgtatt actgtgcaac aaactatgtt    360
ggtagcatct ttgactactg gggccaagga accctggtca ccgtctcctc agcctccacc    420
```

-continued

```
aagggcccat cggtcttccc cctggcaccc tcctccaaga gcacctctgg gggcacagcg      480
gccctgggct gcctggtcaa ggactacttc cccgaaccgg tgacggtgtc gtggaactca      540
ggcgccctga ccagcggcgt gcacaccttc ccggctgtcc tacagtcctc aggactctac      600
tccctcagca gcgtggtgac cgtgccctcc agcagcttgg gcacccagac ctacatctgc      660
aacgtgaatc acaagcccag caacaccaag gtggacaaga agttgagcc caaatcttgt       720
gacaaaactc acacatgccc accgtgccca gcacctgaac tcctgggggg accgtcagtc      780
ttcctcttcc ccccaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc cccatcgaga aaaccatctc caaagccaaa     1080
gggcagcccc gagaaccaca ggtgtacacc ctgcccccat cccgggatga gctgaccaag     1140
aaccaggtca gcctgacctg cctggtcaaa ggcttctatc ccagcgacat cgccgtggag     1200
tgggagagca atgggcagcc ggagaacaac tacaagacca cgcctcccgt gctggactcc     1260
gacggctcct tcttcctcta cagcaagctc accgtggaca agagcaggtg gcagcagggg     1320
aacgtcttct catgctccgt gatgcatgag gctctgcaca accactacac gcagaagagc     1380
ctctccctgt ctccgggtaa atga                                            1404
```

<210> SEQ ID NO 163
<211> LENGTH: 448
<212> TYPE: PRT
<213> ORGANISM: Artificial Sequence
<220> FEATURE:
<223> OTHER INFORMATION: Full Length Humanized Hu2B8 Heavy Chain (Hv1f.1
      Variable Region)

<400> SEQUENCE: 163

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Thr Tyr
            20                  25                  30

Trp Met His Trp Val Gln Gln Ala Pro Gly Lys Gly Leu Glu Trp Met
        35                  40                  45

Gly Glu Ile Asn Pro Thr Asn Gly His Thr Asn Tyr Asn Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Tyr Val Gly Ser Ile Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
                   180                 185                 190
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 164
<211> LENGTH: 412
<212> TYPE: DNA
<213> ORGANISM: Artificial Sequence
<220> FEATURE:
<223> OTHER INFORMATION: Humanized Hu2B8 Hv5a.1 Heavy Chain Variable
      Region

<400> SEQUENCE: 164 atgggtcaa ccgccatcct cgccctcctc ctggctgttc tccaaggagt ctgtgccgaa      60
gtgcagctgg tgcagtctgg agcagaggtg aaaaagcccg gggagtctct gaggatctcc    120
tgtaagggtt ctggatacag ctttaccacc tactggatgc actgggtgcg ccagatgccc    180
gggaaaggcc tggagtggat gggggagatt aatcctacca acggtcatac taactacaat    240
ccgtccttcc aaggccacgt caccatctca gctgacaagt ccatcagcac tgcctacctg    300
cagtggagca gcctgaaggc ctcggacacc gccatgtatt actgtgcgag aaactatgtt    360
ggtagcatct ttgactactg gggccaagga accctggtca ccgtctcctc ag            412

<210> SEQ ID NO 165
<211> LENGTH: 118
<212> TYPE: PRT
```

<213> ORGANISM: Artificial Sequence
<220> FEATURE:
<223> OTHER INFORMATION: Humanized Hu2B8 Hv5a.1 Heavy Chain Variable Region

<400> SEQUENCE: 165

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
            100                 105                 110

Leu Val Thr Val Ser Ser
        115

<210> SEQ ID NO 166
<211> LENGTH: 1404
<212> TYPE: DNA
<213> ORGANISM: Artificial Sequence
<220> FEATURE:
<223> OTHER INFORMATION: Full length Humanized Hu2B8 Heavy Chain (Hv5a.1 Variable Region)

<400> SEQUENCE: 166

```
atggggtcaa ccgccatcct cgccctcctc ctggctgttc tccaaggagt ctgtgccgaa      60
gtgcagctgg tgcagtctgg agcagaggtg aaaaagcccg ggagtctct gaggatctcc      120
tgtaagggtt ctggatacag ctttaccacc tactggatgc actgggtgcg ccagatgccc     180
gggaaaggcc tggagtggat gggggagatt aatcctacca acggtcatac taactacaat    240
ccgtccttcc aaggccacgt caccatctca gctgacaagt ccatcagcac tgcctacctg    300
cagtggagca gcctgaaggc ctcggacacc gccatgtatt actgtgcgag aaactatgtt    360
ggtagcatct ttgactactg gggccaagga accctggtca ccgtctcctc agcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720
gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
```

-continued

```
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                         1404
```

<210> SEQ ID NO 167
<211> LENGTH: 448
<212> TYPE: PRT
<213> ORGANISM: Artificial Sequence
<220> FEATURE:
<223> OTHER INFORMATION: Full length Humanized Hu2B8 Heavy Chain (Hv5a.1 Variable Region)

<400> SEQUENCE: 167

```
Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

```
<210> SEQ ID NO 168
<211> LENGTH: 412
<212> TYPE: DNA
<213> ORGANISM: Artificial Sequence
<220> FEATURE:
<223> OTHER INFORMATION: Humanized Hu2B8 Hv5-51.1 Heavy Chain Variable
      Region

<400> SEQUENCE: 168
atggggtcaa ccgccatcct cgccctcctc ctggctgttc tccaaggagt ctgtgccgaa      60
gtgcagctgg tgcagtctgg agcagaggtg aaaaagcccg ggagtctctc gaagatctcc     120
tgtaagggtt ctggatacag ctttaccacc tactggatgc actgggtgcg ccagatgccc     180
gggaaaggcc tggagtggat gggggagatt aatcctacca cggtcatac taactacaat      240 ccgtccttcc aaggccaggt caccatctca gctgacaagt ccatcagcac tgcctacctg     300
cagtggagca gcctgaaggc ctcggacacc gccatgtatt actgtgcgag aaactatgtt     360
ggtagcatct ttgactactg gggccaagga accctggtca ccgtctcctc ag             412

<210> SEQ ID NO 169
<211> LENGTH: 118
<212> TYPE: PRT
<213> ORGANISM: Artificial Sequence
<220> FEATURE:
<223> OTHER INFORMATION: Humanized Hu2B8 Hv5-51.1 Heavy Chain Variable
      Sequence

<400> SEQUENCE: 169
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys

```
                    85                  90                  95
Ala Arg Asn Tyr Val Gly Ser Ile Phe Asp Tyr Trp Gly Gln Gly Thr
            100                 105                 110
Leu Val Thr Val Ser Ser
        115

<210> SEQ ID NO 170
<211> LENGTH: 1404
<212> TYPE: DNA
<213> ORGANISM: Artificial Sequence
<220> FEATURE:
<223> OTHER INFORMATION: Full Length Humanized Hu2B8 Heavy Chain
      (Hv5-51.1 Variable Region)

<400> SEQUENCE: 170 atgggtcaa ccgccatcct cgccctcctc ctggctgttc tccaaggagt ctgtgccgaa      60
gtgcagctgg tgcagtctgg agcagaggtg aaaaagcccg gggagtctct gaagatctcc    120
tgtaagggtt ctggatacag ctttaccacc tactggatgc actgggtgcg ccagatgccc    180
gggaaaggcc tggagtggat gggggagatt aatcctacca cggtcatac taactacaat     240 ccgtccttcc aaggccaggt caccatctca gctgacaagt ccatcagcac tgcctacctg    300
cagtggagca gcctgaaggc ctcggacacc gccatgtatt actgtgcgag aaactatgtt    360
ggtagcatct ttgactactg gggccaagga accctggtca ccgtctcctc agcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720 gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404

<210> SEQ ID NO 171
<211> LENGTH: 448
<212> TYPE: PRT
<213> ORGANISM: Artificial Sequence
<220> FEATURE:
<223> OTHER INFORMATION: Full Length Humanized Hu2B8 Heavy Chain
      (Hv5-51.1 Variable Region)

<400> SEQUENCE: 171

Glu Val Gln Leu Val Gln Ser Gly Ala Glu Val Lys Lys Pro Gly Glu
```

-continued

```
1               5                   10                  15
Ser Leu Lys Ile Ser Cys Lys Gly Ser Gly Tyr Ser Phe Thr Thr Tyr
                20                  25                  30

Trp Met His Trp Val Arg Gln Met Pro Gly Lys Gly Leu Glu Trp Met
                35                  40                  45

Gly Glu Ile Asn Pro Thr Asn Gly His Thr Asn Tyr Asn Pro Ser Phe
                50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430
```

Leu His Asn His Tyr Thr Gln Lys Ser Leu Ser Leu Ser Pro Gly Lys
        435                 440                 445

<210> SEQ ID NO 172
<211> LENGTH: 388
<212> TYPE: DNA
<213> ORGANISM: Artificial Sequence
<220> FEATURE:
<223> OTHER INFORMATION: Humanized Hu2B8 Kv1-39.1 Kappa Chain Variable
      Region

<400> SEQUENCE: 172
atggacatga gggtccccgc tcagctcctg gggctcctgc tactctggct ccgaggtgcc      60
agatgtgaca tccagatgac ccagtctcca tcctccctgt ctgcatctgt aggagacaga     120
gtcaccatca cttgcaaggc cagtgagaat gtggtttctt atgtatcctg gtatcagcag     180
aaaccaggga agcccctaa gctcctgatc tatggggcat ccaaccggaa cactggggtc      240
ccatcaaggt tcagtggcag tggatctggg acagatttca ctctcaccat cagcagtctg     300
caacctgaag attttgcaac ttactactgt gggcagagtt acaactatcc gtacacgttt     360
ggccagggga ccaagctgga gatcaaac                                        388

<210> SEQ ID NO 173
<211> LENGTH: 107
<212> TYPE: PRT
<213> ORGANISM: Artificial Sequence
<220> FEATURE:
<223> OTHER INFORMATION: Humanized Hu2B8 Kv1-39.1 Kappa Chain Variable
      Region

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Val Ser Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Asn Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Asn Tyr Pro Tyr
                85                  90                  95

Thr Phe Gly Gln Gly Thr Lys Leu Glu Ile Lys
            100                 105

<210> SEQ ID NO 174
<211> LENGTH: 323
<212> TYPE: DNA
<213> ORGANISM: Artificial Sequence
<220> FEATURE:
<223> OTHER INFORMATION: Human Kappa Chain Constant Region (Km(3)
      allotype) (allele 2)

<400> SEQUENCE: 174
gaactgtggc tgcaccatct gtcttcatct tcccgccatc tgatgagcag ttgaaatctg      60
gaactgcctc tgttgtgtgc ctgctgaata acttctatcc cagagaggcc aaagtacagt     120
ggaaggtgga taacgccctc caatcgggta actcccagga gagtgtcaca gagcaggaca     180
gcaaggacag cacctacagc ctcagcagca ccctgacgct gagcaaagca gactacgaga     240

```
aacacaaagt ctacgcctgc gaagtcaccc atcagggcct gagctcgccc gtcacaaaga    300
gcttcaacag gggagagtgt tga                                            323
```

<210> SEQ ID NO 175
<211> LENGTH: 107
<212> TYPE: PRT
<213> ORGANISM: Artificial Sequence
<220> FEATURE:
<223> OTHER INFORMATION: Human Kappa Chain Constant Region (Km(3) allotype) (allele 2)

<400> SEQUENCE: 175

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 176
<211> LENGTH: 711
<212> TYPE: DNA
<213> ORGANISM: Artificial Sequence
<220> FEATURE:
<223> OTHER INFORMATION: Full Length Humanized Hu2B8 Light Chain (Kv-39.1 Variable Region)

<400> SEQUENCE: 176

```
atggacatga gggtccccgc tcagctcctg gggctcctgc tactctggct ccgaggtgcc     60
agatgtgaca tccagatgac ccagtctcca tcctccctgt ctgcatctgt aggagacaga   120
gtcaccatca cttgcaaggc cagtgagaat gtggtttctt atgtatcctg gtatcagcag   180
aaaccaggga agcccctaa gctcctgatc tatggggcat ccaaccggaa cactggggtc    240
ccatcaaggt tcagtggcag tggatctggg acagatttca ctctcaccat cagcagtctg   300
caacctgaag attttgcaac ttactactgt gggcagagtt acaactatcc gtacacgttt   360
ggccagggga ccaagctgga gatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata cgccctcca atcgggtaac    540 tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgttg a            711
```

<210> SEQ ID NO 177
<211> LENGTH: 214
<212> TYPE: PRT
<213> ORGANISM: Artificial Sequence
<220> FEATURE:
<223> OTHER INFORMATION: Full Length Humanized Hu2B8 Light Chain (Kv-39.1 Variable Region)

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Val Ser Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Asn Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 178
<211> LENGTH: 382
<212> TYPE: DNA
<213> ORGANISM: Artificial Sequence
<220> FEATURE:
<223> OTHER INFORMATION: Humanized Hu2B8 Kv3-15.1 Light Chain Variable
      Region

<400> SEQUENCE: 178
atggaagccc cagcgcagct tctcttcctc ctgctactct ggctcccaga taccactgga      60
gaaatagtga tgacgcagtc tccagccacc ctgtctgtgt ctccagggga aagagccacc     120
ctctcctgca aggccagtga gaatgtggtt tcttatgtat cctggtacca gcagaaacct     180
ggccaggctc ccaggctcct catctatggg gcatccaacc ggaacactgg tatcccagcc     240
aggttcagtg gcagtgggtc tgggacagag ttcactctca ccatcagcag cctgcagtct     300
gaagattttg cagtttatta ctgtgggcag agttacaact atccgtacac gtttggccag     360
gggaccaagc tggagatcaa ac                                              382

<210> SEQ ID NO 179
<211> LENGTH: 107
<212> TYPE: PRT
<213> ORGANISM: Artificial Sequence
<220> FEATURE:
<223> OTHER INFORMATION: Humanized Hu2B8 Kv3-15.1 Light Chain Variable
      Region

<400> SEQUENCE: 179

Glu Ile Val Met Thr Gln Ser Pro Ala Thr Leu Ser Val Ser Pro Gly
1               5                   10                  15

Glu Arg Ala Thr Leu Ser Cys Lys Ala Ser Glu Asn Val Val Ser Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Asn Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gly Gln Ser Tyr Asn Tyr Pro Tyr
                85                  90                  95

Thr Phe Gly Gln Gly Thr Lys Leu Glu Ile Lys
            100                 105

<210> SEQ ID NO 180
<211> LENGTH: 705
<212> TYPE: DNA
<213> ORGANISM: Artificial Sequence
<220> FEATURE:
<223> OTHER INFORMATION: Full Length Humanized Hu2B8 Light Chain
      (Kv3-15.1 Variable Region)

<400> SEQUENCE: 180

```
atggaagccc cagcgcagct tctcttcctc ctgctactct ggctcccaga taccactgga      60
gaaatagtga tgacgcagtc tccagccacc ctgtctgtgt ctccagggga agagccacc     120
ctctcctgca aggccagtga aatgtggtt tcttatgtat cctggtacca gcagaaacct     180
ggccaggctc ccaggctcct catctatggg gcatccaacc ggaacactgg tatcccagcc     240
aggttcagtg gcagtgggtc tgggacagag ttcactctca ccatcagcag cctgcagtct     300
gaagattttg cagtttatta ctgtgggcag agttacaact atccgtacac gtttggccag     360
gggaccaagc tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttga                    705
```

<210> SEQ ID NO 181
<211> LENGTH: 214
<212> TYPE: PRT
<213> ORGANISM: Artificial Sequence
<220> FEATURE:
<223> OTHER INFORMATION: Full Length Humanized Hu2B8 Light Chain
      (Kv3-15.1 Variable Region)

<400> SEQUENCE: 181

Glu Ile Val Met Thr Gln Ser Pro Ala Thr Leu Ser Val Ser Pro Gly
1               5                   10                  15

Glu Arg Ala Thr Leu Ser Cys Lys Ala Ser Glu Asn Val Val Ser Tyr
            20                  25                  30

Val Ser Trp Tyr Gln Gln Lys Pro Gly Gln Ala Pro Arg Leu Leu Ile
        35                  40                  45

```
Tyr Gly Ala Ser Asn Arg Asn Thr Gly Ile Pro Ala Arg Phe Ser Gly
        50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gly Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 182
<211> LENGTH: 412
<212> TYPE: DNA
<213> ORGANISM: Artificial Sequence
<220> FEATURE:
<223> OTHER INFORMATION: Humanized LR2B8HC Heavy Chain Variable Region

<400> SEQUENCE: 182

```
atgggctggt catatattat tctctttctt gttgctaccg ctaccgatgt gcactctcaa      60
gtccaactcg tacaaccagg cgctgaagtc gtaaaacccg gaacatctgt taaactctca     120
tgcaaagcct caggatacac tttcacaact tactggatgc attgggtcaa tcaagccccc     180
ggacaaggcc tcgaatggat tggcgaaatt aacccaacta acggacatac taattataat     240
gaaaaattta aggcaaagc tacactcacc gtcgataaat caacctctac agcttatatg     300
gaactttcat ccctgagatc agaagataca gccgtctact attgcgccag aaactacgta     360
ggatcaatat tcgattactg gggtcaaggc actctcctca cagtcagctc ag             412
```

<210> SEQ ID NO 183
<211> LENGTH: 118
<212> TYPE: PRT
<213> ORGANISM: Artificial Sequence
<220> FEATURE:
<223> OTHER INFORMATION: Humanized LR2B8HC Heavy Chain Variable Region

<400> SEQUENCE: 183

```
Gln Val Gln Leu Val Gln Pro Gly Ala Glu Val Val Lys Pro Gly Thr
 1               5                  10                  15

Ser Val Lys Leu Ser Cys Lys Ala Ser Gly Tyr Thr Phe Thr Thr Tyr
             20                  25                  30

Trp Met His Trp Val Asn Gln Ala Pro Gly Gln Gly Leu Glu Trp Ile
         35                  40                  45

Gly Glu Ile Asn Pro Thr Asn Gly His Thr Asn Tyr Asn Glu Lys Phe
     50                  55                  60
```

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser
        115

<210> SEQ ID NO 184
<211> LENGTH: 992
<212> TYPE: DNA
<213> ORGANISM: Artificial Sequence
<220> FEATURE:
<223> OTHER INFORMATION: Human IgG1 Heavy Chain Constant Region (G1m(3)
      allotype) (allele 1)

<400> SEQUENCE: 184
ccagcacaaa gggcccatcg gtcttccccc tggcaccctc ctccaagagc acctctgggg      60
gcacagcggc cctgggctgc ctggtcaagg actacttccc cgaaccggtg acggtgtcgt    120
ggaactcagg cgccctgacc agcggcgtgc acaccttccc ggctgtccta cagtcctcag    180
gactctactc cctcagcagc gtggtgaccg tgccctccag cagcttgggc acccagacct    240
acatctgcaa cgtgaatcac aagcccagca acaccaaggt ggacaagaga gttgagccca    300
aatcttgtga caaaactcac acatgtccac cgtgcccagc acctgaactc ctggggggac    360
cgtcagtctt cctcttcccc ccaaaaccca aggacaccct catgatctcc cggacccctg    420
aggtcacatg cgtggtggtg gacgtgagcc acgaagaccc tgaggtcaag ttcaactggt    480
acgtggacgg cgtggaggtg cataatgcca agacaaagcc gcgggaggag cagtacaaca    540
gcacgtaccg tgtggtcagc gtcctcaccg tcctgcacca ggactggctg aatggcaagg    600
agtacaagtg caaggtctcc aacaaagccc tcccagcccc catcgagaaa accatctcca    660
aagccaaagg gcagccccga gaaccacagg tgtacaccct gcccccatcc cgggaggaga    720
tgaccaagaa ccaggtcagc ctgacctgcc tggtcaaagg cttctatccc agcgacatcg    780
ccgtggagtg ggagagcaat gggcagccgg agaacaacta caagaccacg cctcccgtgc    840
tggactccga cggctccttc ttcctctata gcaagctcac cgtggacaag agcaggtggc    900
agcaggggaa cgtcttctca tgctccgtga tgcatgaggc tctgcacaac cactacacgc    960
agaagagcct ctccctgtcc ccgggtaaat ga                                  992

<210> SEQ ID NO 185
<211> LENGTH: 330
<212> TYPE: PRT
<213> ORGANISM: Artificial Sequence
<220> FEATURE:
<223> OTHER INFORMATION: Human IgG1 Heavy Chain Constant Region (G1m(3)
      allotype) (allele 1 or 2)

<400> SEQUENCE: 185

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

| | | | | | | | | | | | | | | |
|---|---|---|---|---|---|---|---|---|---|---|---|---|---|---|
|Leu|Ser|Ser|Val|Val|Thr|Val|Pro|Ser|Ser|Leu|Gly|Thr|Gln|Thr|
|65| | | |70| | | |75| | | |80| | |
|Tyr|Ile|Cys|Asn|Val|Asn|His|Lys|Pro|Ser|Asn|Thr|Lys|Val|Asp|Lys|
| | | | |85| | | |90| | | |95| | |
|Arg|Val|Glu|Pro|Lys|Ser|Cys|Asp|Lys|Thr|His|Thr|Cys|Pro|Pro|Cys|
| | | |100| | | | |105| | | | |110| | |
|Pro|Ala|Pro|Glu|Leu|Leu|Gly|Gly|Pro|Ser|Val|Phe|Leu|Phe|Pro|Pro|
| | | |115| | | | |120| | | | |125| | |
|Lys|Pro|Lys|Asp|Thr|Leu|Met|Ile|Ser|Arg|Thr|Pro|Glu|Val|Thr|Cys|
| | | |130| | | | |135| | | | |140| | |
|Val|Val|Val|Asp|Val|Ser|His|Glu|Asp|Pro|Glu|Val|Lys|Phe|Asn|Trp|
|145| | | | |150| | | | |155| | | | |160|
|Tyr|Val|Asp|Gly|Val|Glu|Val|His|Asn|Ala|Lys|Thr|Lys|Pro|Arg|Glu|
| | | | |165| | | | |170| | | | |175| |
|Glu|Gln|Tyr|Asn|Ser|Thr|Tyr|Arg|Val|Val|Ser|Val|Leu|Thr|Val|Leu|
| | | | |180| | | | |185| | | | |190| |
|His|Gln|Asp|Trp|Leu|Asn|Gly|Lys|Glu|Tyr|Lys|Cys|Lys|Val|Ser|Asn|
| | | |195| | | | |200| | | | |205| | |
|Lys|Ala|Leu|Pro|Ala|Pro|Ile|Glu|Lys|Thr|Ile|Ser|Lys|Ala|Lys|Gly|
| | | |210| | | | |215| | | | |220| | |
|Gln|Pro|Arg|Glu|Pro|Gln|Val|Tyr|Thr|Leu|Pro|Pro|Ser|Arg|Glu|Glu|
|225| | | | |230| | | | |235| | | | |240|
|Met|Thr|Lys|Asn|Gln|Val|Ser|Leu|Thr|Cys|Leu|Val|Lys|Gly|Phe|Tyr|
| | | | |245| | | | |250| | | | |255| |
|Pro|Ser|Asp|Ile|Ala|Val|Glu|Trp|Glu|Ser|Asn|Gly|Gln|Pro|Glu|Asn|
| | | |260| | | | |265| | | | |270| | |
|Asn|Tyr|Lys|Thr|Thr|Pro|Pro|Val|Leu|Asp|Ser|Asp|Gly|Ser|Phe|Phe|
| | |275| | | | |280| | | | |285| | | |
|Leu|Tyr|Ser|Lys|Leu|Thr|Val|Asp|Lys|Ser|Arg|Trp|Gln|Gln|Gly|Asn|
| | |290| | | | |295| | | | |300| | | |
|Val|Phe|Ser|Cys|Ser|Val|Met|His|Glu|Ala|Leu|His|Asn|His|Tyr|Thr|
|305| | | | |310| | | | |315| | | | |320|
|Gln|Lys|Ser|Leu|Ser|Leu|Ser|Pro|Gly|Lys| | | | | | |
| | |325| | | | |330| | | | | | | | |

```
<210> SEQ ID NO 186
<211> LENGTH: 1404
<212> TYPE: DNA
<213> ORGANISM: Artificial Sequence
<220> FEATURE:
<223> OTHER INFORMATION: Full Length Humanized LR2B8HC Heavy Chain

<400> SEQUENCE: 186
atgggctggt catatattat tctctttctt gttgctaccg ctaccgatgt gcactctcaa      60
gtccaactcg tacaaccagg cgctgaagtc gtaaaaccgg aacatctgt  taaactctca     120
tgcaaagcct caggatacac tttcacaact tactggatgc attgggtcaa tcaagccccc    180
ggacaaggcc tcgaatggat tggcgaaatt aacccaacta acggacatac taattataat    240
gaaaaattta agggcaaagc tacactcacc gtcgataaat caacctctac agcttatatg    300
gaactttcat ccctgagatc agaagataca gccgtctact attgcgccag aaactacgta    360
ggatcaatat tcgattactg gggtcaaggc actctcctca cagtcagctc agccagcaca    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
```

-continued

```
ggcgccctga ccagcggcgt gcacaccttc ccggctgtcc tacagtcctc aggactctac      600
tccctcagca gcgtggtgac cgtgccctcc agcagcttgg gcacccagac ctacatctgc      660
aacgtgaatc acaagcccag caacaccaag gtggacaaga gagttgagcc caaatcttgt      720
gacaaaactc acacatgtcc accgtgccca gcacctgaac tcctgggggg accgtcagtc      780
ttcctcttcc ccccaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc cccatcgaga aaaccatctc caaagccaaa     1080
gggcagcccc gagaaccaca ggtgtacacc ctgcccccat cccgggagga gatgaccaag     1140
aaccaggtca gcctgacctg cctggtcaaa ggcttctatc ccagcgacat cgccgtggag     1200
tgggagagca atgggcagcc ggagaacaac tacaagacca cgcctcccgt gctggactcc     1260
gacggctcct tcttcctcta tagcaagctc accgtggaca agagcaggtg gcagcagggg     1320
aacgtcttct catgctccgt gatgcatgag gctctgcaca accactacac gcagaagagc     1380
ctctccctgt ccccgggtaa atga                                            1404
```

<210> SEQ ID NO 187
<211> LENGTH: 448
<212> TYPE: PRT
<213> ORGANISM: Artificial Sequence
<220> FEATURE:
<223> OTHER INFORMATION: Full Length Humanized LR2B8HC Heavy Chain

<400> SEQUENCE: 187

```
Gln Val Gln Leu Val Gln Pro Gly Ala Glu Val Val Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Asn Gln Ala Pro Gly Gln Gly Leu Glu Trp Ile
        35                  40                  45

Gly Glu Ile Asn Pro Thr Asn Gly His Thr Asn Tyr Asn Glu Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

| | | | | | | | | | | | |
|---|---|---|---|---|---|---|---|---|---|---|---|
|Asn|Thr|Lys|Val|Asp|Lys|Arg|Val|Glu|Pro|Lys|Ser|Cys|Asp|Lys|Thr|
| |210| | | |215| | | |220| | |

Asn Thr Lys Val Asp Lys Arg Val Glu Pro Lys Ser Cys Asp Lys Thr
    210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
            245             250             255

Thr Pro Glu Val Thr Cys Val Val Asp Val Ser His Glu Asp Pro
        260             265             270

Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
        340             345             350

Pro Pro Ser Arg Glu Glu Met Thr Lys Asn Gln Val Ser Leu Thr Cys
        355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
        420             425             430

Leu His Asn His Tyr Thr Gln Lys Ser Leu Ser Leu Ser Pro Gly Lys
        435             440             445

<210> SEQ ID NO 188
<211> LENGTH: 412
<212> TYPE: DNA
<213> ORGANISM: Artificial Sequence
<220> FEATURE:
<223> OTHER INFORMATION: Humanized LRMR2B8HC Heavy Chain Variable Region

<400> SEQUENCE: 188
atgggttggt catatattat actctttctc gtagccaccg ccaccgacgt acactctcag     60
gttcaactcg tacaacccgg cgccgaagtc aagaaaccag gaacatcagt caaactctca    120
tgtaaagcaa gcggatacac ctttactact tattggatgc attgggtaag acaagccccc    180
ggacaaggac tcgaatggat aggcgaaata atcccacta atggacatac aaattataat    240 caaaatttc aaggacgcgc tacactcacc gtcgataaat caacctcaac cgcatacatg    300
gaactcagct ccctccgatc cgaagacact gccgtttatt attgtgccag aaactatgta    360
ggatctattt tcgattactg gggacaagga acacttctca ccgtaagctc ag            412

<210> SEQ ID NO 189
<211> LENGTH: 118
<212> TYPE: PRT
<213> ORGANISM: Artificial Sequence
<220> FEATURE:
<223> OTHER INFORMATION: Humanized LRMR2B8HC Heavy Chain Variable Region

<400> SEQUENCE: 189

```
Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly His Thr Asn Tyr Asn Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
                100                 105                 110

Leu Leu Thr Val Ser Ser
            115
```

<210> SEQ ID NO 190
<211> LENGTH: 1404
<212> TYPE: DNA
<213> ORGANISM: Artificial Sequence
<220> FEATURE:
<223> OTHER INFORMATION: Full Length Humanized LRMR2B8HC Heavy Chain

<400> SEQUENCE: 190

```
atgggttggt catatattat actctttctc gtagccaccg ccaccgacgt acactctcag     60
gttcaactcg tacaacccgg cgccgaagtc aagaaaccag gaacatcagt caaactctca    120
tgtaaagcaa gcggatacac ctttactact tattggatgc attgggtaag acaagccccc    180
ggacaaggac tcgaatggat aggcgaaata atcccacta atggacatac aaattataat    240
caaaaatttc aaggacgcgc tacactcacc gtcgataaat caacctcaac cgcatacatg    300
gaactcagct ccctccgatc cgaagacact gccgtttatt attgtgccag aaactatgta    360
ggatctattt tcgattactg gggacaagga acacttctca ccgtaagctc agccagcaca    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgtcc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca gagcaggtg gcagcagggg   1320
```
aacgtcttct catgctccgt gatgcatgag gctctgcaca accactacac gcagaagagc    1380 ctctcccctgt ccccgggtaa atga                                          1404

<210> SEQ ID NO 191
<211> LENGTH: 448
<212> TYPE: PRT
<213> ORGANISM: Artificial Sequence
<220> FEATURE:
<223> OTHER INFORMATION: Full Length Humanized LRMR2B8HC Heavy Chain

<400> SEQUENCE: 191

Gln Val Gln Leu Val Gln Pro Gly Ala Glu Val Lys Lys Pro Gly Thr
1               5                   10                  15

Ser Val Lys Leu Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly His Thr Asn Tyr Asn Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Val Gly Ser Ile Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 192
<211> LENGTH: 360
<212> TYPE: DNA
<213> ORGANISM: Artificial Sequence
<220> FEATURE:
<223> OTHER INFORMATION: Humanized LR2B8LC Light Chain Variable Region

<400> SEQUENCE: 192
atggaaagtc agaccttgt attcatctct attcttcttt ggttgtatgg agcagacggc    60
gacattgtga tgacccaatc ccccgatagt atggccatga gtgtaggaga aagagtcacc   120
cttaattgca aagcctccga aaatgtcgtt tcatatgtgt cttggtatca acaaaaaccc   180
ggccaatcac ccaaacttct catatacggc gcttcaaaca gaaacacagg cgttcccgac   240
agatttagtg gatccggatc agctacagat ttcacccta ccatcagttc agttcaagca   300
gaagacgttg cagactatca ttgcggacaa tcttataact cccttacac attcggacaa   360

<210> SEQ ID NO 193
<211> LENGTH: 107
<212> TYPE: PRT
<213> ORGANISM: Artificial Sequence
<220> FEATURE:
<223> OTHER INFORMATION: Humanized LR2B8LC Light Chain Variable Region

<400> SEQUENCE: 193

Asp Ile Val Met Thr Gln Ser Pro Asp Ser Met Ala Met Ser Val Gly
1               5                   10                  15

Glu Arg Val Thr Leu Asn Cys Lys Ala Ser Glu Asn Val Val Ser Tyr
            20                  25                  30

Val Ser Trp Tyr Gln Gln Lys Pro Gly Gln Ser Pro Lys Leu Leu Ile
        35                  40                  45

Tyr Gly Ala Ser Asn Arg Asn Thr Gly Val Pro Asp Arg Phe Ser Gly
    50                  55                  60

Ser Gly Ser Ala Thr Asp Phe Thr Leu Thr Ile Ser Ser Val Gln Ala
65                  70                  75                  80

Glu Asp Val Ala Asp Tyr His Cys Gly Gln Ser Tyr Asn Tyr Pro Tyr
                85                  90                  95

Thr Phe Gly Gln Gly Thr Lys Leu Glu Ile Lys
            100                 105

<210> SEQ ID NO 194
<211> LENGTH: 323
<212> TYPE: DNA
<213> ORGANISM: Artificial Sequence
<220> FEATURE:
<223> OTHER INFORMATION: Human Kappa Chain Constant Region (Km(3)
``` allotype) (allele 1)

<400> SEQUENCE: 194

```
gtacggtggc tgcaccatct gtcttcatct tcccgccatc tgatgagcag ttgaaatctg    60
gaactgcctc tgttgtgtgc ctgctgaata acttctatcc cagagaggcc aaagtacagt   120
ggaaggtgga taacgccctc caatcgggta actcccagga gagtgtcaca gagcaggaca   180
gcaaggacag cacctacagc ctcagcagca ccctgacgct gagcaaagca gactacgaga   240
aacacaaagt ctacgcctgc gaagtcaccc atcagggcct gagctcgccc gtcacaaaga   300
gcttcaacag gggagagtgt tag                                           323
```

<210> SEQ ID NO 195
<211> LENGTH: 107
<212> TYPE: PRT
<213> ORGANISM: Artificial Sequence
<220> FEATURE:
<223> OTHER INFORMATION: Human Kappa Chain Constant Region (Km(3) allotype) (allele 1)

<400> SEQUENCE: 195

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 196
<211> LENGTH: 705
<212> TYPE: DNA
<213> ORGANISM: Artificial Sequence
<220> FEATURE:
<223> OTHER INFORMATION: Full Length Humanized LR2B8LC Light Chain

<400> SEQUENCE: 196

```
atggaaagtc agacccttgt attcatctct attcttcttt ggttgtatgg agcagacggc    60
gacattgtga tgacccaatc ccccgatagt atggccatga gtgtaggaga aagagtcacc   120
cttaattgca aagcctccga aaatgtcgtt tcatatgtgt cttggtatca acaaaaaccc   180
ggccaatcac ccaaacttct catatacggc gcttcaaaca gaaacacagg cgttcccgac   240
agatttagtg gatccggatc agctacagat ttcacccctta ccatcagttc agttcaagca   300
gaagacgttg cagactatca ttgcggacaa tcttataact acccttacac attcggacaa   360
ggaaccaaac tcgaaattaa acgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag cacccctgacg   600
ctgagcaaag cagactacga gaaacacaaa gtctacgcct gcgaagtcac ccatcagggc   660
```
ctgagctcgc cgtcacaaa gagcttcaac aggggagagt gttag                      705

<210> SEQ ID NO 197
<211> LENGTH: 214
<212> TYPE: PRT
<213> ORGANISM: Artificial Sequence
<220> FEATURE:
<223> OTHER INFORMATION: Full Length Humanized LR2B8LC Light Chain

<400> SEQUENCE: 197

Asp Ile Val Met Thr Gln Ser Pro Asp Ser Met Ala Met Ser Val Gly
1               5                   10                  15

Glu Arg Val Thr Leu Asn Cys Lys Ala Ser Glu Asn Val Val Ser Tyr
            20                  25                  30

Val Ser Trp Tyr Gln Gln Lys Pro Gly Gln Ser Pro Lys Leu Leu Ile
        35                  40                  45

Tyr Gly Ala Ser Asn Arg Asn Thr Gly Val Pro Asp Arg Phe Ser Gly
    50                  55                  60

Ser Gly Ser Ala Thr Asp Phe Thr Leu Thr Ile Ser Ser Val Gln Ala
65                  70                  75                  80

Glu Asp Val Ala Asp Tyr His Cys Gly Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 198
<211> LENGTH: 382
<212> TYPE: DNA
<213> ORGANISM: Artificial Sequence
<220> FEATURE:
<223> OTHER INFORMATION: Humanized LRMR2B8LC Light Chain Variable Region

<400> SEQUENCE: 198
atggaatccc aaaccttgt tttcatctct atccttctct ggctttatgg cgccgacgga      60
gacatcgtaa tgacacaatc ccctgactct cttgctatga gcttgggcga acgagtaaca    120
cttaactgca aagcatccga aaatgtcgta tcttacgtat cctggtatca gcaaaaacct    180
ggtcaaagtc ctaaacttct tatatatggt gcaagtaatc gtgaaagtgg cgtcccagac    240
agatttagcg gttcaggttc agcaactgac tttacactta caatttctag cgttcaggcc    300
gaagacgttg cagactatca ttgtggacaa tcttataact atccttatac tttcggacaa    360
ggcactaaac ttgaaattaa ac                                             382

<210> SEQ ID NO 199
<211> LENGTH: 107
<212> TYPE: PRT
<213> ORGANISM: Artificial Sequence
<220> FEATURE:
<223> OTHER INFORMATION: Humanized LRMR2B8LC Light Chain Variable Region

<400> SEQUENCE: 199

```
Asp Ile Val Met Thr Gln Ser Pro Asp Ser Leu Ala Met Ser Leu Gly
 1               5                  10                  15

Glu Arg Val Thr Leu Asn Cys Lys Ala Ser Glu Asn Val Val Ser Tyr
            20                  25                  30

Val Ser Trp Tyr Gln Gln Lys Pro Gly Gln Ser Pro Lys Leu Leu Ile
        35                  40                  45

Tyr Gly Ala Ser Asn Arg Glu Ser Gly Val Pro Asp Arg Phe Ser Gly
 50                  55                  60

Ser Gly Ser Ala Thr Asp Phe Thr Leu Thr Ile Ser Ser Val Gln Ala
 65                  70                  75                  80

Glu Asp Val Ala Asp Tyr His Cys Gly Gln Ser Tyr Asn Tyr Pro Tyr
                85                  90                  95

Thr Phe Gly Gln Gly Thr Lys Leu Glu Ile Lys
            100                 105
```

<210> SEQ ID NO 200
<211> LENGTH: 705
<212> TYPE: DNA
<213> ORGANISM: Artificial Sequence
<220> FEATURE:
<223> OTHER INFORMATION: Full Length Humanized LRMR2B8LC Light Chain

<400> SEQUENCE: 200

```
atggaatccc aaaccttgt tttcatctct atccttctct ggctttatgg cgccgacgga      60
gacatcgtaa tgacacaatc ccctgactct cttgctatga gcttgggcga acgagtaaca    120
cttaactgca aagcatccga aaatgtcgta tcttacgtat cctggtatca gcaaaaacct    180
ggtcaaagtc ctaaacttct tatatatggt gcaagtaatc gtgaaagtgg cgtcccagac    240
agatttagcg gttcaggttc agcaactgac tttacactta caattctag cgttcaggcc     300
gaagacgttg cagactatca ttgtggacaa tcttataact atccttatac tttcggacaa    360
ggcactaaac ttgaaattaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc     660
ctgagctcgc ccgtcacaaa gagcttcaac aggggagagt gttag                    705
```

<210> SEQ ID NO 201
<211> LENGTH: 214
<212> TYPE: PRT
<213> ORGANISM: Artificial Sequence
<220> FEATURE:
<223> OTHER INFORMATION: Full Length Humanized LRMR2B8LC Light Chain

<400> SEQUENCE: 201

```
Asp Ile Val Met Thr Gln Ser Pro Asp Ser Leu Ala Met Ser Leu Gly
 1               5                  10                  15

Glu Arg Val Thr Leu Asn Cys Lys Ala Ser Glu Asn Val Val Ser Tyr
```

-continued

```
                    20                  25                  30
Val Ser Trp Tyr Gln Gln Lys Pro Gly Gln Ser Pro Lys Leu Leu Ile
         35                  40                  45
Tyr Gly Ala Ser Asn Arg Glu Ser Gly Val Pro Asp Arg Phe Ser Gly
     50                  55                  60
Ser Gly Ser Ala Thr Asp Phe Thr Leu Thr Ile Ser Ser Val Gln Ala
 65                  70                  75                  80
Glu Asp Val Ala Asp Tyr His Cys Gly Gln Ser Tyr Asn Tyr Pro Tyr
                 85                  90                  95
Thr Phe Gly Gln Gly Thr Lys Leu Glu Ile Lys Arg Thr Val Ala Ala
             100                 105                 110
Pro Ser Val Phe Ile Phe Pro Pro Ser Asp Glu Gln Leu Lys Ser Gly
         115                 120                 125
Thr Ala Ser Val Val Cys Leu Leu Asn Asn Phe Tyr Pro Arg Glu Ala
     130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 202
<211> LENGTH: 17
<212> TYPE: PRT
<213> ORGANISM: Artificial Sequence
<220> FEATURE:
<223> OTHER INFORMATION: Heavy Chain CDR2 sequence of Humanized Hu2B8
      Hv1f.1 antibody

<400> SEQUENCE: 202

Glu Ile Asn Pro Thr Asn Gly His Thr Asn Tyr Asn Glu Lys Phe Gln
 1               5                  10                  15
Gly

<210> SEQ ID NO 203
<211> LENGTH: 17
<212> TYPE: PRT
<213> ORGANISM: Artificial Sequence
<220> FEATURE:
<223> OTHER INFORMATION: Heavy Chain CDR2 sequence of humanized Hu2B8
      Hv5a.1 antibody

<400> SEQUENCE: 203

Glu Ile Asn Pro Thr Asn Gly His Thr Asn Tyr Asn Pro Ser Phe Gln
 1               5                  10                  15
Gly

<210> SEQ ID NO 204
<211> LENGTH: 17
<212> TYPE: PRT
<213> ORGANISM: Artificial Sequence
<220> FEATURE:
<223> OTHER INFORMATION: Heavy Chain CDR2 sequence of humanized LR2B8HC
      antibody
```

```
<400> SEQUENCE: 204

Glu Ile Asn Pro Thr Asn Gly His Thr Asn Tyr Asn Glu Lys Phe Lys
1               5                   10                  15

Gly

<210> SEQ ID NO 205
<211> LENGTH: 17
<212> TYPE: PRT
<213> ORGANISM: Artificial Sequence
<220> FEATURE:
<223> OTHER INFORMATION: Heavy Chain CDR2 sequence of humanized
      LRMR2B8HC antibody

<400> SEQUENCE: 205

Glu Ile Asn Pro Thr Asn Gly His Thr Asn Tyr Asn Gln Lys Phe Gln
1               5                   10                  15

Gly

<210> SEQ ID NO 206
<211> LENGTH: 7
<212> TYPE: PRT
<213> ORGANISM: Artificial Sequence
<220> FEATURE:
<223> OTHER INFORMATION: Light Chain CDR2 sequence of humanized
      LRMR2B8LC antibody

<400> SEQUENCE: 206

Gly Ala Ser Asn Arg Glu Ser
1               5

<210> SEQ ID NO 207
<211> LENGTH: 992
<212> TYPE: DNA
<213> ORGANISM: Artificial Sequence
<220> FEATURE:
<223> OTHER INFORMATION: Human IgG1 Heavy Chain Constant Region (G1m(3)
      allotype) (allele 2)

<400> SEQUENCE: 207
cctccaccaa gggcccatcg gtcttccccc tggcaccctc ctccaagagc acctctgggg      60
gcacagcggc cctgggctgc ctggtcaagg actacttccc cgaaccggtg acggtgtcgt     120
ggaactcagg cgccctgacc agcggcgtgc acaccttccc ggctgtccta cagtcctcag     180
gactctactc cctcagcagc gtggtgaccg tgccctccag cagcttgggc acccagacct     240
acatctgcaa cgtgaatcac aagcccagca acaccaaggt ggacaagaga gttgagccca     300
aatcttgtga caaaactcac acatgcccac cgtgcccagc acctgaactc ctggggggac     360
cgtcagtctt cctcttcccc ccaaaaccca aggacaccct catgatctcc cggacccctg     420
aggtcacatg cgtggtggtg gacgtgagcc acgaagaccc tgaggtcaag ttcaactggt     480
acgtggacgg cgtggaggtg cataatgcca agacaaagcc gcgggaggag cagtacaaca     540
gcacgtaccg tgtggtcagc gtcctcaccg tcctgcacca ggactggctg aatggcaagg     600
agtacaagtg caaggtctcc aacaaagccc tcccagcccc catcgagaag accatctcca     660
aagccaaagg gcagccccga gaaccacagg tgtacaccct gcccccatcc cgggaggaga     720
tgaccaagaa ccaggtcagc ctgacctgcc tggtcaaagg cttctatccc agcgacatcg     780
ccgtggagtg ggagagcaat gggcagccgg agaacaacta caagaccacg cctcccgtgc     840
tggactccga cggctccttc ttcctctaca gcaagctcac cgtggacaag agcaggtggc     900
agcaggggaa cgtcttctca tgctccgtga tgcatgaggc tctgcacaac cactacacgc     960
```
agaagagcct ctccctgtct ccgggtaaat ga              992

<210> SEQ ID NO 208
<211> LENGTH: 330
<212> TYPE: PRT
<213> ORGANISM: Artificial Sequence
<220> FEATURE:
<223> OTHER INFORMATION: Human IgG1 Heavy Chain Constant Region (G1m(3) allotype) (allele 1 or 2)

<400> SEQUENCE: 208

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 209

<211> LENGTH: 1404
<212> TYPE: DNA
<213> ORGANISM: Artificial Sequence
<220> FEATURE:
<223> OTHER INFORMATION: Full Length Humanized Hu2B8 Heavy Chain
      (Hv5-51.1 Variable region)

<400> SEQUENCE: 209

| | | | | | |
|---|---|---|---|---|---|
| atggggtcaa | ccgccatcct | cgccctcctc | ctggctgttc | tccaaggagt | ctgtgccgaa | 60 |
| gtgcagctgg | tgcagtctgg | agcagaggtg | aaaaagcccg | gggagtctct | gaagatctcc | 120 |
| tgtaagggtt | ctggatacag | ctttaccacc | tactggatgc | actgggtgcg | ccagatgccc | 180 |
| gggaaaggcc | tggagtggat | gggggagatt | aatcctacca | acggtcatac | taactacaat | 240 |
| ccgtccttcc | aaggccaggt | caccatctca | gctgacaagt | ccatcagcac | tgcctacctg | 300 |
| cagtggagca | gcctgaaggc | ctcggacacc | gccatgtatt | actgtgcgag | aaactatgtt | 360 |
| ggtagcatct | ttgactactg | gggccaagga | accctggtca | ccgtctcctc | agcctccacc | 420 |
| aagggcccat | cggtcttccc | cctggcaccc | tcctccaaga | gcacctctgg | gggcacagcg | 480 |
| gccctgggct | gcctggtcaa | ggactacttc | cccgaaccgg | tgacggtgtc | gtggaactca | 540 |
| ggcgccctga | ccagcggcgt | gcacaccttc | ccggctgtcc | tacagtcctc | aggactctac | 600 |
| tccctcagca | gcgtggtgac | cgtgccctcc | agcagcttgg | gcacccagac | ctacatctgc | 660 |
| aacgtgaatc | acaagcccag | caacaccaag | gtggacaaga | gagttgagcc | caaatcttgt | 720 |
| gacaaaactc | acacatgccc | accgtgccca | gcacctgaac | tcctgggggg | accgtcagtc | 780 |
| ttcctcttcc | ccccaaaacc | caaggacacc | ctcatgatct | cccggacccc | tgaggtcaca | 840 |
| tgcgtggtgg | tggacgtgag | ccacgaagac | cctgaggtca | agttcaactg | gtacgtggac | 900 |
| ggcgtggagg | tgcataatgc | caagacaaag | ccgcgggagg | agcagtacaa | cagcacgtac | 960 |
| cgtgtggtca | gcgtcctcac | cgtcctgcac | caggactggc | tgaatggcaa | ggagtacaag | 1020 |
| tgcaaggtct | ccaacaaagc | cctcccagcc | cccatcgaga | agaccatctc | caaagccaaa | 1080 |
| gggcagcccc | gagaaccaca | ggtgtacacc | ctgcccccat | cccgggagga | gatgaccaag | 1140 |
| aaccaggtca | gcctgacctg | cctggtcaaa | ggcttctatc | ccagcgacat | cgccgtggag | 1200 |
| tgggagagca | atgggcagcc | ggagaacaac | tacaagacca | cgcctcccgt | gctggactcc | 1260 |
| gacggctcct | tcttcctcta | cagcaagctc | accgtggaca | agagcaggtg | gcagcagggg | 1320 |
| aacgtcttct | catgctccgt | gatgcatgag | gctctgcaca | accactacac | gcagaagagc | 1380 |
| ctctccctgt | ctccgggtaa | atga | | | | 1404 |

<210> SEQ ID NO 210
<211> LENGTH: 448
<212> TYPE: PRT
<213> ORGANISM: Artificial Sequence
<220> FEATURE:
<223> OTHER INFORMATION: Full Length Humanized Hu2B8 Heavy Chain
      (Hv5-51.1 Variable region)

<400> SEQUENCE: 210

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Met His Trp Val Arg Gln Met Pro Gly Lys Gly Leu Glu Trp Met
        35                  40                  45

Gly Glu Ile Asn Pro Thr Asn Gly His Thr Asn Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Tyr Val Gly Ser Ile Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 211
<211> LENGTH: 2209
<212> TYPE: DNA
<213> ORGANISM: Artificial Sequence
<220> FEATURE:

<223> OTHER INFORMATION: Synthetic HGF mhm (V495-L585)

<400> SEQUENCE: 211

```
atgatgtggg ggaccaaact tctgccggtc ctgttgctgc agcatgtcct cctgcacctc      60
ctcctgcttc atgtcgccat cccctatgca gaaggacaga agaaaagaag aaatacactt     120
catgaattta aaaagtcagc aaaaactact cttaccaagg aagacccatt actgaagatt     180
aaaaccaaaa aagtgaactc tgcagatgag tgtgccaaca ggtgtatcag gaacaggggc     240
tttacgttca gcttgcaaggc cttcgttttt gataagtcaa gaaaacgatg ctactggtat     300
cctttcaata gtatgtcaag tggagtgaaa aaagggtttg ccatgaatt tgacctctat     360
gaaaacaaag actatattag aaactgcatc attggtaaag gaggcagcta taagggacg     420
gtatccatca ctaagagtgg catcaaatgc agccttgga attccatgat cccccatgaa     480
cacagctttt tgccttcgag ctatcgcggt aaagacctac aggaaaacta ctgtcgaaat     540
cctcgagggg aagaagggg accctggtgt ttcacaagca atccagaggt acgctacgaa     600
gtctgtgaca ttcctcagtg ttcagaagtt gaatgcatga cctgcaatgg tgaaagctac     660
agaggtccca tggatcacac agaatcaggc aagacttgtc agcgctggga ccagcagaca     720
ccacaccggc acaagttctt gccagaaaga tatcccgaca agggctttga tgataattat     780
tgccgcaatc ctgatggcaa gccgaggcca tggtgctaca ctcttgaccc tgacaccact     840
tgggagtatt gtgcaattaa acgtgcgct cacagtgctg tgaatgagac tgatgtccct     900
atggaaacaa ctgaatgcat tcaaggccaa ggagaaggtt acaggggaac cagcaatacc     960
atttggaatg gaattccctg tcagcgttgg gattcgcagt accctcacaa gcatgatatc    1020
actcccgaga acttcaaatg caaggaccct agagaaaatt attgccgcaa tccagatggg    1080
gctgaatcac catggtgttt taccactgac ccaaacatcc gagttggcta ctgctctcag    1140
attcccaagt gtgacgtgtc aagtggacaa gattgttatc gtggcaatgg aaaaaattac    1200
atgggcaact tatccaaaac aaggtctgga cttacatgtt ccatgtggga caagaatatg    1260
gaggatttac accgtcatat cttctgggag ccagatgcta gcaaattgaa taagaattac    1320
tgccggaatc ctgatgatga tgcccatgga ccttggtgct acacggggaa tcctctatt    1380
ccttgggatt attgccctat ttcccgttgt gaaggagata ctacacctac aattgtcaat    1440
ttggaccatc ctgtaatatc ctgtgccaaa acaaaacaac tgcgggttgt aaatgggatt    1500
ccaacacgaa caaacatagg atggatggtt agtttgagat acagaaataa acatatctgc    1560
ggaggatcat tgataaagga gagttgggtt cttactgcac gacagtgttt cccttctcga    1620
gacttgaaag attatgaagc ttggcttgga attcatgatg tccacggaag aggagatgag    1680
aaatgcaaac aggttctcaa tgtttcccag ctggtatatg gccctgaagg atcagatctg    1740
gttttaatga gcttgctcg acctgcaatc ctggataact ttgtcagtac aattgattta    1800
cctagttatg ttgtacaat ccctgaaaag accacttgca gtatttacgg ctggggctac    1860
actggattga tcaacgcgga tggtttatta cgagtagctc atctgtatat tatgggggaat    1920
gagaaatgca gtcagcacca tcaaggcaag gtgactttga atgagtctga gttatgtgct    1980
ggggctgaaa agattggatc aggaccatgt gagggagatt atggtggccc actcatttgt    2040
gaacaacaca aatgagaat ggttcttggt gtcattgttc ctggtcgtgg atgtgccatc    2100
ccaaatcgtc ctgttatttt tgttcgagta gcatatattg caaaatggat acacaaagta    2160
attttgacat acaagttgtg cggccgccat caccatcacc atcactaag             2209
```

<210> SEQ ID NO 212
<211> LENGTH: 680
<212> TYPE: PRT
<213> ORGANISM: Artificial Sequence
<220> FEATURE:
<223> OTHER INFORMATION: Synthetic HGF mhm495-585 active

<400> SEQUENCE: 212

```
Pro Leu Leu Lys Ile Lys Thr Lys Lys Val Asn Ser Ala Asp Glu Cys
1               5                   10                  15

Ala Asn Arg Cys Ile Arg Asn Arg Gly Phe Thr Phe Thr Cys Lys Ala
            20                  25                  30

Phe Val Phe Asp Lys Ser Arg Lys Arg Cys Tyr Trp Tyr Pro Phe Asn
        35                  40                  45

Ser Met Ser Ser Gly Val Lys Lys Gly Phe Gly His Glu Phe Asp Leu
    50                  55                  60

Tyr Glu Asn Lys Asp Tyr Ile Arg Asn Cys Ile Ile Gly Lys Gly Gly
65                  70                  75                  80

Ser Tyr Lys Gly Thr Val Ser Ile Thr Lys Ser Gly Ile Lys Cys Gln
                85                  90                  95

Pro Trp Asn Ser Met Ile Pro His Glu His Ser Phe Leu Pro Ser Ser
            100                 105                 110

Tyr Arg Gly Lys Asp Leu Gln Glu Asn Tyr Cys Arg Asn Pro Arg Gly
        115                 120                 125

Glu Glu Gly Gly Pro Trp Cys Phe Thr Ser Asn Pro Glu Val Arg Tyr
    130                 135                 140

Glu Val Cys Asp Ile Pro Gln Cys Ser Glu Val Glu Cys Met Thr Cys
145                 150                 155                 160

Asn Gly Glu Ser Tyr Arg Gly Pro Met Asp His Thr Glu Ser Gly Lys
                165                 170                 175

Thr Cys Gln Arg Trp Asp Gln Gln Thr Pro His Arg His Lys Phe Leu
            180                 185                 190

Pro Glu Arg Tyr Pro Asp Lys Gly Phe Asp Asp Asn Tyr Cys Arg Asn
        195                 200                 205

Pro Asp Gly Lys Pro Arg Pro Trp Cys Tyr Thr Leu Asp Pro Asp Thr
    210                 215                 220

Thr Trp Glu Tyr Cys Ala Ile Lys Thr Cys Ala His Ser Ala Val Asn
225                 230                 235                 240

Glu Thr Asp Val Pro Met Glu Thr Thr Glu Cys Ile Gln Gly Gln Gly
                245                 250                 255

Glu Gly Tyr Arg Gly Thr Ser Asn Thr Ile Trp Asn Gly Ile Pro Cys
            260                 265                 270

Gln Arg Trp Asp Ser Gln Tyr Pro His Lys His Asp Ile Thr Pro Glu
        275                 280                 285

Asn Phe Lys Cys Lys Asp Leu Arg Glu Asn Tyr Cys Arg Asn Pro Asp
    290                 295                 300

Gly Ala Glu Ser Pro Trp Cys Phe Thr Thr Asp Pro Asn Ile Arg Val
305                 310                 315                 320

Gly Tyr Cys Ser Gln Ile Pro Lys Cys Asp Val Ser Ser Gly Gln Asp
                325                 330                 335

Cys Tyr Arg Gly Asn Gly Lys Asn Tyr Met Gly Asn Leu Ser Lys Thr
            340                 345                 350

Arg Ser Gly Leu Thr Cys Ser Met Trp Asp Lys Asn Met Glu Asp Leu
        355                 360                 365

His Arg His Ile Phe Trp Glu Pro Asp Ala Ser Lys Leu Asn Lys Asn
```

```
            370            375            380
Tyr Cys Arg Asn Pro Asp Asp Ala His Gly Pro Trp Cys Tyr Thr
385                 390                 395                 400

Gly Asn Pro Leu Ile Pro Trp Asp Tyr Cys Pro Ile Ser Arg Cys Glu
                405                 410                 415

Gly Asp Thr Thr Pro Thr Ile Val Asn Leu Asp His Pro Val Ile Ser
            420                 425                 430

Cys Ala Lys Thr Lys Gln Leu Arg Val Val Asn Gly Ile Pro Thr Arg
            435                 440                 445

Thr Asn Ile Gly Trp Met Val Ser Leu Arg Tyr Arg Asn Lys His Ile
450                 455                 460

Cys Gly Gly Ser Leu Ile Lys Glu Ser Trp Val Leu Thr Ala Arg Gln
465                 470                 475                 480

Cys Phe Pro Ser Arg Asp Leu Lys Asp Tyr Glu Ala Trp Leu Gly Ile
                485                 490                 495

His Asp Val His Gly Arg Gly Asp Glu Lys Cys Lys Gln Val Leu Asn
            500                 505                 510

Val Ser Gln Leu Val Tyr Gly Pro Glu Gly Ser Asp Leu Val Leu Met
            515                 520                 525

Lys Leu Ala Arg Pro Ala Ile Leu Asp Asn Phe Val Ser Thr Ile Asp
530                 535                 540

Leu Pro Ser Tyr Gly Cys Thr Ile Pro Glu Lys Thr Thr Cys Ser Ile
545                 550                 555                 560

Tyr Gly Trp Gly Tyr Thr Gly Leu Ile Asn Ala Asp Gly Leu Leu Arg
                565                 570                 575

Val Ala His Leu Tyr Ile Met Gly Asn Glu Lys Cys Ser Gln His His
            580                 585                 590

Gln Gly Lys Val Thr Leu Asn Glu Ser Glu Leu Cys Ala Gly Ala Glu
            595                 600                 605

Lys Ile Gly Ser Gly Pro Cys Glu Gly Asp Tyr Gly Gly Pro Leu Ile
            610                 615                 620

Cys Glu Gln His Lys Met Arg Met Val Leu Gly Val Ile Val Pro Gly
625                 630                 635                 640

Arg Gly Cys Ala Ile Pro Asn Arg Pro Val Ile Phe Val Arg Val Ala
                645                 650                 655

Tyr Tyr Ala Lys Trp Ile His Lys Val Ile Leu Thr Tyr Lys Leu Cys
                660                 665                 670

Gly Arg His His His His His His
        675                 680

<210> SEQ ID NO 213
<211> LENGTH: 2194
<212> TYPE: DNA
<213> ORGANISM: Artificial Sequence
<220> FEATURE:
<223> OTHER INFORMATION: Synthetic HGF mhm (I499-R556)

<400> SEQUENCE: 213
atgatgtggg ggaccaaact tctgccggtc ctgttgctgc agcatgtcct cctgcacctc      60
ctcctgcttc atgtcgccat ccctatgca gaaggacaga agaaaagaag aaatacactt     120
catgaattta aaaagtcagc aaaaactact cttaccaagg aagacccatt actgaagatt     180
aaaaccaaaa aagtgaactc tgcagatgag tgtgccaaca ggtgtatcag gaacaggggc     240
tttacgttca cttgcaaggc cttcgttttt gataagtcaa gaaaacgatg ctactggtat     300
```

-continued

```
cctttcaata gtatgtcaag tggagtgaaa aaagggtttg gccatgaatt tgacctctat    360
gaaaacaaag actatattag aaactgcatc attggtaaag gaggcagcta taagggacg     420 gtatccatca ctaagagtgg catcaaatgc cagccttgga attccatgat cccccatgaa    480
cacagctatc gcggtaaaga cctacaggaa aactactgtc gaaatcctcg aggggaagaa    540
gggggaccct ggtgtttcac aagcaatcca gaggtacgct acgaagtctg tgacattcct    600
cagtgttcag aagttgaatg catgacctgc aatggtgaaa gctacagagg tcccatggat    660
cacacagaat caggcaagac ttgtcagcgc tgggaccagc agacaccaca ccggcacaag    720
ttcttgccag aaagatatcc cgacaagggc tttgatgata attattgccg caatcctgat    780
ggcaagccga ggccatggtg ctacactctt gaccctgaca ccccttggga gtattgtgca    840
attaaaacgt gcgctcacag tgctgtgaat gagactgatg tccctatgga acaactgaa     900 tgcattcaag gccaaggaga aggttacagg ggaaccagca ataccatttg aatggaatt     960 ccctgtcagc gttgggattc gcagtaccct cacaagcatg atatcactcc cgagaacttc   1020
aaatgcaagg accttagaga aaattattgc cgcaatccag atggggctga atcaccatgg   1080
tgttttacca ctgacccaaa catccgagtt ggctactgct ctcagattcc caagtgtgac   1140
gtgtcaagtg acaagattg ttatcgtggc aatgggaaaa attacatggg caacttatcc    1200
aaaacaaggt ctggacttac atgttccatg tgggacaaga atatgagga tttacaccgt    1260 catatcttct gggagccaga tgctagcaaa ttgaataaga attactgccg gaatcctgat   1320
gatgatgccc atggacctg gtgctacacg gggaatcctc ttattccttg ggattattgc    1380
cctatttccc gttgtgaagg agatactaca cctacaattg tcaatttgga ccatcctgta   1440
atatcctgtg ccaaaacaaa acaactgcgg gttgtaaatg ggattccaac acgaacaaac   1500
ataggatgga tggttagttt gagatacaga aataaacata tctgcggagg atcattgata   1560
aaggagagtt gggttcttac tgcacgacag tgtttccctt ctcgagactt gaaagattat   1620
gaagcttggc ttggaattca tgatgtccac ggaagaggag aggagaaaag aaaacagatt   1680
ctcaatattt cccagctggt tatggccct gaaggatcag atctggtttt actgaagctt    1740
gctcgacctg caatcctgga taactttgtc agtacaattg atttacctag ttatggttgt   1800
acaatccctg aaaagaccac ttgcagtatt tacggctggg gctacactgg attgatcaac   1860
gcggatggtt tattacgagt agctcatctg tatattatgg gaatgagaa atgcagtcag    1920 caccatcaag gcaaggtgac tttgaatgag tctgagttat gtgctggggc tgaaaagatt   1980
ggatcaggac catgtgaggg agattatggt ggcccactca tttgtgaaca acacaaaatg   2040
agaatggttc ttggtgtcat tgttcctggt cgtggatgtg ccatcccaaa tcgtcctggt   2100
atttttgttc gagtagcata ttatgcaaaa tggatacaca agtaatttt gacatacaag    2160 ttgtgcggcc gccatcacca tcaccatcac taag                               2194
```

<210> SEQ ID NO 214
<211> LENGTH: 675
<212> TYPE: PRT
<213> ORGANISM: Artificial Sequence
<220> FEATURE:
<223> OTHER INFORMATION: Synthetic HGF mhm 499-556 active

<400> SEQUENCE: 214

```
Pro Leu Leu Lys Ile Lys Thr Lys Lys Val Asn Ser Ala Asp Glu Cys
1               5                   10                  15

Ala Asn Arg Cys Ile Arg Asn Arg Gly Phe Thr Phe Thr Cys Lys Ala
            20                  25                  30
```

-continued

```
Phe Val Phe Asp Lys Ser Arg Lys Arg Cys Tyr Trp Tyr Pro Phe Asn
         35                  40                  45
Ser Met Ser Ser Gly Val Lys Lys Gly Phe Gly His Glu Phe Asp Leu
         50                  55                  60
Tyr Glu Asn Lys Asp Tyr Ile Arg Asn Cys Ile Ile Gly Lys Gly Gly
 65                  70                  75                  80
Ser Tyr Lys Gly Thr Val Ser Ile Thr Lys Ser Gly Ile Lys Cys Gln
                 85                  90                  95
Pro Trp Asn Ser Met Ile Pro His Glu His Ser Tyr Arg Gly Lys Asp
                100                 105                 110
Leu Gln Glu Asn Tyr Cys Arg Asn Pro Arg Gly Glu Glu Gly Gly Pro
            115                 120                 125
Trp Cys Phe Thr Ser Asn Pro Glu Val Arg Tyr Glu Val Cys Asp Ile
            130                 135                 140
Pro Gln Cys Ser Glu Val Glu Cys Met Thr Cys Asn Gly Glu Ser Tyr
145                 150                 155                 160
Arg Gly Pro Met Asp His Thr Glu Ser Gly Lys Thr Cys Gln Arg Trp
                165                 170                 175
Asp Gln Gln Thr Pro His Arg His Lys Phe Leu Pro Glu Arg Tyr Pro
            180                 185                 190
Asp Lys Gly Phe Asp Asp Asn Tyr Cys Arg Asn Pro Asp Gly Lys Pro
            195                 200                 205
Arg Pro Trp Cys Tyr Thr Leu Asp Pro Asp Thr Pro Trp Glu Tyr Cys
        210                 215                 220
Ala Ile Lys Thr Cys Ala His Ser Ala Val Asn Glu Thr Asp Val Pro
225                 230                 235                 240
Met Glu Thr Thr Glu Cys Ile Gln Gly Gln Gly Glu Gly Tyr Arg Gly
                245                 250                 255
Thr Ser Asn Thr Ile Trp Asn Gly Ile Pro Cys Gln Arg Trp Asp Ser
                260                 265                 270
Gln Tyr Pro His Lys His Asp Ile Thr Pro Glu Asn Phe Lys Cys Lys
            275                 280                 285
Asp Leu Arg Glu Asn Tyr Cys Arg Asn Pro Asp Gly Ala Glu Ser Pro
        290                 295                 300
Trp Cys Phe Thr Thr Asp Pro Asn Ile Arg Val Gly Tyr Cys Ser Gln
305                 310                 315                 320
Ile Pro Lys Cys Asp Val Ser Ser Gly Gln Asp Cys Tyr Arg Gly Asn
                325                 330                 335
Gly Lys Asn Tyr Met Gly Asn Leu Ser Lys Thr Arg Ser Gly Leu Thr
                340                 345                 350
Cys Ser Met Trp Asp Lys Asn Met Glu Asp Leu His Arg His Ile Phe
            355                 360                 365
Trp Glu Pro Asp Ala Ser Lys Leu Asn Lys Asn Tyr Cys Arg Asn Pro
        370                 375                 380
Asp Asp Asp Ala His Gly Pro Trp Cys Tyr Thr Gly Asn Pro Leu Ile
385                 390                 395                 400
Pro Trp Asp Tyr Cys Pro Ile Ser Arg Cys Glu Gly Asp Thr Thr Pro
                405                 410                 415
Thr Ile Val Asn Leu Asp His Pro Val Ile Ser Cys Ala Lys Thr Lys
            420                 425                 430
Gln Leu Arg Val Val Asn Gly Ile Pro Thr Arg Thr Asn Ile Gly Trp
        435                 440                 445
```

```
Met Val Ser Leu Arg Tyr Arg Asn Lys His Ile Cys Gly Gly Ser Leu
    450                 455                 460
Ile Lys Glu Ser Trp Val Leu Thr Ala Arg Gln Cys Phe Pro Ser Arg
465                 470                 475                 480
Asp Leu Lys Asp Tyr Glu Ala Trp Leu Gly Ile His Asp Val His Gly
                485                 490                 495
Arg Gly Glu Glu Lys Arg Lys Gln Ile Leu Asn Ile Ser Gln Leu Val
            500                 505                 510
Tyr Gly Pro Glu Gly Ser Asp Leu Val Leu Lys Leu Ala Arg Pro
        515                 520                 525
Ala Ile Leu Asp Asn Phe Val Ser Thr Ile Asp Leu Pro Ser Tyr Gly
    530                 535                 540
Cys Thr Ile Pro Glu Lys Thr Thr Cys Ser Ile Tyr Gly Trp Gly Tyr
545                 550                 555                 560
Thr Gly Leu Ile Asn Ala Asp Gly Leu Leu Arg Val Ala His Leu Tyr
                565                 570                 575
Ile Met Gly Asn Glu Lys Cys Ser Gln His Gln Gly Lys Val Thr
            580                 585                 590
Leu Asn Glu Ser Glu Leu Cys Ala Gly Ala Lys Ile Gly Ser Gly
        595                 600                 605
Pro Cys Glu Gly Asp Tyr Gly Gly Pro Leu Ile Cys Glu Gln His Lys
    610                 615                 620
Met Arg Met Val Leu Gly Val Ile Val Pro Gly Arg Gly Cys Ala Ile
625                 630                 635                 640
Pro Asn Arg Pro Gly Ile Phe Val Arg Val Ala Tyr Tyr Ala Lys Trp
                645                 650                 655
Ile His Lys Val Ile Leu Thr Tyr Lys Leu Cys Gly Arg His His His
            660                 665                 670
His His His
        675

<210> SEQ ID NO 215
<211> LENGTH: 2194
<212> TYPE: DNA
<213> ORGANISM: Artificial Sequence
<220> FEATURE:
<223> OTHER INFORMATION: Synthetic HGF mhm (W507-L585)

<400> SEQUENCE: 215
atgatgtggg ggaccaaact tctgccggtc ctgttgctgc agcatgtcct cctgcacctc      60
ctcctgcttc atgtcgccat ccctatgca gaaggacaga agaaagaag aaatacactt      120 catgaattta aaagtcagc aaaaactact cttaccaagg aagacccatt actgaagatt      180
aaaaccaaaa aagtgaactc tgcagatgag tgtgccaaca ggtgtatcag gaacaggggc     240
tttacgttca cttgcaaggc cttcgttttt gataagtcaa gaaaacgatg ctactggtat     300
cctttcaata gtatgtcaag tggagtgaaa aaagggtttg gccatgaatt tgacctctat     360
gaaaacaaag actatattag aaactgcatc attggtaaag gaggcagcta taaggggacg     420
gtatccatca ctaagagtgg catcaaatgc cagccttgga attccatgat cccccatgaa     480
cacagctatc gcgtaaaga cctacaggaa aactactgtc gaaatcctcg aggggaagaa     540
gggggaccct ggtgtttcac aagcaatcca gaggtacgct acgaagtctg tgacattcct     600
cagtgttcag aagttgaatg catgacctgc aatggtgaaa gctacagagg tcccatggat     660
cacacagaat caggcaagac ttgtcagcgc tgggaccagc agacaccaca ccggcacaag     720
```

-continued

```
ttcttgccag aaagatatcc cgacaagggc tttgatgata attattgccg caatcctgat    780
ggcaagccga ggccatggtg ctacactctt gaccctgaca cccccttggga gtattgtgca    840
attaaaacgt gcgctcacag tgctgtgaat gagactgatg tccctatgga aacaactgaa    900
tgcattcaag gccaaggaga aggttacagg ggaaccagca ataccatttg aatggaatt    960
ccctgtcagc gttgggattc gcagtaccct cacaagcatg atatcactcc cgagaacttc   1020
aaatgcaaga accttagaga aaattattgc cgcaatccag atgggctga atcaccatgg   1080
tgttttacca ctgacccaaa catccgagtt ggctactgct ctcagattcc caagtgtgac   1140
gtgtcaagtg gacaagattg ttatcgtggc aatgggaaaa attacatggg caacttatcc   1200
aaaacaaggt ctggacttac atgttccatg tgggacaaga atatggagga tttacaccgt   1260
catatcttct gggagccaga tgctagcaaa ttgaataaga attactgccg gaatcctgat   1320
gatgatgccc atggaccttg gtgctacacg gggaatcctc ttattccttg ggattattgc   1380
cctatttccc gttgtgaagg agatactaca cctacaattg tcaatttgga ccatcctgta   1440
atatcctgtg ccaaaacaaa acaactgcgg gttgtaaatg ggattccaac acaaacaaca   1500
gtaggatgga tggttagttt gagatacaga aataaacata tctgcggagg atcattgata   1560
aaggagagtt gggttcttac tgcacgacag tgtttcccctt ctcgagactt gaaagattat   1620
gaagcttggc ttggaattca tgatgtccac ggaagaggag atgagaaatg caaacaggtt   1680
ctcaatgttt cccagctggt atatggccct gaaggatcag atctggtttt aatgaagctt   1740
gctcgacctg caatcctgga taactttgtc agtacaattg atttacctag ttatggttgt   1800
acaatccctg aaaagaccac ttgcagtatt tacggctggg gctacactgg attgatcaac   1860
gcggatggtt tattacgagt agctcatctg tatattatgg ggaatgagaa atgcagtcag   1920
caccatcaag gcaaggtgac tttgaatgag tctgagttat gtgctggggc tgaaaagatt   1980
ggatcaggac catgtgaggg agattatggt ggcccactca tttgtgaaca acacaaaatg   2040
agaatggttc ttggtgtcat tgttcctggt cgtggatgtg ccatcccaaa tcgtcctggt   2100
attttttgttc gagtagcata ttatgcaaaa tggatacaca agtaattttt gacatacaag   2160
ttgtgcggcc gccatcacca tcaccatcac taag                                2194
```

<210> SEQ ID NO 216
<211> LENGTH: 675
<212> TYPE: PRT
<213> ORGANISM: Artificial Sequence
<220> FEATURE:
<223> OTHER INFORMATION: Synthetic HGF mhm507-585 active

<400> SEQUENCE: 216

```
Pro Leu Leu Lys Ile Lys Thr Lys Lys Val Asn Ser Ala Asp Glu Cys
1               5                   10                  15

Ala Asn Arg Cys Ile Arg Asn Arg Gly Phe Thr Phe Thr Cys Lys Ala
            20                  25                  30

Phe Val Phe Asp Lys Ser Arg Lys Arg Cys Tyr Trp Tyr Pro Phe Asn
        35                  40                  45

Ser Met Ser Ser Gly Val Lys Lys Gly Phe Gly His Glu Phe Asp Leu
    50                  55                  60

Tyr Glu Asn Lys Asp Tyr Ile Arg Asn Cys Ile Ile Gly Lys Gly Gly
65                  70                  75                  80

Ser Tyr Lys Gly Thr Val Ser Ile Thr Lys Ser Gly Ile Lys Cys Gln
                85                  90                  95

Pro Trp Asn Ser Met Ile Pro His Glu His Ser Tyr Arg Gly Lys Asp
```

-continued

```
                100               105               110
Leu Gln Glu Asn Tyr Cys Arg Asn Pro Arg Gly Glu Glu Gly Gly Pro
            115                 120                 125

Trp Cys Phe Thr Ser Asn Pro Glu Val Arg Tyr Glu Val Cys Asp Ile
        130                 135                 140

Pro Gln Cys Ser Glu Val Glu Cys Met Thr Cys Asn Gly Glu Ser Tyr
145                 150                 155                 160

Arg Gly Pro Met Asp His Thr Glu Ser Gly Lys Thr Cys Gln Arg Trp
                165                 170                 175

Asp Gln Gln Thr Pro His Arg His Lys Phe Leu Pro Glu Arg Tyr Pro
            180                 185                 190

Asp Lys Gly Phe Asp Asp Asn Tyr Cys Arg Asn Pro Asp Gly Lys Pro
        195                 200                 205

Arg Pro Trp Cys Tyr Thr Leu Asp Pro Asp Thr Pro Trp Glu Tyr Cys
210                 215                 220

Ala Ile Lys Thr Cys Ala His Ser Ala Val Asn Glu Thr Asp Val Pro
225                 230                 235                 240

Met Glu Thr Thr Glu Cys Ile Gln Gly Gln Gly Glu Gly Tyr Arg Gly
                245                 250                 255

Thr Ser Asn Thr Ile Trp Asn Gly Ile Pro Cys Gln Arg Trp Asp Ser
        260                 265                 270

Gln Tyr Pro His Lys His Asp Ile Thr Pro Glu Asn Phe Lys Cys Lys
    275                 280                 285

Asp Leu Arg Glu Asn Tyr Cys Arg Asn Pro Asp Gly Ala Glu Ser Pro
        290                 295                 300

Trp Cys Phe Thr Asp Pro Asn Ile Arg Val Gly Tyr Cys Ser Gln
305                 310                 315                 320

Ile Pro Lys Cys Asp Val Ser Ser Gly Gln Asp Cys Tyr Arg Gly Asn
                325                 330                 335

Gly Lys Asn Tyr Met Gly Asn Leu Ser Lys Thr Arg Ser Gly Leu Thr
            340                 345                 350

Cys Ser Met Trp Asp Lys Asn Met Glu Asp Leu His Arg His Ile Phe
        355                 360                 365

Trp Glu Pro Asp Ala Ser Lys Leu Asn Lys Asn Tyr Cys Arg Asn Pro
    370                 375                 380

Asp Asp Asp Ala His Gly Pro Trp Cys Tyr Thr Gly Asn Pro Leu Ile
385                 390                 395                 400

Pro Trp Asp Tyr Cys Pro Ile Ser Arg Cys Glu Gly Asp Thr Thr Pro
                405                 410                 415

Thr Ile Val Asn Leu Asp His Pro Val Ile Ser Cys Ala Lys Thr Lys
            420                 425                 430

Gln Leu Arg Val Val Asn Gly Ile Pro Thr Gln Thr Thr Val Gly Trp
        435                 440                 445

Met Val Ser Leu Arg Tyr Arg Asn Lys His Ile Cys Gly Gly Ser Leu
    450                 455                 460

Ile Lys Glu Ser Trp Val Leu Thr Ala Arg Gln Cys Phe Pro Ser Arg
465                 470                 475                 480

Asp Leu Lys Asp Tyr Glu Ala Trp Leu Gly Ile His Asp Val His Gly
                485                 490                 495

Arg Gly Asp Glu Lys Cys Lys Gln Val Leu Asn Val Ser Gln Leu Val
            500                 505                 510

Tyr Gly Pro Glu Gly Ser Asp Leu Val Leu Met Lys Leu Ala Arg Pro
        515                 520                 525
```

-continued

```
Ala Ile Leu Asp Asn Phe Val Ser Thr Ile Asp Leu Pro Ser Tyr Gly
        530             535             540

Cys Thr Ile Pro Glu Lys Thr Thr Cys Ser Ile Tyr Gly Trp Gly Tyr
545             550             555                         560

Thr Gly Leu Ile Asn Ala Asp Gly Leu Leu Arg Val Ala His Leu Tyr
                565             570                 575

Ile Met Gly Asn Glu Lys Cys Ser Gln His His Gln Gly Lys Val Thr
            580             585             590

Leu Asn Glu Ser Glu Leu Cys Ala Gly Ala Glu Lys Ile Gly Ser Gly
        595             600             605

Pro Cys Glu Gly Asp Tyr Gly Gly Pro Leu Ile Cys Glu Gln His Lys
    610             615             620

Met Arg Met Val Leu Gly Val Ile Val Pro Gly Arg Gly Cys Ala Ile
625             630             635                         640

Pro Asn Arg Pro Gly Ile Phe Val Arg Val Ala Tyr Tyr Ala Lys Trp
                645             650                 655

Ile His Lys Val Ile Leu Thr Tyr Lys Leu Cys Gly Arg His His His
            660             665             670

His His His
        675
```

HEPATOCYTE GROWTH FACTOR (HGF) BINDING ANTIBODY

RELATED APPLICATIONS

This application claims the benefit and priority to U.S. Provisional Application Nos. 60/810,714, filed Jun. 2, 2006, and 60/860,509, filed Nov. 21, 2006, the disclosures of which are incorporated by reference herein.

FIELD OF THE INVENTION

The field of the invention is molecular biology, immunology and oncology. More particularly, the field is antibody-based binding proteins that bind human hepatocyte growth factor (HGF).

BACKGROUND

Hepatocyte Growth Factor (HGF), also known as Scatter Factor (SF), is a multi-functional heterodimeric protein produced predominantly by mesenchymal cells, and is an effector of cells expressing the Met tyrosine kinase receptor (Bottaro et al. (1991) SCIENCE 251: 802-804, Rubin et al. (1993) BIOCHIM. BIOPHYS. ACTA 1155: 357-371). The human Met receptor is also known as "c-Met." Mature HGF contains two polypeptide chains, the α-chain and the β-chain. Published studies suggest it is the α-chain that contains HGF's c-Met receptor binding domain.

When it binds to its cognate receptor, HGF mediates a number of cellular activities. The HGF-Met signaling pathway plays a role in liver regeneration, wound healing, neural regeneration, angiogenesis and malignancies. See, e.g., Cao et al. (2001) PROC. NATL. ACAD. SCI. USA 98: 7443-7448, Burgess et al. (2006) CANCER RES. 66: 1721-1729, and U.S. Pat. Nos. 5,997,868 and 5,707,624. Investigators have been developing a number of HGF modulators, including antibodies, to treat various disorders that involve HGF activity, for example, certain HGF responsive cancers. See, e.g., International Application Publication No. WO 2005/017107.

The basic structure common to all antibodies is shown schematically in FIG. 1. Antibodies are multimeric proteins that contain four polypeptide chains. Two of the polypeptide chains are called heavy or H chains and two of the polypeptide chains are called light or L chains. The immunoglobulin heavy and light chains are connected by an interchain disulfide bond. The immunoglobulin heavy chains are connected by a number of interchain disulfide bonds. A light chain is composed of one variable region ($V_L$ in FIG. 1) and one constant region ($C_L$ in FIG. 1), while the heavy chain is composed of one variable region ($V_H$ in FIG. 1) and at least three constant regions ($CH_1$, $CH_2$ and $CH_3$ in FIG. 1). The variable regions determine the specificity of the antibody and the constant regions have other functions.

Amino acid and structural information indicate that each variable region comprises three hypervariable regions (also known as complementarity determining regions or CDRs) flanked by four relatively conserved framework regions or FRs. The three CDRs, referred to as $CDR_1$, $CDR_2$, and $CDR_3$, are responsible for the binding specificity of individual antibodies. When antibodies are to be used as diagnostic and therapeutic agents, typically it is desirable to create antibodies that have the highest binding specificity and affinity to the target molecule. It is believed that differences in the variable regions can have profound effects on the specificity and affinity of the antibody.

U.S. Pat. No. 5,707,624 describes the use of anti-HGF antibodies in the treatment of Kaposi's sarcoma. Similarly, U.S. Pat. No. 5,997,868 describes treating a tumor by administering an anti-HGF antibody to the patient to be treated so as to block the ability of endogenous HGF to promote angiogenesis in the tumor. More recently, investigators propose that antibodies that bind the β-chain of HGF may have potential as therapeutic agents in patients with HGF-dependent tumors (Burgess (2006) supra).

Notwithstanding, there is still a need for additional HGF modulators that can be used as therapeutic and diagnostic agents.

SUMMARY OF THE INVENTION

The invention is based, in part, upon the discovery of a family of binding proteins that specifically bind HGF, in particular, human HGF. The binding proteins are antibody-based in so far as they contain antigen (i.e., HGF) binding sites based on the CDRs of a family of antibodies that specifically bind HGF. The CDRs confer the binding specificity of the binding proteins to HGF. The binding proteins can be used as diagnostic and therapeutic agents. When used as a therapeutic agent, the binding proteins are engineered (e.g., humanized) so as to reduce or eliminate the risk of inducing an immune response against the binding protein when administered to the recipient (e.g., a human).

The binding proteins neutralize the activity of HGF and, therefore, can be used as a therapeutic agent. In certain embodiments, the binding proteins prevent HGF from binding to its cognate receptor, c-Met, thereby neutralizing HGF activity. In other embodiments, the binding proteins bind to HGF and neutralize its biological activity but without preventing HGF from binding to the c-Met receptor. Because HGF has been implicated in the growth and proliferation of cancer cells, the binding proteins can be used to inhibit the proliferation of cancer cells. Furthermore, when administered to a mammal, the binding proteins can inhibit or reduce tumor growth in the mammal.

These and other aspects and advantages of the invention will become apparent upon consideration of the following figures, detailed description, and claims.

DESCRIPTION OF THE DRAWINGS

The invention can be more completely understood with reference to the following drawings.

FIG. 2 is a schematic diagram showing the amino acid sequence defining the complete immunoglobulin heavy chain variable region of the antibodies denoted as 1A3, 1 D3, 1F3, 2B8, 2F8, 3A12, 3B6 and 3D11. The amino acid sequences for each antibody are aligned against one another and the regions defining the signal peptide, $CDR_1$, $CDR_2$, and $CDR_3$ are identified in boxes. The unboxed sequences represent FR sequences.

FIG. 3 is a schematic diagram showing the $CDR_1$, $CDR_2$, and $CDR_3$ sequences for each of the immunoglobulin heavy chain variable region sequences presented in FIG. 2.

FIG. 4 is a schematic diagram showing the amino acid sequence defining the complete immunoglobulin light chain variable region of the antibodies 1A3, 1D3, 1F3, 2B8, 2F8, 3A12, 3B6, and 3D11. The amino acid sequences for each antibody are aligned against one another and the regions defining the signal peptide, $CDR_1$, $CDR_2$, and $CDR_3$ are identified in boxes. The unboxed sequences represent FR sequences.

FIG. 5 is a schematic diagram showing the $CDR_1$, $CDR_2$, and $CDR_3$ sequences for each of the immunoglobulin light chain variable region sequences presented in FIG. 4.

FIG. 8 is a table summarizing surface plasmon resonance data on antigen-binding affinity and kinetics of interaction between human HGF and chimeric, chimeric/humanized, or humanized 2B8 antibodies. The table lists the pairs of Kappa light chain and IgG1 heavy chain tested. Those antibodies with standard deviations (STDEV) listed were analyzed in three independent experiments.

DETAILED DESCRIPTION OF THE INVENTION

Figure 1:
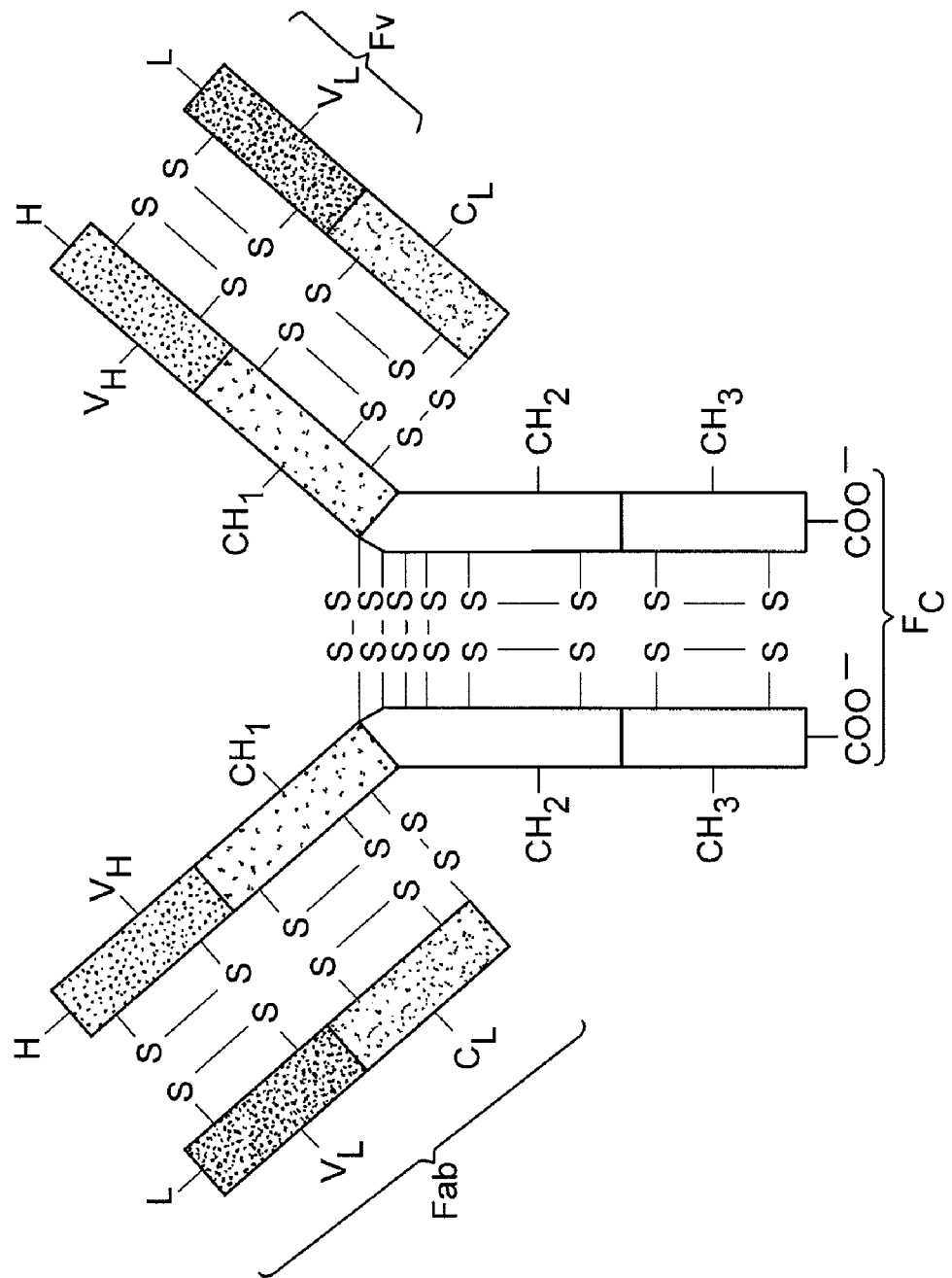
FIG. 1 is a schematic representation of a typical antibody.

The invention is based, in part, upon the discovery of a family of binding proteins that specifically bind, and neutralize the activity of, HGF, in particular, human HGF. The binding proteins can be used in a variety of diagnostic and therapeutic applications. The binding proteins are based upon the antigen binding sites of certain monoclonal antibodies that have been selected for their ability to bind, and neutralize the activity of, HGF. In particular, the binding proteins contain immunoglobulin variable region CDR sequences that together define a binding site for HGF.

In view of the neutralizing activity of these antibodies, they are particularly useful in modulating the growth and/or proliferation of HGF responsive cells, for example, cancer cells. When used as a therapeutic agent, the binding proteins can be engineered so as to minimize or eliminate the risk of inducing an immune response against the binding proteins when administered to the recipient. Furthermore, depending upon the particular application, it is contemplated that the binding proteins can be conjugated to other moieties, for example, detectable labels, for example, radiolabels, and effector molecules, for example, other protein and small molecule-based therapeutics. Each of these features and aspects of the invention are discussed in more detail below.

I—Binding Proteins that Bind HGF

In one aspect, the invention provides an isolated binding protein that binds human HGF. The binding protein comprises (i) an immunoglobulin light chain variable region comprising the structure $CDR_{L1}$-$CDR_{L2}$-$CDR_{L3}$, and (ii) an immunoglobulin heavy chain variable region comprising three complementarity determining regions (CDRs), wherein the immunoglobulin light chain variable region and the immunoglobulin heavy chain variable region together define a single binding site for binding human HGF. $CDR_{L1}$ comprises the amino acid sequence $X_1$ $X_2$ Ser $X_4$ $X_5$ $X_6$ $X_7$ $X_8$ $X_9$ $X_{10}$ $X_{11}$ $X_{12}$ $X_{13}$ $X_{14}$ $X_{15}$, wherein amino acid $X_1$ is Arg, Lys, or Ser, $X_2$ is Ala or Thr, $X_4$ is Glu, Gln, or Ser, $X_5$ is Asn, Asp, or Ser, $X_6$ is Ile or Val, $X_7$ is Asp, Lys, Ser, Val, or Tyr, $X_8$ is a peptide bond or Tyr, $X_9$ is a peptide bond or Asp, $X_{10}$ is a peptide bond or Gly, $X_{11}$ is a peptide bond or Asn, $X_{12}$ is a peptide bond, Ile, or Ser, $X_{13}$ is Asn or Tyr, $X_{14}$ is Ile, Leu, Met, or Val, $X_{15}$ is Ala, Asn, His, or Ser. $CDR_{L2}$ comprises the amino acid sequence $X_{16}$ $X_{17}$ $X_{18}$ $X_{19}$ $X_{20}$ $X_{21}$ $X_{22}$, wherein amino acid $X_{16}$ is Ala, Asp, Arg, Gly, or Val, $X_{17}$ is Ala, Thr, or Val, $X_{18}$ is Asn, Ser, or Thr, $X_{19}$ is Arg, Asn, Lys, or His, $X_{20}$ is Leu or Arg, $X_{21}$ is Ala, Asn, Glu, Val, or Pro, $X_{22}$ is Asp, Ser, or Thr. $CDR_{L3}$ comprises the amino acid sequence $X_{23}$ $X_{24}$ $X_{25}$ $X_{26}$ $X_{27}$ $X_{28}$ Pro $X_{30}$ Thr, wherein amino acid $X_{23}$ is Leu, Gly, or Gln, $X_{24}$ is His or Gln, $X_{25}$ is Phe, Ser, Trp, or Tyr, $X_{26}$ is Asp, Ile, Ser, Trp, or Tyr, $X_{27}$ is Gly, Glu, Asn, or Ser, $X_{28}$ is Asp, Asn, Phe, Thr, or Tyr, $X_{30}$ is Leu, Phe, Pro, or Tyr.

In another aspect, the invention provides an isolated binding protein that binds human HGF comprising (i) an immunoglobulin heavy chain variable region comprising the structure $CDR_{H1}$-$CDR_{H2}$-$CDR_{H3}$ and (ii) an immunoglobulin light chain variable region comprising three complementarity determining regions (CDRs), wherein the immunoglobulin heavy chain variable region and the immunoglobulin light chain variable region together define a single binding site for binding human HGF. $CDR_{H1}$ comprises the amino acid sequence $X_1$ Tyr $X_3$ $X_4$ $X_5$, wherein amino acid $X_1$ is Asp, Asn, Ser, or Thr, $X_3$ is Phe, Ser, Trp, or Tyr, $X_4$ is Ile, Leu, or Met, $X_5$ is Asn, His, or Ser. $CDR_{H2}$ comprises the amino acid sequence $X_6$ Ile $X_8$ $X_9$ $X_{10}$ $X_{11}$ Gly $X_{13}$ $X_{14}$ $X_{15}$ Tyr $X_{17}$ $X_{18}$ $X_{19}$ $X_{20}$ $X_{21}$ $X_{22}$, wherein amino acid $X_6$ is Lys, Gln, Glu, Val, or Tyr, $X_8$ is Asn, Gly, Ser, Trp, or Tyr, $X_9$ is Ala, Pro or Ser, $X_{10}$ is Gly or Thr, $X_{11}$ is a peptide bond, Asp, Asn, Gly, or Ser, $X_{13}$ is Asp, Asn, His, or Ser, $X_{14}$ is Ser or Thr, $X_{15}$ is Asn or Tyr, $X_{17}$ is Asn or Pro, $X_{18}$ is Ala, Asp, Gly, Gln, Glu, Pro, or Ser, $X_{19}$ is Asn, Lys, Met, or Ser, $X_{20}$ is Leu, Phe or Val, $X_{21}$ is Lys, Met, or Gln, $X_{22}$ is Asp, Gly or Ser. $CDR_{H3}$ comprises the amino acid sequence $X_{23}$ $X_{24}$ $X_{25}$ $X_{26}$ $X_{27}$ $X_{28}$ $X_{29}$ $X_{30}$ $X_{31}$ $X_{32}$ $X_{33}$ $X_{34}$ Tyr, wherein amino acid $X_{23}$ is Arg, Asn, Gln, or Glu, $X_{24}$ is Gly, Leu, Arg, or Tyr, $X_{25}$ is a peptide bond, Asp, or Gly, $X_{26}$ is a peptide bond or Gly, $X_{27}$ is a peptide bond or Tyr, $X_{28}$ is a peptide bond, Leu, or Tyr, $X_{29}$ is a peptide bond, Gly, Leu, Arg, or Val, $X_{30}$ is a peptide bond, Asp, Gly, or Glu, $X_{31}$ is a peptide bond, Asn, Arg, Ser, or Tyr, $X_{32}$ is peptide bond, Ala, Gly, Ile, or Tyr, $X_{33}$ is Met or Phe, $X_{34}$ is Ala or Asp.

It is understood that the binding protein can comprise both the immunoglobulin light chain and the immunoglobulin heavy chain sequences or the fragments thereof, noted above. Furthermore, it is understood that the binding protein can be an intact antibody or an antigen binding fragment thereof, or a biosynthetic antibody site.

In certain embodiments, the CDR sequences of the immunoglobulin light chain and the immunoglobulin heavy chain are interposed with framework regions (FR).

In certain other embodiments, the CDR sequences of the immunoglobulin light chain and the immunoglobulin heavy chain are interposed between human or humanized framework regions.

In another aspect, the invention provides an isolated binding protein that specifically binds human HGF. The binding protein comprises: (a) an immunoglobulin light chain variable region comprising the structure $CDR_{L1}$-$CDR_{L2}$-$CDR_{L3}$ and (b) immunoglobulin heavy chain variable region, wherein the immunoglobulin light chain variable region and the immunoglobulin heavy chain variable region together define a single binding site for binding human HGF. The $CDR_{L1}$ comprises a sequence selected from the group consisting of SEQ ID NO. 8 (1A3), SEQ ID NO. 18 (2B8), SEQ ID NO. 28 (2F8), SEQ ID NO. 38 (3B6), SEQ ID NO. 48 (3D11), SEQ ID NO. 58 (1D3), SEQ ID NO. 68 (1F3), and SEQ ID NO. 78 (3A12). The $CDR_{L2}$ comprises a sequence selected from the group consisting of SEQ ID NO. 9 (1A3), SEQ ID NO. 19 (2B8), SEQ ID NO. 29 (2F8), SEQ ID NO. 39 (3B6), SEQ ID NO. 49 (3D11), SEQ ID NO. 59 (1D3), SEQ ID NO. 69 (1F3), SEQ ID NO. 79 (3A12) and SEQ ID NO. 206 (LRMR2B8LC). The $CDR_{L3}$ comprises a sequence selected from the group consisting of SEQ ID NO. 10 (1A3), SEQ ID NO. 20 (2B8), SEQ ID NO. 30 (2F8), SEQ ID NO. 40 (3B6), SEQ ID NO. 50 (3D11), SEQ ID NO. 60 (1D3), SEQ ID NO. 70 (1F3), and SEQ ID NO. 80 (3A12). Throughout the specification and claims, the sequences denoted by a particular SEQ ID NO. are followed in parentheses by the antibody that was the origin of the particular sequence. By way of example, SEQ ID NO. 8 (1A3) indicates that the sequence of SEQ ID NO. 8 is based upon the sequence present in antibody 1A3.

In one embodiment, the binding protein comprises an immunoglobulin light chain variable region comprising a $CDR_{L1}$ comprising the sequence of SEQ ID NO. 8 (1A3), a $CDR_{L2}$ comprising the sequence of SEQ ID NO. 9 (1A3), and a $CDR_{L3}$ comprising the sequence of SEQ ID NO. 10 (1A3).

In another embodiment, the binding protein comprises an immunoglobulin light chain variable region comprising a $CDR_{L1}$ comprising the sequence of SEQ ID NO. 18 (2B8), a $CDR_{L2}$ comprising the sequence of SEQ ID NO. 19 (2B8) or SEQ ID NO. 206 (LRMR2B8LC), and a $CDR_{L3}$ comprising the sequence of SEQ ID NO. 20 (2B8).

In another embodiment, the binding protein comprises an immunoglobulin light chain variable region comprising a $CDR_{L1}$ comprising the sequence of SEQ ID NO. 28 (2F8), a $CDR_{L2}$ comprising the sequence of SEQ ID NO. 29 (2F8), and a $CDR_{L3}$ comprising the sequence of SEQ ID NO. 30 (2F8).

In another embodiment, the binding protein comprises an immunoglobulin light chain variable region comprising a $CDR_{L1}$ comprising the sequence of SEQ ID NO. 38 (3B6), a $CDR_{L2}$ comprising the sequence of SEQ ID NO. 39 (3B6), and a $CDR_{L3}$ comprising the sequence of SEQ ID NO. 40 (3B6).

In another embodiment, the binding protein comprises an immunoglobulin light chain variable region comprising a $CDR_{L1}$ comprising the sequence of SEQ ID NO. 48 (3D11), a $CDR_{L2}$ comprising the sequence of SEQ ID NO. 49 (3D11), and a $CDR_{L3}$ comprising the sequence of SEQ ID NO. 50 (3D11).

In another embodiment, the binding protein comprises an immunoglobulin light chain variable region comprising a $CDR_{L1}$ comprising the sequence of SEQ ID NO. 58 (1D3), a $CDR_{L2}$ comprising the sequence of SEQ ID NO. 59 (1D3), and a $CDR_{L3}$ comprising the sequence of SEQ ID NO. 60 (1D3).

In another embodiment, the binding protein comprises an immunoglobulin light chain variable region comprising a $CDR_{L1}$ comprising the sequence of SEQ ID NO. 68 (1F3), a $CDR_{L2}$ comprising the sequence of SEQ ID NO. 69 (1F3), and a $CDR_{L3}$ comprising the sequence of SEQ ID NO. 70 (1F3).

In another embodiment, the binding protein comprises an immunoglobulin light chain variable region comprising a $CDR_{L1}$ comprising the sequence of SEQ ID NO. 78 (3A12), a $CDR_{L2}$ comprising the sequence of SEQ ID NO. 79 (3A12), and a $CDR_{L3}$ comprising the sequence of SEQ ID NO. 80 (3A12).

In each of the foregoing embodiments, the $CDR_{L1}$, $CDR_{L2}$, and $CDR_{L3}$ sequences preferably are interposed between human or humanized immunoglobulin FRs. It is understood that the binding protein can be an intact antibody, an antigen binding fragment thereof, or a biosynthetic antibody site.

In another aspect, the invention provides an isolated binding protein that binds human HGF. The binding protein comprises (a) an immunoglobulin heavy chain variable region comprising the structure $CDR_{H1}$-$CDR_{H2}$-$CDR_{H3}$, and (b) an immunoglobulin light chain variable region, wherein the immunoglobulin heavy chain variable region and the immunoglobulin light chain variable region together define a single binding site for binding human HGF. The $CDR_{H1}$ comprises a sequence selected from the group consisting of SEQ ID NO. 5 (1A3), SEQ ID NO. 15 (2B8), SEQ ID NO. 25 (2F8), SEQ ID NO. 35 (3B6), SEQ ID NO. 45 (3D11), SEQ ID NO. 55 (1D3), SEQ ID NO. 65 (1F3), and SEQ ID NO. 75 (3A12); the $CDR_{H2}$ comprises a sequence selected from the group consisting of SEQ ID NO. 6 (1A3), SEQ ID NO. 16 (2B8), SEQ ID NO. 26 (2F8), SEQ ID NO. 36 (3B6), SEQ ID NO. 46 (3D11), SEQ ID NO. 56 (1D3), SEQ ID NO. 66 (1F3), SEQ ID NO. 76 (3A12), SEQ ID NO. 202 (Hu2B8 Hv1f.1), SEQ ID NO. 203 (Hu2B8 Hv5a.1 or Hu2B8 Hv5-51.1), SEQ ID NO. 204 (LR2B8HC) and SEQ ID NO. 205 (LRMR2B8HC); and the $CDR_{H3}$ comprises a sequence selected from the group consisting of SEQ ID NO. 7 (1A3), SEQ ID NO. 17 (2B8), SEQ ID NO. 27 (2F8), SEQ ID NO. 37 (3B6), SEQ ID NO. 47 (3D11), SEQ ID NO. 57 (1D3), SEQ ID NO. 67 (1F3), and SEQ ID NO. 77 (3A12).

In one embodiment, the binding protein comprises an immunoglobulin heavy chain variable region comprising: a $CDR_{H1}$ comprising the sequence of SEQ ID NO. 5 (1A3); a $CDR_{H2}$ comprising the sequence of SEQ ID NO. 6 (1A3); and a $CDR_{H3}$ comprising the sequence of SEQ ID NO. 7 (1A3).

In another embodiment, the binding protein comprises an immunoglobulin heavy chain variable region comprising: a $CDR_{H1}$ comprising the sequence of SEQ ID NO. 15 (2B8); a $CDR_{H2}$ comprising the sequence of SEQ ID NO. 16 (2B8), SEQ ID NO. 202 (Hu2B8 Hv1f.1), SEQ ID NO. 203 (Hu2B8 Hv5a.1 or Hu2B8 Hv5-51.1), SEQ ID NO. 204 (LR2B8HC) or SEQ ID NO. 205 (LRMR2B8HC); and a $CDR_{H3}$ comprising the sequence of SEQ ID NO. 17 (2B8).

In another embodiment, the binding protein comprises an immunoglobulin heavy chain variable region comprising: a $CDR_{H1}$ comprising the sequence of SEQ ID NO. 25 (2F8); a $CDR_{H2}$ comprising the sequence of SEQ ID NO. 26 (2F8); and a $CDR_{H3}$ comprising the sequence of SEQ ID NO. 27 (2F8).

In another embodiment, the binding protein comprises an immunoglobulin heavy chain variable region comprising a $CDR_{H1}$ comprising the sequence of SEQ ID NO. 35 (3B6); a $CDR_{H2}$ comprising the sequence of SEQ ID NO. 36 (3B6); and a $CDR_{H3}$ comprising the sequence of SEQ ID NO. 37 (3B6).

In another embodiment, the binding protein comprises an immunoglobulin heavy chain variable region comprising: a $CDR_{H1}$ comprising the sequence of SEQ ID NO. 45 (3D11); a $CDR_{H2}$ comprising the sequence of SEQ ID NO. 46 (3D11); and a $CDR_{H3}$ comprising the sequence of SEQ ID NO. 47 (3D11).

In another embodiment, the binding protein comprises an immunoglobulin heavy chain variable region comprising: a $CDR_{H1}$ comprising the sequence of SEQ ID NO. 55 (1D3); a $CDR_{H2}$ comprising the sequence of SEQ ID NO. 56 (1D3); and a $CDR_{H3}$ comprising the sequence of SEQ ID NO. 57 (1D3).

In another embodiment, the binding protein comprises an immunoglobulin heavy chain variable region comprising: a $CDR_{H1}$ comprising the sequence of SEQ ID NO. 65 (1F3); a $CDR_{H2}$ comprising the sequence of SEQ ID NO. 66 (1F3); and a $CDR_{H3}$ comprising the sequence of SEQ ID NO. 67 (1F3).

In another embodiment, the binding protein comprises an immunoglobulin heavy chain variable region comprising: a $CDR_{H1}$ comprising the sequence of SEQ ID NO. 75 (3A12); a $CDR_{H2}$ comprising the sequence of SEQ ID NO. 76 (3A12); and a $CDR_{H3}$ comprising the sequence of SEQ ID NO. 77 (3A12).

In each of the foregoing embodiments, the $CDR_{H1}$, $CDR_{H2}$, and $CDR_{H3}$ sequences preferably are interposed between human or humanized immunoglobulin FRs. It is understood that the binding protein can be an intact antibody, an antigen binding fragment thereof, or a biosynthetic antibody site.

In another aspect, the invention provides a binding protein that binds human HGF. The binding protein comprises an immunoglobulin heavy chain variable region selected from the group consisting of residues 20-141 of SEQ ID NO. 2 (1A3), residues 20-137 of SEQ ID NO. 12 (2B8), residues 20-137 of SEQ ID NO. 22 (2F8), residues 20-139 of SEQ ID NO. 32 (3B6), residues 20-132 of SEQ ID NO. 42 (3D11), residues 20-141 of SEQ ID NO. 52 (1D3), residues 20-141 of SEQ ID NO. 62 (1F3), and residues 20-141 of SEQ ID NO. 72 (3A12) and an immunoglobulin light chain variable region selected from the group consisting of residues 21-127 of SEQ ID NO. 4 (1A3), residues 21-127 of SEQ ID NO. 14 (2B8), residues 20-131 of SEQ ID NO. 24 (2F8), residues 23-129 of SEQ ID NO. 34 (3B6), residues 23-128 of SEQ ID NO. 44 (3D11), residues 21-127 of SEQ ID NO. 54 (1D3), residues 21-127 of SEQ ID NO. 64 (1F3), and residues 21-127 of SEQ ID NO. 74 (3A12).

In another embodiment, the binding protein comprises an immunoglobulin heavy chain variable region comprising the amino acid sequence of residues 20-141 of SEQ ID NO. 2 (1A3), and an immunoglobulin light chain variable region comprising the amino acid sequence of residues 21-127 of SEQ ID NO. 4 (1A3).

In one embodiment, the binding protein comprises an immunoglobulin heavy chain variable region comprising the amino acid sequence of residues 20-137 of SEQ ID NO. 12 (2B8), and an immunoglobulin light chain variable region comprising the amino acid sequence of residues 21-127 of SEQ ID NO. 14 (2B8).

In another embodiment, the binding protein comprises an immunoglobulin heavy chain variable region comprising the amino acid sequence of residues 20-137 of SEQ ID NO. 22 (2F8), and an immunoglobulin light chain variable region comprising the amino acid sequence of residues 20-131 of SEQ ID NO. 24 (2F8).

In another embodiment, the binding protein comprises an immunoglobulin heavy chain variable region comprising the amino acid sequence of residues 20-139 of SEQ ID NO. 32 (3B6), and an immunoglobulin light chain variable region comprising the amino acid sequence of residues 23-129 of SEQ ID NO. 34 (3B6).

In another embodiment, the binding protein comprises an immunoglobulin heavy chain variable region comprising the amino acid sequence of residues 20-132 of SEQ ID NO. 42 (3D11), and an immunoglobulin light chain variable region comprising the amino acid sequence of residues 23-128 of SEQ ID NO. 44 (3D11).

In another embodiment, the binding protein comprises an immunoglobulin heavy chain variable region comprising the amino acid sequence of residues 20-141 of SEQ ID NO. 52 (1D3), and an immunoglobulin light chain variable region comprising the amino acid sequence of residues 21-127 of SEQ ID NO. 54 (1D3).

In another embodiment, the binding protein comprises an immunoglobulin heavy chain variable region comprising the amino acid sequence of residues 20-141 of SEQ ID NO. 62 (1F3), and an immunoglobulin light chain variable region comprising the amino acid sequence of residues 21-127 of SEQ ID NO. 64 (1F3).

In another embodiment, the binding protein comprises an immunoglobulin heavy chain variable region comprising the amino acid sequence of residues 20-141 of SEQ ID NO. 72 (3A12), and an immunoglobulin light chain variable region comprising the amino acid sequence of residues 21-127 of SEQ ID NO. 74 (3A12).

In each of the foregoing embodiments, the binding protein can be an intact antibody, an antigen binding fragment thereof, or a biosynthetic antibody site.

In another aspect, the invention provides an isolated binding protein that binds human HGF. The binding protein comprises (i) an immunoglobulin light chain variable region selected from the group consisting of SEQ ID NO. 173 (Hu2B8 Kv1-39.1 light chain variable region), SEQ ID NO. 179 (Hu2B8 Kv3-15.1 light chain variable region), SEQ ID NO. 193 (LR2B8LC light chain variable region), and SEQ ID NO. 199 (LRMR2B8LC light chain variable region); and (ii) an immunoglobulin heavy chain variable region selected from the group consisting of SEQ ID NO. 159 (Hu2B8 Hv1f.1 heavy chain variable region), SEQ ID NO. 165 (Hu2B8 Hv5a.1 heavy chain variable region), SEQ ID NO. 169 (Hu2B8 Hv5-51.1 heavy chain variable region), SEQ ID NO. 183 (LR2B8HC heavy chain variable region), and SEQ ID NO. 189 (LRMR2B8HC heavy chain variable region). The binding protein can be an intact antibody, an antigen binding fragment thereof, or a biosynthetic antibody site.

In another aspect, the invention provides an isolated binding protein that binds human HGF. The binding protein comprises (i) an immunoglobulin light chain selected from the group consisting of SEQ ID NO. 177 (Hu2B8 Kv1-39.1+ kappa constant (Km(3) allotype (allele 2)), SEQ ID NO. 181 (Hu2B8 Kv3-15.1+Kappa constant (Km(3) allotype (allele 2)), SEQ ID NO. 197 (LR2B8LC+Kappa constant (Km(3) allotype (allele 1)), and SEQ ID NO. 201 (LRMR2B8LC+ Kappa constant (Km(3) allotype (allele 1)); and (ii) an immunoglobulin heavy chain selected from the group consisting of SEQ ID NO. 163 (Hu2B8 Hv1f.1+IgG1 Constant (G1m(17, 1) allotype)), SEQ ID NO. 167 (Hu2B8 Hv5a.1+IgG1 Constant (G1m(17,1) allotype)), SEQ ID NO. 171 (Hu2B8 Hv5-51.1+IgG1 Constant (G1m(17,1) allotype)), SEQ ID NO. 187 (LR2B8HC+IgG1 Constant (G1m(3) allotype) (allele 1)), and SEQ ID NO. 191 (LRMR2B8HC+IgG1 Constant (G1m (3) allotype) (allele 1)). The binding protein can be an intact antibody, an antigen binding fragment thereof, or a biosynthetic antibody site.

In another aspect, the invention provides an isolated binding protein that binds reduced human HGF. The binding protein comprises (i) an immunoglobulin light chain variable region comprising three CDRs, and (ii) an immunoglobulin heavy chain variable region comprising three CDRs. The CDRs typically are interposed between FRs. The CDRs of the immunoglobulin light chain and the immunoglobulin heavy chain together define a binding site that binds reduced human HGF, for example, the α-chain of reduced HGF. Reduced HGF refers to HGF treated with an amount of reducing agent, for example, dithiothreitol (DTT), 2-mercaptoethanol, or glutathione sufficient to reduce the disulfide linkage between the α-chain and the β-chain. Exemplary concentrations include, for example, 100 mM DTT and 5% 2-mercaptoethanol.

In certain embodiments, the binding protein comprises an immunoglobulin light chain variable region comprising at least one CDR selected from the group consisting of $CDR_{L1}$, $CDR_{L2}$ and $CDR_{L3}$. Optionally, the binding protein comprises two CDRs, for example, $CDR_{L1}$ and $CDR_{L2}$, or $CDR_{L1}$ and $CDR_{L3}$, or $CDR_{L1}$ and $CDR_{L3}$. Optionally, the binding protein comprises all three CDRs, i.e., $CDR_{L1}$, $CDR_{L2}$ and $CDR_{L3}$. $CDR_{L1}$ comprises the amino acid sequence $X_1 X_2$ Ser $X_4 X_5 X_6 X_7 X_8 X_9 X_{10} X_{11} X_{12} X_{13} X_{14} X_{15}$, wherein amino acid $X_1$ is Arg or Lys, $X_2$ is Ala or Thr, $X_4$ is Glu or Gln, $X_5$ is Asn, Ser, or Asp, $X_6$ is Ile or Val, $X_7$ is Tyr, Asp, or Lys, $X_8$ is a peptide bond or Tyr, $X_9$ is a peptide bond or Asp, $X_{10}$ is a peptide bond or Gly, $X_{11}$ is a peptide bond or Asn, $X_{12}$ is a peptide bond or Ser, $X_{13}$ is Asn or Tyr, $X_{14}$ is Ile or Leu, $X_{15}$ is Ala, Asn, or Ser. $CDR_{L2}$ comprises the amino acid sequence $X_{16} X_{17} X_{18} X_{19}$ Leu $X_{21} X_{22}$, wherein amino acid $X_{16}$ is Ala, Asp, Val, or Arg, $X_{17}$ is Ala or Val, $X_{18}$ is Asn, Ser, or Thr, $X_{19}$ is Arg, Asn, or His, $X_{21}$ is Ala, Glu, Val, or Pro, $X_{22}$ is Asp or Ser. $CDR_{L3}$ comprises the amino acid sequence $X_{23} X_{24} X_{25} X_{26} X_{27} X_{28}$ Pro $X_{30}$ Thr, wherein amino acid $X_{23}$ is Leu or Gln, $X_{24}$ is His or Gln, $X_{25}$ is Phe, Ser, or Tyr, $X_{26}$ is Asp, Ile, or Trp, $X_{27}$ is Gly or Glu, $X_{28}$ is Asp, Phe, or Thr, $X_{30}$ is Phe, Pro, or Tyr.

In another embodiment, the binding protein comprises an immunoglobulin heavy chain variable region comprising at least one CDR selected from the group consisting of $CDR_{H1}$, $CDR_{H2}$, and $CDR_{H3}$. Optionally, the binding protein comprises two CDRs, for example, $CDR_{H1}$ and $CDR_{H2}$, or $CDR_{H1}$ and $CDR_{H3}$, or $CDR_{H1}$ and $CDR_{H3}$. Optionally, the binding protein comprises all three CDRs, i.e., $CDR_{H1}$, $CDR_{H2}$ and $CDR_{H3}$. $CDR_{H1}$ comprises the amino acid sequence $X_1$ Tyr $X_3 X_4 X_5$, wherein amino acid $X_1$ is Asp, Asn, Ser, or Thr, $X_3$ is Phe, Trp, or Tyr, $X_4$ is Ile or Met, $X_5$ is Asn, His, or Ser. $CDR_{H2}$ comprises the amino acid sequence $X_6$ Ile $X_8 X_9$ Gly $X_{11}$ Gly $X_{13} X_{14} X_{15}$ Tyr $X_{17} X_{18} X_{19} X_{20}$ Lys $X_{22}$, wherein amino acid $X_6$ is Lys, Gln, or Tyr, $X_8$ is Gly, Ser, or Tyr, $X_9$ is Pro or Ser, $X_{11}$ is Asp, Gly, or Ser, $X_{13}$ is Asp or Ser, $X_{14}$ is Ser or Thr, $X_{15}$ is Asn or Tyr, $X_{17}$ is Asn or Pro, $X_{18}$ is Ala, Asp, Gly, or Glu, $X_{19}$ is Asn, Met, or Ser, $X_{20}$ is Phe or Val, $X_{22}$ is Asp or Gly. $CDR_{H3}$ comprises the amino acid sequence $X_{23} X_{24} X_{25} X_{26} X_{27} X_{28} X_{29} X_{30} X_{31} X_{32} X_{33}$ Asp Tyr, wherein amino acid $X_{23}$ is Arg or Gln, $X_{24}$ is Gly or Leu, $X_{25}$ is Asp, Gly, or a peptide bond, $X_{26}$ is Gly or a peptide bond, $X_{27}$ is a peptide bond or Tyr, $X_{28}$ is Leu, a peptide bond or Tyr, $X_{29}$ is a Gly, Arg or Leu, $X_{30}$ is Asp, Gly or Glu, $X_{31}$ is a Tyr, Arg or Asn, $X_{32}$ is Ala, Gly or Tyr, $X_{33}$ is Met or Phe.

It is understood that the binding protein can comprise both the immunoglobulin heavy chain and the immunoglobulin light chain sequences or the fragments thereof, noted above. Furthermore, it is understood that the binding protein can be an intact antibody or an antigen binding fragment thereof, or a biosynthetic antibody site.

In certain embodiments, the binding protein comprises an immunoglobulin light chain variable region comprising (i) a $CDR_{L1}$ having a sequence selected from the group consisting of SEQ ID NO. 8 (1A3), SEQ ID NO. 28 (2F8), SEQ ID NO. 38 (3B6), SEQ ID NO. 58 (1D3), and SEQ ID NO. 68 (1F3), (ii) a $CDR_{L2}$ having a sequence selected from the group consisting of SEQ ID NO. 9 (1A3), SEQ ID NO. 29 (2F8), SEQ ID NO. 39 (3B6), SEQ ID NO. 59 (1D3), and SEQ ID NO. 69 (1F3), and (iii) a $CDR_{L3}$ having a sequence selected from the group consisting of SEQ ID NO. 10 (1A3), SEQ ID NO. 30 (2F8), SEQ ID NO. 40 (3B6), SEQ ID NO. 60 (1D3), and SEQ ID NO. 70 (1F3). The CDR sequences can be interposed between human or humanized FRs. In other embodiments, the binding protein comprises an immunoglobulin light chain variable region comprising an amino acid sequence selected from the group consisting of residues 21-127 of SEQ ID NO. 4 (1A3), residues 20-131 of SEQ ID NO. 24 (2F8), residues 23-129 of SEQ ID NO. 34 (3B6), residues 21-127 of SEQ ID NO. 54 (1D3), and residues 21-127 of SEQ ID NO. 64 (1F3).

In certain other embodiments, the binding protein comprises an immunoglobulin heavy chain variable region comprising (i) a $CDR_{H1}$ having a sequence selected from the group consisting of SEQ ID NO. 5 (1A3), SEQ ID NO. 25 (2F8), SEQ ID NO. 35 (3B6), SEQ ID NO. 55 (1D3), and SEQ ID NO. 65 (1F3), (ii) a $CDR_{H2}$ having a sequence selected from the group consisting of SEQ ID NO. 6 (1A3), SEQ ID NO. 26 (2F8), SEQ ID NO. 36 (3B6), SEQ ID NO. 56 (1D3), and SEQ ID NO. 66 (1F3), and (iii) a $CDR_{H3}$ having a sequence selected from the group consisting of SEQ ID NO. 7 (1A3), SEQ ID NO. 27 (2F8), SEQ ID NO. 37 (3B6), SEQ ID NO. 57 (1D3), and SEQ ID NO. 67 (1F3). The CDR sequences can be interposed between human or humanized FRs. In another embodiment, the immunoglobulin heavy chain variable region comprises an amino acid sequence selected from the group consisting of residues 20-141 of SEQ ID NO. 2 (1A3), residues 20-137 of SEQ ID NO. 22 (2F8), residues 20-139 of SEQ ID NO. 32 (3B6), residues 20-141 of SEQ ID NO. 52 (1D3), and residues 20-141 of SEQ ID NO. 62 (1F3).

In another aspect, the invention provides an isolated binding protein that binds human HGF and comprises an immunoglobulin light chain variable region and an immunoglobulin heavy chain variable region. The isolated binding protein competes for binding to HGF with at least one reference antibody selected from the group consisting of (i) an antibody having an immunoglobulin light chain variable region of residues 20-131 of SEQ ID NO. 24 (2F8), and an immunoglobulin heavy chain variable region of residues 20-137 of SEQ ID NO. 22 (2F8), (ii) an antibody having an immunoglobulin light chain variable region of residues 23-129 of SEQ ID NO. 34 (3B6), and an immunoglobulin heavy chain variable region of residues 20-139 of SEQ ID NO. 32 (3B6), and (iii) an antibody having an immunoglobulin light chain variable region of residues 23-128 of SEQ ID NO. 44 (3D11), and an immunoglobulin heavy chain variable region of residues 20-132 of SEQ ID NO. 42 (3D11). Under certain circumstances, the binding protein binds the same epitope of HGF as one of the reference antibodies.

It is understood that each of the binding proteins discussed above can be an intact antibody, for example, a monoclonal antibody. Alternatively, the binding protein can be an antigen binding fragment of an antibody, or can be a biosynthetic antibody binding site. Antibody fragments include Fab, Fab', (Fab')$_2$ or Fv fragments. Techniques for making such antibody fragments are known to those skilled in the art. A number of biosynthetic antibody binding sites are known in the art and include, for example, single Fv or sFv molecules, described, for example, in U.S. Pat. No. 5,476,786. Other biosynthetic antibody binding sites include bispecific or bifunctional binding proteins, for example, bispecific or bifunctional antibodies, which are antibodies or antibody fragments that bind at least two different antigens. For example, bispecific binding proteins can bind HGF, for example, human HGF, and another antigen of interest. Methods for making bispecific antibodies are known in art and, include, for example, by fusing hybridomas or by linking Fab' fragments. See, e.g., Songsivilai et al. (1990) CLIN. EXP. IMMUNOL. 79: 315-325; Kostelny et al. (1992) J. IMMUNOL. 148: 1547-1553.

The binding proteins of the invention can bind hHGF containing a cysteine to arginine substitution at position 561 or a glycine to glutamate substitution at position 555.

In another aspect, the invention provides an isolated binding protein that binds human HGF with a $k_d$ of $4.0 \times 10^{-5}$ $s^{-1}$ or lower, $3.0 \times 10^{-5}$ $s^{-1}$ or lower, or $2.0 \times 10^{-5}$ $s^{-1}$ or lower. The isolated binding proteins can bind human HGF with a $k_d$ from $5.0 \times 10^{-5}$ $s^{-1}$ to $0.5 \times 10^{-5}$ $s^{-1}$, or from $4.0 \times 10^{-5}$ $s^{-1}$ to $1.0 \times 10^{-5}$ $s^{-1}$, or from $3.0 \times 10^{-5}$ $s^{-1}$ to $1.5 \times 10^{-5}$ $s^{-1}$. In another aspect, the invention provides an isolated binding protein that binds human HGF with a $K_D$ of 100 pM or lower, or 20 pM or lower, or 10 pM or lower, or 5 pM or lower. The isolated binding proteins can bind human HGF with a $K_D$ from 100 pM to 5 pM, or from 20 pM to 5 pM, or from 15 pM to 10 pM, or from 20 pM to 10 pM, or from 15 pM to 5 pM. Unless otherwise specified, $K_D$ values are determined by the methods, and under the conditions, described in Example 6.

In another aspect, the invention provides an isolated binding protein that binds human HGF, wherein the antibody binds to human HGF with lower $K_D$ at 37° C. than at 25° C. The binding protein binding optionally binds human HGF with a $K_D$ less than 5 pM at 37° C.

In other aspects and embodiments, the binding proteins can inhibit hHGF from binding to c-Met. For example, the binding proteins can have an $IC_{50}$ (concentration at 50% of maximum inhibition) of at least about 4.0, 4.5, 5.0, 5.5, 6.0, 6.5, and 7.0 nM when assayed using the protocol described in Example 7(a). In certain other embodiments, the binding proteins can neutralize HGF BrdU incorporation in 4 MBr-5 cells (ATCC, Catalog No. CCL208) using the method described in Example 7(b).

The binding proteins have an $IC_{50}$ of 50 nM or lower, preferably 45, 40, 35, 30, 25, 20, 15, 10, 5, 1, 0.5 nM or lower, when assayed using the protocol described in Example 7(b). In certain other embodiments, the binding proteins can be used to inhibit HGF stimulated c-Met phosphorylation in PC-3 cells (ATCC, Manassus, Va. Catalog No. CRL-1435) using the assay described in Example 9. The binding proteins inhibit HGF-stimulated (1.25 nM) c-Met phosphorylation in PC-3 cells with an $IC_{50}$ of 2 nM or less (Table 8), using the assay described in Example 9.

II—Production of Binding Proteins

Binding proteins of the invention can be produced in various ways using approaches know in the art. For example, DNA molecules encoding light chain variable regions and heavy chain variable regions can be chemically synthesized, using a commercial synthesizer and sequence information provided herein. Such synthetic DNA molecules can be ligated to other appropriate nucleotide sequences, including, e.g., constant region coding sequences, and expression control sequences, to produce conventional gene expression constructs encoding the desired binding proteins. Production of defined gene constructs is within routine skill in the art.

Alternatively, the sequences provided herein can be cloned out of hybridomas by conventional hybridization techniques or PCR techniques, using synthetic nucleic acid probes whose sequences are based on sequence information provided herein or prior art sequence information regarding genes encoding the heavy and light chains of murine antibodies in hybridoma cells. Production and use of such probes is within ordinary skill in the art.

The nucleic acids encoding the desired binding proteins can be introduced (ligated) into expression vectors, which can be introduced into a host cell via standard transfection or transformation techniques known in the art. Exemplary host cells include, for example, E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce immunoglobulin protein. Transfected host cells can be grown under conditions that permit the host cells to express the genes of interest, for example, the genes that encode the immunoglobulin light or heavy chain variable regions. The resulting expression products can be harvested using techniques known in the art.

The particular expression and purification conditions will vary depending upon what expression system is employed. For example, if the gene is to be expressed in E. coli, it is first cloned into an expression vector. This is accomplished by positioning the engineered gene downstream from a suitable bacterial promoter, e.g., Trp or Tac, and a signal sequence, e.g., a sequence encoding fragment B of protein A (FB). The resulting expressed fusion protein typically accumulates in refractile or inclusion bodies in the cytoplasm of the cells, and may be harvested after disruption of the cells by French press or sonication. The refractile bodies then are solubilized, and the expressed proteins refolded and cleaved by the methods already established for many other recombinant proteins.

If the engineered gene is to be expressed in eukaryotic host cells, for example, myeloma cells or CHO cells, it is first inserted into an expression vector containing a suitable eukaryotic promoter, a secretion signal, immunoglobulin enhancers, and various introns. This expression vector optionally can contain sequences encoding all or part of a constant region, enabling an entire, or a part of, a heavy or light chain to be expressed. The gene construct can be transfected into myeloma cells or CHO cells using established transfection protocols. Such transfected cells can express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a protein domain having another function (e.g., cytotoxicity).

III—Modifications to the Binding Proteins

It is understood that the binding proteins can be modified to optimize performance depending upon the intended use of the binding proteins. For example, when the binding protein is being used as a therapeutic agent, the binding protein can be modified to reduce its immunogenicity in the intended recipient. Alternatively or in addition, the binding protein can be fused or coupled to another protein or peptide, for example, a growth factor, cytokine, or cytotoxin. Such modifications can be achieved by using routine gene manipulation techniques known in the art.

Various techniques for reducing the antigenicity of antibodies and antibody fragments are known in the art. These techniques can be used to reduce or eliminate the antigenicity of the binding proteins of the invention. For example, when the binding proteins are to be administered to a human, the binding proteins preferably are engineered to reduce their antigenicity in humans. This process often is referred to as humanization. Preferably, the humanized binding proteins have the same or substantially the same affinity for the antigen as the original non-humanized binding protein it was derived from.

In one well known humanization approach, chimeric proteins are created in which immunoglobulin constant regions of antibodies from one species, e.g., mouse, are replaced with immunoglobulin constant regions from a second, different species, e.g., a human. In this example, the resulting antibody is a mouse-human chimera, where the human constant region sequences, in principle, are less immunogenic than the counterpart murine sequences. This type of antibody engineering is described, for example, Morrison, et al. (1984) PROC. NAT. ACAD. SCI. 81: 6851-6855, Neuberger et al. (1984) NATURE 312: 604-608; U.S. Pat. No. 6,893,625 (Robinson); U.S. Pat. No. 5,500,362 (Robinson); and U.S. Pat. No. 4,816,567 (Cabilly).

In another approach, known as CDR grafting, the CDRs of the light and heavy chain variable regions of an antibody of interest are grafted into frameworks (FRs) from another species. For example, murine CDRs can be grafted into human FR sequences. In some embodiments, the CDRs of the light and heavy chain variable regions of an anti-HGF antibody are grafted into human FRs or consensus human FRs. In order to create consensus human FRs, FRs from several human heavy chain or light chain amino acid sequences are aligned to identify a consensus amino acid sequence. CDR grafting is described, for example, in U.S. Pat. No. 7,022,500 (Queen); U.S. Pat. NO. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); U.S. Pat. NO. Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "superhumanization," antibodies in which human immunogenicity is reduced or eliminated are created by an alternative form of grafting. In superhumanization, human FR sequences are chosen from a set of human germline genes based on the structural similarity of the human CDRs to those of the mouse antibody to be humanized. This approach is described, for example, in U.S. Pat. No. 6,881,557 (Foote) and in Tan et al. (2002) J. IMMUNOL 169: 1119-1125.

Other approaches to reduce immunogenicity include, techniques are known as "reshaping," "hyperchimerization," or "veneering/resurfacing" to produce humanized antibodies. See, e.g., Vaswami et al. (1998) ANNALS OF ALLERGY, ASTHMA, & IMMUNOL. 81: 105; Roguska et al. (1996) PROT. ENGINEER 9: 895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, for example, in U.S. Pat. No. 5,639,641 (Pedersen).

One exemplary approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of immunoglobulin heavy and light chains are said to be produced. See, e.g., U.S. Pat. Nos. 6,706,477 (Zauderer); U.S. Pat. NO. 6,800,442 (Zauderer); and U.S. Pat. No. 6,872,518 (Zauderer).

Another exemplary approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another exemplary approach for modifying a mouse antibody into a form suitable for medical use in humans is HUMAN ENGINEERING™ (HE™) technology, which is practiced commercially by XOMA (US) LLC. See, e.g., International Application Publication No. WO 93/11794 and U.S. Pat. Nos. 5,766,886; 5,770,196; 5,821,123; and 5,869,619.

Any suitable approach, including any of the above approaches, can be used to reduce or eliminate human immunogenicity of a binding protein of interest.

In addition, it is possible to create fully human antibodies in mice. In this approach, human antibodies are prepared using a transgenic mouse in which the mouse's antibody-producing genes have been replaced by a substantial portion of the human antibody producing genes. Such mice produce human immunoglobulin instead of murine immunoglobulin molecules. See, e.g., WO 98/24893 (Jacobovitz et al.) and Mendez et al. (1997) NATURE GENETICS 15: 146-156. Fully human anti-HGF monoclonal antibodies can be produced using the following approach. Transgenic mice containing human immunoglobulin genes are immunized with the antigen of interest, e.g., HGF. Lymphatic cells from the mice then are obtained from the mice, which are then fused with a myeloid-type cell line to prepare immortal hybridoma cell lines. The hybridoma cell lines are screened and selected to identify hybridoma cell lines that produce antibodies specific to HGF.

Binding proteins of the invention can be conjugated with other molecules, depending upon their intended use. For example, if the binding protein is going to be used as a therapeutic, then the binding protein can be conjugated with another agent, for example, an effector molecule that modulates or otherwise promotes the therapy. To the extent that the effector is non-protein based agent, for example, a small molecule drug, a radiolabel or toxin, then, the agent can be chemically coupled to the binding protein using standard in vitro coupling chemistries. If, on the other hand, the effector molecule is a protein or peptide, for example, an enzyme, receptor, toxin, growth factor, cytokine or other immunomodulator, then the binding protein can either be chemically coupled to the effector using in vitro coupling chemistries or can be coupled to the effector as a fusion protein. Fusion proteins can be constructed and expressed using the techniques similar to those discussed in section II.

IV—Use of Binding Proteins

The binding proteins described herein can be used as a diagnostic agent or a therapeutic agent.

(1) Therapeutic Applications

Because the binding proteins of the invention neutralize the activity of HGF, they can be used in various therapeutic applications. For example, certain binding proteins of the invention are useful in the prevention or treatment of hyperproliferative diseases or disorders, e.g., various forms of cancer.

The binding proteins can be used to inhibit or reduce the proliferation of tumor cells. In such an approach, the tumor cells are exposed to a therapeutically effective amount of the binding protein so as to inhibit or reduce proliferation of the tumor cell. In certain embodiments, the binding proteins inhibit tumor cell proliferation by at least 50%, 60%, 70%, 80%, 90%, 95% or 100%.

In certain embodiments, the binding protein is used to inhibit or reduce proliferation of a tumor cell wherein the binding protein reduces the ability of hHGF to bind to c-Met. In other embodiments, the binding protein is used to inhibit or reduce the proliferation of a tumor cell even when the binding protein binds hHGF but does not substantially inhibit hHGF binding to c-Met, as shown by antibody 3B6 in Tables 5 and 6.

In addition, the binding protein can be used to inhibit, or slow down tumor growth or development in a mammal. In such a method, an effective amount of the binding protein is administered to the mammal so as to inhibit or slow down tumor growth in the mammal. Accordingly, the binding proteins can be used to treat tumors, for example, in a mammal. The method comprises administering to the mammal a therapeutically effective amount of the binding protein. The binding protein can be administered alone or in combination with another pharmaceutically active molecule, so as to treat the tumor.

It is contemplated that the binding proteins of the invention can be used in the treatment of a variety of HGF responsive disorders, including, for example, HGF responsive tumor cells in lung cancer, breast cancer, colon cancer, prostate cancer, ovarian cancer, head and neck cancer, ovarian cancer, multiple myeloma, liver cancer, gastric cancer, esophageal cancer, kidney cancer, nasopharyngeal cancer, pancreatic cancer, mesothelioma, melanoma and glioblastoma.

As used herein, "treat, "treating" and "treatment" refer to the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the binding protein delivered, the formulation of the binding protein, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments of the invention, the binding protein, e.g., monoclonal antibody, is lyophilized and reconstituted in buffered saline at the time of administration.

The binding proteins may be administered either alone or in combination with other pharmaceutically active ingredients. The other active ingredients, e.g., immunomodulators, can be administered together with the binding protein, or can be administered before or after the binding protein.

Formulations containing the binding proteins for therapeutic use, typically include the binding proteins combined with a pharmaceutically acceptable carrier. As used herein, "pharmaceutically acceptable carrier" means buffers, carriers, and excipients, that are, within the scope of sound medical judgment, suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers, in this regard, are intended to include any and all buffers, solvents, dispersion media, coatings, isotonic and absorption delaying agents, and the like, compatible with pharmaceutical administration. The use of such media and agents for pharmaceutically active substances is known in the art.

The formulations can be conveniently presented in a dosage unit form and can be prepared by any suitable method, including any of the methods well known in the pharmacy art. A pharmaceutical composition of the invention should be formulated to be compatible with its intended route of administration. Examples of routes of administration include parenteral administration or non-parenteral administration, for example, intravenous, intradermal, inhalation, transdermal (topical), transmucosal, and rectal administration. Useful solutions for oral or parenteral administration can be prepared by any of the methods well known in the pharmaceutical art, described, for example, in *Remington's Pharmaceutical Sciences,* 18th ed. (Mack Publishing Company, 1990).

Formulations suitable for oral administration can be in the form of: discrete units such as injectables, capsules, gelatin capsules, sachets, tablets, troches, or lozenges, each containing a predetermined amount of the binding protein; a powder or granular composition; a solution or a suspension in an aqueous liquid or non-aqueous liquid; or an oil-in-water emulsion or a water-in-oil emulsion.

Formulations suitable for parenteral administration include, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In general, compositions suitable for injectable use include aqueous solutions (where water soluble) or dispersions and powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished, for example, by filtration through sterile filtration membranes. Where the composition is lyophilized, sterilization using this method can be conducted prior to or following lyophilization and reconstitution. Once the pharmaceutical composition has been formulated, it can be stored, for example, in vials as a solution, suspension, gel, emulsion, solid, or as a dehydrated or lyophilized powder.

(2) Diagnostic Applications

Whenever the binding proteins are used for diagnostic purposes, either in vitro or in vivo, the binding proteins typically are labeled either directly or indirectly with a detectable moiety. The detectable moiety can be any moiety which is capable of producing, either directly or indirectly, a detectable signal. For example, the detectable moiety may be a radioisotope, such as $^3$Hydrogen ($^3$H), $^{14}$Carbon ($^{14}$C), $^{32}$Phosphorus ($^{32}$P), $^{35}$Sulfur ($^{35}$S), or $^{125}$Iodine ($^{125}$I); a fluorescent or chemiluminescent compound, such as fluorescein isothiocyanate, rhodamine, or luciferin; an enzyme, such as alkaline phosphatase, beta-galactosidase, or horseradish peroxidase; a spin probe, such as a spin label; or a colored particle, for example, a latex or gold particle. It is understood that the binding protein can be conjugated to the detectable moiety using a number of approaches known in the art, for example, as described in Hunter et al. (1962) NATURE 144: 945; David et al. (1974) BIOCHEMISTRY 13: 1014; Pain et al. (1981) J. IMMUNOL. METH. 40: 219; and Nygren (1982) J. HISTOCHEM. AND CYTOCHEM. 30: 407. The labels may be detected, e.g., visually or with the aid of a spectrophotometer or other detector.

The binding proteins can be employed in a wide range of immunoassay techniques available in the art. Exemplary immunoassays include, for example, sandwich immunoassays, competitive immunoassays, immunohistochemical procedures.

In a sandwich immunoassay, two antibodies that bind an analyte or antigen of interest are used, e.g., one immobilized onto a solid support, and one free in solution and labeled with a detectable moiety. When a sample containing the antigen is introduced into this system, the antigen binds to both the immobilized antibody and the labeled antibody, to form a "sandwich" immune complex on the surface of the support. The complexed protein is detected by washing away non-bound sample components and excess labeled antibody, and measuring the amount of labeled antibody complexed to protein on the support's surface. Alternatively, the antibody free in solution can be detected by a third antibody labeled with a detectable moiety which binds the free antibody. A detailed review of immunological assay design, theory and protocols can be found in numerous texts, including Butt, ed., (1984) PRACTICAL IMMUNOLOGY, Marcel Dekker, New York; Harlow et al. eds. (1988) ANTIBODIES, A LABORATORY APPROACH, Cold Spring Harbor Laboratory; and Diamandis et al., eds. (1996) IMMUNOASSAY, Academic Press, Boston.

It is contemplated that the labeled binding proteins are useful as in vivo imaging agents, whereby the binding proteins can target the imaging agents to particular tissues of interest in the recipient. A preferred remotely detectable moiety for in vivo imaging includes the radioactive atom Technetium$^{-99m}$ ($^{99m}$Tc), a gamma emitter with a half-life of about six hours. Non-radioactive moieties also useful in in vivo imaging include nitroxide spin labels as well as lanthanide and transition metal ions all of which induce proton relaxation in situ. In addition to immunoimaging, the complexed radioactive moieties may be used in standard radioimmunotherapy protocols to destroy the targeted cell. Preferred nucleotides for high dose radioimmunotherapy include the radioactive atoms $^{90}$Yttrium ($^{90}$Yt), $^{131}$Iodine ($^{131}$I) and $^{111}$Indium ($^{111}$In). The binding protein can be labeled with 131I, $^{111}$In and $^{99m}$TC using coupling techniques known in the imaging arts. Similarly, procedures for preparing and administering the imaging agent as well as capturing and processing images are well known in the imaging art and so are not discussed in detail herein. Similarly, methods for performing antibody-based immunotherapies are well known in the art. See, for example, U.S. Pat. No. 5,534,254.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

The following Examples discuss the production and characterization of a number of anti-hHGF monoclonal antibodies.

Example 1

Production of Anti-hHGF Monoclonal Antibodies

This Example describes the production of a number of anti-hHGF monoclonal antibodies.

Immunizations, fusions, and primary screens were conducted at MBS Inc. (Portland, Me.), following the Repetitive Immunization Multiple Sites (RIMMS) protocol. Five AJ mice and Five Balb/c mice were immunized with recombinant human HGF (R&D Systems, Minneapolis, Minn.; Catalog No. 294-HGN-025). Two mice with sera displaying highest anti-HGF activity by Enzyme Linked Immunosorbent Assay (ELISA) were chosen for subsequent fusion. Spleens and lymph nodes from the appropriate mice were harvested. B-cells then were harvested and fused with an myeloma line. Fusion products were serially diluted on one or more plates to near clonality. Supernatants from the resulting fusions were screened for their binding to hHGF by ELISA. Supernatants identified as containing antibodies to HGF were further characterized by in vitro functional testing as discussed in the following examples. A panel of hybridomas was selected and the hybridomas were subcloned and expanded. The monoclonal antibodies then were purified by affinity chromatography on Protein A/G resin under standard conditions.

Example 2

Sequence Analysis of Anti-hHGF Monoclonal Antibodies

This Example describes isotype and sequence analyses of the anti-hHGF monoclonal antibodies produced in Example 1.

a. Determination of HGF Murine Monoclonal Antibody Isotypes

The light-chain type and heavy chain isotype of each monoclonal antibody were determined using the IsoStrip Mouse Monoclonal Antibody Isotyping Kit in accordance the manufacturer's instructions (Roche Applied Science).

All the antibodies were determined to contain a Kappa immunoglobulin light chain and an IgG1 immunoglobulin heavy chain.

b. Determination of Nucleotide Sequences Encoding Immunoglobulin Heavy and Light Chain Variable Regions Total RNA was extracted from each monoclonal hybridoma cell line using the RNeasy Miniprep kit according to the manufacturer's instructions (Qiagen Venlo, The Netherlands). Full-length first strand cDNA was generated using the BD SMART™ RACE cDNA Amplification Kit according to the manufacturer's instructions (Clontech) using the oligonucleotide primers BD SMART II A (5' aagcagtggtatcaacgcagagtacgcggg 3') (SEQ ID NO. 85) and 5'-RACE CDS Primer (5' tttttttttttttttttttttttttttvn 3', where v=a, g, or c and n=a, g, c, or t) (SEQ ID NO. 86) for the purpose of 5' RACE (Rapid Amplification of cDNA Ends).

The variable regions of the Kappa and Heavy (IgG1) immunoglobulin chains were amplified by PCR (Polymerase Chain Reaction) using the Expand High-Fidelity PCR System (Roche Applied Science) according to the manufacturer's instructions. Heavy chain variable regions were amplified with the 5' oligonucleotide primer mix Universal Primer Mix A (mix of 5' ctaatacgactcactatagggcaagcagtggtatcaacgcagagt 3' (SEQ ID NO. 87) and 5' ctaatacgactcactatagggc 3'(SEQ ID NO. 88)) and a 3' IgG1 Constant Region specific primer, either 5' tatgcaaggcttacaaccaca 3' (SEQ ID NO. 89) or 5' gccagtggatagacagatgggggtgtcg 3' (SEQ ID NO. 90). Kappa chain variable regions were amplified with the 5' oligonucleotide primer mix Universal Primer Mix A and a 3' Kappa Constant Region specific primer, either 5' ctcattcctgttgaagctcttgacaat 3' (SEQ ID NO. 91) or 5' cgactgaggcacctccagatgtt 3' (SEQ ID NO. 92).

Individual PCR products were fractionated by agarose gel electrophoresis and purified using the Qiaquick Gel Purification kit according to the manufacturer's instructions (Qiagen). The PCR products were subsequently cloned into the pCR2.1 TOPO plasmid using the topoisomerase based cloning kit TOPO TA Cloning® Kit (with pCR®2.1-TOPO® vector) according to the manufacturer's instructions (Invitrogen, Carlsbad, Calif.) and transformed into DH5 bacteria using standard transformation techniques. Plasmid DNA isolated from transformed bacterial clones was sequenced using T7 (5' TAATACGACTCACTATAGGG 3') (SEQ ID NO. 93), M13 Forward (5' GTAAAACGACGGCCAGT 3') (SEQ ID NO. 94), and M13 Reverse primers (5' CAGGAAACAGCTATGACC 3') (SEQ ID NO. 95) by Agencourt Bioscience using standard dideoxy DNA sequencing methods to identify the sequence of the variable region sequences. The sequences were analyzed using Vector NTI software (Invitrogen, Carlsbad, Calif.) and the IMGT/V-Quest webserver (http://imgt.cines.fr/textes/vquest) to identify and confirm variable region sequences.

c. Determination of Nucleotide Sequences Encoding Immunoglobulin Heavy and Light Chain Constant Region Sequences for 1A3, 1D3, 1F3, and 2B8 Kappa and IgG1 Chains Full Length cDNAs for the 1A3, 1D3, and 1F3 IgG1 chains were PCR amplified from the cDNA created above using the forward primer 5' ggggacaagtttgtacaaaaaagcaggctgccacc atgaactttgggctcagattgattttcc 3' (start codon underlined) (SEQ ID NO. 96) and the reverse primer 5' ggggaccactttgtacaagaaagctgggttcatttaccaggagagtgggagagg 3' (stop codon underlined) (SEQ ID NO. 97). Full Length cDNA for the 2B8 IgG1 chain was amplified from the cDNA created above using the forward primer 5' ggggacaagtttgtacaaaaaagcaggctgccacc atggatggagctatatcatcctcttt 3' (start codon underlined) (SEQ ID NO. 98) and reverse primer 5' ggggaccactttgtacaagaaagctgggttcatttaccaggagagtgggagag 3' (stop codon underlined) (SEQ ID NO. 99).

Full Length cDNA for the 2B8 Kappa Chain was amplified using the forward primer 5' ggggacaagtttgtacaaaaaagcaggctgccaccatgaatcacagactctggtcttcata 3' (start codon underlined) (SEQ ID NO. 100) and the reverse primer 5' ggggaccactttgtacaagaaagctgggtctaacactcattcctgttgaagctc 3' (stop codon underlined) (SEQ ID NO. 101). PCR fragments were subcloned into pDONR221 (Invitrogen, Carlsbad, Calif.) by Gateway BP recombination reaction (Invitrogen, Carlsbad, Calif.) and sequenced by Agencourt Bioscience using standard dideoxy DNA sequencing methods to identify the sequence of the constant region and further confirm variable region sequences.

d. Sequence Analysis

Variable Regions (normal text) were identified using IMGT/V-QUEST webserver software (http://imgt.cines.fr/textes/vquest/). Signal Peptide sequences were predicted based on identification of the in frame start codon (ATG) that was upstream of the identified Variable Region. Signal Peptide sequences were identified and are underlined below.

The last nucleotide of each variable region is the first base of the next codon generated by the variable/constant region junction. This nucleotide is included in the variable region cause it is part of that exon. Amino acid sequences of the constant regions listed below include the translation of this junction codon.

In order to create the complete heavy or kappa chain antibody sequences, the variable region sequences noted below are combined with their respective constant region sequences (the signal sequences are underlined).

(1) 1A3 Heavy Chain Variable Region (SEQ ID NO. 1)

```
  1 atgaactttg ggctcagatt gatttttcctt gtccttgttt
    taaaaggtgt gaagtgtgaa 61 gtgcagctgg tggagtctgg gggaggctta gtgcagcctg
    gagggtccct gaaactctcc 121 tgtgcagcct ctgaattcac tttcagtaac tattacatgt
    cttgggttcg ccagactcca 181 gagaagaggc tgcagtgggt cgcatacatt agtcctggtg
    gtggtagctc ctactatcca 241 gccagtgtga agggtcgatt caccatctcc agagacaatg
    ccaagaacac cctgtacctg 301 caaatgagca gtctgaagtc tgaggacaca gccatgtatt
    actgtgcaag acaaggggat
```

```
361 ggttactacg gggactatgc tatggactac tggggtcaag
    gaacctcagt caccgtctcc 421 tcag
```

(2) 1A3 Kappa Light Chain Variable Region (SEQ ID NO. 3)

```
  1 atgagtgtgc ccactcaggt cctgggttg ctgctgctgt
    ggcttacaga tgccagatgt 61 gacatccaga tgactcagtc tccagcctcc ctatctgttt
    ctgtgggaga aactgtcacc 121 atcacatgtc gagcaagtga gaatatttat agtaatttag
    catggtatca gcagaaacag 181 ggaaaatctc ctcagctcct ggtctatgct gcaacaaact
    tagcagatgg tgtgccatca 241 aggttcagtg gcagtggatc aggcacacag ttttcccctca
    agatcaacag cctgcagtct 301 gaagattttg ggacttatta ctgtcaacat ttttggggta
    ctccgtacac gttcggaggg 361 gggaccaagc tggaaataaa ac
```

(3) 2B8 Heavy Chain Variable Region (SEQ ID NO. 11)

```
  1 atgggatgga gctatatcat cctcttttg gtagcaacag
    ctacagatgt ccactcccag 61 gtccaactga gcagcctgg ggctgaactg gtgaagcctg
    ggacttcagt gaagctgtcc 121 tgcaaggctt ctggctacac cttcaccacc tactggatgc
    actgggtgaa tcagaggcct 181 ggacaaggcc ttgagtggat tggagagatt aatcctacca
    acggtcatac taactacaat 241 gagaagttca gagcaaggc cacactgact gtagacaaat
    cctccagcac agcctacatg 301 caactcagca gcctgacatc tgaggactct gcggtctatt
    actgtgcaag aaactatgtt 361 ggtagcatct ttgactactg gggccaaggc accactctca
    cagtctcctc ag
```

(4) 2B8 Kappa Light Chain Variable Region (SEQ ID NO. 13)

```
  1 atggaatcac agactctggt cttcatatcc atactgctct
    ggttatatgg tgctgatggg 61 aacattgtaa tgacccaatc tcccaaaatc atgtccatgt
    cagtaggaga gagggtcacc 121 ttgagctgca aggccagtga gaatgtggtt tcttatgtat
    cctggtatca acagaaacca 181 gcgcagtctc ctaaactgct gatatacggg gcatccaacc
    ggaacactgg ggtccccgat 241 cgcttcacag gcagtggatc tgcaacagat ttcactctga
    ccatcagcag tgtgcgggct 301 gaagaccttg cagattatca ctgtgggcag agttacaact
    atccgtacac gttcggaggg 361 gggaccaggc tggaaataaa ac
```

(5) 2F8 Heavy Chain Variable Region (SEQ ID NO. 21)

```
  1 atggaatgga gctgggtctt tctcttcctc ctgtcagtaa
    ctgcaggtgt ccactgccag
```

```
 61 gtccagctga agcagtctgg agctgagctg gtgaggcctg
    ggacttcagt gaagatgtcc 121 tgcaaggctt ctggctacac cttcactacc tactatatac
    actgggtgaa tcagaggcct 181 ggacagggcc ttgagtggat tggaaagatt ggtcctggaa
    gtggtagtac ttactacaat 241 gagatgttca agacaaggc cacattgact gtagacacat
    cctccagcac agcctacatg 301 cagctcagca gcctgacatc tgacgactct gcggtctatt
    tctgtgcaag aaggggactg 361 ggacgtggct tgactactg gggccaaggc accactctca
    cagtctcctc ag
```

(6) 2F8 Kappa Light Chain Variable Region (SEQ ID NO. 23)

```
  1 atggagacag acacaatcct gctatgggtg ctgctgctct
    gggttccagg ctccactggt 61 gacattgtgc tgacccaatc tccagcttct ttggctgtgt
    ctctagggca gagggccacc 121 atctcctgca aggccagcca agtgttgat tatgatggta
    atagttatat caactggtac 181 caacagaaac aggacagcc acccaaagtc ctcatctatg
    ttgcatccaa tctagaatct 241 gggatcccag ccaggtttag tggcagtggg tctgggacag
    acttcaccct caacatccat 301 cctgtggagg aggaggatgc tgcaacctat tactgtcagc
    aaagtattga ggatcctccc 361 acgttcggtg ctgggaccaa gctggagctg aaac
```

(7) 3B6 Heavy Chain Variable Region (SEQ ID NO. 31)

```
  1 atggaatggc cttgtatctt tctcttcctc ctgtcagtaa
    ctgaaggtgt ccactcccag 61 gttcagctgc agcagtctgg ggctgaactg gtgaggcctg
    ggtcctcagt gaagatttcc 121 tgcaaggctt ctggctatgt attcagtagc tactggatga
    actgggtgaa gcagaggcct 181 ggacagggtc ttgagtggat tggacagatt tatcctggag
    atggtgatag taactacaat 241 ggaaacttca aggtaaagc cacactgact gcagacaaat
    cctccagtac agcctacatg 301 cagctcagca gcctaacatc tgaggactct gcggtctatt
    tctgtgcatc ccagctcggg 361 ctacgtgaga actactttga ctactgggc caaggcacca
    ctctcacagt ctcctcag
```

(8) 3B6 Kappa Light Chain Variable Region (2 possible ATG start codons (uppercase)) (SEQ ID NO. 33)

```
  1 ATGgacATGa ggaccctgc tcagtttctt ggaatcttgt
    tgctctggtt tccaggtatc 61 aaatgtgaca tcaagatgac ccagtctcca tcttccatgt
    atgcatctct aggagagaga
```

-continued

```
121 gtcacaatca cttgcaaggc gagtcaggac attaaaagct
    atttaagctg gttccagcag 181 aaaccaggga atctcctaa gaccctgatc tatcgtgtaa
    acagattggt agatggggtc 241 ccatcaaggt tcagtggcag tggatctggg caagattctt
    ctctcaccat caccagcctg 301 gagaatgaag atatgggaat ttattattgt ctacagtatg
    atgagtttcc gttcacgttc 361 ggagggggga ccaagctgga aataaagc
```

(9) 3D11 Heavy Chain Variable Region (SEQ ID NO. 41)
```
  1 atggctgtcc cggtgctgtt cctctgcctg gttgcatttc
    caagctgtgt cctgtcccag 61 gtacagctga aggagtcagg acctggcctg gtggcgccct
    cacagagcct gtccatcact 121 tgcactgtct ctgggttttc attaaccagc tatagtttac
    actgggttcg ccagcctcca 181 ggaaagggtc tggaatggct gggagtaata tgggctggtg
    gaaacacaaa ttataattcg 241 tctctcatgt ccagactgac catcaggaaa gacaactcca
    agagccaagt tttcttaaaa 301 atgaacagtc tgcaaactga tgacacagcc atgtactact
    gtgccagaga gaggtttgct 361 tactggggcc aagggactct ggtcactgtc tctgcag
```

(10) 3D11 Kappa Light Chain Variable Region (SEQ ID NO. 43)
```
  1 atggattttc aagtgcagat tttcagcttc ctgctaatca
    gtgcctcagt caaaatatcc 61 agaggacaaa ttgttctcac ccagtctcca gcaatcatgt
    ctgcatatcc aggggagaag 121 gtcaccatga cctgcagtgc cagctcaagt gtaagttaca
    tgcactggta ccagcagaag 181 tcaggcacct cccccaaaag atggatttat gacacatcca
    aactggcttc tggagtccct 241 gctcgcttca gtggcagtgg gtctgggacc tcttactccc
    tcacaatcag tagtatggag 301 gctgaagatg ctgccactta ttactgccag cagtggagta
    gtaacccact cacgttcggt 361 gctgggacca agctggagct gaaac
```

(11) 1D3 Heavy Chain Variable Region (SEQ ID NO. 51)
```
  1 atgaactttg ggctcagatt gattttcctt gtccttgttt
    taaaaggtgt gaagtgtgaa 61 gtgcagctgg tggagtctgg gggaggctta gtgcagcctg
    gagggtccct gaaactctcc 121 tgtgcagcct ctggattcac tttcagtgac tattacatgt
    cttgggttcg ccagactcca 181 gagaagaggc tggagtgggt cgcatacatt agtagtggtg
    gtggtagcac ctactatcca 241 gacagtgtga aggtcgatt caccatctcc agagacaatg
    ccaagaacac cctgtacctg 301 caaatgagca gtctgaagtc tgaggacaca gccatgtatt
    actgtgtgag acaagggggat
```

```
361 ggttattacg gggactatgc taiggactac tggggtcaag
    gaacctcagt catcgtctcc 421 tcag
```

(12) 1D3 Kappa Light Chain Variable Region (SEQ ID NO. 53)
```
  1 atgagtgtgc ccactcaggt cctggggttg ctgctgctgt
    ggcttacaga tgtcagatgt 61 gacatccaga tgactcagtc tccagcctcc ctatctgtat
    ctgtgggaga aactgtcacc 121 atcacatgtc gaacaagtga aaatatttac agtaatttag
    cgtggtatca gcagaaacag 181 ggaaaatctc ctcagctcct aatctatgct gcaacaaact
    tagcagatgg tgtgccatca 241 aggttcagtg gcagtggatc aggcacacag ttttccctca
    ggatcaacag cctgcagtct 301 gaagattttg ggaggttatta ctgtcaacat ttttggggga
    ctccgtacac gttcggaggg 361 gggaccaaac tggaaataaa ac
```

(13) 1F3 Heavy Chain Variable Region (SEQ ID NO. 61)
```
  1 atgaactttg ggctcagatt gattttcctt gtccttgttt
    taaaaggtgt gaagtgtgag 61 gtgcagctgg tggagtctgg gggaggctta gtgcagtctg
    gagggtccct gaaactctcc 121 tgtgcggcct ctggattcac tttcagtaac tatttcatgt
    cttgggttcg ccagactcca 181 gagaagaggc tggagtgggt cgcatatatt agtagtggtg
    gtggtagcac ctactatcca 241 gacagtgtga aggtcgatt caccatctct agagacaatg
    ccaagaacac cctgtacctg 301 caaatgagca gtctgaagtc tgaggacaca gccatgtatt
    actgtgtaag acaagggggat 361 ggttactacg gggactatgc tatggactac tggggtcaag
    gaacctcagt caccgtctcc 421 tcag
```

(14) 1F3 Kappa Light Chain Variable Region (SEQ ID NO. 63)
```
  1 atgagtgtgc ccactcaggt cctggggttg ctgctgctgt
    ggcttacaga tgccagatgt 61 gacatccaga tgactcagtc tccagcctcc ctatctgtat
    ctgtgggaga aactgtcacc 121 atcacatgtc gagcaagtga aaatatttac agtaatttag
    catggtatca gcagaaacag 181 ggaaaatctc ctcagctcct ggtctatgat gcaacacact
    taccagatgg tgtgccatca 241 aggttcagtg gcagtggatc aggcacacag ttttccctca
    agatcaacag cctgcagtct 301 gaagatttg ggagttatta ctgtcaacat ttttgggta
    ctccgtacac gttggagggg 361 gggaccagac tggaaattaa ac
```

(15) 3A12 Heavy Chain Variable Region (SEQ ID NO. 71)
```
  1 atgaactttg ggctcagatt gattttcctt gtccttgttt
    taaaaggtgt gaagtgtgaa
```

```
 61 gtgcagctgg tggagtctgg gggaggctta gtgcagcctg
    gagggtccct gaaaatctcc 121 tgtgcagcct ctggatttac tttcagtaac tatttcatgt
    cttgggttcg ccagactcca 181 gagaagaggc tggagtgggt cgcatacatt agtagtggtg
    gtggtagcac ctactatcca 241 gacagtgtga agggtcgatt caccatctcc agagacaatg
    ccaagaacac cctgtacctg 301 caaatgaaca gtctgaagtc tgaggacaca gccatgtatt
    actgtgtaag acaaggagat 361 ggttactatg ggactatgc tatggactac tggggtcaag
    gaacctcagt caccgtctcc 421 tcag
```

(16) 3A12 Kappa Light Chain Variable Region (SEQ ID NO. 73)
```
  1 atgagtgtgc ccactcaggt cctggggttg ctgctgctgt
    ggcttacaga tgccagatgt 61 gacatccaga tgactcagtc gccagcctcc ctatctgtat
    ctgtgggaga aactgtcacc 121 atcacatgtc gagcaagtga gaatatttac attaatttag
    catggtatca gcagaaacag 181 ggaaaatctc ctcagctcct ggtccatgct gcaacaaagt
    tagcagatgg tgtgccatca 241 aggttcagtg gcagtggatc aggcacacag tattccctca
    agatcaacag cctgcagtct 301 gaagattttg ggagttatta ctgtcaacat ttttggggta
    ctccgtacac gttcggaggg 361 gggaccaaac tagaaataaa ac
```

(17) Reference Mouse IgG1 Heavy Chain Constant Region (J00453) (SEQ ID NO. 81)
```
  1 ccaaaacgac accccatct gtctatccac tggcccctgg
    atctgctgcc caaactaact 61 ccatggtgac cctgggatgc ctggtcaagg gctatttccc
    tgagccagtg acagtgacct 121 ggaactctgg atccctgtcc agcggtgtgc acaccttccc
    agctgtcctg gagtctgacc 181 tctacactct gagcagctca gtgactgtcc cctccagccc
    tcggcccagc gagaccgtca 241 cctgcaacgt tgcccacccg ccagcagca ccaaggtgga
    caagaaaatt gtgcccaggg 301 attgtggttg taagccttgc atatgtacag tcccagaagt
    atcatctgtc ttcatcttcc 361 ccccaaagcc caaggatgtg ctcaccatta ctctgactcc
    taaggtcacg tgtgttgtgg 421 tagacatcag caaggatgat cccgaggtcc agttcagctg
    gtttgtagat gatgtggagg 481 tgcacacagc tcagacgcaa ccccgggagg agcagttcaa
    cagcactttc cgctcagtca 541 gtgaacttcc catcatgcac caggactggc tcaatggcaa
    ggagttcaaa tgcagggtca 601 acagtgcagc tttccctgcc cccatcgaga aaaccatctc
    caaaaccaaa ggcagaccga 661 aggctccaca ggtgtacacc attccacctc ccaaggagca
    gatggccaag ataaagtca
```

```
721 gtctgacctg catgataaca gacttcttcc ctgaagacat
    tactgtggag tggcagtgga 781 atgggcagcc agcggagaac tacaagaaca ctcagcccat
    catgaacacg aatggctctt 841 acttcgtcta cagcaagctc aatgtgcaga gagcaactg
    ggaggcagga aatactttca 901 cctgctctgt gttacatgag ggcctgcaca accaccatac
    tgagaagagc ctctcccact 961 ctcctggtaa atga
```

(18) Mouse IgG1 Heavy Chain Constant Region Determined for 1A3, 1D3, 1F3, and 2B8 (derived from AJ strain mice) (SEQ ID NO. 82)
```
  1 ccaaaacgac accccatct gtctatccac tggcccctgg
    atctgctgcc caaactaact 61 ccatggtgac cctgggatgc ctggtcaagg gctatttccc
    tgagccagtg acagtgacct 121 ggaactctgg atccctgtcc agcggtgtgc acaccttccc
    agctgtcctg cagtctgacc 181 tctacactct gagcagctca gtgactgtcc cctccagcac
    ctggcccagc gagaccgtca 241 cctgcaacgt tgcccacccg ccagcagca ccaaggtgga
    caagaaaatt gtgcccaggg 301 attgtggttg taagccttgc atatgtacag tcccagaagt
    atcatctgtc ttcatcttcc 361 ccccaaagcc caaggatgtg ctcaccatta ctctgactcc
    taaggtcacg tgtgttgtgg 421 tagacatcag caaggatgat cccgaggtcc agttcagctg
    gtttgtagat gatgtggagg 481 tgcacacagc tcagacgcaa ccccgggagg agcagttcaa
    cagcactttc cgctcagtca 541 gtgaacttcc catcatgcac caggactggc tcaatggcaa
    ggagttcaaa tgcagggtca 601 acagtgcagc tttccctgcc cccatcgaga aaaccatctc
    caaaaccaaa ggcagaccga 661 aggctccaca ggtgtacacc attccacctc ccaaggagca
    gatggccaag ataaagtca 721 gtctgacctg catgataaca gacttcttcc ctgaagacat
    tactgtggag tggcagtgga 781 atgggcagcc agcggagaac tacaagaaca ctcagcccat
    catggacaca gatggctctt 841 acttcgtcta cagcaagctc aatgtgcaga gagcaactg
    ggaggcagga aatactttca 901 cctgctctgt gttacatgag ggcctgcaca accaccatac
    tgagaagagc ctctcccact 961 ctcctggtaa atga
```

(19) Reference Mouse Kappa Light Chain Constant Region (V00807) and Mouse Kappa Light Chain Constant Region Determined for 1D3, 1F3, and 2B8 (derived from AJ strain mice) (SEQ ID NO. 83)
```
  1 gggctgatgc tgcaccaact gtatccatct tcccaccatc
    cagtgagcag ttaacatctg 61 gaggtgcctc agtcgtgtgc ttcttgaaca acttctaccc
    caaagacatc aatgtcaagt
```

-continued

```
121 ggaagattga tggcagtgaa cgacaaaatg gcgtcctgaa
    cagttggact gatcaggaca 181 gcaaagacag cacctacagc atgagcagca ccctcacgtt
    gaccaaggac gagtatgaac 241 gacataacag ctatacctgt gaggccactc acaagacatc
    aacttcaccc attgtcaaga 301 gcttcaacag gaatgagtgt tag
```

(20) Mouse Kappa Light Chain Constant Region Determined for 1A3 containing one altered nucleotide compared to 1D3, 1F3, and 2B8 (underlined) (SEQ ID NO. 84)

```
  1 gggctgatgc tgcaccaact gtatccatct tcccaccatc
    cagtgagcag ttaacatctg 61 gaggtgcctc agtcgtgtgc ttcttgaaca acttctaccc
    caaagacatc aatgtcaagt 121 ggaagattga tggcagtgaa cgacaaaatg gcgtcctgaa
    cagttggact gatcaggaca 181 gcaaagacag cacctacagc atgagcagca ccctcatgtt
    gaccaaggac gagtatgaac 241 gacataacag ctatacctgt gaggccactc acaagacatc
    aacttcaccc attgtcaaga 301 gcttcaacag gaatgagtgt tag
```

Each of the amino acid sequences defining the immunoglobulin heavy chain variable regions for the antibodies produced in Example 1 are set forth in FIG. 2. Each of the sequences are aligned with one another and the sequences defining the signal peptide, $CDR_1$, $CDR_2$ and $CDR_3$ are identified by boxes. FIG. 3 shows an alignment of the separate $CDR_1$, $CDR_2$ and $CDR_3$ sequences for each of the antibodies.

Each of the amino acid sequences defining the immunoglobulin light chain variable regions for each of the antibodies produced in Example 1 are set forth in FIG. 4. Each of the sequences are aligned with one another and the sequences defining the signal peptide, $CDR_1$, $CDR_2$ and $CDR_3$ are identified by boxes. FIG. 5 shows an alignment of the separate $CDR_1$, $CDR_2$ and $CDR_3$ sequences for each of the antibodies.

For convenience, Table 1 provides a concordance chart showing the correspondence between the antibody sequences discussed in this Example with those presented in the Sequence Listing.

TABLE 1

| SEQ. ID NO. | Protein or Nucleic Acid |
| --- | --- |
| 1 | Heavy Chain Variable Region 1A3 - nucleic acid |
| 2 | Heavy Chain Variable Region 1A3 - protein |
| 3 | Light (kappa) Chain Variable Region 1A3 - nucleic acid |
| 4 | Light (kappa) Chain Variable Region 1A3 - protein |
| 5 | Heavy Chain $CDR_1$ 1A3 |
| 6 | Heavy Chain $CDR_2$ 1A3 |
| 7 | Heavy Chain $CDR_3$ 1A3 |
| 8 | Light (kappa) Chain $CDR_1$ 1A3 |
| 9 | Light (kappa) Chain $CDR_2$ 1A3 |
| 10 | Light (kappa) Chain $CDR_3$ 1A3 |
| 11 | Heavy Chain Variable Region 2B8 - nucleic acid |
| 12 | Heavy Chain Variable Region 2B8 - protein |
| 13 | Light (kappa) Chain Variable Region 2B8 - nucleic acid |
| 14 | Light (kappa) Chain Variable Region 2B8 - protein |
| 15 | Heavy Chain $CDR_1$ 2B8 |
| 16 | Heavy Chain $CDR_2$ 2B8 |
| 17 | Heavy Chain $CDR_3$ 2B8 |
| 18 | Light (kappa) Chain $CDR_1$ 2B8 |
| 19 | Light (kappa) Chain $CDR_2$ 2B8 |
| 20 | Light (kappa) Chain $CDR_3$ 2B8 |
| 21 | Heavy Chain Variable Region 2F8 - nucleic acid |
| 22 | Heavy Chain Variable Region 2F8 - protein |
| 23 | Light (kappa) Chain Variable Region 2F8 - nucleic acid |
| 24 | Light (kappa) Chain Variable Region 2F8 - protein |
| 25 | Heavy Chain $CDR_1$ 2F8 |
| 26 | Heavy Chain $CDR_2$ 2F8 |
| 27 | Heavy Chain $CDR_3$ 2F8 |
| 28 | Light (kappa) Chain $CDR_1$ 2F8 |
| 29 | Light (kappa) Chain $CDR_2$ 2F8 |
| 30 | Light (kappa) Chain $CDR_3$ 2F8 |
| 31 | Heavy Chain Variable Region 3B6 - nucleic acid |
| 32 | Heavy Chain Variable Region 3B6 - protein |
| 33 | Light (kappa) Chain Variable Region 3B6 - nucleic acid |
| 34 | Light (kappa) Chain Variable Region 3B6 - protein |
| 35 | Heavy Chain $CDR_1$ 3B6 |
| 36 | Heavy Chain $CDR_2$ 3B6 |
| 37 | Heavy Chain $CDR_3$ 3B6 |
| 38 | Light (kappa) Chain $CDR_1$ 3B6 |
| 39 | Light (kappa) Chain $CDR_2$ 3B6 |
| 40 | Light (kappa) Chain $CDR_3$ 3B6 |
| 41 | Heavy Chain Variable Region 3D11 - nucleic acid |
| 42 | Heavy Chain Variable Region 3D11 - protein |
| 43 | Light (kappa) Chain Variable Region 3D11 - nucleic acid |
| 44 | Light (kappa) Chain Variable Region 3D11 - protein |
| 45 | Heavy Chain $CDR_1$ 3D11 |
| 46 | Heavy Chain $CDR_2$ 3D11 |
| 47 | Heavy Chain $CDR_3$ 3D11 |
| 48 | Light (kappa) Chain $CDR_1$ 3D11 |
| 49 | Light (kappa) Chain $CDR_2$ 3D11 |
| 50 | Light (kappa) Chain $CDR_3$ 3D11 |
| 51 | Heavy Chain Variable Region 1D3 - nucleic acid |
| 52 | Heavy Chain Variable Region 1D3 - protein |
| 53 | Light (kappa) Chain Variable Region 1D3 - nucleic acid |
| 54 | Light (kappa) Chain Variable Region 1D3 - protein |
| 55 | Heavy Chain $CDR_1$ 1D3 |
| 56 | Heavy Chain $CDR_2$ 1D3 |
| 57 | Heavy Chain $CDR_3$ 1D3 |
| 58 | Light (kappa) Chain $CDR_1$ 1D3 |
| 59 | Light (kappa) Chain $CDR_2$ 1D3 |
| 60 | Light (kappa) Chain $CDR_3$ 1D3 |
| 61 | Heavy Chain Variable Region 1F3 - nucleic acid |
| 62 | Heavy Chain Variable Region 1F3 - protein |
| 63 | Light (kappa) Chain Variable Region 1F3 - nucleic acid |
| 64 | Light (kappa) Chain Variable Region 1F3 - protein |
| 65 | Heavy Chain $CDR_1$ 1F3 |
| 66 | Heavy Chain $CDR_2$ 1F3 |
| 67 | Heavy Chain $CDR_3$ 1F3 |
| 68 | Light (kappa) Chain $CDR_1$ 1F3 |
| 69 | Light (kappa) Chain $CDR_2$ 1F3 |
| 70 | Light (kappa) Chain $CDR_3$ 1F3 |
| 71 | Heavy Chain Variable Region 3A12 - nucleic acid |
| 72 | Heavy Chain Variable Region 3A12 - protein |
| 73 | Light (kappa) Chain Variable Region 3A12 - nucleic acid |
| 74 | Light (kappa) Chain Variable Region 3A12 - protein |
| 75 | Heavy Chain $CDR_1$ 3A12 |
| 76 | Heavy Chain $CDR_2$ 3A12 |
| 77 | Heavy Chain $CDR_3$ 3A12 |
| 78 | Light (kappa) Chain $CDR_1$ 3A12 |
| 79 | Light (kappa) Chain $CDR_2$ 3A12 |
| 80 | Light (kappa) Chain $CDR_3$ 3A12 |

Also, for convenience, the following sequences represent the actual or contemplated full length heavy and light chain sequences (i.e., containing both the variable and constant region sequences) for each of the antibodies described in this Example. It is noted that the constant regions of the murine antibodies 2F8, 3A12, 3B6, and 3D11 were not sequenced but are presumed to have the same constant region sequences as the 1D3, 1F3, and 2B8 antibodies, which were sequenced, as they were all derived from AJ strain mice. It is appreciated, however, that the variable region sequences described herein can be ligated to each of a number of other constant region sequences known to those skilled in the art to produce active full length immunoglobulin heavy and light chains.

(1) Nucleic Acid Sequence Encoding the Full Length 1A3 Heavy Chain Sequence (1A3 Heavy Chain Variable Region and IgG1 Constant Region) (signal sequence underlined) (SEQ ID NO. 122)

```
   1 atgaactttg ggctcagatt gattttcctt gtccttgttt
     taaaaggtgt gaagtgtgaa 61 gtgcagctgg tggagtctgg gggaggctta gtgcagcctg
     gagggtccct gaaactctcc 121 tgtgcagcct ctgaattcac tttcagtaac tattacatgt
     cttgggttcg ccagactcca 181 gagaagaggc tgcagtgggt cgcatacatt agtcctggtg
     gtggtagctc ctactatcca 241 gccagtgtga agggtcgatt caccatctcc agagacaatg
     ccaagaacac cctgtacctg 301 caaatgagca gtctgaagtc tgaggacaca gccatgtatt
     actgtgcaag acaaggggat 361 ggttactacg ggactatgc tatggactac tggggtcaag
     gaacctcagt caccgtctcc 421 tcagccaaaa cgacaccccc atctgtctat ccactggccc
     ctggatctgc tgcccaaact 481 aactccatgg tgaccctggg atgcctggtc aagggctatt
     tccctgagcc agtgacagtg 541 acctggaact ctggatccct gtccagcggt gtgcacacct
     tcccagctgt cctgcagtct 601 gacctctaca ctctgagcag ctcagtgact gtcccctcca
     gcacctggcc cagcgagacc 661 gtcacctgca acgttgccca cccggccagc agcaccaagg
     tggacaagaa aattgtgccc 721 agggattgtg gttgtaagcc ttgcatatgt acagtcccag
     aagtatcatc tgtcttcatc 781 ttccccccaa agcccaagga tgtgctcacc attactctga
     ctcctaaggt cacgtgtgtt 841 gtggtagaca tcagcaagga tgatcccgag gtccagttca
     gctggtttgt agatgatgtg 901 gaggtgcaca cagctcagac gcaaccccgg gaggagcagt
     tcaacagcac tttccgctca 961 gtcagtgaac ttcccatcat gcaccaggac tggctcaatg
     gcaaggagtt caaatgcagg 1021 gtcaacagtg cagctttccc tgcccccatc gagaaaacca
     tctccaaaac caaaggcaga 1081 ccgaaggctc cacaggtgta caccattcca cctcccaagg
     agcagatggc caaggataaa 1141 gtcagtctga cctgcatgat aacagacttc ttccctgaag
     acattactgt ggagtggcag 1201 tggaatgggc agccagcgga gaactacaag aacactcagc
     ccatcatgga cacagatggc 1261 tcttacttcg tctacagcaa gctcaatgtg cagaagagca
     actgggaggc aggaaatact 1321 ttcacctgct ctgtgttaca tgaggcctg cacaaccacc
     atactgagaa gagcctctcc 1381 cactctcctg gtaaatga
```

(2) Protein Sequence Defining the Full Length 1A3 Heavy Chain Sequence (1A3 Heavy Chain Variable Region and IgG1 Constant Region) (without signal sequence) (SEQ ID NO. 123)

```
   1 evqlvesggg lvqpggslkl scaaseftfs nyymswvrqt
     pekrlqwvay ispgggssyy 61 pasvkgrfti srdnakntly lqmsslksed tamyycarqg
     dgyygdyamd ywgqgtsvtv 121 ssakttppsv yplapgsaaq tnsmvtlgcl vkgyfpepvt
     vtwnsgslss gvhtfpavlq 181 sdlytlsssv tvpsstwpse tvtcnvahpa sstkvdkkiv
     prdcgckpci ctvpevssvf 241 ifppkpkdvl titltpkvtc vvvdiskddp evqfswfvdd
     vevhtaqtqp reeqfnstfr 301 svselpimhq dwlngkefkc rvnsaafpap iektisktkg
     rpkapqvyti pppkeqmakd 361 kvsltcmitd ffpeditvew qwngqpaeny kntqpimdtd
     gsyfvyskln vqksnweagn 421 tftcsvlheg lhnhhteksl shspgk
```

(3) Nucleic Acid Sequence Encoding the Full Length 1A3 Light Chain Sequence (1A3 Kappa Variable Region and Constant Region) (signal sequence underlined) (SEQ ID NO. 124)

```
   1 atgagtgtgc ccactcaggt cctggggttg ctgctgctgt
     ggcttacaga tgccagatgt 61 gacatccaga tgactcagtc tccagcctcc ctatctgttt
     ctgtgggaga aactgtcacc 121 atcacatgtc gagcaagtga gaatatttat agtaatttag
     catggtatca gcagaaacag 181 ggaaaatctc ctcagctcct ggtctatgct gcaacaaact
     tagcagatgg tgtgccatca 241 aggttcagtg gcagtggatc aggcacacag ttttccctca
     agatcaacag cctgcagtct 301 gaagattttg ggacttatta ctgtcaacat ttttggggta
     ctccgtacac gttcggaggg 361 gggaccaagc tggaaataaa acgggctgat gctgcaccaa
     ctgtatccat cttcccacca 421 tccagtgagc agttaacatc tggaggtgcc tcagtcgtgt
     gcttcttgaa caacttctac 481 cccaaagaca tcaatgtcaa gtggaagatt gatggcagtg
     aacgacaaaa tggcgtcctg 541 aacagttgga ctgatcagga cagcaaagac agcacctaca
     gcatgagcag caccctcatg 601 ttgaccaagg acgagtatga acgacataac agctatacct
     gtgaggccac tcacaagaca 661 tcaacttcac ccattgtcaa gagcttcaac aggaatgagt
     gttag
```

(4) Protein Sequence Defining the Full Length 1A3 Light Chain Sequence (1A3 Kappa Variable Region and Constant Region) (without signal sequence) (SEQ ID NO. 125)

```
   1 diqmtqspas lsvsvgetvt itcraseniy snlawyqqkq
     gkspqllvya atnladgvps 61 rfsgsgsgtq fslkinslqs edfgtyycqh fwgtpytfgg
     gtkleikrad aaptvsifpp
```

```
121 sseqltsgga svvcflnnfy pkdinvkwki dgserqngvl
    nswtdqdskd stysmsstlm 181 ltkdeyerhn sytceathkt stspivksfn rnec
```

(5) Nucleic Acid Sequence Encoding the Full Length 2B8 Heavy Chain Sequence (2B8 Heavy Chain Variable Region and IgG1 Constant Region) (signal sequence underlined) (SEQ ID NO. 126)

```
   1 atgggatgga gctatatcat cctcttttg gtagcaacag
     ctacagatgt ccactccag 61 gtccaactgc agcagcctgg ggctgaactg gtgaagcctg
     ggacttcagt gaagctgtcc 121 tgcaaggctt ctggctacac cttcaccacc tactggatgc
     actgggtgaa tcagaggcct 181 ggacaaggcc ttgagtggat tggagagatt aatcctacca
     acggtcatac taactacaat 241 gagaagttca gagcaaggc cacactgact gtagacaaat
     cctccagcac agcctacatg 301 caactcagca gcctgacatc tgaggactct gcggtctatt
     actgtgcaag aaactatgtt 361 ggtagcatct ttgactactg gggccaaggc accactctca
     cagtctcctc agccaaaacg 421 acacccccat ctgtctatcc actggcccct ggatctgctg
     cccaaactaa ctccatggtg 481 accctgggat gcctggtcaa gggctatttc cctgagccag
     tgacagtgac ctggaactct 541 ggatccctgt ccagcggtgt gcacaccttc ccagctgtcc
     tgcagtctga cctctacact 601 ctgagcagct cagtgactgt ccctccagc acctggccca
     gcgagaccgt cacctgcaac 661 gttgccaccc ggccagcag caccaaggtg gacaagaaaa
     ttgtgcccag ggattgtggt 721 tgtaagcctt gcatatgtac agtcccagaa gtatcatctg
     tcttcatctt ccccccaaag 781 cccaaggatg tgctcaccat tactctgact cctaaggtca
     cgtgtgttgt ggtagacatc 841 agcaaggatg atcccgaggt ccagttcagc tggtttgtag
     atgatgtgga ggtgcacaca 901 gctcagacgc aaccccggga ggagcagttc aacagcactt
     tccgctcagt cagtgaactt 961 cccatcatgc accaggactg gctcaatggc aaggagttca
     aatgcagggt caacagtgca 1021 gctttccctg cccccatcga gaaaaccatc tccaaaacca
     aaggcagacc gaaggctcca 1081 caggtgtaca ccattccacc tcccaaggag cagatggcca
     aggataaagt cagtctgacc 1141 tgcatgataa cagacttctt ccctgaagac attactgtgg
     agtggcagtg gaatgggcag 1201 ccagcggaga actacaagaa cactcagccc atcatggaca
     cagatggctc ttacttcgtc 1261 tacagcaagc tcaatgtgca gaagagcaac tggggaggcag
     gaaatacttt cacctgctct 1321 gtgttacatg agggcctgca caaccaccat actgagaaga
     gcctctccca ctctcctggt 1381 aaatga
```

(6) Protein Sequence Defining the Full Length 2B8 Heavy Chain Sequence (2B8 Heavy Chain Variable Region and IgG1 Constant Region) (without signal sequence) (SEQ ID NO. 127)

```
   1 qvqlqqpgae lvkpgtsvkl sckasgytft tywmhwvnqr
     pgqglewige inptnghtny 61 nekfkskatl tvdkssstay mqlssltsed savyycarny
     vgsifdywgq gttltvssak 121 ttppsvypla pgsaaqtnsm vtlgclvkgy fpepvtvtwn
     sgslssgvht fpavlqsdly 181 tlsssvtvps stwpsetvtc nvahpasstk vdkkivprdc
     gckpcictvp evssvfifpp 241 kpkdvltitl tpkvtcvvvd iskddpevqf swfvddvevh
     taqtqpreeq fnstfrsvse 301 lpimhqdwln gkefkcrvns aafpapiekt isktkgrpka
     pqvytipppk eqmakdkvsl 361 tcmitdffpe ditvewqwng qpaenykntq pimdtdgsyf
     vysklnvqks nweagntftc 421 svlheglhnh htekslshsp gk
```

(7) Nucleic Acid Sequence Encoding the Full Length 2B8 Light Chain Sequence (2B8 Kappa Variable Region and Constant Region) (signal sequence underlined) (SEQ ID NO. 128)

```
   1 atggaatcac agactctggt cttcatatcc atactgctct
     ggttatatgg tgctgatggg 61 aacattgtaa tgacccaatc tcccaaatcc atgtccatgt
     cagtaggaga gagggtcacc 121 ttgagctgca aggccagtga gaatgtggtt tcttatgtat
     cctggtatca acagaaacca 181 gcgcagtctc ctaaactgct gatatacggg gcatccaacc
     ggaacactgg ggtccccgat 241 cgcttcacag gcagtggatc tgcaacagat ttcactctga
     ccatcagcag tgtgcgggct 301 gaagaccttg cagattatca ctgtgggcag agttacaact
     atccgtacac gttcggaggg 361 gggaccaggc tggaaataaa acgggctgat gctgcaccaa
     ctgtatccat cttcccacca 421 tccagtgagc agttaacatc tggaggtgcc tcagtcgtgt
     gcttcttgaa caacttctac 481 cccaaagaca tcaatgtcaa gtggaagatt gatggcagtg
     aacgacaaaa tggcgtcctg 541 aacagttgga ctgatcagga cagcaaagac agcacctaca
     gcatgagcag caccctcacg 601 ttgaccaagg acgagtatga acgacataac agctataccct
     gtgaggccac tcacaagaca 661 tcaacttcac ccattgtcaa gagcttcaac aggaatgagt
     gttag
```

(8) Protein Sequence Defining the Full Length 2B8 Light Chain Sequence (2B8 Kappa Variable Region and Constant Region) (without signal sequence) (SEQ ID NO. 129)

```
   1 nivmtqspks msmsvgervt lsckasenvv syvswyqqkp
     aqspkliyg asnrntgvpd 61 rftgsgsatd ftltissvra edladyhcgq synypytfgg
     gtrleikrad aaptvsifpp
```

(9) Nucleic Acid Sequence Encoding the Full Length 2F8 Heavy Chain Sequence (2F8 Heavy Chain Variable Region and IgG1 Constant Region) (signal sequence underlined) (SEQ ID NO. 130)

```
  1 atggaatgga gctgggtctt tctcttcctc ctgtcagtaa
    ctgcaggtgt ccactgccag 61 gtccagctga agcagtctgg agctgagctg gtgaggcctg
    ggacttcagt gaagatgtcc 121 tgcaaggctt ctggctacac cttcactacc tactatatac
    actgggtgaa tcagaggcct 181 ggacagggcc ttgagtggat tggaaagatt ggtcctggaa
    gtggtagtac ttactacaat 241 gagatgttca aagacaaggc cacattgact gtagacacat
    cctccagcac agcctacatg 301 cagctcagca gcctgacatc tgacgactct gcggtctatt
    tctgtgcaag aaggggactg 361 ggacgtggct ttgactactg gggccaaggc accactctca
    cagtctcctc agccaaaacg 421 acacccccat ctgtctatcc actggcccct ggatctgctg
    cccaaactaa ctccatggtg 481 accctgggat gcctggtcaa gggctatttc cctgagccag
    tgacagtgac ctggaactct 541 ggatccctgt ccagcggtgt gcacaccttc ccagctgtcc
    tgcagtctga cctctacact 601 ctgagcagct cagtgactgt cccctccagc acctggccca
    gcgagaccgt cacctgcaac 661 gttgcccacc cggccagcag caccaaggtg gacaagaaaa
    ttgtgcccag ggattgtggt 721 tgtaagcctt gcatatgtac agtcccagaa gtatcatctg
    tcttcatctt ccccccaaag 781 cccaaggatg tgctcaccat tactctgact cctaaggtca
    cgtgtgttgt ggtagacatc 841 agcaaggatg atcccgaggt ccagttcagc tggtttgtag
    atgatgtgga ggtgcacaca 901 gctcagacgc aaccccggga ggagcagttc aacagcactt
    tccgctcagt cagtgaactt 961 cccatcatgc accaggactg gctcaatggc aaggagttca
    aatgcagggt caacagtgca 1021 gctttccctg cccccatcga gaaaaccatc tccaaaacca
     aaggcagacc gaaggctcca 1081 caggtgtaca ccattccacc tcccaaggag cagatggcca
     aggataaagt cagtctgacc 1141 tgcatgataa cagacttctt ccctgaagac attactgtgg
     agtggcagtg gaatgggcag 1201 ccagcggaga actacaagaa cactcagccc atcatggaca
     cagatggctc ttacttcgtc 1261 tacagcaagc tcaatgtgca gaagagcaac tgggaggcag
     gaaatacttt cacctgctct 1321 gtgttacatg agggcctgca caaccaccat actgagaaga
     gcctctccca ctctcctggt 1381 aaatga
```

(10) Protein Sequence Defining the Full Length 2F8 Heavy Chain Sequence (2F8 Heavy Chain Variable Region and IgG1 Constant Region) (without signal sequence) (SEQ ID NO. 131)

```
  1 qvqlkqsgae lvrpgtsvkm sckasgytft tyyihwvngr
    pgqglewigk igpgsgstyy 61 nemfkdkatl tvdtssstay mqlssltsdd savyfcarrg
    lgrgfdywgq gttltvssak 121 ttppsvypla pgsaaqtnsm vtlgclvkgy fpepvtvtwn
    sgslssgvht fpavlqsdly 181 tlsssvtvps stwpsetvtc nvahpasstk vdkkivprdc
    gckpcictvp evssvfifpp 241 kpkdvltitl tpkvtcvvvd iskddpevqf swfvddvevh
    taqtqpreeq fnstfrsvse 301 lpimhqdwln gkefkcrvns aafpapiekt isktkgrpka
    pqvytipppk eqmakdkvsl 361 tcmitdffpe ditvewqwng qpaenykntq pimdtdgsyf
    vysklnvqks nweagntftc 421 svlheglhnh htekslshsp gk
```

(11) Nucleic Acid Sequence Encoding the Full Length 2F8 Light Chain Sequence (2F8 Kappa Variable Region and Constant Region) (signal sequence underlined) (SEQ ID NO. 132)

```
  1 atggagacag acacaatcct gctatgggtg ctgctgctct
    gggttccagg ctccactggt 61 gacattgtgc tgacccaatc tccagcttct ttggctgtgt
    ctctagggca gagggccacc 121 atctcctgca aggccagcca agtgttgat tatgatggta
    atagttatat caactggtac 181 caacagaaac caggacagcc acccaaagtc ctcatctatg
    ttgcatccaa tctagaatct 241 gggatcccag ccaggtttag tggcagtggg tctgggacag
    acttcaccct caacatccat 301 cctgtggagg aggaggatgc tgcaacctat tactgtcagc
    aaagtattga ggatcctccc 361 acgttcggtg ctgggaccaa gctggagctg aaacgggctg
    atgctgcacc aactgtatcc 421 atcttccac catccagtga gcagttaaca tctggaggtg
    cctcagtcgt gtgcttcttg 481 aacaacttct accccaaaga catcaatgtc aagtggaaga
    ttgatggcag tgaacgacaa 541 aatggcgtcc tgaacagttg gactgatcag gacagcaaag
    acagcaccta cagcatgagc 601 agcaccctca cgttgaccaa ggacgagtat gaacgacata
    acagctatac ctgtgaggcc 661 actcacaaga catcaacttc acccattgtc aagagcttca
    acaggaatga gtgttag
```

(12) Protein Sequence Defining the Full Length 2F8 Light Chain Sequence (2F8 Kappa Variable Region and Constant Region) (without signal sequence) (SEQ ID NO. 133)

```
  1 divltqspas lavslgqrat isckasqsvd ydgnsyinwy
    qqkpgqppkv liyvasnles 61 giparfsgsg sgtdftlnih pveeedaaty ycqqsiedpp
    tfgagtklel kradaaptvs
```

-continued 121 ifppsseqlt sggasvvcfl nnfypkdinv kwkidgserq
    ngvlnswtdq dskdstysms 181 stltltkdey erhnsytcea thktstspiv ksfnrnec

(13) Nucleic Acid Sequence Encoding the Full Length 3B6 Heavy Chain Sequence (3B6 Heavy Chain Variable Region and IgG1 Constant Region) (signal sequence underlined) (SEQ ID NO. 134)
  1 atggaatggc cttgtatctt tctcttcctc ctgtcagtaa
    ctgaaggtgt ccactcccag 61 gttcagctga gcagtctgg ggctgaactg gtgaggcctg
    ggtcctcagt gaagatttcc 121 tgcaaggctt ctggctatgt attcagtagc tactggatga
    actgggtgaa gcagaggcct 181 ggacaggtc ttgagtggat tggacagatt tatcctggag
    atggtgatag taactacaat 241 ggaaacttca agggtaaagc cacactgact gcagacaaat
    cctccagtac agcctacatg 301 cagctcagca gcctaacatc tgaggactct gcggtctatt
    tctgtgcatc ccagctcggg 361 ctacgtgaga actactttga ctactggggc caaggcacca
    ctctcacagt ctcctcagcc 421 aaaacgacac ccccatctgt ctatccactg gcccctggat
    ctgctgccca aactaactcc 481 atggtgaccc tgggatgcct ggtcaagggc tatttccctg
    agccagtgac agtgacctgg 541 aactctggat ccctgtccag cggtgtgcac accttcccag
    ctgtcctgca gtctgacctc 601 tacactctga gcagctcagt gactgtcccc tccagcacct
    ggcccagcga gaccgtcacc 661 tgcaacgttg cccaccgc cagcagcacc aaggtggaca
    agaaaattgt gcccaggat 721 tgtggttgta agccttgcat atgtacagtc ccagaagtat
    catctgtctt catcttcccc 781 ccaaagccca aggatgtgct caccattact ctgactccta
    aggtcacgtg tgttgtggta 841 gacatcagca aggatgatcc cgaggtccag ttcagctggt
    ttgtagatga tgtggaggtg 901 cacacagctc agacgcaacc ccgggaggag cagttcaaca
    gcactttccg ctcagtcagt 961 gaacttccca tcatgcacca ggactggctc aatggcaagg
    agttcaaatg cagggtcaac 1021 agtgcagctt ccctgcccc catcgagaaa accatctcca
    aaaccaaagg cagaccgaag 1081 gctccacagg tgtacaccat tccacctccc aaggagcaga
    tggccaagga taaagtcagt 1141 ctgacctgca tgataacaga cttcttccct gaagacatta
    ctgtggagtg gcagtggaat 1201 gggcagccag cggagaacta caagaacact cagcccatca
    tggacacaga tggctcttac 1261 ttcgtctaca gcaagctcaa tgtgcagaag agcaactggg
    aggcaggaaa actttcacc 1321 tgctctgtgt tacatgaggg cctgcacaac caccatactg
    agaagagcct ctcccactct 1381 cctggtaaat ga

(14) Protein Sequence Defining the Full Length 3B6 Heavy Chain Sequence (3B6 Heavy Chain Variable Region and IgG1 Constant Region) (without signal sequence) (SEQ ID NO. 135)
  1 qvqlqqsgae lvrpgssvki sckasgyvfs sywmnwvkqr
    pgqglewigq iypgdgdsny 61 ngnfkgkatl tadkssstay mqlssltsed savyfcasql
    glrenyfdyw gqgttltvss 121 akttppsvyp lapgsaaqtn smvtlgclvk gyfpepvtvt
    wnsgslssgv htfpavlqsd 181 lytlsssvtv psstwpsetv tcnvahpass tkvdkkivpr
    dcgckpcict vpevssvfif 241 ppkpkdvlti tltpkvtcvv vdiskddpev qfswfvddve
    vhtaqtqpre eqfnstfrsv 301 selpimhqdw lngkefkcrv nsaafpapie ktisktkgrp
    kapqvytipp pkeqmakdkv 361 sltcmitdff peditvewqw ngqpaenykn tqpimdtdgs
    yfvysklnvq ksnweagntf 421 tcsvlheglh nhhtekslsh spgk

(15) Nucleic Acid Sequence Encoding the Full Length 3B6 Light Chain Sequence (3B6 Kappa Variable Region and Constant Region) (signal sequence underlined) (SEQ ID NO. 136)
  1 ATGgacATGa ggacccctgc tcagtttctt ggaatcttgt
    tgctctggtt tccaggtatc 61 aaatgtgaca tcaagatgac ccagtctcca tcttccatgt
    atgcatctct aggagagaga 121 gtcacaatca cttgcaaggc gagtcaggac attaaaagct
    atttaagctg gttccagcag 181 aaaccaggga atctcctaa gaccctgatc tatcgtgtaa
    acagattggt agatggggtc 241 ccatcaaggt tcagtggcag tggatctggg caagattctt
    ctctcaccat caccagcctg 301 gagaatgaag atatgggaat ttattattgt ctacagtatg
    atgagttcc gttcacgttc 361 ggaggggga ccaagctgga aataaagcgg gctgatgctg
    caccaactgt atccatcttc 421 ccaccatcca gtgagcagtt aacatctgga ggtgcctcag
    tcgtgtgctt cttgaacaac 481 ttctaccca aagacatcaa tgtcaagtgg aagattgatg
    gcagtgaacg acaaaatggc 541 gtcctgaaca gttggactga tcaggacagc aaagacagca
    cctacagcat gagcagcacc 601 ctcacgttga ccaaggacga gtatgaacga cataacagct
    atacctgtga ggccactcac 661 aagacatcaa cttcacccat tgtcaagagc ttcaacagga
    atgagtgtta g

(16) Protein Sequence Defining the Full Length 3B6 Light Chain Sequence (3B6 Kappa Variable Region and Constant Region) (without signal sequence) (SEQ ID NO. 137)
  1 dikmtqspss myaslgervt itckasqdik sylswfqqkp
    gkspktliyr vnrlvdgvps 61 rfsgsgsgqd ssltitslen edmgiyyclq ydefpftfgg
    gtkleikrad aaptvsifpp 121 sseqltsgga svvcflnnfy pkdinvkwki dgserqngvl
    nswtdqdskd stysmsstlt 181 ltkdeyerhn sytcceathkt stspivksfn rnec

(17) Nucleic Acid Sequence Encoding the Full
Length 3D11 Heavy Chain Sequence (3D11 Heavy Chain
Variable Region and IgG1 Constant Region) (signal
sequence underlined) (SEQ ID NO. 138)
   1 <u>atgctgtcc cggtgctgtt cctctgcctg gttgcatttc
     caagctgtgt cctgtcccag</u>

61 gtacagctga aggagtcagg acctggcctg gtggcgccct
     cacagagcct gtccatcact 121 tgcactgtct ctgggttttc attaaccagc tatagtttac
     actgggttcg ccagcctcca 181 ggaaaggggtc tggaatggct gggagtaata tgggctggtg
     gaaacacaaa ttataattcg 241 tctctcatgt ccagactgac catcaggaaa gacaactcca
     agagccaagt tttcttaaaa 301 atgaacagtc tgcaaactga tgacacagcc atgtactact
     gtgccagaga gaggtttgct 361 tactggggcc aagggactct ggtcactgtc tctgcagcca
     aaacgacacc cccatctgtc 421 tatccactgg cccctggatc tgctgcccaa actaactcca
     tggtgaccct gggatgcctg 481 gtcaaggggct atttccctga gccagtgaca gtgacctgga
     actctggatc cctgtccagc 541 ggtgtgcaca cctttccagc tgtcctgcag tctgacctct
     acactctgag cagctcagtg 601 actgtcccct ccagcacctg cccagcgag accgtcacct
     gcaacgttgc ccacccggcc 661 agcagcacca aggtggacaa gaaaattgtg cccagggatt
     gtggttgtaa gccttgcata 721 tgtacagtcc cagaagtatc atctgtcttc atcttccccc
     caaagcccaa ggatgtgctc 781 accattactc tgactcctaa ggtcacgtgt gttgtggtag
     acatcagcaa ggatgatccc 841 gaggtccagt tcagctggtt tgtagatgat gtggaggtgc
     acacagctca gacgcaaccc 901 cgggaggagc agttcaacag cactttccgc tcagtcagtg
     aacttcccat catgcaccag 961 gactggctca atggcaagga gttcaaatgc agggtcaaca
     gtgcagcttt ccctgccccc 1021 atcgagaaaa ccatctccaa aaccaaaggc agaccgaagg
     ctccacaggt gtacaccatt 1081 ccacctccca aggagcagat ggccaaggat aaagtcagtc
     tgacctgcat gataacagac 1141 ttcttccctg aagacattac tgtggagtgg cagtggaatg
     ggcagccagc ggagaactac 1201 aagaacactc agcccatcat ggacacagat ggctcttact
     tcgtctacag caagctcaat 1261 gtgcagaaga gcaactggga ggcaggaaat actttcacct
     gctctgtgtt acatgagggc 1321 ctgcacaacc accatactga gaagagcctc tcccactctc
     ctggtaaatg a

(18) Protein Sequence Defining the Full Length
3D11 Heavy Chain Sequence (3D11 Heavy Chain Varia-
ble Region and IgG1 Constant Region) (without sig-
nal sequence) (SEQ ID NO. 139)
   1 qvqlkesgpg lvapsqslsi tctvsgfslt syslhwvrqp
     pgkglewlgv iwaggntnyn 61 sslmsrltir kdnskqqvfl kmnslqtddt amyycarerf
     aywgqgtlvt vsaaktttpps 121 vyplapgsaa qtnsmvtlgc lvkgyfpepv tvtwnsgsls
     sgvhtfpavl qsdlytlsss 181 vtvpsstwps etvtcnvahp asstkvdkki vprdcgckpc
     ictvpevssv fifppkpkdv 241 ltiltpkvt cvvvdiskdd pevqfswfvd dvevhtaqtq
     preeqfnstf rsvselpimh 301 qdwlngkefk crvnsaafpa piektisktk grpkapqvyt
     ipppkeqmak dkvsltcmit 361 dffpeditve wqwngqpaen ykntqpimdt dgsyfvyskl
     nvqksnweag ntftcsvlhe 421 glhnhhteks lshspgk

(19) Nucleic Acid Sequence Encoding the Full
Length 3D11 Light Chain Sequence (3D11 Kappa Var-
iable Region and Constant Region) (signal sequence
underlined) (SEQ ID NO. 140)
   1 <u>atggattttc aagtgcagat tttcagcttc ctgctaatca
     gtgcctcagt caaaatatcc</u>

61 <u>agagga</u>caaa ttgttctcac ccagtctcca gcaatcatgt
     ctgcatatcc aggggagaag 121 gtcaccatga cctgcagtgc cagctcaagt gtaagttaca
     tgcactggta ccagcagaag 181 tcaggcacct cccccaaaag atggatttat gacacatcca
     aactggcttc tggagtccct 241 gctcgcttca gtggcagtgg gtctgggacc tcttactccc
     tcacaatcag tagtatggag 301 gctgaagatg ctgccactta ttactgccag cagtggagta
     gtaacccact cacgttcggt 361 gctgggacca agctggagct gaaacgggct gatgctgcac
     caactgtatc catcttccca 421 ccatccagtg agcagttaac atctggaggt gcctcagtcg
     tgtgcttctt gaacaacttc 481 taccccaaag acatcaatgt caagtggaag attgatggca
     gtgaacgaca aaatggcgtc 541 ctgaacagtt ggactgatca ggacagcaaa gacagcacct
     acagcatgag cagcaccctc 601 acgttgacca ggacgagta tgaacgacat aacagctata
     cctgtgaggc cactcacaag 661 acatcaactt cacccattgt caagagcttc aacaggaatg
     agtgttag

(20) Protein Sequence Defining the Full Length
3D11 Light Chain Sequence (3D11 Kappa Variable Re-
gion and Constant Region) (without signal se-
quence) (SEQ ID NO. 141)
   1 qivltqspai msaypgekvt mtcsasssvs ymhwyqqksg
     tspkrwiydt sklasgvpar 61 fsgsgsgtsy sltissmeae daatyycqqw ssnpltfgag
     tklelkrada aptvsifpps 121 seqltsggas vvcflnnfyp kdinvkwkid gserqngvln
    swtdqdskds tysmsstltl 181 tkdeyerhns ytceathkts tspivksfnr nec

(21) Nucleic Acid Sequence Encoding the Full
Length 1D3 Heavy Chain Sequence (1D3 Heavy Chain
Variable Region and IgG1 Constant Region) (signal
sequence underlined) (SEQ ID NO. 142)

```
  1 atgaactttg ggctcagatt gattttcctt gtccttgttt
    taaaaggtgt gaagtgtgaa 61 gtgcagctgg tggagtctgg gggaggctta gtgcagcctg
    gagggtccct gaaactctcc 121 tgtgcagcct ctggattcac tttcagtgac tattacatgt
    cttgggttcg ccagactcca 181 gagaagaggc tggagtgggt cgcatacatt agtagtggtg
    gtggtagcac ctactatcca 241 gacagtgtga agggtcgatt caccatctcc cgagacaatg
    ccaagaacac cctgtacctg 301 caaatgagca gtctgaagtc tgaggacaca gccatatatt
    actgtgtgag acaaggggat 361 ggttattacg gggactatgc tatggactac tggggtcaag
    gaacctcagt catcgtctcc 421 tcagccaaaa cgacaccccc atctgtctat ccactggccc
    ctggatctgc tgcccaaact 481 aactccatgg tgaccctggg atgcctggtc aagggctatt
    tccctgagcc agtgacagtg 541 acctggaact ctggatccct gtccagcggt gtgcacacct
    tcccagctgt cctgcagtct 601 gacctctaca ctctgagcag ctcagtgact gtcccctcca
    gcacctggcc cagcgagacc 661 gtcacctgca acgttgccca cccggccagc agcaccaagg
    tggacaagaa aattgtgccc 721 agggattgtg gttgtaagcc ttgcatatgt acagtcccag
    aagtatcatc tgtcttcatc 781 ttccccccaa agcccaagga tgtgctcacc attactctga
    ctcctaaggt cacgtgtgtt 841 gtggtagaca tcagcaagga tgatcccgag gtccagttca
    gctggtttgt agatgatgtg 901 gaggtgcaca cagctcagac gcaacccccgg gaggagcagt
    tcaacagcac tttccgctca 961 gtcagtgaac ttcccatcat gcaccaggac tggctcaatg
    gcaaggagtt caaatgcagg 1021 gtcaacagtg cagctttccc tgcccccatc gagaaaacca
     tctccaaaac caaaggcaga 1081 ccgaaggctc cacaggtgta caccattcca cctcccaagg
     agcagatggc caaggataaa 1141 gtcagtctga cctgcatgat aacagacttc ttccctgaag
     acattactgt ggagtggcag 1201 tggaatgggc agccagcgga gaactacaag aacactcagc
     ccatcatgga cacagatggc 1261 tcttacttcg tctacagcaa gctcaatgtg cagaagagca
     actgggaggc aggaaatact 1321 ttcacctgct ctgtgttaca tgagggcctg cacaaccacc
     atactgagaa gagcctctcc 1381 cactctcctg gtaaatga
```

(22) Protein Sequence Defining the Full Length 1D3
Heavy chain sequence (1D3 Heavy Chain Variable Region and IgG1 Constant Region) (without signal sequence) (SEQ ID NO. 143)

```
  1 evqlvesggg lvqpggslkl scaasgftfs dyymswvrqt
    pekrlewvay issgggstyy 61 pdsvkgrfti srdnakntly lqmsslksed taiyycvrqg
    dgyygdyamd ywgqgtsviv 121 ssakttppsv yplapgsaaq tnsmvtlgcl vkgyfpepvt
    vtwnsgslss gvhtfpavlq 181 sdlytlsssv tvpsstwpse tvtcnvahpa sstkvdkkiv
    prdcgckpci ctvpevssvf 241 ifppkpkdvl titltpkvtc vvvdiskddp evqfswfvdd
    vevhtaqtqp reeqfnstfr 301 svselpimhq dwlngkefkc rvnsaafpap iektisktkg
    rpkapqvyti pppkeqmakd 361 kvsltcmitd ffpeditvew qwngqpaeny kntqpimdtd
    gsytvyskln vqksnweagn 421 tttcsvlheg lhnhhteksl shspgk
```

(23) Nucleic Acid Sequence Encoding the Full
Length 1D3 Light Chain Sequence (1D3 Kappa Variable Region and Constant Region) (signal sequence underlined) (SEQ ID NO. 144)

```
  1 atgagtgtgc ccactcaggt cctggggttg ctgctgctgt
    ggcttacaga tgtcagatgt 61 gacatacaga tgactcagtc tccagcctcc ctatctgtat
    ctgtgggaga aactgtcacc 121 atcacatgtc gaacaagtga gaatatttac agtaatttag
    cgtggtatca gcagaaacag 181 ggaaaatctc ctcagctcct aatctatgct gcaacaaact
    tagcagatgg tgtgccatca 241 aggttcagtg gcagtggatc aggcacacag ttttccctca
    ggatcaacag cctgcagtct 301 gaagattttg ggaggtatta ctgtcaacat ttttggggga
    ctccgtacac gttcggaggg 361 gggaccaaac tggaaataaa acgggctgat gctgcaccaa
    ctgtatccat cttcccacca 421 tccagtgagc agttaacatc tggaggtgcc tcagtcgtgt
    gcttcttgaa caacttctac 481 cccaaagaca tcaatgtcaa gtggaagatt gatggcagtg
    aacgacaaaa tggcgtcctg 541 aacagttgga ctgatcagga cagcaaagac agcacctaca
    gcatgagcag caccctcacg 601 ttgaccaagg acgagtatga acgacataac agctatacct
    gtgaggccac tcacaagaca 661 tcaacttcac ccattgtcaa gagcttcaac aggaatgagt
    gttag
```

(24) Protein Sequence Defining the Full Length 1D3
Light Chain Sequence (1D3 Kappa Variable Region and Constant Region) (without signal sequence) (SEQ ID NO. 145)

```
  1 diqmtqspas lsvsvgetvt itcrtseniy snlawyqqkq
    gkspqlliya atnladgvps 61 rfsgsgsgtq fslrinslqs edfgryycqh fwgtpytfgg
    gtkleikrad aaptvsifpp
```

```
121  sseqltsgga svvcflnnfy pkdinvkwki dgserqngvl
     nswtdqdskd stysmssstlt 181  ltkdeyerhn sytceathkt stspivksfn rnec
```

(25) Nucleic Acid Sequence Encoding the Full Length 1F3 Heavy Chain Sequence (1F3 Heavy Chain Variable Region and IgG1 Constant Region) (signal sequence underlined) (SEQ ID NO. 146)

```
   1 atgaactttg ggctcagatt gattttcctt gtccttgttt
     taaaaggtgt gaagtgtgag 61 gtgcagctgg tggagtctgg gggaggctta gtgcagtctg
     gagggtccct gaaactctcc 121 tgtgcggcct ctggattcac tttcagtaac tatttcatgt
     cttgggttcg ccagactcca 181 gagaagaggc tggagtgggt cgcatatatt agtagtggtg
     gtggtagcac ctactatcca 241 gacagtgtga agggtcgatt caccatctct agagacaatg
     ccaagaacac cctgtacctg 301 caaatgagca gtctgaagtc tgaggacaca gccatgtatt
     actgtgtaag acaaggggat 361 ggttactacg gggactatgc tatggactac tggggtcaag
     gaacctcagt caccgtctcc 421 tcagccaaaa cgacaccccc atctgtctat ccactggccc
     ctggatctgc tgcccaaact 481 aactccatgg tgaccctggg atgcctggtc aagggctatt
     tccctgagcc agtgacagtg 541 acctggaact ctggatccct gtccagcggt gtgcacacct
     tcccagctgt cctgcagtct 601 gacctctaca ctctgagcag ctcagtgact gtcccctcca
     gcacctggcc cagcgagacc 661 gtcacctgca acgttgccca cccggccagc agcaccaagg
     tggacaagaa aattgtgccc 721 agggattgtg gttgtaagcc ttgcatatgt acagtcccag
     aagtatcatc tgtcttcatc 781 ttccccccaa agcccaagga tgtgctcacc attactctga
     ctcctaaggt cacgtgtgtt 841 gtggtagaca tcagcaagga tgatcccgag gtccagttca
     gctggtttgt agatgatgtg 901 gaggtgcaca cagctcagac gcaacccggg gaggagcagt
     tcaacagcac tttccgctca 961 gtcagtgaac ttcccatcat gcaccaggac tggctcaatg
     gcaaggagtt caaatgcagg 1021 gtcaacagtg cagctttccc tgcccccatc gagaaaacca
     tctccaaaac caaaggcaga 1081 ccgaaggctc cacaggtgta caccattcca cctcccaagg
     agcagatggc caaggataaa 1141 gtcagtctga cctgcatgat aacagacttc ttccctgaag
     acattactgt ggagtggcag 1201 tggaatgggc agccagcgga gaactacaag aacactcagc
     ccatcatgga cacagatggc 1261 tcttacttcg tctacagcaa gctcaatgtg cagaagagca
     actgggaggc aggaaatact 1321 ttcacctgct ctgtgttaca tgaggccctg cacaaccacc
     atactgagaa gagcctctcc 1381 cactctcctg gtaaatga
```

(26) Protein Sequence Defining the Full Length 1F3 Heavy Chain Sequence (1F3 Heavy Chain Variable Region and IgG1 Constant Region) (without signal sequence) (SEQ ID NO. 147)

```
   1 evqlvesggg lvqsggslkl scaasgftfs nyfmswvrqt
     pekrlewvay issgggstyy 61 pdsvkgrfti srdnakntly lqmsslksed tamyycvrqg
     dgyygdyamd ywgqgtsvtv 121 ssakttppsv yplapgsaaq tnsmvtlgcl vkgyfpepvt
     vtwnsgslss gvhtfpavlq 181 sdlytlsssv tvpsstwpse tvtcnvahpa sstkvdkkiv
     prdcgckpci ctvpevssvf 241 ifppkpkdvl titltpkvtc vvvdiskddp evqfswfvdd
     vevhtaqtqp reeqfnstfr 301 svselpimhq dwlngkefkc rvnsaafpap iektisktkg
     rpkapqvyti pppkeqmakd 361 kvsltcmitd ffpeditvew qwngqpaeny kntqpimdtd
     gsyfvyskln vqksnweagn 421 tftcsvlheg lhnhhteksl shspgk
```

(27) Nucleic Acid Sequence Encoding the Full Length 1F3 Light Chain Sequence (1F3 Kappa Variable Region and Constant Region) (signal sequence underlined) (SEQ ID NO. 148)

```
   1 atgagtgtgc ccactcaggt cctggggttg ctgctgctgt
     ggcttacaga tgccagatgt 61 gacatccaga tgactcagtc tccagcctcc ctatctgtat
     ctgtgggaga aactgtcacc 121 atcacatgtc gagcaagtga aaatatttac agtaatttag
     catggtatca gcagaaacag 181 ggaaaatctc ctcagctcct ggtctatgat gcaacacact
     taccagatgg tgtgccatca 241 aggttcagtg gcagtggatc aggcacacag ttttccctca
     agatcaacag cctgcagtct 301 gaagattttg ggagttatta ctgtcaacat tttggggta
     ctccgtacac gtttggaggg 361 ggaccagac tggaaattaa acgggctgat gctgcaccaa
     ctgtatccat cttcccacca 421 tccagtgagc agttaacatc tggaggtgcc tcagtcgtgt
     gcttcttgaa caacttctac 481 cccaaagaca tcaatgtcaa gtggaagatt gatggcagtg
     aacgacaaaa tggcgtcctg 541 aacagttgga ctgatcagga cagcaaagac agcacctaca
     gcatgagcag caccctcacg 601 ttgaccaagg acgagtatga acgacataac agctatacct
     gtgaggccac tcacaagaca 661 tcaacttcac ccattgtcaa gagcttcaac aggaatgagt
     gttag
```

(28) Protein Sequence Defining the Full Length 1F3 Light Chain Sequence (1F3 Kappa Variable Region and Constant Region) (without signal sequence) (SEQ ID NO. 149)

```
   1 diqmtqspas lsvsvgetvt itcraseniy snlawyqqkq
     gkspqllvyd athlpdgvps 61 rfsgsgsgtq fslkinslqs edfgsyycqh fwgtpytfgg
     gtrleikrad aaptvsifpp
```

121 sseqltsgga svvcflnnfy pkdinvkwki dgserqngvl
    nswtdqdskd stysmsstlt 181 ltkdeyerhn sytceathkt stspivksfn rnec

(29) Nucleic Acid Sequence Encoding the Full
Length 3A12 Heavy Chain Sequence (3A12 Heavy Chain
Variable Region and IgG1 Constant Region) (signal
sequence underlined) (SEQ ID NO. 150)

```
   1 atgaactttg ggctcagatt gattttcctt gtccttgttt
     taaaaggtgt gaagtgtgaa 61 gtgcagctgg tggagtctgg gggaggctta gtgcagcctg
     gagggtccct gaaaatctcc 121 tgtgcagcct ctggatttac tttcagtaac tatttcatgt
     cttgggttcg ccagactcca 181 gagaagaggc tggagtgggt cgcatacatt agtagtggtg
     gtggtagcac ctactatcca 241 gacagtgtga agggtcgatt caccatctcc agagacaatg
     ccaagaacac cctgtacctg 301 caaatgaaca gtctgaagtc tgaggacaca gccatgtatt
     actgtgtaag acaaggagat 361 ggttactatg gggactatgc tatggactac tggggtcaag
     gaacctcagt caccgtctcc 421 tcagccaaaa cgacaccccc atctgtctat ccactggccc
     ctggatctgc tgcccaaact 481 aactccatgg tgaccctggg atgcctggtc aagggctatt
     tccctgagcc agtgacagtg 541 acctggaact ctggatccct gtccagcggt gtgcacacct
     tcccagctgt cctgcagtct 601 gacctctaca ctctgagcag ctcagtgact gtcccctcca
     gcacctggcc cagcgagacc 661 gtcacctgca acgttgccca cccggccagc agcaccaagg
     tggacaagaa aattgtgccc 721 agggattgtg gttgtaagcc ttgcatatgt acagtcccag
     aagtatcatc tgtcttcatc 781 ttccccccaa agcccaagga tgtgctcacc attactctga
     ctcctaaggt cacgtgtgtt 841 gtggtagaca tcagcaagga tgatcccgag gtccagttca
     gctggtttgt agatgatgtg 901 gaggtgcaca cagctcagac gcaaccccgg gaggagcagt
     tcaacagcac tttccgctca 961 gtcagtgaac ttcccatcat gcaccaggac tggctcaatg
     gcaaggagtt caaatgcagg 1021 gtcaacagtg cagctttccc tgcccccatc gagaaaacca
     tctccaaaac caaaggcaga 1081 ccgaaggctc cacaggtgta caccattcca cctcccaagg
     agcagatggc caaggataaa 1141 gtcagtctga cctgcatgat aacagacttc ttccctgaag
     acattactgt ggagtggcag 1201 tggaatgggc agccagcgga gaactacaag aacactcagc
     ccatcatgga cacagatggc 1261 tcttacttcg tctacagcaa gctcaatgtg cagaagagca
     actgggaggc aggaaatact 1321 ttcacctgct ctgtgttaca tgagggcctg cacaaccacc
     atactgagaa gagcctctcc 1381 cactctcctg gtaaatga
```

(30) Protein Sequence Defining the Full Length
3A12 Heavy Chain Sequence (3A12 Heavy Chain Variable Region and IgG1 Constant Region) (without signal sequence) (SEQ ID NO. 151)

```
   1 evqlvesggg lvqpggslki scaasgftfs nyfmswvrqt
     pekrlewvay issgggstyy 61 pdsvkgrfti srdnakntly lqmnslksed tamyycvrqg
     dgyygdyamd ywgqgtsvtv 121 ssakttppsv yplapgsaaq tnsmvtlgcl vkgyfpepvt
     vtwnsgslss gvhtfpavlq 181 sdlytlsssv tvpsstwpse tvtcnvahpa sstkvdkkiv
     prdcgckpci ctvpevssvf 241 ifppkpkdvl titltpkvtc vvvdiskddp evqfswfvdd
     vevhtaqtqp reeqfnstfr 301 svselpimhq dwlngkefkc rvnsaafpap iektisktkg
     rpkapqvyti pppkeqmakd 361 kvsltcmitd ffpeditvew qwngqpaeny kntqpimdtd
     gsyfvyskln vqksnweagn 421 tftcsvlheg lhnhhteksl shspgk
```

(31) Nucleic Acid Sequence Encoding the Full
Length 3A12 Light Chain Sequence (3A12 Kappa Variable Region and Constant Region) (signal sequence
underlined) (SEQ ID NO. 152)

```
   1 atgagtgtgc ccactcaggt cctggggttg ctgctgctgt
     ggcttacaga tgccagatgt 61 gacatccaga tgactcagtc gccagcctcc ctatctgtat
     ctgtgggaga aactgtcacc 121 atcacatgtc gagcaagtga gaatatttac attaatttag
     catggtatca gcagaaacag 181 ggaaaatctc ctcagctcct ggtccatgct gcaacaaagt
     tagcagatgg tgtgccatca 241 aggttcagtg gcagtggatc aggcacacag tattccctca
     agatcaacag cctgcagtct 301 gaagattttg ggagttatta ctgtcaacat ttttggggta
     ctccgtacac gttcggaggg 361 gggaccaaac tagaaataaa acgggctgat gctgcaccaa
     ctgtatccat cttcccacca 421 tccagtgagc agttaacatc tggaggtgcc tcagtcgtgt
     gcttcttgaa caacttctac 481 cccaaagaca tcaatgtcaa gtggaagatt gatggcagtg
     aacgacaaaa tggcgtcctg 541 aacagttgga ctgatcagga cagcaaagac agcacctaca
     gcatgagcag cacccttacg 601 ttgaccaagg acgagtatga acgacataac agctataccl
     gtgaggccac tcacaagaca 661 tcaacttcac ccattgtcaa gagcttcaac aggaatgagt
     gttag
```

(32) Protein Sequence Defining the Full Length
3A12 Light Chain Sequence (3A12 Kappa Variable Region and Constant Region) (without signal sequence) (SEQ ID NO. 153)

```
   1 diqmtqspas lsvsvgetvt itcraseniy inlawyqqkq
     gkspqllvha atkladgvps 61 rfsgsgsgtq yslkinslqs edfgsyycqh fwgtpytfgg
     gtkleikrad aaptvsifpp
```

-continued

```
121 sseqltsgga svvcflnnfy pkdinvkwki dgserqngvl
    nswtdqdskd stysmsstlt 181 ltkdeyerhn sytceathkt stspivksfn rnec
```

For convenience, Table 2 provides a concordance chart showing the correspondence between the full length sequences of the antibodies discussed in this Example with those presented in the Sequence Listing.

TABLE 2

| SEQ. ID NO. | Protein or Nucleic Acid |
|---|---|
| 122 | 1A3 Heavy Variable + IgG1 constant - nucleic acid |
| 123 | 1A3 Heavy Variable + IgG1 constant - protein |
| 124 | 1A3 Light Variable + constant - nucleic acid |
| 125 | 1A3 Light Variable + constant - protein |
| 126 | 2B8 Heavy Variable + IgG1 constant - nucleic acid |
| 127 | 2B8 Heavy Variable + IgG1 constant - protein |
| 128 | 2B8 Light Variable + constant - nucleic acid |
| 129 | 2B8 Light Variable + constant - protein |
| 130 | 2F8 Heavy Variable + IgG1 constant - nucleic acid |
| 131 | 2F8 Heavy Variable + IgG1 constant - protein |
| 132 | 2F8 Light Variable + constant - nucleic acid |
| 133 | 2F8 Light Variable + constant - protein |
| 134 | 3B6 Heavy Variable + IgG1 constant - nucleic acid |
| 135 | 3B6 Heavy Variable + IgG1 constant - protein |
| 136 | 3B6 Light Variable + constant - nucleic acid |
| 137 | 3B6 Light Variable + constant - protein |
| 138 | 3D11 Heavy Variable + IgG1 constant - nucleic acid |
| 139 | 3D11 Heavy Variable + IgG1 constant - protein |
| 140 | 3D11 Light Variable + constant - nucleic acid |
| 141 | 3D11 Light Variable + constant - protein |
| 142 | 1D3 Heavy Variable + IgG1 constant - nucleic acid |
| 143 | 1D3 Heavy Variable + IgG1 constant - protein |
| 144 | 1D3 Light Variable + constant - nucleic acid |
| 145 | 1D3 Light Variable + constant - protein |
| 146 | 1F3 Heavy Variable + IgG1 constant - nucleic acid |
| 147 | 1F3 Heavy Variable + IgG1 constant - protein |
| 148 | 1F3 Light Variable + constant - nucleic acid |
| 149 | 1F3 Light Variable + constant - protein |
| 150 | 3A12 Heavy Variable + IgG1 constant - nucleic acid |
| 151 | 3A12 Heavy Variable + IgG1 constant - protein |
| 152 | 3A12 Light Variable + constant - nucleic acid |
| 153 | 3A12 Light Variable + constant - protein |

Example 3

Production of Various Recombinant hHGF Proteins

This Example describes the cloning and expression of a number of recombinant proteins used to characterize the antibodies created in Example 1 and in Example 14. In particular, this Example describes the cloning and expression of recombinant hHGF protein, a recombinant hHGF protein containing a glycine to glutamate substitution at position 555 (G555E), a recombinant hHGF protein containing a cysteine to arginine substitution at position 561 (C561R), a recombinant mouse-human-mouse (mhm) chimeric HGF protein containing the human V495-L585 HGF sequence disposed within mouse HGF sequence, a recombinant mhm chimeric HGF protein containing the human I499-R566 HGF sequence disposed within mouse HGF sequence, and a recombinant mhm chimeric HGF protein containing human W507-L585 HGF sequence disposed within mouse HGF sequence.

The following expression constructs were generated using standard molecular techniques and the resulting cDNA sequences were confirmed by DNA sequencing:

a. hHGF-Fc

In a first round of PCR, two overlapping PCR fragments were generated introducing a Not I site and encoding a 6×His tag between hHGF and hIgFc. The overlapping PCR fragments served as template in a second round to amplify hHGF-his-IgFc. The resulting fragment was digested by NheI and BamHI and cloned into pcDNA5/FRT (Invitrogen, #35-3014). Then, hHGF was amplified from Invitrogen clone ID: IOH29794 (human HGF cDNA). The sequence was found to correspond to the sequence deposited at the NCBI under accession number NM_000601.4.

```
(1) 5'hHGF NheI Primer
                                   (SEQ ID NO. 102)
ACTGGCTAGCATGTGGGTGACCAAACTCCT (2) 3' hHGF NotI His Tag Primer
                                   (SEQ ID NO. 103)
GTGATGGTGATGGTGATGGCGGCCGCATGACTGTGGTACCTTATATG (3) 5' HisIgFc Primer
                                   (SEQ ID NO. 104)
ACTGGCGGCCGCCATCACCATCACCATCAC (4) 3' IgFc BamHI Primer
                                   (SEQ ID NO. 105)
ACTGGGATCCTCACTATTTACCCGGGGACAG
``` hHGF-Fc mutants G555E and C561R were generated by site directed mutagenesis using the QuikChange II XL site-directed mutagenesis kit (Stratagene) according to manufacturer's instructions.

```
(1) hHGF-Fc (G555E) Sense Primer
                                   (SEQ ID NO. 106)
CATGATGTCCACGAAAGAGGAGATGAG (2) hHGF-Fc (G555E) Anti-sense Primer
                                   (SEQ ID NO. 107)
CTCATCTCCTCTTTCGTGGACATCATG (3) hHGF-Fc (C561R) Sense Primer
                                   (SEQ ID NO. 108)
GGAAGAGGAGATGAGAAACGCAAACAGGTTCTCAATG (4) hHGF-Fc (C561R) Anti-sense Primer
                                   (SEQ ID NO. 109)
CATTGAGAACCTGTTTGCGTTTCTCATCTCCTCTTCC
```

The mouse-human-mouse chimera IgFc construct contains mHGF alpha chain-hHGF, β-chain amino acids Val 495-Leu 585 of human HGF, and mHGF C-terminal beta chain followed by 6×His tag and IgG-Fc.

Human HGF cDNA encoding amino acids V495-L585 was amplified from Invitrogen clone ID: IOH29794 (human HGF cDNA). The sequence corresponds to the sequence deposited at the NCBI under accession number NM_000601.4. Mouse HGF sequences were amplified by RT-PCR from mouse liver total RNA (Clontech, # 636603) using the Super Script One Step RT-PCR kit from Invitrogen (#10928-034) according to manufacturer's instructions. The mHGF cDNA sequence corresponds to the sequence deposited at the NCBI under accession number D10213.1.

Three fragments, referred to as Fragments 1, 2, and 3, were generated using overlapping PCR primers and annealed in consecutive rounds of PCR amplification. The final product was cleaved with NheI and NotI and cloned into pcDNA5/FRT IgGFc.

(1) Fragment 1 Primers for mHGF alpha chain 5'NheI (SEQ ID NO. 110)
5' ATCGGCTAGCATGATGTGGGGGACCAAAC (SEQ ID NO. 111)
3' GAATCCCATTTACAACCCGCAGTTGTTTTGTTTTGG (2) Fragment 2 Primers for hHGF beta chain aa V495-L585

(SEQ ID NO. 112)
5' CCAAAACAAAACAACTGCGGGTTGTAAATGGGATTC (SEQ ID NO. 113)
3' CAGGATTGCAGGTCGAGCAAGCTTCATTAAAACCAGATCT (3) Fragment 3 Primer for mHGF beta chain C-terminus 3'NotI (SEQ ID NO. 114)
5' AGATCTGGTTTTAATGAAGCTTGCTCGACCTGCAATCCTG (SEQ ID NO. 115)
3' GTAATTTTGACATACAAGTTGTGCGGCCGCCATCACCATCACCATCAC d. Construction of hHGF and mhm Chimera The vectors encoding hHGF and mhm chimera (V495-L585), pcDNA5/FRT hHGF and pcDNA5/FRT-mhm chimera (V495-L585), without Fc-tag were generated by site directed mutagenesis. A stop codon was introduced 3' of the 6×His tag using the QuikChange II XL site-directed mutagenesis kit (Stratagene) according to manufacturer's instructions. The mutagenesis primer included Primer 1: CATCACCATCACCATCAC-TAAGCGGGTCTGGTGCCACG (SEQ ID NO. 116), and Primer 2: CGTGGCACCAGACCCGCTTAGTGATGGT-GATGGTGATG (SEQ ID NO. 117).

In addition, two additional mhm chimeras were created from the pcDNA5/FRT-mhm (V495-L585) construct by site directed mutagenesis using the QuikChange II XL site-directed mutagenesis kit (Stratagene) according to manufacturer's instructions. One mhm construct contained the region of I499-R556 of hHGF disposed between murine sequences. The other mhm construct contained the region of W507-L585 of hHGF disposed between murine sequences.

For the mhm chimera (I499-R556), the following point mutations were made in order in the template pcDNA5/FRT-mhm chimera (V495-L585) construct: D558E, C561R, V564I, V567I and M583L, using the appropriate oligonucleotide sequences. For the mhm chimera (W507-L585), the following point mutations were introduced in one step in the template pcDNA5/FRT-mhm chimera (V495-L585) construct: Q502R, $N_{504}T$ and I505V, using the appropriate oligonucleotide sequences.

The resulting nucleotide sequence of the hHGF-Fc protein is set forth as SEQ ID NO. 118, including signal sequence (nucleotides 1-93) and prodomain (nucleotides 94-162). The amino acid sequence of the hHGF-Fc protein is set forth as SEQ ID NO. 119.

The resulting nucleotide sequence encoding the mhm (V495-L585)-Fc chimeric protein is set forth in SEQ ID NO. 120, including signal sequence (nucleotides 1-96) and prodomain (nucleotides 97-165). The amino acid sequence of the mhm (V495-L585)-Fc chimeric protein is set forth in SEQ ID NO. 121.

The resulting nucleotide sequence encoding, and the protein sequence defining, the mhm (V495-L585) construct are set forth in SEQ ID NOS. 211 and 212, respectively. The nucleic acid sequence set forth in SEQ ID NO. 211 includes the signal sequence (nucleotides 1-96) and the prodomain (nucleotides 97-165), and the protein sequence set forth in SEQ ID NO. 212 includes the active protein sequence (without the signal sequence or the prodomain). The resulting nucleotide sequence encoding, and the protein sequence defining, the mhm (I499-R556) construct are set forth in SEQ ID NOS. 213 and 214, respectively. The nucleic acid sequence set forth in SEQ ID NO. 213 includes the signal sequence (nucleotides 1-96) and the prodomain (nucleotides 97-165), and the protein sequence set forth in SEQ ID NO. 214 includes the active protein sequence (without the signal sequence or the prodomain). The resulting nucleotide sequence encoding, and the protein sequence defining, the mhm (W507-L585) are set forth in SEQ ID NOS. 215 and 216, respectively. The nucleic acid sequence set forth in SEQ ID NO. 215 includes the signal sequence (nucleotides 1-96) and the prodomain (nucleotides 97-165), and the protein sequence set forth in SEQ ID NO. 216 includes the active protein sequence (without the signal sequence or the prodomain).

e. Protein Expression (1) Cell Culture

CHO FlpIn cells (Invitrogen, Catalog No. R758-07)) were grown in F12K media (ATCC, Catalog No. 30-2004), 10% FCS (Invitrogen, Catalog No. 10438026), 1% Penicillin (10000 units/mL)/Streptomycin (10,000 µg/mL) (Invitrogen, Catalog No. 15140-122) at 37° C., 5% $CO_2$, 100 µg/mL Zeocin (Invitrogen, Catalog No. R250-01).

(2) Generation of Stable CHO FlpIn Cell Lines

CHO FlpIn host cells were transfected with a 9:1 ratio of pOG44:pcDNA5/FRT expression plasmid DNA using lipofectamine 2000 according to the manufacturer's instructions (Invitrogen, Catalog No. 11668-027). As controls, cells were transfected with empty pcDNA5/FRT vector/pOG44 and pOG44 plasmid (Invitrogen, Catalog No. 35-3018) alone. Twenty four hours after transfection, the cells were split, and after forty eight hours 0.5 mg/mL Hygromycin B (Sigma, Catalog No. H0654-SPEC) was added to the cells. Polyclonal selection of stable cells was performed in F12K, 10% FCS, 1% Penicillin/Streptomycin, 0.5 mg/mL Hygromycin B.

(3) Protein Expression in Stable CHO FlpIn Cell Lines

Approximately $2 \times 10^6$ cells were seeded in 15 cm plates and grown in F12K (ATCC, Catalog No. 30-2004)/DMEM high.glucose (Invitrogen, Catalog No. 11995065) 1:1, 5% ultra low IgG FCS (Invitrogen, #16250-78) at 37° C., 5% $CO_2$ for 5-6 days. Supernatants were harvested and resulting proteins analyzed by ELISA and by surface plasmon resonance.

Example 4

Binding Characteristics of Anti-hHGF Monoclonal Antibodies

The monoclonal antibodies produced in Example 1 were characterized by their ability to bind hHGF, and certain of the recombinant HGF proteins produced in Example 3.

The antibodies were analyzed by surface-plasmon resonance using a BIAcore T100 instrument to assess their ability to bind HGF and certain of the fusion proteins discussed in Example 3. Each antibody was immobilized on a carboxymethylated dextran CM5 sensor chip (BIAcore, Catalog No. BR-1006-68) by amine coupling (BIAcore, Catalog No. BR-1000-50) using a standard coupling protocol according to manufacturer's instructions.

Analyses were performed at 25° C. using PBS (GIBCO, Catalog No. 14040-133) containing 0.05% surfactant P20 (BIAcore, Catalog No. R-1000-54), 2 mg/mL BSA (EMD, Catalog No. 2930) and 10 mg/mL CM-Dextran Sodium salt (Fluka, Catalog No. 86524) as running buffer. Supernatant containing different HGF fusion proteins or supernatant from cells transfected with empty vector were injected over each antibody at a flow rate of 30 μL/min for 3 minutes. The resulting binding was determined as resonance units (RU) over baseline 30 seconds after the end of injection. Binding was compared to human HGF (R&D Systems, Catalog No. 294-HGN-025) diluted in running buffer. Non-specific binding was monitored by comparing binding to a control surface where mouse IgG (Rockland, Catalog No. 010-0102) was immobilized using the same amine coupling procedure.

The results are summarized in the Table 3.

TABLE 3

| Antibody | rhHGF (R&D Systems) | rmHGF (R&D Systems) | mhm chimera (V495-L585) | human HGF | G555E | C561R |
| --- | --- | --- | --- | --- | --- | --- |
| 1A3 | Yes | No | No | Yes | Yes | Yes |
| 1D3 | Yes | No | Yes | Yes | Yes | Yes |
| 1F3 | Yes | Yes | Yes | Yes | Yes | Yes |
| 2B8 | Yes | No | Yes | Yes | Yes | Yes |
| 2F8 | Yes | Yes | No | Yes | Yes | Yes |
| 3A12 | Yes | No | No | Yes | Yes | Yes |
| 3B6 | Yes | No | No | Yes | Yes | Yes |
| 3D11 | Yes | No | No | Yes | Yes | Yes |

The results in Table 3 demonstrate that each of the antibodies bind rHGF and purified human HGF. Furthermore, all of the antibodies bind hHGF containing point mutations G555E and $C^{561}R$. In general, all of the antibodies except for 1F3 and 2F8 did not bind murine HGF demonstrating that the antibodies 1A3, 1D3, 2B8, 3A12, 3B6, and 3D11 specifically bind human HGF. Antibodies 1D3, 1F3, and 2B8 bind the mouse-human-mouse chimera whereas the remaining antibodies did not. The results suggest that the antibodies 1D3 and 2B8 at least in part bind to residues 495-585 of human HGF. The antibodies 1A3, 3A12, 3B6, and 3D11 appear to bind portions of human hHGF other than residues 495-585. At present, it is uncertain why 2F8 does not bind the mhm chimera as it appears to bind both hHGF and mHGF.

Example 5

Ability of Anti-hHGF Monoclonal Antibodies to Bind Reduced and Non-Reduced HGF

In this Example, the anti-hHGF monoclonal antibodies produced in Example 1 were analyzed for their ability to bind reduced and non-reduced HGF.

The reactivity of the anti-HGF sera with the recombinant hHGF was assessed by immunoblotting. Eight μg of recombinant hHGF protein in NuPAGE MOPS SDS running buffer (Invitrogen) with or without NuPAGE sample reducing buffer (Invitrogen) was fractionated on a 4-12% Bis-Tris 1.0 mm×2D well gel (Invitrogen, Carlsbad, Calif.). The fractionated proteins then were transferred onto a nitrocellulose membrane using standard procedures. The nitrocellulose membranes were blocked with 5% nonfat milk powder solution in Tris buffered Saline with 0.1% Tween-20® (TBST), and then mounted onto a Mini Protean II Multi-Screen apparatus (BioRad) for further blocking.

The resulting membranes were probed with the purified antibodies on a Multi-Screen apparatus. The purified antibodies were diluted to 5 μg/mL in blocking buffer. The nitrocellulose membrane then was removed from the apparatus, and incubated with horseradish peroxidase-labeled anti-mouse IgG antibodies. The results are summarized in Table 4, where the numbers reflect the extent of binding with — representing the least (little or no binding) and 3+ representing the most binding.

TABLE 4

| Antibody | Reduced (exposure: 3-5 min) | Non-Reduced (exposure: 20 sec) |
| --- | --- | --- |
| 1A3 | 2+ | 2+ |
| 1D3 | 2+ | 2+ |

TABLE 4-continued

| Antibody | Reduced (exposure: 3-5 min) | Non-Reduced (exposure: 20 sec) |
| --- | --- | --- |
| 1F3 | 2+ | 2+ |
| 2B8 | — | 1+ |
| 2F8 | 2+ | 2+ |
| 3A12 | — | 2+ |
| 3B6 | 3+ | 2+ |
| 3D11 | — | 3+ |

The data in Table 4 demonstrate that all the antibodies bind non-reduced rhHGF. In contrast, monoclonal antibodies 1A3, 1D3, 1F3, 2F8, 3B6 bound reduced rhHGF but antibodies 2B8, 3A12, and 3D11 did not bind to reduced rhHGF.

Example 6

Binding Affinities

The binding affinities and kinetics of interaction of each of the antibodies produced in Example 1 against hHGF were measured by surface plasmon resonance.

Rabbit anti-mouse immunoglobulins (BIAcore, Catalog No. BR-1005-14) were immobilized on carboxymethylated dextran CM5 sensor chips (BIAcore, Catalog No. BR-1006-68) by amine coupling (BIAcore, Catalog No. BR-1000-50) using a standard coupling protocol according to manufacturer's instructions. The analyses were performed at 25° C. using PBS (GIBCO, Catalog No. 14040-133) containing 0.05% surfactant P20 (BIAcore, Catalog No. BR-1000-54), 2 mg/mL BSA (EMD, Catalog No. 2930), and 10 mg/mL CM-Dextran Sodium salt (Fluka, Catalog No. 86524) as running buffer.

The antibodies were captured in an individual flow cell at a flow rate of 10 μL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 µL/min. The dissociation phase was monitored for 15 or 90 minutes, depending on concentration. The surface then was regenerated with 10 mM Glycine-HCl, pH 1.7 (BIAcore, Catalog No. BR-1003-54) injected for 3 minutes at a flow rate of 60 µL/min before another cycle was initiated. HGF concentrations tested were 0.46 nM to 7.5 nM.

Kinetic parameters were determined using the kinetic function of the BIAevalutation software with reference subtraction. Kinetic parameters for each antibody, $k_a$ (association rate constant), $k_d$ (dissociation rate constant) and $K_D$ (equilibrium dissociation constant) are summarized in Table 5.

TABLE 5

| Antibody | ka (1/Ms) | SE (ka) | kd (1/s) | SE (kd) | $K_D$ (pM) | SD |
|---|---|---|---|---|---|---|
| 1A3 | $1.7 \times 10^6$ | $7.3 \times 10^4$ | $5.2 \times 10^{-5}$ | $8.4 \times 10^{-7}$ | 30.1 | 5.6 |
| 1D3 | $1.7 \times 10^6$ | $3.1 \times 10^4$ | $8.2 \times 10^{-5}$ | $1.7 \times 10^{-6}$ | 54.2 | 27.4 |
| 1F3 | $1.5 \times 10^6$ | $5.0 \times 10^4$ | $2.6 \times 10^{-5}$ | $6.6 \times 10^{-7}$ | 18.1 | 8.2 |
| 2B8 | $1.6 \times 10^6$ | $2.9 \times 10^4$ | $2.1 \times 10^{-5}$ | $1.4 \times 10^{-7}$ | 13.5 | 4.4 |
| 3A12 | $1.6 \times 10^6$ | $3.7 \times 10^4$ | $1.6 \times 10^{-4}$ | $1.6 \times 10^{-6}$ | 103.0 | 10.4 |
| 3B6 | $2.0 \times 10^6$ | $6.5 \times 10^4$ | $3.9 \times 10^{-5}$ | $3.2 \times 10^{-7}$ | 17.0 | 3.4 |

The data in Table 5 demonstrate that the antibodies bind hHGF with a $K_D$ of about 100 pM or less, about 50 pM or less, or 20 pM or less.

Example 7

Neutralization Activity of Anti-hHGF Antibodies

In this Example, the antibodies produced in Example 1 were characterized for their ability to (a) inhibit the binding of hHGF to c-Met, and (b) inhibit HGF stimulated BrdU incorporation in 4 MBr-5 cells.

a. HGF-Met Binding Inhibition Assay (Neutralization Assay)

The antibodies were tested by ELISA for their ability to inhibit hHGF binding to c-Met.

Specifically, Wallac 96-well DELFIA assay plates (Wallac Inc., Catalog No. AAAND-0001) were coated with 100 µL of 6.25 µg/mL HGF (R&D Systems, Catalog No. 294-HGN-025) in carbonate coating buffer (15 mM $Na_2CO_3$ and 34 mM $NaHCO_3$, pH 9.0) for 16 hours at 4° C. The plates then were blocked with 200 µL of 5% non-fat dry milk in PBS for 1 hour at room temperature. The antibodies were prepared in a separate plate by adding increasing concentrations of the antibodies under investigation (0.033-667 nM, 3-fold-serial dilution) to 2 nM c-Met (R&D Systems, Catalog No. 358-MT/CF) in 5% non-fat dry milk in PBS. 100 µL of sample per well was transferred to the assay plate and incubated overnight at 4° C. The assay plates then were washed 3 times with PBS-0.1% Tween 20, and incubated for 2 hours at room temperature with 100 µL/well of 2 µg/mL biotinylated anti-human c-Met antibody (R&D Systems, Catalog No. BAF358) prepared in 5% non-fat dry milk in PBS.

The resulting plates then were washed three times with PBS-0.1% Tween 20, and incubated for 1 hour at room temperature with Eu-labeled Streptavidin (Wallac, Catalog No. 1244-360) diluted 1:1000 in DELFIA assay buffer (Wallac, Catalog No. 4002-0010). The resulting plates were washed 3 times with DELFIA wash solution (Wallac, Catalog No. 4010-0010) and incubated with 100 µL/well DELFIA enhancement solution (Wallac #4001-0010) for 15 minutes at room temperature with agitation.

The plates were read on Victor³V instrument (Perkin Elmer) using the Europium method. The $IC_{50}$ values were calculated and are summarized in Table 6.

TABLE 6

| Antibody | $IC_{50}$ (nM) | SD |
|---|---|---|
| 1A3 | 5.65 | 0.91 |
| 1D3 | 4.43 | 2.27 |
| 1F3 | 6.57 | 0.28 |
| 2B8 | 5.57 | 1.19 |
| 2F8 | 5.36 | 0.88 |
| 3A12 | 5.26 | 2.11 |
| 3B6 | — | — |
| 3D11 | 5.66 | 2.75 |

The results demonstrate that all the antibodies (i.e., 1D3, 1A3, 2B8, 3A12, 1F3, 3D11, and 2F8) other than 3B6 efficiently neutralize HGF binding to c-Met.

b. Neutralization of HGF Stimulated BrdU Incorporation in 4 MBr-5 Cells

Ten µL of 12.5 nM of hHGF was dispensed into individual wells of a 96-well tissue culture microtiter plate (Costar Catalog No. 3903). Ten µL of serially diluted antibodies at concentrations of 6667, 2222, 740, 247, 82, 27, 9.1, 3.0, 1.0, 0.33 nM were added to each well. The HGF antibody mixture then was incubated at room temperature for 30 minutes. Monkey bronchial epithelial cells 4 MBr-5 (ATCC, CCL208) cultured in F-12K (ATCC, 30-2004), 15% FBS (Gibco 10438-026), 30 ng/mL EGF (Sigma E9644), 1% penicillin/streptomycin (PS, Gibco Catalog No. 15140-122) were dissociated with Trypsin (Gibco Catalog No. 25200-056), resuspended in assay media (F-12K, 2.5% FBS, 1% PS) at 75,000 cells/mL, and 80 µL of the cell suspension was dispensed to the HGF antibody mixture.

The resulting cells were incubated at 37° C., 5% $CO_2$. Forty eight hours later, 10 µL of 100 µM BrdU (Roche Catalog No. 1669915) was added. Seventy two hours later, the media was removed, the plates were dried with a hair dryer and were processed with the BrdU ELISA in accordance with manufacturer's instructions (Roche Catalog No. 1669915).

The luminescent signal was quantified by a Synergy HT plate reader (Bio-Tek). The data were fit to a sigmoidal dose response with variable slope with the equation y=bottom+(top−bottom)/(1+10^(log(EC50−x)*hill slope)) in GraphPad Prism (GraphPad Software). Each experiment was repeated at least 3 times in duplicates, and average $EC_{50}$ values are presented in Table 7.

TABLE 7

| Antibody | $IC_{50}$ (nM) |
|---|---|
| 1A3 | 4.69 |
| 1D3 | 4.99 |
| 1F3 | 1.94 |
| 2B8 | 1.41 |
| 2F8 | 19.24 |
| 3A12 | 30.30 |
| 3B6 | 36.08 |
| 3D11 | 51.12 |

The results in Table 7 demonstrate that all of the antibodies, 1A3, 1D3, 1F3, 2B8, 2F8, 3A12, 3B6, and 3D11 inhibit HGF induced proliferation in 4 MBr-5 cells.

53

Example 8

Anti-Scatter Activity of Anti-hHGF Antibodies

This Example describes a characterization of the antibodies produced in Example 1 for their ability to inhibit HGF induced scatter activity. HGF induces "scattering" (motility) of clusters in MDCK cells (ATCC, Manassas, Va., Catalog No. CCL-34).

MDCK cells were seeded in 96-well Costar tissue culture plates (Corning Incorporated, Corning, N.Y., Catalog No. 3595) at a density of $4\times10^3$ cells per well in 80 μL MEM (ATCC, Manassas, Va., Catalog No. 30-2003) containing 10% Fetal Bovine Serum (Invitrogen Catalog No. 10438026), and 1% penicillin-streptomycin (Invitrogen Catalog No. 15140122). Each of the antibodies to be investigated was diluted to 6,667 nM in MEM containing 10% Fetal Bovine Serum and 1% penicillin-streptomycin. Each of the different antibody dilutions, as well as MEM containing 10% Fetal Bovine Serum and 1% penicillin-streptomycin without antibody, then was separately combined with an equal volume of MEM containing 10% Fetal Bovine Serum and 1% penicillin-streptomycin, and 100 ng/ml HGF (R&D Systems Catalog No. 294-HGN-025). The antibody/HGF dilutions were incubated for 30 minutes at 25° C. Twenty μL of each antibody/HGF dilution was added separately to individual wells, yielding a final antibody concentration of 666.7 nM, and a final HGF concentration of 10 ng/ml. The MDCK cells then were incubated for 24 hours at 37° C. with 5% $CO_2$.

After 24 hours incubation, the MDCK cells were carefully washed once with 100 μL per well of ice-cold PBS (Invitrogen Catalog No. 14190144), and fixed with 100 μL per well of ice-cold methanol while rocking for 10 minutes at 25° C. The plates then were washed carefully once with distilled water. A volume of 100 μL crystal violet solution, consisting of 0.5% crystal violet (Sigma, St. Louis, Mo., Catalog No. C3886) and 50% ethanol in distilled water, was added to each well, and the cells were incubated for 20 minutes at 25° C. while rocking.

Following staining with crystal violet solution, the cells were washed carefully three times with distilled water. Then, PBS was added to each well to prevent drying of samples. The cells were imaged using the Leica DMIRB microscope (Leica Microsystems GmbH, Wetzler, Germany), DC500 camera (Leica Microsystems GmbH, Wetzler, Germany), and MagnaFire 2.1C software (Optronics, Goleta, Calif.), and samples were rated for level of scattering. The results are summarized in Table 8.

TABLE 8

Inhibition of HGF-induced MDCK Cell Scattering

| Antibody | Trial 1 | Trial 2 |
| --- | --- | --- |
| 1A3 | ++ | + |
| 1D3 | ++ | ++ |
| 1F3 | + | + |
| 2B8 | +++ | +++ |
| 2F8 | + | + |
| 3A12 | − | −/+ |
| 3B6 | ++ | ++ |
| 3D11 | − | − |

− No Inhibition
+++ Very strong, nearly complete inhibition
++ Strong inhibition
+ Detectable inhibition

54

The results in Table 8 demonstrate that antibody 2B8 inhibited HGF-induced scattering more than the other antibodies. Antibodies 1D3 and 3B6 displayed an intermediate level of inhibition; antibody 1A3 displayed a low to intermediate level of inhibition: antibodies 1F3 and 2F8 displayed a low level of inhibition; and antibodies 3A12 and 3D11 gave little or no detectable inhibition.

Example 9

Inhibition of HGF-Stimulated c-Met Phosphorylation

This Example describes a characterization of the antibodies produced in Example 1 for their ability to inhibit the HGF-stimulated c-Met phosphorylation in PC-3 cells. HGF induces phosphorylation of Met in PC-3 cells (ATCC No. CRL-1435).

PC-3 cells were seeded into individual wells of 96-well Costar tissue culture plates (Corning Catalog No. 3595) at a density of $4.5\times10^4$ cells per well in 100 μL F-12K (ATCC, Manassas, Va., Catalog No. 30-2004) containing 10% Fetal Bovine Serum (Invitrogen Catalog No. 10438026) and 1% penicillin-streptomycin (Invitrogen Catalog No. 15140122). After 24 hours at 37° C. with 5% $CO_2$, the media was removed, and cells were rinsed once with serum-free F-12K containing 1% penicillin-streptomycin. Cells then were incubated for 24 hours in 100 μL serum-free F-12K containing 1% penicillin-streptomycin.

The following 10 different dilutions of each of the antibodies being investigated were prepared in serum-free F-12K containing 1% penicillin-streptomycin: 6667 nM, 2222 nM, 741 nM, 247 nM, 82.3 nM, 27.4 nM, 9.1 nM, 3.0 nM, 1.0 nM, and 0.3 nM. Each antibody dilution, and, serum-free F-12K containing 1% penicillin-streptomycin without antibody, were separately combined with an equal volume of serum-free F-12K containing 1% penicillin-streptomycin and 500 ng/mL HGF (R&D Systems Catalog No. 294-HGN-025). These antibody/HGF dilutions were incubated for 30 minutes at 25° C. This resulted in a final concentration of 1.25 nM HGF.

The PC-3 cells then were rinsed once with serum-free F-12K containing 1% penicillin-streptomycin. Next, 70 μL of serum-free F-12K containing 1% penicillin-streptomycin was added to the cells, followed by 10 μL of 10 mM $Na_3VO_4$ (Sigma Catalog No. S6508) in serum-free F-12K containing 1% penicillin-streptomycin. The cells then were incubated for 60 minutes at 37° C. with 5% $CO_2$. Following this incubation, 20 μL of each antibody/HGF dilution was added separately to separate wells, yielding a final HGF concentration of 50 ng/mL, and the following final concentrations of each antibody: 666.7 nM, 222.2 nM, 74.1 nM, 24.7 nM, 8.23 nM, 2.74 nM, 0.91 nM, 0.30 nM, 0.10 nM, 0.03 nM. The cells then were incubated for 10 minutes at 37° C. with 5% $CO_2$, after which point the media/antibody/HGF mixture was removed, the plates were placed on ice. The cells then were rinsed once with 100 μL per well of ice-cold PBS (Invitrogen Catalog No. 14190144) containing 1 mM $Na_3VO_4$. The cells then were incubated for 30 minutes at 4° C. in 100 μL per well ice-cold lysis buffer consisting of 1% OmniPur Triton X-100 (MERCK KGaA, Darmstadt, Germany, Catalog No. 9410), 50 mM Tris-HCl pH 8.0, 100 mM NaCl, 0.3 mM $Na_3VO_4$, 1× protease inhibitor cocktail (Sigma Catalog No. P8340), and 1× phosphatase inhibitor cocktail 2 (Sigma Catalog No. 5726).

Biotinylated anti-human HGF-R (c-met) antibody (R&D Systems Catalog No. BAF358) was diluted to a concentration of 2 µg/mL in DELFIA Assay Buffer (PerkinElmer, Turku, Finland, Catalog No. 4002-0010) containing 1% bovine serum albumin (Sigma Catalog No. A2153), and 50 µL of this dilution was added per well of yellow streptavidin microtitration plates (PerkinElmer Catalog No. AAAND-0005). The plates then were incubated with antibody for 30 minutes at 25° C. with rocking. Following incubation, the plates were washed with DELFIA wash solution (PerkinElmer Catalog No. 4010-0010), and 80 µL of each of the different PC-3 cell lysates was added separately to individual wells of the washed streptavidin microtitration plates.

The streptavidin microtitration plates containing PC-3 cell lysates were incubated for 60 minutes at 25° C. with shaking, and then washed with DELFIA wash solution. 100 µL of 600 ng/mL DELFIA Eu-N1 P-Tyr-100 antibody (PerkinElmer Catalog No. AD0159) diluted in DELFIA Assay Buffer containing 1% bovine serum albumin was added to each well of the washed streptavidin microtitration plates previously incubated with PC-3 cell lysates. The plates were incubated for 60 minutes at 25° C., with rocking. The plates were washed a final time with DELFIA wash solution. Then 200 µL of DELFIA Enhancement Solution (PerkinElmer Catalog No. 4001-0010) was added to each well of the washed streptavidin microtitration plates, and the plates were incubated in the dark for 5 minutes at 25° C., with shaking.

Signal then was measured using the Europium protocol on the Victor3V reader (PerkinElmer). $EC_{50}$ values were calculated using Prism 4 for Windows (GraphPad Software, Inc., San Diego, Calif.) and the sigmoidal dose-response equation.

The results summarized as EC50s in nM are tabulated in Table 9.

TABLE 9

| Antibody | Average of Two Trials | Standard Deviation |
| --- | --- | --- |
| 1A3 | 0.684 | 0.242 |
| 1D3 | 0.984 | 0.129 |
| 1F3 | 1.19 | 1.01 |
| 2B8 | 0.287 | 0.104 |
| 2F8 | 1.39 | 2.12 |
| 3A12 | 2.00 | 0.553 |
| 3B6 | 1.01 | 1.11 |
| 3D11 | 2.28 | N/A |

The data in Table 9 demonstrate that all eight antibodies are potent inhibitors of HGF-induced c-Met phosphorylation in PC-3 cells.

Example 10

Tumor Inhibition in U87MG Xenograft Model

The ability of murine monoclonal antibodies of the invention to inhibit tumor growth was tested in an U87MG xenograft model. U87MG cells (ATCC) were expanded in culture at 37° C. in an atmosphere containing 5% CO2 and 95% air, using a medium comprising Dulbecco's Modified Eagle medium (DMEM) with 10% fetal bovine serum, 100 units/mL penicillin and 100 µg/mL streptomycin. The cells were subcultured and maintained by detaching the cells from the wall of the culture dish using trypsin-EDTA.

Near-confluent cells were collected by trypsinization and then $5 \times 10^6$ cells in 50% Matrigel (BD Biosciences; catalog no. 356237) were injected subcutaneously into the upper dorsal area between the shoulder blades of 7-week old female ICR SCID mice (Taconic Labs). The long (L) and short (W) diameters (mm) of tumors were measured with a caliper. Tumor volume (vol.) was calculated as: volume (mm³)=L× W²/2. When the tumors grew to approximately 200 mm³, the tumor-bearing mice were randomized into 5 groups of 10 mice each. One group received PBS. Each of the other 4 groups received one of the antibody 1A3, 1D3, 1F3 or 2B8. All antibodies were dosed at 1 mg/kg body weight, twice per week, by intra-peritoneal injections of 5 doses. Tumor volumes and mouse body weights were recorded twice per week. Tumor growth inhibition was analyzed using Student's t-test. The results are summarized in FIG. 6 and Table 10.

TABLE 10

| Percent Inhibition | | |
| --- | --- | --- |
| 2B8 vs PBS | 93% | p = 0.001 |
| 1A3 vs PBS | 73% | p = 0.0075 |
| 1D3 vs PBS | 51% | p = 0.075 |
| 1F3 vs PBS | 60% | p = 0.027 |

Figure 6:
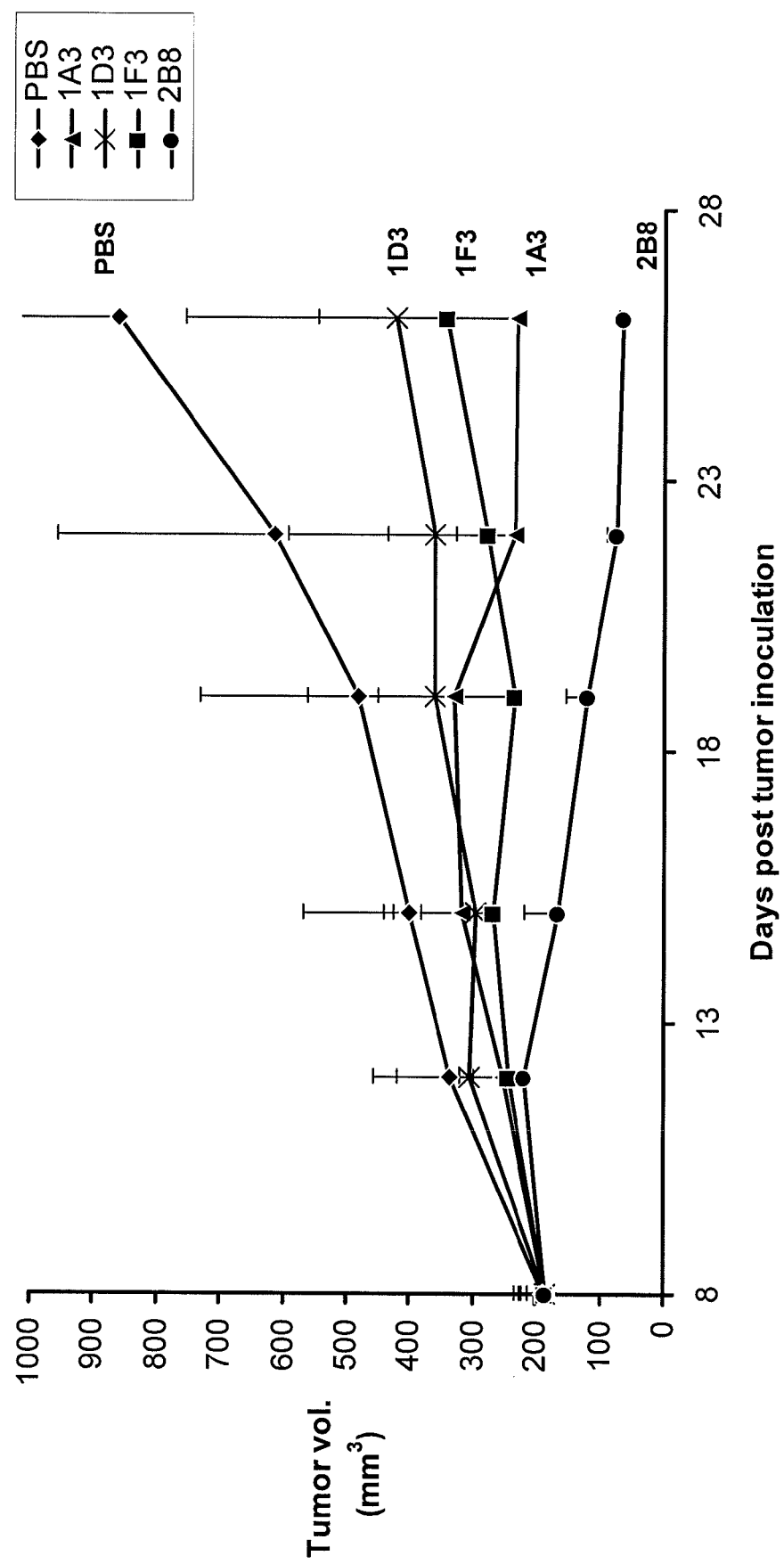
FIG. 6 is a graph summarizing results from an experiment to measure tumor inhibitory activity of anti-HGF antibodies 1D3, 1F3, 1A3 and 2B8 in a U87MG xenograft model. Diamonds correspond to PBS; triangles correspond to anti-HGF antibody 1A3; X corresponds to anti-HGF antibody 1D3; squares correspond to anti-HGF antibody 1F3, and circles correspond to anti-HGF antibody 2B8.

Partial regression was achieved in 2B8 treated group (FIG. 6). Statistically significant growth inhibition was observed in the 1A3-treated and 1F3-treated groups (Table 10). There was 51% tumor growth inhibition for 1D3 with a p value of 0.075. No significant body weight loss was observed.

Example 11

Tumor Inhibition in U118 Xenograft Model

The ability of the antibodies 1A3, 1D3, 1F3 and 2B8 to inhibit tumor growth was tested in an U118 xenograft model. U118 cells (ATCC) were expanded as described in Example 10 (above) with respect to the U87MG cells.

Subcutaneous tumors were established as described in Example 10 above, except that the mice used were 7 weeks old female NCr nude mice (Taconic), and treatment was started when the tumors grew to approximately 80 mm³. As in the U87MG model, all the antibodies were dosed at 1 mg/kg body weight twice a week by intra-peritoneal injections for 4 doses. Tumor volumes and body weights of the mice were recorded twice per week. Tumor growth inhibition was analyzed using Student's t-test. The results are summarized in FIG. 7 and Table 11.

TABLE 11

| Percent Inhibition | | |
| --- | --- | --- |
| 2B8 vs IgG | 75% | p = 0.007 |
| 1A3 vs IgG | 57% | p = 0.01 |
| 1D3 vs IgG | 47% | p = 0.12 |
| 1F3 vs IgG | 30% | p = 0.39 |

Figure 7:
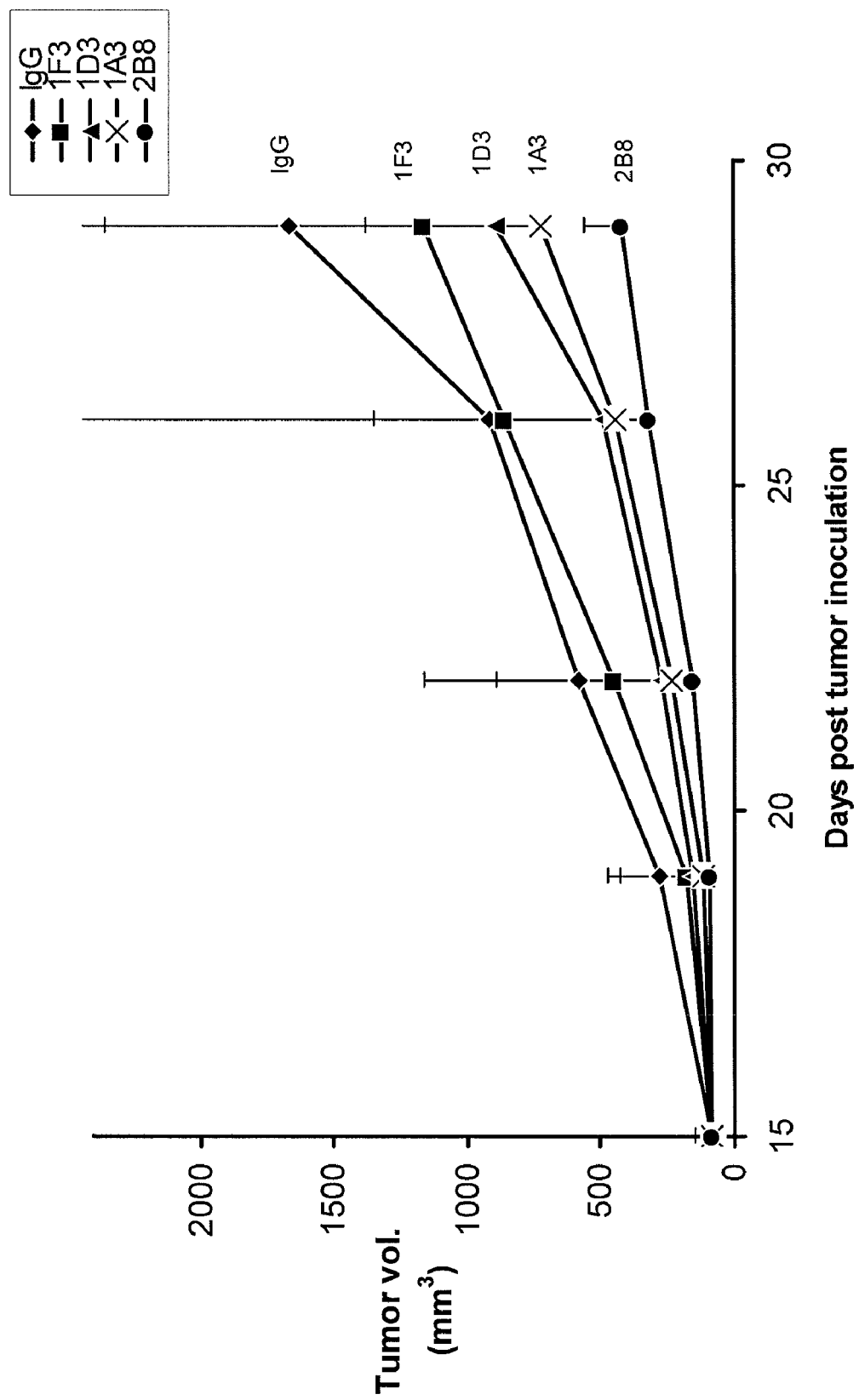
FIG. 7 is a graph summarizing results from an experiment to measure tumor inhibitory activity of anti-HGF antibodies 1D3, 1F3, 1A3 and 2B8 in a U118 xenograft model. Diamonds correspond to IgG; squares correspond to anti-HGF antibody 1F3, triangles to anti-HGF antibody 1D3; X corresponds to anti-HGF antibody 1A3; and circles correspond to anti-HGF antibody 2B8.

Statistically significant tumor growth inhibition was observed in 2B8 and 1A3 treated groups (FIG. 7). There was modest tumor growth inhibition in 1F3 and 1D3 groups with p values less than 0.05, which was defined as statistical significance in this study (Table 11). No significant body weight loss was observed.

Example 12

Humanization of Murine Monoclonal Antibodies

This Example describes the humanization of the murine 2B8 antibody, together with a characterization of the resulting humanized antibodies. The murine 2B8 Heavy and Light Variable Regions were "humanized" by two methods.

A. Humanization Procedure 1

In the first method, three humanized heavy chain variable regions and two humanized kappa light chain variable regions were designed based on the "superhumanization" method described in Hwang et al. (2005) METHODS 36:35-42; Tan et al. (2002) J. IMMUNOL. 169:1119-1125; U.S. Pat. No. 6,881,557.

The Chothia canonical structural class was determined for each mouse 2B8 CDR based on CDR length and amino acid composition. Human germline variable regions consisting of the same Chothia canonical structural class light and heavy variable regions were identified based on known human germline variable region reference alleles described at the International Immunogenetics Information System (IMGT) website (available on the world wide web at imgt.cines.fr and biochem.unizh.ch/antibody/Sequences/index.html). These human germline variable regions of the same structural class were compared to murine 2B8 variable regions by calculating the percent identity or similarity between CDR amino acid residues. Those human germline variable regions with the highest identity and/or similarity with mouse 2B8 CDR residues were chosen for CDR grafting. The framework residues of the human germline variable regions were preserved while the mouse 2B8 CDR residues were used to replace the corresponding human germline variable region residues that were different between mouse 2B8 CDR and human germline CDRs. The human J region that was most similar to the 2B8 mouse J region was then added to the carboxyl terminus of the "superhumanized" variable region. A signal sequence was then added to the amino terminus of the "superhumanized" variable regions and these amino acid sequences were converted into nucleic acid sequences.

The complete variable region nucleic acid sequence was constructed using gene synthesis PCR methods (Young et al. (2004) NUCL. ACIDS RES. 32:e59) and cloned into a mammalian expression vector (based on pcDNA3.2 DEST (Invitrogen)) containing human constant IgG1 (G1m(17,1) allotype) or Kappa (Km(3) allotype (allele 2)) regions (downstream of the variable regions) using standard molecular biology techniques. All four heavy chain IgG1 antibodies (chimeric 2B8 and 3 humanized heavy chains (Hu2B8 Hv1-f.1, Hu2B8 Hv5-a.1, Hu2B8 Hv5-51.1) were expressed in the possible combinations with all 3 kappa chain antibodies (chimera 2B8 and 2 humanized light chains (Hu2B8 Kv1-39.1 and Hu2B8 Kv3-15.1) creating 12 different antibody proteins. Binding of the chimeric, chimeric/humanized, and humanized antibodies to human HGF was then measured as described below and the results are summarized in FIG. 8. Each of the possible combinations of immunoglobulin heavy chain and immunoglobulin light chain variable regions are set forth below in Table 12A.

TABLE 12A

| Heavy Chain Variable Region | Light Chain Variable Region |
| --- | --- |
| Chimeric 2B8 (SEQ ID NO: 12) | Chimeric 2B8 (SEQ ID NO: 14) |
| Chimeric 2B8 (SEQ ID NO: 12) | Hu2B8 Kv1-39.1 (SEQ ID NO: 173) |
| Chimeric 2B8 (SEQ ID NO: 12) | Hu2B8 Kv3-15.1 (SEQ ID NO: 179) |
| Hu2B8 Hv1-f.1 (SEQ ID NO: 159) | Chimeric 2B8 (SEQ ID NO: 14) |
| Hu2B8 Hv1-f.1 (SEQ ID NO: 159) | Hu2B8 Kv1-39.1 (SEQ ID NO: 173) |
| Hu2B8 Hv1-f.1 (SEQ ID NO: 159) | Hu2B8 Kv3-15.1 (SEQ ID NO: 179) |
| Hu2B8 Hv5-a.1 (SEQ ID NO: 165) | Chimeric 2B8 (SEQ ID NO: 14) |
| Hu2B8 Hv5-a.1 (SEQ ID NO: 165) | Hu2B8 Kv1-39.1 (SEQ ID NO: 173) |
| Hu2B8 Hv5-a.1 (SEQ ID NO: 165) | Hu2B8 Kv3-15.1 (SEQ ID NO: 179) |
| Hu2B8 Hv5-51.1 (SEQ ID NO: 169) | Chimeric 2B8 (SEQ ID NO: 14) |
| Hu2B8 Hv5-51.1 (SEQ ID NO: 169) | Hu2B8 Kv1-39.1 (SEQ ID NO: 173) |
| Hu2B8 Hv5-51.1 (SEQ ID NO: 169) | Hu2B8 Kv3-15.1 (SEQ ID NO: 179) |

Each of the possible combinations of immunoglobulin heavy chains and immunoglobulin light chains are set forth below in Table 12B.

TABLE 12B

| Immunoglobulin Heavy Chain | Immunoglobulin Light Chain |
| --- | --- |
| Chimeric 2B8 IgG1 (SEQ ID NO: 155) | Chimeric 2B8 Kappa (Km(3)) (SEQ ID NO: 157) |
| Chimeric 2B8 IgG1 (SEQ ID NO: 155) | Hu2B8 Kv1-39.1 + Kappa Constant (Km(3) allotype) (allele 2) (SEQ ID NO: 177) |
| Chimeric 2B8 IgG1 (SEQ ID NO: 155) | Hu2B8 Kv3-15.1 + Kappa Constant (Km(3) allotype) (allele 2) (SEQ ID NO: 181) |
| Hu2B8 Hv1-f.1 + IgG1 Constant (G1M(17, 1)) allotype (SEQ ID NO: 163) | Chimeric 2B8 Kappa (Km(3)) (SEQ ID NO: 157) |
| Hu2B8 Hv1-f.1 + IgG1 Constant (G1M(17, 1)) allotype (SEQ ID NO: 163) | Hu2B8 Kv1-39.1 + Kappa Constant (Km(3) allotype) (allele 2) (SEQ ID NO: 177) |
| Hu2B8 Hv1-f.1 + IgG1 Constant (G1M(17, 1)) allotype (SEQ ID NO: 163) | Hu2B8 Kv3-15.1 + Kappa Constant (Km(3) allotype) (allele 2) (SEQ ID NO: 181) |
| Hu2B8 Hv5-a.1 + IgG1 Constant (G1M(17, 1)) allotype (SEQ ID NO: 167) | Chimeric 2B8 Kappa (Km(3)) (SEQ ID NO: 157) |
| Hu2B8 Hv5-a.1 + IgG1 Constant (G1M(17, 1)) allotype (SEQ ID NO: 167) | Hu2B8 Kv1-39.1 + Kappa Constant (Km(3) allotype) (allele 2) (SEQ ID NO: 177) |
| Hu2B8 Hv5-a.1 + IgG1 Constant (G1M(17, 1)) allotype (SEQ ID NO: 167) | Hu2B8 Kv3-15.1 + Kappa Constant (Km(3) allotype) (allele 2) (SEQ ID NO: 181) |
| Hu2B8 Hv5-51.1 + IgG1 Constant (G1M(17, 1)) allotype (SEQ ID NO: 171) | Chimeric 2B8 Kappa (Km(3)) (SEQ ID NO: 157) |
| Hu2B8 Hv5-51.1 + IgG1 Constant (G1M(17, 1)) allotype (SEQ ID NO: 171) | Hu2B8 Kv1-39.1 + Kappa Constant (Km(3) allotype) (allele 2) (SEQ ID NO: 177) |
| Hu2B8 Hv5-51.1 + IgG1 Constant (G1M(17, 1)) allotype (SEQ ID NO: 171) | Hu2B8 Kv3-15.1 + Kappa Constant (Km(3) allotype) (allele 2) (SEQ ID NO: 181) |

Two of the possible antibody constructs containing the full length immunoglobulin heavy and light chains containing humanized variable regions are designated below:

sh2B8-9 (G1m(17,1))=hu2B8 Hv5-51.1 (+IgG1 constant region (G1m(17,1) allotype) (SEQ ID NO. 171) plus hu2B8 Kv 1-39.1 (+Kappa constant region (Km(3) allotype (allele 2))) (SEQ ID NO. 177)

sh2B8-12 (G1m(17,1))=hu2B8 Hv5-51.1 (+IgG1 constant region (G1m(17,1) allotype)) (SEQ ID NO. 171) plus hu2B8 Kv 3-15.1 (+Kappa constant region (Km(3) allotype (allele 2))) (SEQ ID NO. 181).

The nucleic acid sequences encoding and the protein sequences defining each of the humanized antibodies are summarized below. In this section, the last nucleotide of each variable region is the first base of the next codon generated by the variable/constant region junction. This nucleotide is included in the Variable Region because it is part of that exon. Amino acid sequences of Constant Regions listed below include the translation of this junction codon.

(1) Nucleic Acid Sequence Encoding the Full Length Chimeric 2B8 Heavy Chain (Mouse Variable Region and Human IgG1 Constant Region) (allotype G1m(17, 1)) (signal sequence underlined) (SEQ ID NO. 154)

```
   1 atgggatgga gctatatcat cctcttttg gtagcaacag
     ctacagatgt ccactcccag 61 gtccaactgc agcagcctgg ggctgaactg gtgaagcctg
     ggacttcagt gaagctgtcc 121 tgcaaggctt ctggctacac cttcaccacc tactggatgc
     actgggtgaa tcagaggcct 181 ggacaaggcc ttgagtggat tggagagatt aatcctacca
     acggtcatac taactacaat 241 gagaagttca agagcaaggc cacactgact gtagacaaat
     cctccagcac agcctacatg 301 caactcagca gcctgacatc tgaggactct gcggtctatt
     actgtgcaag aaactatgtt 361 ggtagcatct ttgactactg gggccaaggc accactctca
     ccgtctcctc agcctccacc 421 aagggcccat cggtcttccc cctggcaccc tcctccaaga
     gcacctctgg gggcacagcg 481 gccctgggct gcctggtcaa ggactacttc cccgaaccgg
     tgacggtgtc gtggaactca 541 ggcgccctga ccagcggcgt gcacaccttc ccggctgtcc
     tacagtcctc aggactctac 601 tccctcagca gcgtggtgac cgtgccctcc agcagcttgg
     gcacccagac ctacatctgc 661 aacgtgaatc acaagcccag caacaccaag gtggacaaga
     aagttgagcc caaatcttgt 721 gacaaaactc acacatgccc accgtgccca gcacctgaac
     tcctgggggg accgtcagtc 781 ttcctcttcc ccccaaaacc caaggacacc ctcatgatct
     cccggacccc tgaggtcaca 841 tgcgtggtgg tggacgtgag ccacgaagac cctgaggtca
     agttcaactg gtacgtggac 901 ggcgtggagg tgcataatgc caagacaaag ccgcgggagg
     agcagtacaa cagcacgtac 961 cgtgtggtca gcgtcctcac cgtcctgcac caggactggc
     tgaatggcaa ggagtacaag
```

```
1021 tgcaaggtct ccaacaaagc cctcccagcc cccatcgaga
     aaaccatctc caaagccaaa 1081 gggcagcccc gagaaccaca ggtgtacacc ctgcccccat
     cccgggatga gctgaccaag 1141 aaccaggtca gcctgacctg cctggtcaaa ggcttctatc
     ccagcgacat cgccgtggag 1201 tgggagagca atgggcagcc ggagaacaac tacaagacca
     cgcctcccgt gctggactcc 1261 gacggctcct tcttcctcta cagcaagctc accgtggaca
     agagcaggtg gcagcagggg 1321 aacgtcttct catgctccgt gatgcatgag gctctgcaca
     accactacac gcagaagagc 1381 ctctccctgt ctccgggtaa atga
```

(2) Protein Sequence Defining the Full Length Chimeric 2B8 Heavy Chain (Chimeric 2B8 IgG1 (G1m(17, 1) allotype) (without signal sequence) (SEQ ID NO. 155)

```
   1 qvqlqqpgae lvkpgtsvkl sckasgytft tywmhwvnqr
     pgqglewige inptnghtny 61 nekfkskatl tvdkssstay mqlssltsed savyycarny
     vgsifdywgq gttltvssas 121 tkgpsvfpla psskstsggt aalgclvkdy tpepvtvswn
     sgaltsgvht fpavlqssgl 181 yslssvvtvp ssslgtqtyi cnvnhkpsnt kvdkkvepks
     cdkthtcppc papellggps 241 vflfppkpkd tlmisrtpev tcvvvdvshe dpevkfnwyv
     dgvevhnakt kpreeqynst 301 yrvvsvltvl hqdwlngkey kckvsnkalp apiektiska
     kgqprepqvy tlppsrdelt 361 knqvsltclv kgfypsdiav ewesngqpen nykttppvld
     sdgsfflysk ltvdksrwqq 421 gnvfscsvmh ealhnhytqk slslspgk
```

(3) Nucleic Acid Sequence Encoding the Full Length Chimeric 2B8 Light Chain (Mouse Variable Region and Human Constant Region) (Chimeric 2B8 Kappa (Km(3))) (signal sequence underlined) (SEQ ID NO. 156)

```
   1 atggaatcac agactctggt cttcatatcc atactgctct
     ggttatatgg tgctgatggg 61 aacattgtaa tgacccaatc tcccaaatcc atgtccatgt
     cagtaggaga gagggtcacc 121 ttgagctgca aggccagtga gaatgtggtt tcttatgtat
     cctggtatca acagaaacca 181 gcgcagtctc ctaaactgct gatatacggg gcatccaacc
     ggaacactgg gtccccgat 241 cgcttcacag gcagtggatc tgcaacagat ttcactctga
     ccatcagcag tgtgcgggct 301 gaagaccttg cagattatca ctgtgggcag agttacaact
     atccgtacac gttcggaggg 361 gggaccaggc tggaaataaa acgaactgtg gctgcaccat
     ctgtcttcat cttcccgcca 421 tctgatgagc agttgaaatc tggaactgcc tctgttgtgt
     gcctgctgaa taacttctat
```

-continued

```
481 cccagagagg ccaaagtaca gtggaaggtg gataacgccc
    tccaatcggg taactcccag 541 gagagtgtca cagagcagga cagcaaggac agcacctaca
    gcctcagcag caccctgacg 601 ctgagcaaag cagactacga gaaacacaaa gtctacgcct
    gcgaagtcac ccatcagggc 661 ctgagctcgc ccgtcacaaa gagcttcaac aggggagagt
    gttga
```

(4) Protein Sequence Defining the Full Length Chimeric 2B8 Light Chain (Chimeric 2B8 Kappa (Km(3))) (without signal sequence) (SEQ ID NO. 157)

```
  1 nivmtqspks msmsvgervt lsckasenvv syvswyqqkp
    aqspklliyg asnrntgvpd 61 rftgsgsatd ftltissvra edladyhcgq synypytfgg
    gtrleikrtv aapsvfifpp 121 sdeqlksgta svvcllnnfy preakvqwkv dnalqsgnsq
    esvteqdskd styslssstlt 181 lskadyekhk vyacevthqg lsspvtksfn rgec
```

(5) Nucleic Acid Sequence Encoding Humanized Hu2B8 Hv1-f.1 Heavy Chain Variable Region (signal sequence underlined) (SEQ ID NO. 158)

```
  1 atggactgca cctggaggat cctcctcttg gtggcagcag
    ctacaggcac ccacgccgag 61 gtccagctgg tacagtctgg ggctgaggtg aagaagcctg
    gggctacagt gaaaatctcc 121 tgcaaggttt ctggatacac cttcaccacc tactggatgc
    actgggtgca acaggccccgt 181 ggaaaagggc ttgagtggat gggagagatt aatcctacca
    acggtcatac taactacaat 241 gagaagttcc agggcagagt caccataacc gcggacacgt
    ctacagacac agcctacatg 301 gagctgagca gcctgagatc tgaggacacg gccgtgtatt
    actgtgcaac aaactatgtt 361 ggtagcatct ttgactactg gggccaagga accctggtca
    ccgtctcctc ag
```

(6) Protein Sequence Defining Humanized Hu2B8 Hv1-f.1 Heavy Chain Variable Region (without signal sequence) (SEQ ID NO. 159)

```
  1 evqlvqsgae vkkpgatvki sckvsgytft tywmhwvqqa
    pgkglewmge inptnghtny 61 nekfqgrvti tadtstdtay melsslrsed tavyycatny
    vgsifdywgq gtlvtvss
```

(7) Nucleic Acid Sequence Encoding Human IgG1 Heavy Chain Constant Region (Glm(17, 1) allotype) (SEQ ID NO. 160)

```
  1 cctccaccaa gggcccatcg gtcttccccc tggcaccctc
    ctccaagagc acctctgggg 61 gcacagcggc cctgggctgc ctggtcaagg actacttccc
    cgaaccggtg acggtgtcgt 121 ggaactcagg cgccctgacc agcggcgtgc acaccttccc
    ggctgtccta cagtcctcag 181 gactctactc cctcagcagc gtggtgaccg tgccctccag
    cagcttgggc acccagacct 241 acatctgcaa cgtgaatcac aagcccagca acaccaaggt
    ggacaagaaa gttgagccca 301 aatcttgtga caaaactcac acatgcccac cgtgcccagc
    acctgaactc ctggggggac 361 cgtcagtctt cctcttcccc ccaaaaccca aggacaccct
    catgatctcc cggacccctg 421 aggtcacatg cgtggtggtg gacgtgagcc acgaagaccc
    tgaggtcaag ttcaactggt 481 acgtggacgg cgtggaggtg cataatgcca agacaaagcc
    gcgggaggag cagtacaaca 541 gcacgtaccg tgtggtcagc gtcctcaccg tcctgcacca
    ggactggctg aatggcaagg 601 agtacaagtg caaggtctcc aacaaagccc tcccagcccc
    catcgagaaa accatctcca 661 aagccaaagg gcagccccga gaaccacagg tgtacaccct
    gcccccatcc cgggatgagc 721 tgaccaagaa ccaggtcagc ctgacctgcc tggtcaaagg
    cttctatccc agcgacatcg 781 ccgtggagtg ggagagcaat gggcagccgg agaacaacta
    caagaccacg cctcccgtgc 841 tggactccga cggctccttc ttcctctaca gcaagctcac
    cgtggacaag agcaggtggc 901 agcaggggaa cgtcttctca tgctccgtga tgcatgaggc
    tctgcacaac cactacacgc 961 agaagagcct ctccctgtct ccgggtaaat ga
```

The first amino acid is derived from translation of the last nucleotide of variable region and beginning two nucleotides of the IgG1 Heavy Chain sequence.

(8) Protein Sequence Defining Human IgG1 Heavy Chain Constant Region (Glm(17.1) allotype).
(SEQ ID NO. 161)

```
  1 astkgpsvfp lapsskstsg gtaalgclvk dyfpepvtvs wnsgaltsgv htfpavlqss 61 glyslssvvt vpssslgtqt yicnvnhkps ntkvdkkvep kscdkthtcp pcpapellgg 121 psvflfppkp kdtlmisrtp evtcvvvdvs hedpevkfnw yvdgvevhna ktkpreeqyn
```

```
181 styrvvsvlt vlhqdwlngk eykckvsnka lpapiektis kakgqprepq vytlppsrde 241 ltknqvsltc lvkgfypsdi avewesngqp ennykttppv ldsdgsffly skltvdksrw 301 qqgnvfscsv mhealhnhyt qkslslspgk
```

(9) Nucleic Acid Sequence Encoding the Full Length Heavy Chain
Humanized Hu2B8 Hv1f.1 Variable Region and Human IgG1 (G1m(17,1)
allotype) Heavy Chain Constant Region (signal sequence underlined)
(SEQ ID NO. 162)

```
   1 atggactgca cctggaggat cctcctcttg gtggcagcag ctacaggcac ccacgccgag 61 gtccagctgg tacagtctgg ggctgaggtg aagaagcctg ggctacagt gaaaatctcc 121 tgcaaggttt ctggatacac cttcaccacc tactggatgc actgggtgca acaggcccct 181 ggaaaagggc ttgagtggat gggagagatt aatcctacca acggtcatac taactacaat 241 gagaagttcc agggcagagt caccataacc gcggacacgt ctacagacac agcctacatg 301 gagctgagca gcctgagatc tgaggacacg gccgtgtatt actgtgcaac aaactatgtt 361 ggtagcatct ttgactactg gggccaagga accctggtca ccgtctcctc agcctccacc 421 aagggcccat cggtcttccc cctggcaccc tcctccaaga gcacctctgg gggcacagcg 481 gccctgggct gcctggtcaa ggactacttc cccgaaccgg tgacggtgtc gtggaactca 541 ggcgccctga ccagcggcgt gcacaccttc ccggctgtcc tacagtcctc aggactctac 601 tccctcagca gcgtggtgac cgtgccctcc agcagcttgg gcacccagac ctacatctgc 661 aacgtgaatc acaagcccag caacaccaag gtggacaaga agttgagcca aatcttgt 721 gacaaaactc acacatgccc accgtgccca gcacctgaac tcctgggggg accgtcagtc 781 ttcctcttcc ccccaaaacc caaggacacc ctcatgatct cccggacccc tgaggtcaca 841 tgcgtggtgg tggacgtgag ccacgaagac cctgaggtca agttcaactg gtacgtggac 901 ggcgtggagg tgcataatgc caagacaaag ccgcgggagg agcagtacaa cagcacgtac 961 cgtgtggtca gcgtcctcac cgtcctgcac caggactggc tgaatggcaa ggagtacaag 1021 tgcaaggtct ccaacaaagc cctcccagcc cccatcgaga aaaccatctc caaagccaaa 1081 gggcagcccc gagaaccaca ggtgtacacc ctgcccccat cccgggatga gctgaccaag 1141 aaccaggtca gcctgacctg cctggtcaaa ggcttctatc cagcgacat cgccgtggag 1201 tgggagagca atgggcagcc ggagaacaac tacaagacca cgcctcccgt gctggactcc 1261 gacggctcct tcttcctcta cagcaagctc accgtggaca agagcaggtg gcagcagggg 1321 aacgtcttct catgctccgt gatgcatgag gctctgcaca accactacac gcagaagagc 1381 ctctccctgt ctccgggtaa atga
```

(10) Protein Sequence Defining the Full Length Heavy Chain Humanized
Hu2B8 Hv1f.1 Variable Region and Human IgG1 Heavy Chain Constant
Region (G1m(17,1) allotype) (without signal sequence)
(SEQ ID NO. 163)

```
   1 evqlvqsgae vkkpgatvki sckvsgytft tywmhwvqqa pgkglewmge inptnghtny 61 nekfqgrvti tadtstdtay melsslrsed tavyycatny vgsifdywgq gtlvtvssas 121 tkgpsvfpla psskstsggt aalgclvkdy fpepvtvswn sgaltsgvht fpavlqssgl 181 yslssvvtvp ssslgtqtyi cnvnhkpsnt kvdkkvepks cdkthtcppc papellggps 241 vflfppkpkd tlmisrtpev tcvvvdvshe dpevkfnwyv dgvevhnakt kpreeqynst 301 yrvvsvltvl hqdwlngkey kckvsnkalp apiektiska kgqprepqvy tlppsrdelt 361 knqvsltclv kgfypsdiav ewesngqpen nykttppvld sdgsfflysk ltvdksrwqq 421 gnvfscsvmh ealhnhytqk slslspgk
```

-continued

(11) Nucleic Acid Sequence Encoding Humanized Hu2B8 Hv5a.1 Heavy Chain Variable Region (signal sequence underlined)

(SEQ ID NO. 164)

```
   1 atggggtcaa ccgccatcct cgccctcctc ctggctgttc tccaaggagt ctgtgccgaa 61 gtgcagctgg tgcagtctgg agcagaggtg aaaaagcccg gggagtctct gaggatctcc 121 tgtaagggtt ctggatacag ctttaccacc tactggatgc actgggtgcg ccagatgccc 181 gggaaaggcc tggagtggat ggggagatt aatcctacca acggtcatac taactacaat 241 ccgtccttcc aaggccacgt caccatctca gctgacaagt ccatcagcac tgcctacctg 301 cagtggagca gcctgaaggc ctcggacacc gccatgtatt actgtgcgag aaactatgtt 361 ggtagcatct ttgactactg gggccaagga accctggtca ccgtctcctc ag
```

(12) Protein Sequence Defining Humanized Hu2B8 Hv5a.1 Heavy Chain Variable Region (without signal sequence)

(SEQ ID NO. 165)

```
   1 evqlvqsgae vkkpgeslri sckgsgysft tywmhwvrqm pgkglewmge inptnghtny 61 npsfqghvti sadksistay lqwsslkasd tamyycarny vgsifdywgq gtlvtvss
```

(13) Nucleic Acid Sequence Encoding the Full Length Humanized Hu2B8 Hv5a.1 Heavy Chain Variable Region and Human IgG1 (G1m (17,1) allotype) Heavy Chain Constant Region (signal sequence underlined)

(SEQ ID NO. 166)

```
   1 atggggtcaa ccgccatcct cgccctcctc ctggctgttc tccaaggagt ctgtgccgaa 61 gtgcagctgg tgcagtctgg agcagaggtg aaaaagcccg gggagtctct gaggatctcc 121 tgtaagggtt ctggatacag ctttaccacc tactggatgc actgggtgcg ccagatgccc 181 gggaaaggcc tggagtggat ggggagatt aatcctacca acggtcatac taactacaat 241 ccgtccttcc aaggccacgt caccatctca gctgacaagt ccatcagcac tgcctacctg 301 cagtggagca gcctgaaggc ctcggacacc gccatgtatt actgtgcgag aaactatgtt 361 ggtagcatct ttgactactg gggccaagga accctggtca ccgtctcctc agcctccacc 421 aagggcccat cggtcttccc cctggcaccc tcctccaaga gcacctctgg gggcacagcg 481 gccctgggct gcctggtcaa ggactacttc cccgaaccgg tgacggtgtc gtggaactca 541 ggcgccctga ccagcggcgt gcacaccttc ccggctgtcc tacagtcctc aggactctac 601 tccctcagca gcgtggtgac cgtgccctcc agcagcttgg gcacccagac ctacatctgc 661 aacgtgaatc acaagcccag caacaccaag gtggacaaga agttgagccc aaatcttgt 721 gacaaaactc acacatgccc accgtgccca gcacctgaac tcctgggggg accgtcagtc 781 ttcctcttcc ccccaaaacc caaggacacc ctcatgatct cccggacccc tgaggtcaca 841 tgcgtggtgg tggacgtgag ccacgaagac cctgaggtca agttcaactg gtacgtggac 901 ggcgtggagg tgcataatgc caagacaaag ccgcgggagg agcagtacaa cagcacgtac 961 cgtgtggtca gcgtcctcac cgtcctgcac caggactggc tgaatggcaa ggagtacaag 1021 tgcaaggtct ccaacaaagc cctcccagcc cccatcgaga aaccatctc caaagccaaa 1081 gggcagcccc gagaaccaca ggtgtacacc ctgcccccat cccgggatga gctgaccaag 1141 aaccaggtca gcctgacctg cctggtcaaa ggcttctatc ccagcgacat cgccgtggag 1201 tgggagagca atgggcagcc ggagaacaac tacaagacca cgcctcccgt gctggactcc 1261 gacggctcct tcttcctcta cagcaagctc accgtggaca agagcaggtg gcagcagggg 1321 aacgtcttct catgctccgt gatgcatgag gctctgcaca accactacac gcagaagagc 1381 ctctccctgt ctccgggtaa atga
```

(14) Protein Sequence Defining the Full Length Humanized Hu2B8 Hv5a.1 Heavy Chain Variable Region and Human IgG1 (G1m(17,1) allotype) Heavy Chain Constant Region (without signal sequence)

-continued (SEQ ID NO. 167)
```
  1 evqlvqsgae vkkpgeslri sckgsgysft tywmhwvrqm pgkglewmge inptnghtny
 61 npsfqghvti sadksistay lqwsslkasd tamyycarny vgsifdywgq gtlvtvssas
121 tkgpsvfpla pssksstsggt aalgclvkdy fpepvtvswn sgaltsgvht fpavlqssgl
181 yslssvvtvp ssslgtqtyi cnvnhkpsnt kvdkkvepks cdkthtcppc papellggps
241 vflfppkpkd tlmisrtpev tcvvvdvshe dpevkfnwyv dgvevhnakt kpreeqynst
301 yrvvsvltvl hqdwlngkey kckvsnkalp apiektiska kgqprepqvy tlppsrdelt
361 knqvsltclv kgfypsdiav ewesngqpen nykttppvld sdgsfflysk ltvdksrwqq
421 gnvfscsvmh ealhnhytqk slslspgk
```

(15) Nucleic Acid Sequence Encoding Humanized Hu2B8 Hv5-51.1 Heavy Chain Variable Region (signal sequence underlined)
(SEQ ID NO. 168)
```
  1 atggggtcaa ccgccatcct cgccctcctc ctggctgttc tccaaggagt ctgtgccgaa
 61 gtgcagctgg tgcagtctgg agcagaggtg aaaaagcccg gggagtctct gaagatctcc
121 tgtaagggtt ctggatacag ctttaccacc tactggatgc actgggtgcg ccagatgccc
181 gggaaaggcc tggagtggat gggggagatt aatcctacca acggtcatac taactacaat
241 ccgtccttcc aaggccaggt caccatctca gctgacaagt ccatcagcac tgcctacctg
301 cagtggagca gcctgaaggc ctcggacacc gccatgtatt actgtgcgag aaactatgtt
361 ggtagcatct ttgactactg ggggccaagga accctggtca ccgtctcctc ag
```

(16) Protein Sequence Defining Humanized Hu2B8 Hv5-51.1 Heavy Chain Variable Sequence (without signal sequence)
(SEQ ID NO. 169)
```
  1 evqlvqsgae vkkpgeslki sckgsgysft tywmhwvrqm pgkglewmge inptnghtny
 61 npsfqgqvti sadksistay lqwsslkasd tamyycarny vgsifdywgq gtlvtvss
```

(17) Nucleic Acid Sequence Encoding the Full Length Humanized Hu2B8 Hv5-51.1 Heavy Chain Variable Region and Human IgG1 (G1m(17,1) allotype) Heavy Chain Constant Region (signal sequence underlined)
(SEQ ID NO. 170)
```
   1 atggggtcaa ccgccatcct cgccctcctc ctggctgttc tccaaggagt ctgtgccgaa
  61 gtgcagctgg tgcagtctgg agcagaggtg aaaaagcccg gggagtctct gaagatctcc
 121 tgtaagggtt ctggatacag ctttaccacc tactggatgc actgggtgcg ccagatgccc
 181 gggaaaggcc tggagtggat gggggagatt aatcctacca acggtcatac taactacaat
 241 ccgtccttcc aaggccaggt caccatctca gctgacaagt ccatcagcac tgcctacctg
 301 cagtggagca gcctgaaggc ctcggacacc gccatgtatt actgtgcgag aaactatgtt
 361 ggtagcatct ttgactactg ggggccaagga accctggtca ccgtctcctc agcctccacc
 421 aagggcccat cggtcttccc cctggcaccc tcctccaaga gcacctctgg gggcacagcg
 481 gccctgggct gcctggtcaa ggactacttc cccgaaccgg tgacggtgtc gtggaactca
 541 ggcgccctga ccagcggcgt gcacaccttc ccggctgtcc tacagtcctc aggactctac
 601 tccctcagca gcgtggtgac cgtgccctcc agcagcttgg gcacccagac ctacatctgc
 661 aacgtgaatc acaagcccag caacaccaag gtggacaaga agttgagccc aaatcttgt
 721 gacaaaactc acacatgccc accgtgccca gcacctgaac tcctgggggg accgtcagtc
 781 ttcctcttcc ccccaaaacc caaggacacc ctcatgatct cccggacccc tgaggtcaca
 841 tgcgtggtgg tggacgtgag ccacgaagac cctgaggtca agttcaactg gtacgtggac
 901 ggcgtggagg tgcataatgc caagacaaag ccgcgggagg agcagtacaa cagcacgtac
 961 cgtgtggtca gcgtcctcac cgtcctgcac caggactggc tgaatggcaa ggagtacaag
1021 tgcaaggtct ccaacaaagc cctcccagcc cccatcgaga aaaccatctc caaagccaaa
```

```
1081 gggcagcccc gagaaccaca ggtgtacacc ctgccccat cccgggatga gctgaccaag 1141 aaccaggtca gcctgacctg cctggtcaaa ggcttctatc cagcgacat cgccgtggag 1201 tgggagagca atgggcagcc ggagaacaac tacaagacca cgcctcccgt gctggactcc 1261 gacggctcct tcttcctcta cagcaagctc accgtggaca agagcaggtg gcagcagggg 1321 aacgtcttct catgctccgt gatgcatgag gctctgcaca accactacac gcagaagagc 1381 ctctccctgt ctccgggtaa atga
```

(18) Protein Sequence Defining the Full Length Humanized Hu2B8 Hv5-51.1 Heavy Chain Variable Region and Human IgG1 (G1m(17,1) allotype) Heavy Chain Constant Region (without signal sequence)

(SEQ ID NO. 171)

```
  1 evqlvqsgae vkkpgeslki sckgsgysft tywmhwvrqm pgkglewmge inptnghtny 61 npsfqgqvti sadksistay lqwsslkasd tamyycarny vgsifdywgq gtlvtvssas 121 tkgpsvfpla pssktstsggt aalgclvkdy fpepvtvswn sgaltsgvht fpavlqssgl 181 yslssvvtvp ssslgtqtyi cnvnhkpsnt kvdkkvepks cdkthtcppc papellggps 241 vflfppkpkd tlmisrtpev tcvvvdvshe dpevkfnwyv dgvevhnakt kpreeqynst 301 yrvvsvltvl hqdwlngkey kckvsnkalp apiektiska kgqprepqvy tlppsrdelt 361 knqvsltclv kgfypsdiav ewesngqpen nykttppvld sdgsfflysk ltvdksrwqq 421 gnvfscsvmh ealhnhytqk slslspgk
```

Two possible start ATGs are shown in uppercase.

(19) Nucleic Acid Sequence Encoding Humanized Hu2B8 Kv1-39.1 Kappa Chain Variable Region (signal sequence underlined).

(SEQ ID NO. 172)

```
  1 ATGgacATGa gggtccccgc tcagctcctg gggctcctgc tactctggct ccgaggtgcc 61 agatgtgaca tccagatgac ccagtctcca tcctccctgt ctgcatctgt aggagacaga 121 gtcaccatca cttgcaaggc cagtgagaat gtggtttctt atgtatcctg gtatcagcag 181 aaaccaggga aagcccctaa gctcctgatc tatggggcat ccaaccggaa cactggggtc 241 ccatcaaggt tcagtggcag tggatctggg acagatttca ctctcaccat cagcagtctg 301 caacctgaag attttgcaac ttactactgt gggcagagtt acaactatcc gtacacgttt 361 ggccagggga ccaagctgga gatcaaac
```

(20) Protein Sequence Defining Humanized Hu2B8 Kv1-39.1 Kappa Chain Variable Region (without signal sequence)

(SEQ ID NO. 173)

```
  1 diqmtqspss lsasvgdrvt itckasenvv syvswyqqkp gkapklliyg asnrntgvps 61 rfsgsgsgtd ftltisslqp edfatyycgq synypytfgq gtkleik
```

(21) Nucleic Acid Sequence Encoding Human Kappa Chain Constant Region (Km(3) allotype) (allele 2)

(SEQ ID NO. 174)

```
  1 gaactgtggc tgcaccatct gtcttcatct tcccgccatc tgatgagcag ttgaaatctg 61 gaactgcctc tgttgtgtgc ctgctgaata acttctatcc cagagaggcc aaagtacagt 121 ggaaggtgga taacgccctc caatcgggta actcccagga gagtgtcaca gagcaggaca 181 gcaaggacag cacctacagc ctcagcagca ccctgacgct gagcaaagca gactacgaga 241 aacacaaagt ctacgcctgc gaagtcaccc atcagggcct gagctcgccc gtcacaaaga 301 gcttcaacag gggagagtgt tga
```

The first amino acid is derived from translation of the last nucleotide of variable region and beginning two nucleotides of the Kappa Light Chain sequence.

(22) Protein Sequence Defining Human Kappa Chain Constant Region (Km(3) allotype) (allele 2).
(SEQ ID NO. 175)

```
  1 rtvaapsvfi fppsdeqlks gtasvvclln nfypreakvq wkvdnalqsg nsqesvteqd 61 skdstyslss tltlskadyc khkvyacevt hqglsspvtk sfnrgec
```

(23) Nucleic Acid Sequence Encoding the Full Length Humanized Hu2B8 Kv1-39.1 Light Chain Variable Region and Human Kappa Chain Constant Region (Km(3) allotype) (allele 2) (signal sequence underlined)
(SEQ ID NO. 176)

```
  1 atggacatga gggtccccgc tcagctcctg gggctcctgc tactctggct ccgaggtgcc 61 agatgtgaca tccagatgac ccagtctcca tcctccctgt ctgcatctgt aggagacaga 121 gtcaccatca cttgcaaggc cagtgagaat gtggtttctt atgtatcctg gtatcagcag 181 aaaccaggga agcccctaa gctcctgatc tatggggcat ccaaccggaa cactggggtc 241 ccatcaaggt tcagtggcag tggatctggg acagatttca ctctcaccat cagcagtctg 301 caacctgaag attttgcaac ttactactgt gggcagagtt acaactatcc gtacacgttt 361 ggccagggga ccaagctgga gatcaaacga actgtggctg caccatctgt cttcatcttc 421 ccgccatctg atgagcagtt gaaatctgga actgcctctg ttgtgtgcct gctgaataac 481 ttctatccca gagaggccaa agtacagtgg aaggtggata acgcctcca atcgggtaac 541 tcccaggaga gtgtcacaga gcaggacagc aaggacagca cctacagcct cagcagcacc 601 ctgacgctga gcaaagcaga ctacgagaaa cacaaagtct acgcctgcga agtcacccat 661 cagggcctga gctcgcccgt cacaaagagc ttcaacaggg gagagtgttg a
```

(24) Protein Sequence Defining the Full Length Humanized Hu2B8 Kv1-39.1 Light Chain Variable Region and Human Kappa Chain Constant Region (Km(3) allotype) (allele 1)
(SEQ ID NO. 177)

```
  1 diqmtqspss lsasvgdrvt itckasenvv syvswyqqkp gkapklliyg asnrntgvps 61 rfsgsgsgtd ftltisslqp edfatyycgq synypyttgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec
```

(25) Nucleic Acid Sequence Encoding Humanized Hu2B8 Kv3-15.1 Light Chain Variable Region (signal sequence underlined)
(SEQ ID NO. 178)

```
  1 atggaagccc cagcgcagct tctcttcctc ctgctactct ggctcccaga taccactgga 61 gaaatagtga tgacgcagtc tccagccacc ctgtctgtgt ctccagggga aagagccacc 121 ctctcctgca aggccagtga gaatgtggtt tcttatgtat cctggtacca gcagaaacct 181 ggccaggctc ccaggctcct catctatggg gcatccaacc ggaacactgg tatcccagcc 241 aggttcagtg gcagtgggtc tgggacagag ttcactctca ccatcagcag cctgcagtct 301 gaagattttg cagtttatta ctgtgggcag agttacaact atccgtacac gtttggccag 361 gggaccaagc tggagatcaa ac
```

(26) Protein Sequence Defining Humanized Hu2B8 Kv3-15.1 Light Chain Variable Region (without signal sequence)
(SEQ ID NO. 179)

```
  1 eivmtqspat lsvspgerat lsckasenvv syvswyqqkp gqaprlliyg asnrntgipa 61 rfsgsgsgte ftltisslqs edfavyycgq synypytfgq gtkleik
```

-continued

(27) Nucleic Acid Encoding the Full Length Humanized Hu2B8 Kv3-15.1
Light Chain Variable Region and Human Kappa Chain Constant Region
(Km(3) allotype) (allele 2) (signal sequence underlined)

(SEQ ID NO. 180)

```
  1 atggaagccc cagcgcagct tctcttcctc ctgctactct ggctcccaga taccactgga 61 gaaatagtga tgacgcagtc tccagccacc ctgtctgtgt ctccagggga agagccacc 121 ctctcctgca aggccagtga gaatgtggtt tcttatgtat cctggtacca gcagaaacct 181 ggccaggctc ccaggctcct catctatggg gcatccaacc ggaacactgg tatcccagcc 241 aggttcagtg gcagtgggtc tgggacagag ttcactctca ccatcagcag cctgcagtct 301 gaagattttg cagtttatta ctgtgggcag agttacaact atccgtacac gtttggccag 361 gggaccaagc tggagatcaa acgaactgtg gctgcaccat ctgtcttcat cttcccgcca 421 tctgatgagc agttgaaatc tggaactgcc tctgttgtgt gcctgctgaa taacttctat 481 cccagagagg ccaaagtaca gtggaaggtg gataacgccc tccaatcggg taactcccag 541 gagagtgtca cagagcagga cagcaaggac agcacctaca gcctcagcag caccctgacg 601 ctgagcaaag cagactacga gaaacacaaa gtctacgcct gcgaagtcac ccatcagggc 661 ctgagctcgc ccgtcacaaa gagcttcaac aggggagagt gttga
```

(28) Protein Sequence Defining Humanized Hu2B8 Kv3-15.1 Light Chain
Variable Region and Human Kappa Chain Constant Region (Km(3)
allotype) (allele 2) (without signal sequence)

(SEQ ID NO. 181)

```
  1 eivmtqspat lsvspgerat lsckasenvv syvswyqqkp gqaprlliyg asnrntgipa 61 rfsgsgsgte ftltisslqs edfavyycgq synypytfgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec
```

(2) Protein Sequence Defining Humanized LR2B8HC Heavy Chain Variable
Region (without signal sequence)

(SEQ ID NO. 183)

```
  1 qvqlvqpgae vvkpqtsvkl sckasgytft tywmhwvnqa pgqglewige inptnghtny 61 nekfkgkatl tvdkststay melsslrsed tavyycarny vgsifdywgq gtlltvss
```

(3) Nucleic Acid Sequence Encoding the Human IgG1 Heavy Chain
Constant Region (G1m(3) allotype) (allele 1)

(SEQ ID NO. 184)

```
  1 ccagcacaaa gggcccatcg gtcttccccc tggcaccctc ctccaagagc acctctgggg 61 gcacagcggc cctgggctgc ctggtcaagg actacttccc cgaaccggtg acggtgtcgt 121 ggaactcagg cgccctgacc agcggcgtgc acaccttccc ggctgtccta cagtcctcag 181 gactctactc cctcagcagc gtggtgaccg tgccctccag cagcttgggc acccagacct 241 acatctgcaa cgtgaatcac aagcccagca acaccaaggt ggacaagaga gttgagccca 301 aatcttgtga caaaactcac acatgtccac cgtgcccagc acctgaactc ctggggggac 361 cgtcagtctt cctcttcccc ccaaaaccca aggacaccct catgatctcc cggacccctg 421 aggtcacatg cgtggtggtg gacgtgagcc acgaagaccc tgaggtcaag ttcaactggt 481 acgtggacgg cgtggaggtg cataatgcca agacsaagcc gcgggaggag cagtacaaca 541 gcacgtaccg tgtggtcagc gtcctcaccg tcctgcacca ggactggctg aatggcaagg 601 agtacaagtg caaggtctcc aacaaagccc tcccagcccc catcgagaaa accatctcca 661 aagccaaagg gcagccccga gaaccacagg tgtacaccct gcccccatcc cggaggagga 721 tgaccaagaa ccaggtcagc ctgacctgcc tggtcaaagg cttctatccc agcgacatcg 781 ccgtggagtg ggagagcaat gggcagccgg agaacaacta caagaccacg cctcccgtgc 841 tggactccga cggctccttc ttcctctata gcaagctcac cgtggacaag agcaggtggc
```

```
901 agcaggggaa cgtcttctca tgctccgtga tgcatgaggc tctgcacaac cactacacgc 961 agaagagcct ctccctgtcc ccgggtaaat ga
```

For convenience, Table 13 provides a concordance chart showing the correspondence between the full length sequences and of the antibodies discussed in this section with those presented in the Sequence Listing.

chains. Variable region nucleic acid sequences were first synthesized by gene synthesis methods and then added to human constant region sequences. These human engineered antibodies were cloned into mammalian protein expression vectors,

TABLE 13

| SEQ. ID. NO. | Protein or Nucleic Acid |
| --- | --- |
| 154 | Chimeric 2B8 IgG1 (G1m(17, 1)) – nucleic acid |
| 155 | Chimeric 2B8 IgG1 (G1m(17, 1)) – protein |
| 156 | Chimeric 2B8 Kappa (Km(3)) – nucleic acid |
| 157 | Chimeric 2B8 Kappa (Km(3)) – protein |
| 158 | Hu2B8 Hv1f.1 Heavy Chain Variable Region – nucleic acid |
| 159 | Hu2B8 Hv1f.1 Heavy Chain Variable Region – protein |
| 160 | Human IgG1 Heavy Chain Constant Region (G1m(17, 1)) allotype – nucleic acid |
| 161 | Human IgG1 Heavy Chain Constant Region (G1m(17, 1)) allotype – protein |
| 162 | Hu2B8 Hv1f.1 + IgG1 Constant (G1m(17, 1) allotype) – nucleic acid |
| 163 | Hu2B8 Hv1f.1 + IgG1 Constant (G1m(17, 1) allotype) – protein |
| 164 | Hu2B8 Hv5a.1 Heavy Chain Variable Region – nucleic acid |
| 165 | Hu2B8 Hv5a.1 Heavy Chain Variable Region – protein |
| 166 | Hu2B8 Hv5a.1 + IgG1 Constant (G1m(17, 1) allotype) – nucleic acid |
| 167 | Hu2B8 Hv5a.1 + IgG1 Constant (G1m(17, 1) allotype) – protein |
| 168 | Hu2B8 Hv5-51.1 Heavy Chain Variable Region – nucleic acid |
| 169 | Hu2B8 Hv5-51.1 Heavy Chain Variable Region – protein |
| 170 | Hu2B8 Hv5-51.1 + IgG1 Constant (G1m(17, 1 allotype) – nucleic acid |
| 171 | Hu2B8 Hv5-51.1 + IgG1 Constant (G1m(17, 1 allotype) – protein |
| 172 | Hu2B8 Kv1-39.1 Kappa Chain Variable Region – nucleic acid |
| 173 | Hu2B8 Kv1-39.1 Kappa Chain Variable Region – protein |
| 174 | Human Kappa Chain Constant Region (Km(3) allotype) (allele 2) – nucleic acid |
| 175 | Human Kappa Chain Constant Region (Km(3) allotype) (allele 2) – protein |
| 176 | Hu2B8 Kv1-39.1 + Kappa Constant (Km(3) allotype) (allele 2) – nucleic acid |
| 177 | Hu2B8 Kv1-39.1 + Kappa Constant (Km(3) allotype) (allele 2) – protein |
| 178 | Hu2B8 Kv3-15.1 Kappa Chain Variable Region – nucleic acid |
| 179 | Hu2B8 Kv3-15.1 Kappa Chain Variable Region – protein |
| 180 | Hu2B8 Kv3-15.1 + Kappa Constant (Km(3) allotype) (allele 2) – nucleic acid |
| 181 | Hu2B8 Kv3-15.1 + Kappa Constant (Km(3) allotype) (allele 2) – protein |

B. Humanization Procedure 2

The second humanization method employed for reducing immunogenicity of the mouse 2B8 antibody is based on the method described in Studnicka et al. (1994) PROTEIN ENG. 7:805-814. The heavy and kappa human germline variable regions most identical (at the amino acid level) to those of mouse 2B8 were identified. Residues that differed between mouse and human were converted into the human sequence depending on the likely risk that such a change would affect binding or immunogenicity. Low risk residues (i.e., residues that when changed would likely not affect antigen binding and would also reduce potential immunogenicity) were changed to the human amino acid in the heavy variable region (creating LR2B8HC) and the kappa variable region (creating LR2B8LC). Additionally, low risk and medium risk (i.e., residues that when changed are somewhat likely to have an effect on antigen binding residues and would also reduce potential immunogenicity) were changed to the human amino acid in the heavy variable region (creating LRMR2B8HC) and the kappa variable region (creating LRMR2B8LC). The human IgG1 heavy chain constant region (G1m(3) allotype (allele 1)) was added to the carboxyl terminus of the two human engineered heavy variable regions and the human Kappa constant region (Km(3) allotype (allele 1)) was added to the carboxyl terminus of two human engineered light variable regions, thus creating four human engineered antibody and protein was expressed in the four possible combinations of heavy chain plus light chain. Binding of the chimeric, chimeric/humanized, or humanized antibodies to human HGF was measured using conventional techniques, as described below.

The nucleic acid sequences encoding and the protein sequences defining each of the humanized antibodies are summarized below. In this section, the last nucleotide of each variable region is the first base of the next codon generated by the variable/constant region junction. This nucleotide is included in the Variable Region because it is part of that exon. Amino acid sequences of Constant Regions listed below include the translation of this junction codon.

```
(1) Nucleic Acid Sequence Encoding the Humanized
LR2B8HC Heavy Chain Variable Region (signal
sequence underlined) (SEQ ID NO. 182)
    1 atgggctggt catatattat tctctttctt gttgctaccg
      ctaccgatgt gcactctcaa 61 gtccaactcg tacaaccagg cgctgaagtc gtaaaacccg
      gaacatctgt taaactctca 121 tgcaaagcct caggatacac tttcacaact tactggatgc
      attgggtcaa tcaagccccc
```

```
181 ggacaaggcc tcgaatggat tggcgaaatt aacccaacta
    acggacatac taattataat 241 gaaaaattta agggcaaagc tacactcacc gtcgataaat
    caacctctac agcttatatg 301 gaactttcat ccctgagatc agaagataca gccgtctact
    attgcgccag aaactacgta 361 ggatcaatat tcgattactg gggtcaaggc actctcctca
    cagtcagctc ag
```

(2) Protein Sequence Defining Humanized LR2B8HC Heavy Chain Variable Region (without signal sequence) (SEQ ID NO. 183)
```
  1 qvqlvqpgae vvkpgtsvkl sekasgytfi tywmhwvnqa
    pgqglewige inptnghtny 61 nekfkgkatl tvdkststay meissirsed tavyycarny
    vgsifdywgq gtlltvss
```

(3) Nucleic Acid Sequence Encoding the Human IgG1 Heavy Chain Constant Region (G1m(3) allotype) (allele 1) (SEQ ID NO. 184)
```
  1 ccagcacaaa gggcccatcg gtcttccccc tggcaccctc
    ctccaagagc acctctgggg 61 gcacagcggc cctgggctgc ctggtcaagg actacttccc
    cgaaccggtg acggtgtcgt 121 ggaactcagg cgccctgacc agcggcgtgc acaccttccc
    ggctgtccta cagtcctcag 181 gactctactc cctcagcagc gtggtgaccg tgccctccag
    cagcttgggc acccagacct 241 acatctgcaa cgtgaatcac aagcccagca acaccaaggt
    ggacaagaga gttgagccca 301 aatcttgtga caaaactcac acatgtccac cgtgcccagc
    acctgaactc ctggggggac 361 cgtcagtctt cctcttcccc ccaaaaccca aggacaccct
    catgatctcc cggacccctg 421 aggtcacatg cgtggtggtg gacgtgagcc acgaagaccc
    tgaggtcaag ttcaactggt 481 acgtggacgg cgtggaggtg cataatgcca agacaaagcc
    gcgggaggag cagtacaaca 541 gcacgtaccg tgtggtcagc gtcctcaccg tcctgcacca
    ggactggctg aatggcaagg 601 agtacaagtg caaggtctcc aacaaagccc tcccagcccc
    catcgagaaa accatctcca 661 aagccaaagg gcagccccga gaaccacagg tgtacaccct
    gcccccatcc cgggaggaga 721 tgaccaagaa ccaggtcagc ctgacctgcc tggtcaaagg
    cttctatccc agcgacatcg 781 ccgtggagtg ggagagcaat gggcagccgg agaacaacta
    caagaccacg cctcccgtgc 841 tggactccga cggctccttc ttcctctata gcaagctcac
    cgtggacaag agcaggtggc 901 agcaggggaa cgtcttctca tgctccgtga tgcatgaggc
    tctgcacaac cactacacg 961 agaagagcct ctccctgtcc ccgggtaaat ga
```

The first amino acid is derived from translation of the last nucleotide of variable region and the beginning two nucleotides of the IgG1 Heavy Chain sequence.

(4) Protein Sequence Defining Human IgG1 Heavy Chain Constant Region (G1m(3) allotype) (allele 1 or 2).
(SEQ ID NO. 185)
```
  1 astkgpsvfp lapsskstsg gtaalgclvk dyfpepvtvs wnsgaltsgv htfpavlqss 61 glyslssvvt vpssslgtqt yicnvnhkps ntkvdkrvep kscdkthtcp pcpapellgg 121 psvflfppkp kdtlmisrtp evtcvvvdvs hedpevkfnw yvdgvevhna ktkpreeqyn 181 styrvvsvlt vlhqdwlngk eykckvsnka lpapiektis kakgqprepq vytlppsree 241 mtknqvsltc lvkgfypsdi avewesngqp ennykttppv ldsdgsffly skltvdksrw 301 qqgnvfscsv mhealhnhyt qkslslspgk
```

(5) Nucleic Acid Sequence Encoding the Full Length Heavy Chain Humanized LR2B8HC Heavy Chain Variable Region and Human IgG1 Heavy Chain Constant Region (G1m(3) allotype) (allele 1) (signal sequence underlined)
(SEQ ID NO. 186)
```
  1 atgggctggt catatattat tctctttctt gttgctaccg ctaccgatgt gcactctcaa 61 gtccaactcg tacaaccagg cgctgaagtc gtaaaacccg gaacatctgt taaactctca 121 tgcaaagcct caggatacac tttcacaact tactggatgc attgggtcaa tcaagccccc 181 ggacaaggcc tcgaatggat tggcgaaatt aacccaacta acggacatac taattataat 241 gaaaaattta agggcaaagc tacactcacc gtcgataaat caacctctac agcttatatg 301 gaactttcat ccctgagatc agaagataca gccgtctact attgcgccag aaactacgta 361 ggatcaatat tcgattactg gggtcaaggc actctcctca cagtcagctc agccagcaca 421 aagggcccat cggtcttccc cctggcaccc tcctccaaga gcacctctgg gggcacagcg
```

-continued

```
 481 gccctgggct gcctggtcaa ggactacttc cccgaaccgg tgacggtgtc gtggaactca 541 ggcgccctga ccagcggcgt gcacaccttc ccggctgtcc tacagtcctc aggactctac 601 tccctcagca gcgtggtgac cgtgccctcc agcagcttgg gcacccagac ctacatctgc 661 aacgtgaatc acaagcccag caacaccaag gtggacaaga gagttgagcc caaatcttgt 721 gacaaaactc acacatgtcc accgtgccca gcacctgaac tcctgggggg accgtcagtc 781 ttcctcttcc ccccaaaacc caaggacacc ctcatgatct cccggacccc tgaggtcaca 841 tgcgtggtgg tggacgtgag ccacgaagac cctgaggtca agttcaactg gtacgtggac 901 ggcgtggagg tgcataatgc caagacaaag ccgcgggagg agcagtacaa cagcacgtac 961 cgtgtggtca gcgtcctcac cgtcctgcac caggactggc tgaatggcaa ggagtacaag 1021 tgcaaggtct ccaacaaagc cctcccagcc cccatcgaga aaccatctc caaagccaaa 1081 gggcagcccc gagaaccaca ggtgtacacc ctgcccccat cccgggagga tgaccaag 1141 aaccaggtca gcctgacctg cctggtcaaa ggcttctatc ccagcgacat cgccgtggag 1201 tgggagagca atgggcagcc ggagaacaac tacaagacca cgcctcccgt gctggactcc 1261 gacggctcct tcttcctcta tagcaagctc accgtggaca agagcaggtg gcagcagggg 1321 aacgtcttct catgctccgt gatgcatgag gctctgcaca accactacac gcagaagagc 1381 ctctccctgt ccccgggtaa atga
```

(6) Protein Sequence Defining the Full Length Heavy Chain Humanized LR2B8HC Heavy Chain Variable Region and Human IgG1 Heavy Chain Constant Region (G1m(3) allotype) (allele 1) (without signal sequence)

(SEQ ID NO. 187)

```
  1 qvqlvqpgae vvkpgtsvkl sckasgytft tywmhwvnqa pgqglewige inptnghtny 61 nekfkgkatl tvdkststay melsslrsed tavyycarny vgsifdywgq gtlltvssas 121 tkgpsvfpla psskstsggt aalgclvkdy tpepvtvswn sgaltsgvht fpavlqssgl 181 yslssvvtvp ssslgtqtyi cnvnhkpsnt kvdkrvepks cdkthtcppc papellggps 241 vflfppkpkd tlmisrtpev tcvvvdvshe dpevkfnwyv dgvevhnakt kpreeqynst 301 yrvvsvltvl hqdwlngkey kckvsnkalp apiektiska kgqprepqvy tlppsreemt 361 knqvsltclv kgfypsdiav ewesngqpen nykttppvld sdgsfflysk ltvdksrwqq 421 gnvfscsvmh ealhnhytqk slslspgk
```

(7) Nucleic Acid Sequence Encoding the Humanized LRMR2B8HC Heavy Chain Variable Region (signal sequence underlined)

(SEQ ID NO. 188)

```
  1 atgggttggt catatattat actctttctc gtagccaccg ccaccgacgt acactctcag 61 gttcaactcg tacaacccgg cgccgaagtc aagaaaccag gaacatcagt caaactctca 121 tgtaaagcaa gcggatacac ctttactact tattggatgc attgggtaag acaagccccc 181 ggacaaggac tcgaatggat aggcgaaata aatcccacta atggacatac aaattataat 241 caaaaatttc aaggacgcgc tacactcacc gtcgataaat caacctcaac cgcatacatg 301 gaactcagct ccctccgatc cgaagacact gccgtttatt attgtgccag aaactatgta 361 ggatctattt tcgattactg ggacaagga acacttctca ccgtaagctc ag
```

(8) Protein Sequence Defining Humanized LRMR2B8HC Heavy Chain Variable Region (without signal sequence)

(SEQ ID NO. 189)

```
  1 qvqlvqpgae vkkpgtsvkl sckasgytft tywmhwvrqa pgqglewige inptnghtny 61 nqkfqgratl tvdkststay melsslrsed tavyycarny vgsifdywgq gtlltvss
```

(9) Nucleic Acid Sequence Encoding the Full Length Heavy Chain
Humanized LRMR2B8HC Heavy Chain Variable Region and Human IgG1 Heavy
Chain Constant Region (G1m(3) allotype) (allele 1) (signal sequence
underlined)

(SEQ ID NO. 190)

```
   1 atgggttggt catatattat actctttctc gtagccaccg ccaccgacgt acactctcag 61 gttcaactcg tacaacccgg cgccgaagtc aagaaaccag gaacatcagt caaactctca 121 tgtaaagcaa gcggatacac ctttactact tattggatgc attgggtaag acaagccccc 181 ggacaaggac tcgaatggat aggcgaaata aatcccacta atggacatac aaattataat 241 caaaaatttc aaggacgcgc tacactcacc gtcgataaat caacctcaac cgcatacatg 301 gaactcagct ccctccgatc cgaagacact gccgtttatt attgtgccag aaactatgta 361 ggatctattt tcgattactg gggacaagga acacttctca ccgtaagctc agccagcaca 421 aagggcccat cggtcttccc cctggcaccc tcctccaaga gcacctctgg gggcacagcg 481 gccctgggct gcctggtcaa ggactacttc cccgaaccgg tgacggtgtc gtggaactca 541 ggcgccctga ccagcggcgt gcacaccttc ccggctgtcc tacagtcctc aggactctac 601 tccctcagca gcgtggtgac cgtgccctcc agcagcttgg gcacccagac ctacatctgc 661 aacgtgaatc acaagcccag caacaccaag gtggacaaga gagttgagcc caaatcttgt 721 gacaaaactc acacatgtcc accgtgccca gcacctgaac tcctgggggg accgtcagtc 781 ttcctcttcc ccccaaaacc caaggacacc ctcatgatct cccggacccc tgaggtcaca 841 tgcgtggtgg tggacgtgag ccacgaagac cctgaggtca agttcaactg gtacgtggac 901 ggcgtggagg tgcataatgc caagacaaag ccgcgggagg agcagtacaa cagcacgtac 961 cgtgtggtca gcgtcctcac cgtcctgcac caggactggc tgaatggcaa ggagtacaag 1021 tgcaaggtct ccaacaaagc cctcccagcc cccatcgaga aaaccatctc aaaagccaaa 1081 gggcagcccc gagaaccaca ggtgtacacc ctgcccccat cccgggagga tgaccaag 1141 aaccaggtca gcctgacctg cctggtcaaa ggcttctatc cagcgacat cgccgtggag 1201 tgggagagca atgggcagcc ggagaacaac tacaagacca cgcctcccgt gctggactcc 1261 gacggctcct tcttcctcta tagcaagctc accgtggaca agagcaggtg gcagcagggg 1321 aacgtcttct catgctccgt gatgcatgag gctctgcaca accactacac gcagaagagc 1381 ctctccctgt ccccgggtaa atga
```

(10) Protein Sequence Defining the Full Length Heavy Chain Humanized
LRMR2B8HC Heavy Chain Variable Region and Human IgG1 Heavy Chain
Constant Region (G1m(3) allotype) (allele 1) (without signal
sequence)

(SEQ ID NO. 191)

```
   1 qvqlvqpgae vkkpgtsvkl sckasgytft tywmhwvrqa pgqglewige inptnghtny 61 nqkfqgratl tvdkststay melsslrsed tavyycarny vgsifdywgq gtlltvssas 121 tkgpsvfpla psskstsggt aalgclvkdy fpepvtvswn sgaltsgvht fpavlqssgl 181 yslssvvtvp ssslgtqtyi cnvnhkpsnt kvdkrvepks cdkthtcppc papellggps 241 vflfppkpkd tlmisrtpev tcvvvdvshe dpevkfnwyv dgvevhnakt kpreeqynst 301 yrvvsvltvl hqdwlngkey kckvsnkalp apiektiska kgqprepqvy tlppsreemt 361 knqvsltclv kgfypsdiav ewesngqpen nykttppvld sdgsfflysk ltvdksrwqq 421 gnvfscsvmh ealhnhytqk slslspgk
```

-continued

(11) Nucleic Acid Sequence Encoding the Humanized LR2B8LC Light Chain
Variable Region (signal sequence underlined)
(SEQ ID NO. 192)

```
  1 atggaaagtc agaccttgt attcatctct attcttcttt ggttgtatgg agcagacggc 61 gacattgtga tgacccaatc ccccgatagt atggccatga gtgtaggaga aagagtcacc 121 cttaattgca aagcctccga aaatgtcgtt tcatatgtgt cttggtatca acaaaaaccc 181 ggccaatcac ccaaacttct catatacggc gcttcaaaca gaaacacagg cgttcccgac 241 agatttagtg gatccggatc agctacagat ttcaccctta ccatcagttc agttcaagca 301 gaagacgttg cagactatca ttgcggacaa tcttataact acccttacac attcggacaa
```

(12) Protein Sequence Defining Humanized LR2B8LC Light Chain Variable
Region (without signal sequence)
(SEQ ID NO. 193)

```
  1 divmtqspds mamsvgervt lnckasenvv syvswyqqkp gqspklliyg asnrntgvpd 61 rfsgsgsatd ftltissvqa edvadyhcgq synypytfgq gtkleik
```

(13) Nucleic Acid Sequence Encoding the Human Kappa Chain Constant
Region (Km(3) allotype) (allele 1)
(SEQ ID NO. 194)

```
  1 gtacggtggc tgcaccatct gtcttcatct tcccgccatc tgatgagcag ttgaaatctg 61 gaactgcctc tgttgtgtgc ctgctgaata acttctatcc cagagaggcc aaagtacagt 121 ggaaggtgga taacgccctc caatcgggta actcccagga gagtgtcaca gagcaggaca 181 gcaaggacag cacctacagc ctcagcagca ccctgacgct gagcaaagca gactacgaga 241 aacacaaagt ctacgcctgc gaagtcaccc atcagggcct gagctcgccc gtcacaaaga 301 gcttcaacag gggagagtgt tag
```

The first amino acid is derived from translation of the last
nucleotide of variable region and the beginning two nucleotides of the Kappa Light Chain sequence.

(14) Protein Sequence Defining the Human Kappa Chain Constant Region
(Km(3) allotype) (allele 1).
(SEQ ID NO. 195)

```
  1 rtvaapsvfi fppsdeqlks gtasvvclln nfypreakvq wkvdnalqsg nsqesvteqd 61 skdstyslss tltlskadye khkvyacevt hqglsspvtk sfnrgec
```

(15) Nucleic Acid Sequence Encoding the Full Length Humanized LR2B8LC
Light Chain Variable Region and the Human Kappa Chain Constant Region
(Km(3) allotype) (allele 1)
(SEQ ID NO. 196)

```
  1 atggaaagtc agaccttgt attcatctct attcttcttt ggttgtatgg agcagacggc 61 gacattgtga tgacccaatc ccccgatagt atggccatga gtgtaggaga aagagtcacc 121 cttaattgca aagcctccga aaatgtcgtt tcatatgtgt cttggtatca acaaaaaccc 181 ggccaatcac ccaaacttct catatacggc gcttcaaaca gaaacacagg cgttcccgac 241 agatttagtg gatccggatc agctacagat ttcaccctta ccatcagttc agttcaagca 301 gaagacgttg cagactatca ttgcggacaa tcttataact acccttacac attcggacaa 361 ggaaccaaac tcgaaattaa acgtacggtg gctgcaccat ctgtcttcat cttcccgcca 421 tctgatgagc agttgaaatc tggaactgcc tctgttgtgt gcctgctgaa taacttctat 481 cccagagagg ccaaagtaca gtggaaggtg gataacgccc tccaatcggg taactcccag 541 gagagtgtca cagagcagga cagcaaggac agcacctaca gcctcagcag caccctgacg 601 ctgagcaaag cagactacga gaaacacaaa gtctacgcct gcgaagtcac ccatcagggc 661 ctgagctcgc ccgtcacaaa gagcttcaac aggggagagt gttag
```

-continued

(16) Protein Sequence Encoding the Full Length Humanized LR2B8LC Light
Chain Variable Region and the Human Kappa Chain Constant Region (Km(3)
allotype) (allele 1)

(SEQ ID NO. 197)

```
  1 divmtqspds mamsvgervt lnckasenvv syvswyqqkp gqspklliyg asnrntgvpd 61 rfsgsgsatd ftltissvqa edvadyhcgq synypytfgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec
```

(17) Nucleic Acid Sequence Encoding the Humanized LRMR2B8LC Light
Chain Variable Region (signal sequence underlined)

(SEQ ID NO. 198)

```
  1 atggaatccc aaacccttgt tttcatctct atccttctct ggctttatgg cgccgacgga 61 gacatcgtaa tgacacaatc ccctgactct cttgctatga gcttgggcga acgagtaaca 121 cttaactgca aagcatccga aaatgtcgta tcttacgtat cctggtatca gcaaaaacct 181 ggtcaaagtc ctaaacttct tatatatggt gcaagtaatc gtgaaagtgg cgtcccagac 241 agatttagcg gttcaggttc agcaactgac tttacactta caatttctag cgttcaggcc 301 gaagacgttg cagactatca ttgtggacaa tcttataact atccttatac tttcggacaa 361 ggcactaaac ttgaaattaa ac
```

(18) Protein Sequence Defining the Humanized LRMR2B8LC Light Chain
Variable Region (without signal sequence)

(SEQ ID NO. 199)

```
  1 divmtqspds lamslgervt lnckasenvv syvswyqqkp gqspklliyg asnresgvpd 61 rfsgsgsatd ftltissvqa edvadyhcgq synypytfgq gtkleik
```

(19) Nucleic Acid Sequence Encoding the Full Length Humanized
LRMR2B8LC Light Chain Variable Region and the Human Kappa Chain
Constant Region (Km(3) allotype) (allele 1) (signal sequence
underlined)

(SEQ ID NO. 200)

```
  1 atggaatccc aaacccttgt tttcatctct atccttctct ggctttatgg cgccgacgga 61 gacatcgtaa tgacacaatc ccctgactct cttgctatga gcttgggcga acgagtaaca 121 cttaactgca aagcatccga aaatgtcgta tcttacgtat cctggtatca gcaaaaacct 181 ggtcaaagtc ctaaacttct tatatatggt gcaagtaatc gtgaaagtgg cgtcccagac 241 agatttagcg gttcaggttc agcaactgac tttacactta caatttctag cgttcaggcc 301 gaagacgttg cagactatca ttgtggacaa tcttataact atccttatac tttcggacaa 361 ggcactaaac ttgaaattaa acgtacggtg ctgcaccat ctgtcttcat cttcccgcca 421 tctgatgagc agttgaaatc tggaactgcc tctgttgtgt gcctgctgaa taacttctat 481 cccagagagg ccaaagtaca gtggaaggtg gataacgccc tccaatcggg taactcccag 541 gagagtgtca cagagcagga cagcaaggac agcacctaca gcctcagcag cacCCtgacg 601 ctgagcaaag cagactacga gaaacacaaa gtctacgcct gcgaagtcac ccatcagggc 661 ctgagctcgc ccgtcacaaa gagcttcaac aggggagagt gttag
```

(20) Protein Sequence Defining the Full Length Humanized LRMR2B8LC
Light Chain Variable Region and the Human Kappa Chain Constant Region
(Km(3) allotype) (allele 1)

(SEQ ID NO. 201)

```
  1 divmtqspds lamslgervt lnckasenvv syvswyqqkp gqspklliyg asnresgvpd 61 rfsgsgsatd ftltissvqa edvadyhcgq synypytfgq gtkleikrtv aapsvfifpp
```

```
121 sdeqlksgta svvcllnnfy preakvqwkv dnalqsgnsq esvteqdskd styslsstlt
181 lskadyekhk vyacevthqg lsspvtksfn rgec
```

For convenience, Table 14 provides a concordance chart showing the correspondence between the full length sequences and of the antibodies discussed in this section with those presented in the Sequence Listing.

TABLE 14

| SEQ. ID NO. | Protein or Nucleic Acid |
| --- | --- |
| 182 | LR2B8HC Heavy Chain Variable Region – nucleic acid |
| 183 | LR2B8HC Heavy Chain Variable Region – protein |
| 184 | Human IgG1 Heavy Chain Constant Region (G1m(3) allotype) (allele 1) – nucleic acid |
| 185 | Human IgG1 Heavy Chain Constant Region (G1m(3) allotype) (allele 1) – protein |
| 186 | LR2B8HC + IgG1 Constant (G1m(3) allotype) (allele 1) – nucleic acid |
| 187 | LR2B8HC + IgG1 Constant (G1m(3) allotype) (allele 1) – protein |
| 188 | LRMR2B8HC Heavy Chain Variable Region – nucleic acid |
| 189 | LRMR2B8HC Heavy Chain Variable Region – protein |
| 190 | LRMR2B8HC + IgG1 Constant (G1m(3) allotype) (allele 1) – nucleic acid |
| 191 | LRMR2B8HC + IgG1 Constant (G1m(3) allotype) (allele 1) – protein |
| 192 | LR2B8LC Light Chain Variable Region – nucleic acid |
| 193 | LR2B8LC Light Chain Variable Region – protein |
| 194 | Human Kappa Chain Constant Region (Km(3) allotype) (allele 1) – nucleic acid |
| 195 | Human Kappa Chain Constant Region (Km(3) allotype) (allele 1) – protein |
| 196 | LR2B8LC + Kappa Constant (Km(3) allotype) (allele 1) – nucleic acid |
| 197 | LR2B8LC + Kappa Constant (Km(3) allotype) (allele 1) – protein |
| 198 | LRMR2B8LC Light Chain Variable Region – nucleic acid |
| 199 | LRMR2B8LC Light Chain Variable Region – protein |
| 200 | LRMR2B8LC + Kappa Constant (Km(3) allotype) (allele 1) – nucleic acid |
| 201 | LRMR2B8LC + Kappa Constant (Km(3) allotype) (allele 1) – protein |

Table 15 summarizes the heavy chain CDR sequences (Kabat Definition) of the humanized 2B8 antibodies prepared by humanization procedure 1 and by humanization procedure 2 described herein above in this Example.

TABLE 15

| Antibody | CDR1 | CDR2 | CDR3 | Full Length Heavy Chain Variable Region |
| --- | --- | --- | --- | --- |
| Murine 2B8 Heavy | TYWMH (SEQ ID NO: 15) | EINPTNGHTNYNEKFKS (SEQ ID NO: 16) | NYVGSIFDY (SEQ ID NO: 17) | SEQ ID NO: 12 |
| Hu2B8 Hv1f.1 | TYWMH (SEQ ID NO: 15) | EINPTNGHTNYNEKFQG (SEQ ID NO: 202) | NYVGSIFDY (SEQ ID NO: 17) | SEQ ID NO: 159 |
| Hu2B8 Hv5a.1 | TYWMH (SEQ ID NO: 15) | EINPTNGHTNYNPSFQG (SEQ ID NO: 203) | NYVGSIFDY (SEQ ID NO: 17) | SEQ ID NO: 165 |
| Hu2B8 Hv5-51.1 | TYWMH (SEQ ID NO: 15) | EINPTNGHTNYNPSFQG (SEQ ID NO: 203) | NYVGSIFDY (SEQ ID NO: 17) | SEQ ID NO: 169 |
| LR2B8HC | TYWMH (SEQ ID NO: 15) | EINPTNGHTNYNEKFKG (SEQ ID NO: 204) | NYVGSIFDY (SEQ ID NO: 17) | SEQ ID NO: 183 |
| LRMR2B8HC | TYWMH (SEQ ID NO: 15) | EINPTNGHTNYNQKFQG (SEQ ID NO: 205) | NYVGSIFDY (SEQ ID NO: 17) | SEQ ID NO: 189 |

Table 16 summarizes the light chain CDR sequences (Kabat Definition) of the humanized 2B8 antibodies prepared by humanization procedure 1 and by humanization procedure 2 described herein above in this Example.

TABLE 16

| Antibody | CDR1 | CDR2 | CDR3 | Full Length Light Chain Variable Region |
|---|---|---|---|---|
| Murine 2B8 Light | KASENVVSYVS (SEQ ID NO: 18) | GASNRNT (SEQ ID NO: 19) | GQSYNYPYT (SEQ ID NO: 20) | SEQ ID NO: 14 |
| Hu2B8 Kv1-39.1 | KASENVVSYVS (SEQ ID NO: 18) | GASNRNT (SEQ ID NO: 19) | GQSYNYPYT (SEQ ID NO: 20) | SEQ ID NO: 173 |
| Hu2B8 Kv3-15.1 | KASENVVSYVS (SEQ ID NO: 18) | GASNRNT (SEQ ID NO: 19) | GQSYNYPYT (SEQ ID NO: 20) | SEQ ID NO: 179 |
| LR2B8LC | KASENVVSYVS (SEQ ID NO: 18) | GASNRNT (SEQ ID NO: 19) | GQSYNYPYT (SEQ ID NO: 20) | SEQ ID NO: 193 |
| LRMR2B8LC | KASENVVSYVS (SEQ ID NO: 18) | GASNRES (SEQ ID NO: 206) | GQSYNYPYT (SEQ ID NO: 20) | SEQ ID NO: 199 |

C. Binding Affinity of Humanized 2B8 Antibodies

Antigen-binding affinity and kinetics of interaction were assessed by surface plasmon resonance technology using a BIAcore T100 instrument. Mouse anti-human immunoglobulins (Jackson ImmunoResearch Labs, 209-005-098) were immobilized on carboxymethylated dextran CM4 sensor chips (BIAcore, Catalog No. BR-1005-34) by amine coupling (BIAcore, Catalog No. BR-1000-50) using a standard coupling protocol according to manufacturer's recommendations. The analyses were performed at 25° C. using PBS (GIBCO, Catalog No. 14040-133) containing 0.05% surfactant P20 (BIAcore, Catalog No. BR-1000-54), 2 mg/mL BSA (EMD, Catalog No. 2930) and 10 mg/mL CM-Dextran Sodium salt (Fluka, Catalog No. 86524) as running buffer.

The antibodies were captured on individual flow cell at a flow rate of 10 µL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 µL/min. The dissociation phase was monitored for 15 or 90 minutes, depending on concentration. The surface then was regenerated with 10 mM Glycine-HCl, pH 2.0 (BIAcore, Catalog No. BR-1003-55) injected for 3 minutes at a flow rate of 60 µL/min before another cycle was initiated. HGF concentrations tested were 1.88, 3.75 and 7.5 nM. Determination of kinetic parameters was achieved using the kinetic function of the BIAevalutation software with reference subtraction. Kinetic parameters for each antibody, $k_a$ (association rate constant), $k_d$ (dissociation rate constant) and $K_D$ (equilibrium dissociation constant) are summarized in FIG. 8.

The results summarized in FIG. 8 show that certain combinations of superhumanized heavy chains (Hu2B8 Hv5a.1, Hu2B8 Hv5-51.1 or Hu2B8 Hv1-f.1) and light chains (Hu2B8 Kv1-39.1 or Hu2B8 Kv3-15.1) retain similar binding affinity ($K_D$) to HGF as chimeric 2B8 (mouse variable regions with human constant regions) and 2B8 (Table 5).

D. Mutually Exclusive Binding Assay

Mutually exclusive binding to HGF was assessed by surface plasmon resonance technology using a BIAcore T100 instrument. Mouse anti-human immunoglobulins (Jackson ImmunoResearch Labs, 209-005-098) were immobilized on carboxymethylated dextran CM5 sensor chips (BIAcore, Catalog No. BR-1006-68) by amine coupling (BIAcore, Catalog No. BR-1000-50) using a standard coupling protocol according to manufacturer's recommendations. The analyses were performed at 25° C. using PBS (GIBCO, Catalog No. 14040-133) containing 0.05% surfactant P20 (BIAcore, #BR-1000-54), 2 mg/mL BSA (EMD, Catalog No. 2930) and 10 mg/ml CM-Dextran Sodium salt (Fluka, Catalog No. 86524) as running buffer.

The humanized antibodies were captured on an individual flow cell at a flow rate of 30 µL/min. Injection time was variable for each antibody to yield approximately 150 RU of antibody captured for each cycle. HGF (R&D Systems, Catalog No. 294-HGN-025) diluted in running buffer at a final concentration of 7.5 µg/mL was injected for 90 sec at 30 µL/min over the captured humanized antibodies. Binding of HGF was monitored before subsequent injection of mouse 2B8 antibody or polyclonal goat anti-HGF antibody (R & D Systems, AF294) for 3 min at 30 µL/min. The surface then was regenerated with 10 mM Glycine-HCl, pH 2.0 (BIAcore, Catalog No. BR-1003-55) injected for 3 min at a flow rate of 60 µL/min before another antibody was tested. The results are summarized in FIG. 9.

Figure 9:
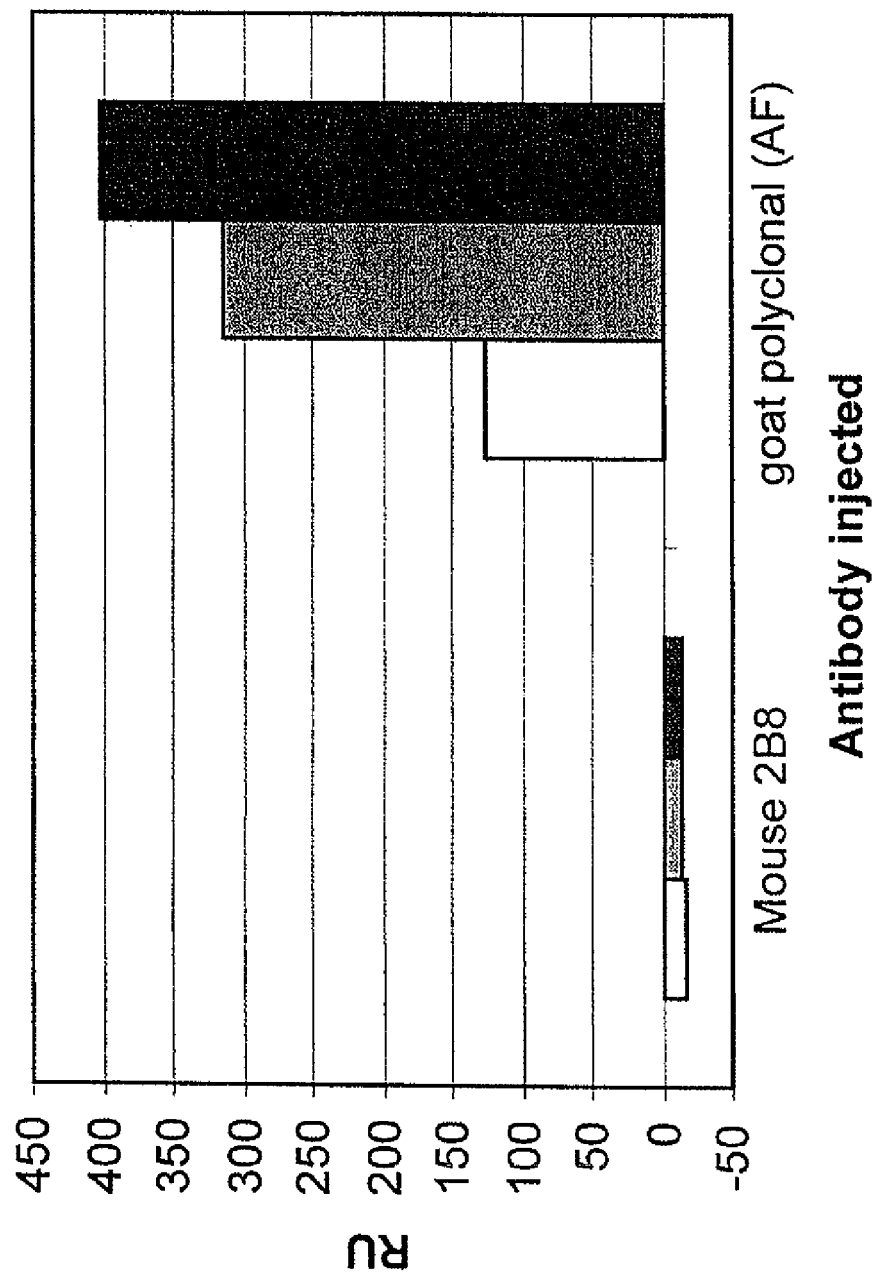
FIG. 9 is a bar chart summarizing experimental data indicating that Hu2B8 binds an epitope mutually exclusive to murine monoclonal antibody 2B8. Humanized or chimeric 2B8 was captured on an anti-human Fc chip. HGF then was bound to the humanized or chimeric 2B8. The ability of mouse 2B8 or the control antibody (polyclonal goat anti-HGF antibody) to bind the captured HGF was measured. Both humanized 2B8 antibodies and chimeric 2B8 prevent murine 2B8 from binding HGF. White bars correspond to the chimeric 2B8 antibody; gray bars correspond to the humanized Hu2B8 antibody (kappa variable region Kv1-39.1 and heavy chain variable region Hv5-51.1); black bars correspond to the humanized Hu2B8 antibody (kappa variable region Kv3-15.1 and heavy chain variable region Hv5-51.1).

Results summarized in FIG. 9 show that both humanized 2B8 antibodies and chimeric 2B8 antibodies prevent murine 2B8 from binding HGF. These results demonstrate that the humanized antibodies still bind the same HGF epitope as the original 2B8 antibody.

Example 13

Production of Humanized 2B8 Variants a. HUMAN ENGINEERED™ Antibodies

Codon- and expression-optimized low risk and low-plus-moderate risk Human Engineered light chain (LR2B8LC and LRMR2B8LC, respectively) and heavy chains (LR2B8HC and LRMR2B8HC, respectively) were cloned in-phase into XOMA's transient antibody expression vectors, which contain human Kappa and Gamma-1 constant regions modules. The four Human Engineered 2B8 variants were produced by transient transfection in HEK293E cells. The following four antibodies were produced:

HE2B8-1=LR2B8HC (+IgG1 constant region (G1m(3) allotype (allele 1)) (SEQ ID NO. 187) plus LR2B8LC (+Kappa constant region (Km(3) allotype (allele 1))) (SEQ ID NO. 197)

HE2B8-2=LR2B8HC (+IgG1 constant region (G1m(3) allotype (allele 1)) (SEQ ID NO. 187) plus LRMR2B8LC (+Kappa constant region (Km(3) allotype (allele 1))) (SEQ ID NO. 201)

HE2B8-3=LRMR2B8HC (+IgG1 constant region (G1m (3) allotype (allele 1)) (SEQ ID NO. 191) plus LR2B8LC (+Kappa constant region (Km(3) allotype (allele 1))) (SEQ ID NO. 197)

HE2B8-4=LRMR2B8HC (+IgG1 constant region (G1m (3) allotype (allele 1)) (SEQ ID NO. 191) plus LRMR2B8LC (+Kappa constant region (Km(3) allotype (allele 1))) (SEQ ID NO. 201)

The light and heavy chains were co-transfected into XOMA's suspension adapted HEK293E cells grown in IS293 media (Irvine Scientific, Irvine, Calif.) using 2 liter shake flasks. After 24 hours in the shake flasks, 200 mL of transfected cells were centrifuged, resuspended in 40 mL of fresh medium and transferred to Integra flasks (Wilson Wolf Manufacturing Inc., MN) for production. After incubation for seven days, the cell suspensions were removed from the Integra flasks, centrifuged and the culture supernatants retained. Antibodies in the culture supernatants were purified on protein A spin columns (Pro-Chem), dialyzed against PBS, concentrated and sterile filtered.

b. SUPERHUMANIZED™ Antibodies

Full length Hu2B8_Hv5-51.1+human IgG1 constant domain (G1 m(3) allotype) cDNA was cloned into pEE6.4 (Lonza Biologics, Berkshire, UK) using HindIII and EcoRI restriction sites. Full length Hu2B8_Kv1-39.1 variable region+human Kappa constant domain cDNA and full length Hu2B8_Kv3-15.1 variable region+human Kappa constant domain cDNA were each cloned into pEE14.4 (Lonza Biologics) using HindIII and EcoRI restriction sites. The hCMV-MIE promoter+full length Hu2B8_Hv5-51.1+human IgG1 constant domain (G1m(3) allotype) cDNA+SV40 poly A fragment (in pEE6.4) was removed by NotI/SalI digestion and inserted into either Kappa chain pEE14.4 vector through NotI/SalI sites, thus creating 2 different expression vectors that each simultaneously express heavy and light chain to make the following antibodies:

- sh2B8-9 (G1m(3))=hu2B8 Hv5-51.1 (+IgG1 constant region (G1m(3) allotype) (allele 2)) (SEQ ID NO. 210) plus hu2B8 Kv 1-39.1 (+Kappa constant region (Km(3) allotype (allele 2))) (SEQ ID NO: 177)
- sh2B8-12 (G1m(3))=hu2B8 Hv5-51.1 (+IgG1 constant region (G1m(3) allotype) (allele 2)) (SEQ ID NO. 210) plus hu2B8 Kv 3-15.1 (+Kappa constant region (Km(3) allotype (allele 2))) (SEQ ID No. 181)

The nucleic acid sequences encoding and the protein sequences defining the human IgG1 Heavy Constant Region G1m(3) allotype (allele 2) and each of the full length heavy chain sequences are set forth below. The light chain sequences were the same as described in Example 12.

(1) Nucleic Acid Sequence Encoding Human IgG1 Heavy Chain Constant Region (G1m(3) allotype) (allele 2) (SEQ ID NO. 207)

```
  1 cctccaccaa gggcccatcg gtcttccccc tggcaccctc
    ctccaagagc acctctgggg
 61 gcacagcggc cctgggctgc ctggtcaagg actacttccc
    cgaaccggtg acggtgtcgt
121 ggaactcagg cgccctgacc agcggcgtgc acaccttccc
    ggctgtccta cagtcctcag
181 gactctactc cctcagcagc gtggtgaccg tgccctccag
    cagcttgggc acccagacct
241 acatctgcaa cgtgaatcac aagcccagca acaccaaggt
    ggacaagaga gttgagccca
301 aatcttgtga caaaactcac acatgcccac cgtgcccagc
    acctgaactc ctggggggac
361 cgtcagtctt cctcttcccc ccaaaaccca aggacaccct
    catgatctcc cggacccctg
421 aggtcacatg cgtggtggtg gacgtgagcc acgaagaccc
    tgaggtcaag ttcaactggt
481 acgtggacgg cgtggaggtg cataatgcca gacaaagcc
    gcgggaggag cagtacaaca
541 gcacgtaccg tgtggtcagc gtcctcaccg tcctgcacca
    ggactggctg aatggcaagg
601 agtacaagtg caaggtctcc aacaaagccc tcccagcccc
    catcgagaag accatctcca
661 aagccaaagg gcagccccga gaaccacagg tgtacaccct
    gcccccatcc cgggaggaga
721 tgaccaagaa ccaggtcagc ctgacctgcc tggtcaaagg
    cttctatccc agcgacatcg
781 ccgtggagtg ggagagcaat gggcagccgg agaacaacta
    caagaccacg cctcccgtgc
841 tggactccga cggctccttc ttcctctaca gcaagctcac
    cgtggacaag agcaggtggc
901 agcaggggaa cgtcttctca tgctccgtga tgcatgaggc
    tctgcacaac cactacacgc
961 agaagagcct ctccctgtct ccgggtaaat ga
```

The first amino acid is derived from translation of the last nucleotide of variable region and the beginning two nucleotides of the IgG1 Heavy Chain sequence.

(2) Protein Sequence Defining Human IgG1 Heavy Chain Constant Region (G1m(3) allotype) (allele 1 or 2).

(SEQ ID NO. 208)

```
  1 astkgpsvfp lapsskstsg gtaalgclvk dyfpepvtvs wnsgaltsgv htfpavlqss
 61 glyslssvvt vpssslgtqt yicnvnhkps ntkvdkrvep kscdkthtcp pcpapellgg
121 psvflfppkp kdtlmisrtp evtcvvvdvs hedpevkfnw yvdgvevhna ktkpreeqyn
181 styrvvsvlt vlhqdwlngk eykckvsnka lpapiektis kakgqprepq vytlppsree
241 mtknqvsltc lvkgfypsdi avewesngqp ennykttppv ldsdgsffly skltvdksrw
301 qqgnvfscsv mhealhnhyt qkslslspgk
```

(3) Nucleic Acid Sequence Encoding the Full Length Chain Containing Humanized Hu2B8 Hv5-51.1 Heavy Chain Variable Region and the Human IgG1 Heavy Chain Constant Region G1m(3) allotype (allele 2) (signal sequence underlined)

-continued (SEQ ID NO. 209)
```
   1 atgggtcaa ccgccatcct cgccctcctc ctggctgttc tccaaggagt ctgtgccgaa
  61 gtgcagctgg tgcagtctgg agcagaggtg aaaaagcccg gggagtctct gaagatctcc
 121 tgtaagggtt ctggatacag ctttaccacc tactgatgc actgggtgcg ccagatgccc
 181 gggaaaggcc tggagtggat gggggagatt aatcctacca cggtcatac taactacaat
 241 ccgtccttcc aaggccaggt caccatctca gctgacaagt ccatcagcac tgcctacctg
 301 cagtggagca gcctgaaggc ctcggacacc gccatgtatt actgtgcgag aaactatgtt
 361 ggtagcatct ttgactactg gggccaagga accctggtca ccgtctcctc agcctccacc
 421 aagggcccat cggtcttccc cctggcaccc tcctccaaga gcacctctgg gggcacagcg
 481 gccctgggct gcctggtcaa ggactacttc cccgaaccgg tgacggtgtc gtggaactca
 541 ggcgccctga ccagcggcgt gcacaccttc ccggctgtcc tacagtcctc aggactctac
 601 tccctcagca gcgtggtgac cgtgccctcc agcagcttgg gcacccagac ctacatctgc
 661 aacgtgaatc acaagcccag caacaccaag gtggacaaga gagttgagcc caaatcttgt
 721 gacaaaactc acacatgccc accgtgccca gcacctgaac tcctgggggg accgtcagtc
 781 ttcctcttcc ccccaaaacc caaggacacc ctcatgatct cccggacccc tgaggtcaca
 841 tgcgtggtgg tggacgtgag ccacgaagac cctgaggtca agttcaactg gtacgtggac
 901 ggcgtggagg tgcataatgc caagacaaag ccgcgggagg agcagtacaa cagcacgtac
 961 cgtgtggtca gcgtcctcac cgtcctgcac caggactggc tgaatggcaa ggagtacaag
1021 tgcaaggtct ccaacaaagc cctcccagcc cccatcgaga agaccatctc caaagccaaa
1081 gggcagcccc gagaaccaca ggtgtacacc ctgcccccat cccgggagga gatgaccaag
1141 aaccaggtca gcctgacctg cctggtcaaa ggcttctatc ccagcgacat cgccgtggag
1201 tgggagagca atgggcagcc ggagaacaac tacaagacca cgcctcccgt gctggactcc
1261 gacggctcct tcttcctcta cagcaagctc accgtggaca agagcaggtg gcagcagggg
1321 aacgtcttct catgctccgt gatgcatgag gctctgcaca accactacac gcagaagagc
1381 ctctccctgt ctccgggtaa atga
```

(4) Protein Sequence Defining the Full Length Heavy Chain Containing
Humanized Hu2B8 Hv5-51.1 and the Human IgG1 Heavy Chain Constant
Region G1m(3) allotype (allele 2) (without signal sequence)

(SEQ ID NO. 210)
```
  1 evqlvqsgae vkkpgeslki sckgsgysft tywmhwvrqm pgkglewmge inptnghtny
 61 npsfqgqvti sadksistay lqwsslkasd tamyycarny vgsifdywgq gtlvtvssas
121 tkgpsvfpla psskstsggt aalgclvkdy fpepvtvswn sgaltsgvht fpavlqssgl
181 yslssvvtvp ssslgtqtyi cnvnhkpsnt kvdkrvepks cdkthtcppc papellggps
241 vflfppkpkd tlmisrtpev tcvvvdvshe dpevkfnwyv dgvevhnakt kpreeqynst
301 yrvvsvltvl hqdwlngkey kckvsnkalp apiektiska kgqprepqvy tlppsreemt
361 knqvsltclv kgfypsdiav ewesngqpen nykttppvld sdgsfflysk ltvdksrwqq
421 gnvfscsvmh ealhnhytqk slslspgk
```

Each dual expression vector was transfected into 293T cells for transient expression using DMEM 10% fetal bovine serum. Forty-eight hours after transfection, cells were washed with and then replaced with serum free medium, IS GRO™ (Irvine Scientific, Santa Ana, Calif.) containing 4 mM L-Glutamine. Supernatant was harvested daily and replaced with fresh media for 10 days. The culture supernatants were centrifuged, filtered (0.45 μm) and concentrated 10-100 fold. Antibodies were purified on ProSep vA resin (Millipore), dialyzed against PBS, concentrated and sterile filtered.

Example 14

Binding Characteristics of Humanized 2B8 Variants

The humanized antibodies produced in Example 13 were characterized by their ability to bind hHGF and the recombinant HGF proteins produced in Example 3.

The antibodies were analyzed by surface-plasmon resonance using a BIAcore T100 instrument to assess their ability to bind hHGF and the fusion proteins discussed in Example 3. Each antibody was immobilized on a carboxymethylated dextran CM5 sensor chip (BIAcore, Catalog No. BR-1006-68) by amine coupling (BIAcore, Catalog No. BR-1000-50) using a standard coupling protocol according to manufacturer's instructions.

Analyses were performed at 25° C. using PBS (GIBCO, Catalog No. 14040-133) containing 0.05% surfactant P20 (BIAcore, Catalog No. R-1000-54), 2 mg/mL BSA (EMD, Catalog No. 2930) and 10 mg/mL CM-Dextran Sodium salt (Fluka, Catalog No. 86524) as running buffer. Supernatant containing different HGF fusion proteins or supernatant from cells transfected with empty vector were injected over each antibody at a flow rate of 30 μL/min for 3 minutes. The resulting binding was determined as resonance units (RU) over baseline 30 seconds after the end of injection. Binding was compared to human HGF (R&D Systems, Catalog No. 294-HGN-025) diluted in running buffer. Non-specific binding was monitored by comparing binding to a control surface. The results are summarized in the Table 17.

Mouse anti-human immunoglobulins (Jackson Labs, Catalog No. 209-005) were immobilized on carboxymethylated dextran CM4 sensor chips (BIAcore, Catalog No. BR-1006-68) by amine coupling (BIAcore, Catalog No. BR-1000-50) using a standard coupling protocol according to manufacturer's instructions. The analyses were performed at 25° C. using PBS (GIBCO, Catalog No. 14040-133) containing 0.05% surfactant P20 (BIAcore, Catalog No. BR-1000-54), and 2 mg/mL BSA (EMD, Catalog No. 2930).

The antibodies were captured in an individual flow cell at a flow rate of 10 μL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 μL/min. The dissociation phase was monitored for 15 or 90 minutes, depending on concentration. The surface then was regenerated with 10 mM Glycine-HCl, pH 2.2 (BIAcore, Catalog No. BR-1003-54) injected for 3 minutes at a flow rate of 60 μL/min before another cycle was initiated. HGF concentrations tested were 0.46 nM to 7.5 nM.

Kinetic parameters were determined using the kinetic function of the BIAevalutation™ software with reference subtraction. Kinetic parameters for each antibody, $k_a$ (association rate constant), $k_d$ (dissociation rate constant) and $K_D$ (equilibrium dissociation constant) are summarized in Table 18.

TABLE 18

| Antibody | $k_a$ (1/Ms) | $k_d$ (1/s) | $K_D$ (pM) | SD |
|---|---|---|---|---|
| 2B8 | $1.4 \times 10^6$ | $1.0 \times 10^{-5}$ | 7.3 | — |
| HE2B8-1 | $2.2 \times 10^6$ | $1.4 \times 10^{-5}$ | 7.1 | 5.2 |
| HE2B8-2 | $1.8 \times 10^6$ | $9.6 \times 10^{-6}$ | 5.2 | 2.7 |
| HE2B8-3 | $2.0 \times 10^6$ | $4.1 \times 10^{-6}$ | 2.0 | 1.1 |
| HE2B8-4 | $1.7 \times 10^6$ | $1.1 \times 10^{-5}$ | 6.5 | 1.3 |
| sh2B8-9 (G1m(17, 1) | $2.0 \times 10^6$ | $1.7 \times 10^{-5}$ | 8.1 | 5.3 |
| sh2B8-12(G1m(17, 1) | $1.9 \times 10^6$ | $2.3 \times 10^{-5}$ | 12 | 0.4 |

TABLE 17

| Antibody | rhHGF (R&D Systems) | rmHGF (R&D Systems) | MHM chimera (495-585) | MHM chimera (507-585) | MHM chimera (499-556) |
|---|---|---|---|---|---|
| 2B8 | Yes | No | Yes | Yes | Yes |
| HE2B8-1 | Yes | No | Yes | Yes | Yes |
| HE2B8-2 | Yes | No | Yes | Yes | Yes |
| HE2B8-3 | Yes | No | Yes | Yes | Yes |
| HE2B8-4 | Yes | No | Yes | Yes | Yes |
| sh2B8-9 (G1m(3)) | Yes | No | Yes | Yes | Yes |
| sh2B8-12 (G1m(3)) | Yes | No | Yes | Yes | Yes |

The results in Table 17 demonstrate that each of the humanized 2B8-based antibodies bind rhHGF and all three mouse-human-mouse chimeras.

Example 15

Binding Affinities of Humanized 2B8 Variants

The binding affinities and kinetics of interaction of the antibodies listed in Table 15 were measured by surface plasmon resonance.

These data show that the humanized antibodies have fast association rates ($k_a$), very slow dissociation rates ($k_d$), and very high affinities ($K_D$). In particular, the antibodies have affinities ranging from 2.0-12 pM.

Example 16

Comparison of Binding Affinities at 25° C. and 37° C.

The binding affinities and kinetics of interaction of antibody HE2B8-4, sh2B8-9, sh2B8-12, and murine 2B8 were measured by surface plasmon resonance under different conditions.

Mouse anti-human immunoglobulins (Jackson Labs, Catalog No. 209-005) or rabbit anti-mouse immunoglobulins (BIAcore, Catalog No. BR-1005-14) were immobilized on carboxymethylated dextran CM4 sensor chips (BIAcore, Catalog No. BR-1006-68) by amine coupling (BIAcore, Catalog No. BR-1000-50) using a standard coupling protocol according to manufacturer's instructions. In the case of 25° C. measurements for sh2b8-9 and sh2B8-12, a CM5 sensor chip (BIAcore, Catalog No. BR-1006-68) was used. The analyses were performed at 25° C. and 37° C. using PBS (GIBCO, Catalog No. 14040-133) containing 0.05% surfactant P20 (BIAcore, Catalog No. BR-1000-54), and 2 mg/mL BSA (EMD, Catalog No. 2930) as running buffer.

The antibodies were captured in an individual flow cell at a flow rate of 10 μL/min. Injection time was variable for each antibody to yield approximately 20 RU of antibody captured for each cycle. Buffer or HGF (R&D Systems, Catalog No. 294-HGN-025) diluted in running buffer was injected sequentially over a reference surface (no antibody captured) and the active surface (antibody to be tested) for 2 minutes at 60 μL/min. The dissociation phase was monitored for 15 or 90 minutes, depending on concentration. The surface of mouse anti-human immunoglobulins sensor chips was then regenerated with 10 mM Glycine-HCl, pH 2.2 (BIAcore, Catalog No. BR-1003-54) injected for 3 minutes at a flow rate of 60 μL/min before another cycle was initiated. The surface of rabbit anti-mouse immunoglobulins sensor chips was regenerated with 10 mM Glycine-HCl, pH 1.7 (BIAcore, Catalog No. BR-1003-54) injected for 3 minutes at a flow rate of 60 μL/min before another cycle was initiated. HGF concentrations tested were 0.46 nM to 7.5 nM.

Kinetic parameters were determined using the kinetic function of the BIAevaluation software with reference subtraction. Kinetic parameters for each antibody, $k_a$ (association rate constant), $k_d$ (dissociation rate constant) and $K_D$ (equilibrium dissociation constant) are summarized below in Table 19.

TABLE 19

| Antibody | Temp. (° C.) | $k_a$ (1/Ms) | $k_d$ (1/s) | $K_D$ (pM) |
|---|---|---|---|---|
| 2B8 | 25 | $1.6 \times 10^6$ | $2.1 \times 10^{-5}$ | 13.5 |
| 2B8 | 37 | $2.8 \times 10^6$ | $1.3 \times 10^{-5}$ | 4.5 |
| HE2B8-4 | 25 | $2.0 \times 10^6$ | $1.2 \times 10^{-5}$ | 5.6 |
| HE2B8-4 | 37 | $3.1 \times 10^6$ | $1.0 \times 10^{-5}$ | 3.3 |
| sh2B8-9 (G1m(17, 1)) | 25 | $2.0 \times 10^6$ | $1.7 \times 10^{-5}$ | 8.1 |
| sh2B8-9 (G1m(3)) | 37 | $2.5 \times 10^6$ | $1.4 \times 10^{-5}$ | 5.8 |
| sh2B8-12 (G1m(17, 1)) | 25 | $1.9 \times 10^6$ | $2.3 \times 10^{-5}$ | 12.0 |
| sh2B8-12 (G1m(3)) | 37 | $2.4 \times 10^6$ | $1.1 \times 10^{-5}$ | 4.8 |

As expected, the association rate constants increased with an increase in the temperature. Surprisingly, the dissociation constants did not change significantly with a corresponding increase in temperature. Consequently, the overall equilibrium dissociation constants ($K_D$) were approximately 1.4 to 3 times smaller (higher affinity) at physiological temperature (37° C.).

Example 17

Neutralization Activity of Humanized 2B8 Variants

The antibodies described in Example 14 were characterized for their ability to (a) inhibit the binding of hHGF to c-Met, and (b) inhibit HGF stimulated BrdU incorporation in 4 MBr-5 cells.

HGF-Met Binding Inhibition Assay (Neutralization Assay) was performed as described in as follows. The antibodies were tested by ELISA for their ability to inhibit hHGF binding to c-Met. Specifically, Wallac 96-well DELFIA assay plates (Wallac Inc., Catalog No. AAAND-0001) were coated with 100 μL of 6.25 μg/mL HGF (R&D Systems, Catalog No. 294-HGN-025) in carbonate coating buffer (15 mM $Na_2CO_3$ and 34 mM $NaHCO_3$, pH 9.0) for 16 hours at 4° C. The plates then were blocked with 200 μL of 5% non-fat dry milk in PBS for 1 hour at room temperature. The antibodies were prepared in a separate plate by adding increasing concentrations of the antibodies under investigation (0.033-250 nM, 2-fold-serial dilution) to 2 nM biotinylated c-Met in 5% non-fat dry milk in PBS. c-Met (R&D Systems, Catalog No. 358-MT/CF) is biotinylated according to manufacturer's instruction at 10:1 biotin to c-Met ratio (Pierce, Catalog No. 21335). 100 μL of sample per well was transferred to the assay plate and incubated for 2 hours at room temperature. The resulting plates were washed three times with PBS-0.1% Tween 20, and incubated for 1 hour at room temperature with Eu-labeled Streptavidin (Wallac, Catalog No. 1244-360) diluted 1:1000 in DELFIA assay buffer (Wallac, Catalog No. 4002-0010). The resulting plates were washed 3 times with DELFIA wash solution (Wallac, Catalog No. 4010-0010) and incubated with 100 μL/well DELFIA enhancement solution (Wallac #4001-0010) for 15 minutes at room temperature with agitation. The plates were read on Victor$^3$V instrument (Perkin Elmer) using the Europium method. The $IC_{50}$ values were calculated using Prism.

The $IC_{50}$ values obtained are shown in Table 20.

TABLE 20

| Antibody | $IC_{50}$ (nM) | SD |
|---|---|---|
| 2B8 | 9.2 | 1.2 |
| HE2B8-1 | 6.0 | 1.2 |
| HE2B8-2 | 5.7 | 1.1 |
| HE2B8-3 | 5.9 | 1.1 |
| HE2B8-4 | 6.5 | 1.2 |
| sh2B8-9 (G1m(3)) | 4.2 | — |
| sh2B8-12 (G1m(3)) | 6.8 | — |

These results from Table 20 demonstrate that the humanized antibodies tested efficiently neutralize HGF binding to c-Met.

The antibodies in Table 17 were also tested in the cell proliferation assay described in Example 7(b). The results are summarized below in Table 21.

TABLE 21

| Antibody | $IC_{50}$ (nM) | SD |
|---|---|---|
| 2B8 | 0.86 | 0.35 |
| HE2B8-1 | 0.47 | 0.15 |

TABLE 21-continued

| Antibody | IC$_{50}$ (nM) | SD |
|---|---|---|
| HE2B8-2 | 0.66 | 0.13 |
| HE2B8-3 | 0.55 | 0.28 |
| HE2B8-4 | 0.58 | 0.26 |
| sh2B8-9 (G1m(3)) | 0.52 | 0.11 |
| sh2B8-12 (G1m(3)) | 0.81 | 0.22 |

The results from Table 21 demonstrate that all the humanized antibodies tested inhibit HGF-induced proliferation of 4 MBr-5 cells.

Example 18

Anti-Scatter Activity of Humanized 2B8 Variants

The antibodies in Table 17 were tested in the anti-scatter assay described in Example 8. The results are summarized below in Table 22.

TABLE 22

Inhibition of HGF-induced MDCK Cell Scattering

| Antibody | Trial 1 | Trial 2 |
|---|---|---|
| 2B8 | ++ | ++ |
| HE2B8-1 | ++ | ++ |
| HE2B8-2 | ++ | ++ |
| HE2B8-3 | ++ | ++ |
| HE2B8-4 | ++ | ++ |
| sh2B8-9 (G1m(3)) | ++ | ++ |
| sh2B8-12 (G1m(3)) | ++ | ++ |

− No Inhibition
+++ Very strong, nearly complete inhibition
++ Strong inhibition
+ Detectable inhibition The results in Table 22 demonstrate that all the humanized antibodies tested inhibited HGF-induced scattering to the same extent as the murine monoclonal antibody 2B8.

Example 19

Inhibition of HGF-Stimulated c-Met Phosphorylation

The antibodies in Table 17 were tested in the c-Met phosphorylation assay described in Example 9. The results are summarized below in Table 23.

TABLE 23

| Antibody | Average of Two Trials | Standard Deviation |
|---|---|---|
| 2B8 | 0.91 | 0.02 |
| he2B8-1 | 0.80 | 0.04 |
| he2B8-2 | 0.88 | 0.15 |
| he2B8-3 | 0.79 | 0.05 |
| he2B8-4 | 0.75 | 0.14 |
| sh2B8-9 (G1m(3)) | 0.93 | 0.03 |
| sh2B8-12 (G1m(3)) | 0.81 | 0.07 |

The results in Table 23 demonstrate that all the humanized antibodies tested are potent inhibitors of HGF-induced c-Met phosphorylation in PC-3 cells.

Example 20

Tumor Inhibition in U87MG Xenograft Model

The ability of the humanized monoclonal antibodies of the invention to inhibit tumor growth was tested in an U87MG xenograft model. U87MG cells (ATCC) were expanded in culture at 37° C. in an atmosphere containing 5% $CO_2$ and 95% air, using a medium comprising Dulbecco's Modified Eagle medium (DMEM) with 10% fetal bovine serum, 100 units/mL penicillin and 100 µg/mL streptomycin. The cells were subcultured and maintained by detaching the cells from the wall of the culture dish using trypsin-EDTA.

Near-confluent cells were collected by trypsinization and then $5 \times 10^6$ cells in 50% Matrigel (BD Biosciences; catalog no. 356237) were injected subcutaneously into the upper dorsal area between the shoulder blades of 7-week old female ICR SCID mice (Taconic Labs). The long (L) and short (W) diameters (mm) of tumors were measured with a caliper. Tumor volume (vol.) was calculated as: volume $(mm^3) = L \times W^2/2$. When the tumors grew to approximately 200 $mm^3$, the tumor-bearing mice were randomized into 5 groups of 10 mice each. One group received PBS and one group received human IgG control. Each of the other 4 groups received one of the humanized antibodies (HE2B8-1, HE2B8-2, HE2B8-3, and HE2B8-4). All the antibodies were dosed at 0.25 mg/kg body weight, twice per week, by intra-peritoneal injections of 5 doses. Tumor volumes and mouse body weights were recorded twice per week. Tumor growth inhibition was analyzed using Student's t-test.

The humanized antibodies tested were active in vivo. There was 57% tumor growth inhibition for HE2B8-1 with a p value of 0.02, 61% tumor growth inhibition for HE2B8-2 with a p value of 0.02, 85% tumor growth inhibition for HE2B8-3, with a p value of 0.0004, and 74% tumor growth inhibition for HE2B8-4 with a p value of 0.001. No significant body weight loss was observed.

A subsequent study was performed as described above in female NCR nude mice (Taconic Labs) bearing subcutaneous U87MG tumors inoculated in the flank. Each group (10 mice each) received one of the following treatments at 0.5 mg/kg: PBS vehicle control, huIgG control, HE2B8-4, or sh2B8-9. Treatment was given intra-peritoneal twice weekly for a minimum of 5 weeks. Each treatment group demonstrated similar tumor regression with tumor growth inhibition of 113% for sh2B8-9 and 115% for HE2B8-4, and a minimum tumor growth delay of 30 days. Both treatments were well-tolerated with no significant body weight loss.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An isolated antibody that binds human hepatocyte growth factor (HGF), comprising:
   (a) an immunoglobulin heavy chain variable region comprising the structure $CDR_{H1}$-$CDR_{H2}$-$CDR_{H3}$, wherein
      (i) $CDR_{H1}$ comprises the amino acid sequence of SEQ ID NO. 15,
      (ii) $CDR_{H2}$ comprises the amino acid sequence of SEQ ID NO. 205, and
      (iii) $CDR_{H3}$ comprises the amino acid sequence of SEQ ID NO. 17, and
   (b) an immunoglobulin light chain variable region comprising the structure $CDR_{L1}$-$CDR_{L2}$-$CDR_{L3}$, wherein
      (i) $CDR_{L1}$ comprises the amino acid sequence of SEQ ID NO. 18,
      (ii) $CDR_{L2}$ comprises the amino acid sequence of SEQ ID NO. 206, and
      (iii) $CDR_{L3}$ comprises the amino acid sequence of SEQ ID NO. 20, or an antigen binding fragment of the antibody.

2. The antibody of claim 1, wherein the CDRs are interposed between human or humanized immunoglobulin framework regions.

3. The antibody of claim 1, wherein the antibody is a monoclonal antibody.

4. The antibody of claim 1, wherein the antibody binds human hepatocyte growth factor with a $k_d$ of $4.0 \times 10^{-5}$ $s^{-1}$ or lower.

5. The antibody of claim 1, wherein the antibody binds human hepatocyte growth factor with a $K_D$ of 20 pM or lower.

6. An isolated antibody that binds human hepatocyte growth factor (HGF) comprising an immunoglobulin light chain variable region comprising the amino acid sequence of SEQ ID NO. 199, and an immunoglobulin heavy chain variable region comprising the amino acid sequence of SEQ ID NO. 189, or an antigen binding fragment of the antibody.

7. An isolated antibody that binds human hepatocyte growth factor (HGF) comprising an immunoglobulin light chain sequence comprising the amino acid sequence of SEQ ID NO. 201, and an immunoglobulin heavy chain sequence comprising the amino acid sequence of SEQ ID NO. 191, or an antigen binding fragment of the antibody.

8. The antibody of claim 6, wherein the antibody is a monoclonal antibody.

9. The antibody of claim 7, wherein the antibody is a monoclonal antibody.

* * * * *